US012435062B2

(12) United States Patent
Su et al.

(10) Patent No.: US 12,435,062 B2
(45) Date of Patent: Oct. 7, 2025

(54) AMIDE COMPOUNDS AND USES THEREOF

(71) Applicant: HUTCHISON MEDIPHARMA LIMITED, Shanghai (CN)

(72) Inventors: Wei-Guo Su, Shanghai (CN); Weihan Zhang, Shanghai (CN); Haibin Yang, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 537 days.

(21) Appl. No.: 17/995,172

(22) PCT Filed: Mar. 29, 2021

(86) PCT No.: PCT/CN2021/083664
§ 371 (c)(1),
(2) Date: Sep. 30, 2022

(87) PCT Pub. No.: WO2021/197276
PCT Pub. Date: Oct. 7, 2021

(65) Prior Publication Data
US 2023/0174513 A1 Jun. 8, 2023

(30) Foreign Application Priority Data
Mar. 30, 2020 (CN) ......................... 202010235798.3

(51) Int. Cl.

| | |
|---|---|
| ***C07D 401/14*** | (2006.01) |
| ***A61K 45/06*** | (2006.01) |
| ***C07D 405/14*** | (2006.01) |
| ***C07D 409/14*** | (2006.01) |
| ***C07D 417/14*** | (2006.01) |
| ***C07D 471/04*** | (2006.01) |
| ***C07D 487/04*** | (2006.01) |

(52) U.S. Cl.
CPC ............ *C07D 401/14* (2013.01); *A61K 45/06* (2013.01); *C07D 405/14* (2013.01); *C07D 409/14* (2013.01); *C07D 417/14* (2013.01); *C07D 471/04* (2013.01); *C07D 487/04* (2013.01); *C07B 2200/05* (2013.01)

(58) Field of Classification Search
CPC .. C07D 401/14; C07D 405/14; C07D 409/14; C07D 417/14; C07D 471/04; C07D 487/04; A61P 35/00
See application file for complete search history.

(56) References Cited

U.S. PATENT DOCUMENTS 9,586,967 B2 3/2017 Inukai et al.

FOREIGN PATENT DOCUMENTS

| | | |
|---|---|---|
| CN | 103565653 A | 2/2014 |
| CN | 110330479 A | 10/2019 |
| EP | 3239147 | 11/2017 |
| EP | 3842425 A1 | 8/2021 |
| WO | WO 2005/117867 A2 | 12/2006 |
| WO | WO 2009/140549 | 11/2009 |
| WO | WO 2011/017142 A1 | 2/2011 |
| WO | WO 2011/095045 A1 | 8/2011 |
| WO | WO 2013/078295 A2 | 5/2013 |
| WO | WO 2014/022117 A1 | 2/2014 |
| WO | WO 2014/145004 A1 | 9/2014 |
| WO | WO 2014/145015 A2 | 9/2014 |
| WO | WO 2015/100117 A1 | 7/2015 |
| WO | WO 2015/164161 A1 | 10/2015 |
| WO | WO 2017/161028 A1 | 9/2017 |
| WO | WO 2018/214867 A1 | 11/2018 |
| WO | WO 2019/036657 A1 | 2/2019 |
| WO | WO 2019/183587 A1 | 9/2019 |
| WO | 2019/213340 A1 | 11/2019 |
| WO | WO 2020/038460 | 2/2020 |
| WO | WO 2020/042618 A1 | 3/2020 |
| WO | WO 2020/198026 A1 | 10/2020 |
| WO | WO2021043217 A1 | 3/2021 |

OTHER PUBLICATIONS

Antonescu, C. R., "The GIST paradigm: lessons for other kinase-driven cancers", J. Pathol. 2011, 223(2), pp. 251-261.
Berenstein, R. "Class III Receptor Tyrosine Kinases in Acute Leukemia Biological Functions and Modern Laboratory Analysis", Biomark Insights. 2015, 10(s3), pp. 1-14.
Cannarile, et al., "Colony-stimulating factor 1 receptor (CSF1R) inhibitors in cancer therapy", J. Immunother Cancer. 2017, 5(1):53.
Garcia, et al., "Colony-stimulating factor (CSF) 1 receptor blockade reduces inflammation in human and murine models of rheumatoid arthritis", Arthritis Res Ther. 2016, 18:75.
Hamilton, J. A., "Colony-stimulating factors in inflammation and autoimmunity", Nat Rev Immunol., 2008, 8(7), pp. 533-544.
Noy, et al., "Tumor-Associated Macrophages: From Mechanisms to Therapy", Immunity, 2014, 41(1), pp. 49-61.
Pyonteck, et al., "CSF-1R inhibition alters macrophage polarization and blocks glioma progression", Nat Med, 2013, 19(10), pp. 1264-1272.

(Continued)

*Primary Examiner* — Kortney L. Klinkel
*Assistant Examiner* — Faidat Jyoti
(74) *Attorney, Agent, or Firm* — Hoxie & Associates LLC

(57) ABSTRACT

The present invention relates to novel amide compounds of formula (I), pharmaceutical compositions comprising same, methods for preparing same, and uses thereof, wherein the definition of each symbol is as described in the description.

(I)

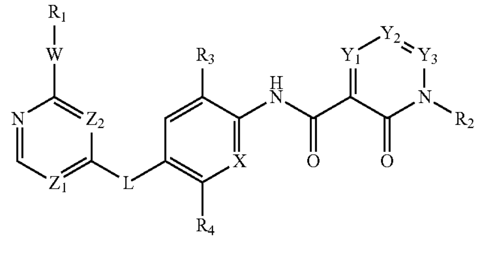

20 Claims, No Drawings

(56) References Cited

OTHER PUBLICATIONS

Settembre, et al., "Lysosomal Adaptation: How the Lysosome Responds to External Cues", Cold Spring Harb Perspect Biol., 2014, 6(6), pp. 1-15.
Tap, et al., "Structure-Guided Blockade of CSFIR Kinase in Tenosynovial Giant-Cell Tumor", N. Engl. J. Med. 2015, 373(5), pp. 428-437.
Duan, Y., et al., "Discovery of novel 2-substituted-4-phenoxypyridine derivatives as potential antitumor agents", Bioorganic & Medicinal Chemistry Letters, 28(3): 254-259 (2018).
Tenin, T., et al., "New aminopyrimidine derivatives as inhibitors of the TAM family", European Journal of Medicinal Chemistry, 70: 789-801 (2013).

AMIDE COMPOUNDS AND USES THEREOF

FIELD OF THE INVENTION

The present invention relates to novel amide compounds, pharmaceutical compositions comprising same, methods for preparing same, and uses thereof.

BACKGROUND OF THE INVENTION

Members of type III tyrosine kinase receptor family include CSF-1R, PDGFRα, PDGFRβ, FLT3 and c-KIT. The members of this family are all composed of an extracellular immunoglobulin-like domain, a transmembrane domain, a juxtamembrane domain and a protein kinase domain, wherein the kinase domain is highly conserved (Nat Rev Cancer. 2012, 12(11):753-66). The phosphorylation signal mediated thereby participates in numerous cell biological functions and plays an important role in the occurrence of diseases. Specifically, there are reports indicating that mutations in the kinase domain of PDGFRα and c-KIT would lead to gastrointestinal tumors (J Pathol. 2011, 223(2): 251-261). In addition, it is found that FLT-3 tandem duplication (FLT3-ITD) is a key pathogenic factor in approximately 20% of patients with acute lymphoblastic leukemia (Biomark Insights. 2015, 10(Suppl 3):1-14).

CSF-1R, i.e. CSF-1 receptor (colony stimulating factor 1 receptor), is encoded by the oncogene c-fms. The human c-fms gene is located at 5q33.3 of chromosome 5, downstream of the β-type platelet-derived growth factor receptor (PDGF_Rβ) gene, and the two genes are connected end to end. Human CSF-1R is a single-chain, transmembrane receptor tyrosine kinase, a transmembrane glycoprotein composed of 972 amino acids, with a molecular weight of 150 Kd. It consists of an extra membrane region with 512 amino acids, a transmembrane region with 25 amino acids, and an intracellular cytoplasmic region with 435 amino acids. The extracellular region has 5 disulfide bonds and 11 possible glycosylation sites, and the intracellular region has a Gly-X-Gly-X-X-Gly motif. Lysine at position 616 is a binding site for ATP, flanked by a kinase insertion region with 72 amino acids. It is speculated that it has the function of recognizing specific substrates (Cold Spring Harb Perspect Biol. 2014, 6(6)).

CSF-1, also called M-CSF (macrophage colony stimulating factor), is encoded by the CSF-1 gene. CSF-1 exerts its biological effects by binding to the only cell surface receptor CSF-1R thereof. After binding to CSF-1, CSF-1R undergoes changes in its conformation and forms a dimer or polymer. After dimerization, the tyrosine kinase activity of the receptor is activated, and the tyrosines at positions 544, 559, 699, 708, 723, 809, 923, etc. are phosphorylated, and subsequently interact with multiple intracellular signaling pathways such as Ras, MAPK, PI3K, JAK, etc. to produce various biological effects in cells (J Cell Biochem. 1988, 38(3):179-87).

The tumor microenvironment is a complex ecosystem, and provides support for the occurrence, growth and metastasis of tumors. Macrophages are particularly abundant in immune cells that migrate to the tumor site, and exist in all stages of tumor development. Studies have shown that tumor-associated macrophages (TAMs) play an important role in the occurrence, growth and metastasis of tumors. For primary tumors, macrophages can stimulate the neovascularization, aid the extravasation, survival and continuous growth of tumor cells, thereby promoting tumor cell metastasis. TAM also exerts an immunosuppressive effect, preventing natural killer cells and T cells from attacking tumor cells (Immunity. 2014, 41(1):49-61). CSF-1R is expressed in macrophages, and the survival and differentiation of macrophages depends on the CSF-1/CSF-1R signaling pathway. The CSF-1/CSF-1R signaling pathway interferes with tumor progression by regulating TAMs to reduce tumor invasiveness and proliferation, as a consequence, the CSF1/CSF1R signaling pathway is a potential target for cancer treatment. Overexpression of CSF-1 or CSF-1R is related to tumor malignant invasiveness and poor prognosis. Studies have shown that the application of CSF-1R inhibitors can affect the exchange of inflammatory factors between TAMs and glioma cells, which significantly reduces the volume of glioblastoma, and reduces tumor invasiveness and proliferation (Nat Med. 2013, 19(10):1264-72). In addition, aberrantly high expression of CSF-1 is the main pathogenesis of tenosynovial giant cell tumor (a type of rare non-metastatic tumor with giant cell tumor and pigmented villonodular synovitis in tendon sheath). Patients with tenosynovial giant cell tumor have obvious clinical benefits after using CSF-1R inhibitors (N Engl J Med. 2015, 373(5):428-37).

In addition to tumors, the CSF-1R signaling pathway plays an important role in autoimmune diseases and inflammatory diseases, including systemic lupus erythematosus, arthritis, atherosclerosis and obesity (Arthritis Res Ther. 2016, 18:75; Nat Rev Immunol. 2008, 8(7):533-44; J Immunother Cancer. 2017, 5(1):53). Therefore, the development of CSF-1R inhibitors may also be used to treat such diseases.

At present, CSF-1R and c-KIT inhibitor Pexidartinib has been approved for marketing by the FDA for the treatment of tenosynovial giant cell tumor in adult patients.

There is still a need to develop novel type III tyrosine kinase receptor inhibitors, especially CSF-1R inhibitors, for the treatment of diseases, such as cancer, autoimmune diseases or inflammatory diseases. The present invention addresses these needs.

SUMMARY OF THE INVENTION

Provided is a compound of formula (I):

(I)

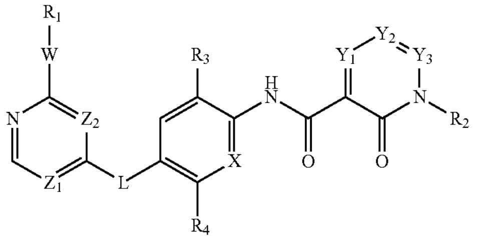

or a pharmaceutically acceptable salt thereof, and/or a deuterate, a solvate, a racemic mixture, an enantiomer, a diastereomer and a tautomer thereof, wherein X is N or $CR_5$;

$Z_1$ and $Z_2$ are each independently N or $CR_6$;

$Y_1$ is N or $CR_7$; $Y_2$ is N or $CR_8$; $Y_3$ is N or $CR_9$;

L is NH, O, S or $CH_2$;

W is absent or NH, O, S or $CH_2$;

$R_1$ is phenyl, 5-12 membered heteroaryl, 4-6 membered heterocyclyl or $C_{3-8}$ cycloalkyl, each of which is optionally substituted with one or more groups chosen from: halogen, —CN, $C_{1-6}$ alkyl, $C_{2-6}$ alkenyl, $C_{2-6}$ alkynyl, $C_{1-6}$ haloalkyl, —($C_{1-6}$ alkylene)$_n$-$NH_2$, —($C_{1-6}$ alkylene)$_n$-NH($C_{1-6}$ alkyl), —($C_{1-6}$ alkylene)$_n$-N($C_{1-6}$ alkyl)$_2$, —($C_{1-6}$ alkylene)$_n$-OH, —($C_{1-6}$ alkylene)$_n$-O—($C_{1-6}$ alkyl) or —($C_{1-6}$ alkylene)$_n$-O—($C_{1-6}$ haloalkyl);

$R_2$ is hydrogen, —CN, $C_{1-6}$ alkyl, $C_{2-6}$ alkenyl, $C_{2-6}$ alkynyl, $C_{1-6}$ haloalkyl, —($C_{1-6}$ alkylene)-$NH_2$, —($C_{1-6}$ alkylene)-NH($C_{1-6}$ alkyl), —($C_{1-6}$ alkylene)-N($C_{1-6}$ alkyl)$_2$, —($C_{1-6}$ alkylene)-O—($C_{1-6}$ alkyl), —($C_{1-6}$ alkylene)-O—($C_{1-6}$ haloalkyl), —($C_{1-6}$ alkylene)-OH, $C_{3-8}$ cycloalkyl or 4-6 membered heterocyclyl;

$R_3$, $R_4$, $R_5$, $R_6$, $R_7$ and $R_8$ are each independently chosen from: hydrogen, halogen, —CN, $C_{1-6}$ alkyl, $C_{1-6}$ haloalkyl, —O($C_{1-6}$ alkyl), —O($C_{1-6}$ haloalkyl) or —OH;

$R_9$ is hydrogen, halogen, —CN, $C_{1-6}$ alkyl, $C_{1-6}$ haloalkyl, —O($C_{1-6}$ alkyl), —O($C_{1-6}$ haloalkyl), —OH, —($C_{1-6}$ alkylene)-OH, —$NH_2$, —NH($C_{1-6}$ alkyl), —N($C_{1-6}$ alkyl)$_2$ or $C_{3-8}$ cycloalkyl;

n is 0 or 1;

or when $Y_3$ is $CR_9$, $R_2$ and $R_9$ together with the N atoms and C atoms to which they are attached form a 5-6 membered heteroaromatic ring or 5-6 membered heterocycle;

or when $Y_2$ is $CR_8$ and $Y_3$ is $CR_9$, $R_8$ and $R_9$ together with the C atoms to which they are attached form a benzene ring;

or

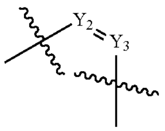

is

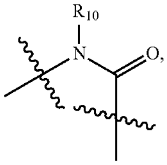

, wherein $R_{10}$ is hydrogen or $C_{1-6}$ alkyl;

provided that when X is CH, $Z_1$ is not N.

Also provided is a pharmaceutical composition, comprising the compound of formula (I) of the present invention (e.g., a compound of any of the examples as described herein) and/or a pharmaceutically acceptable salt thereof, and optionally comprising at least one pharmaceutically acceptable excipient (e.g., a pharmaceutically acceptable carrier).

Also provided is a method of in vivo or in vitro inhibiting the activity of CSF-1R, comprising contacting CSF-1R with an effective amount of at least one compound of formula (I) of the present invention (e.g., a compound of any of the examples as described herein) and/or at least one pharmaceutically acceptable salt thereof.

Also provided is the use of the compound of formula (I) of the present invention (e.g., a compound of any of the examples as described herein) and/or a pharmaceutically acceptable salt thereof for in vivo or in vitro inhibiting the activity of CSF-1R.

Also provided is the use of the compound of formula (I) of the present invention (e.g., a compound of any of the examples as described herein) and/or a pharmaceutically acceptable salt thereof in the manufacture of a medicament for in vivo or in vitro inhibiting the activity of CSF-1R.

Also provided is a method of treating cancer, an autoimmune disease, an inflammatory disease, a metabolic disease, a neurodegenerative disease, obesity or an obesity-related disease in a subject, comprising administering to the subject in need thereof an effective amount of at least one compound of formula (I) of the present invention (e.g., a compound of any of the examples as described herein) and/or at least one pharmaceutically acceptable salt thereof.

Also provided is the use of the compound of formula (I) of the present invention (e.g., a compound of any of the examples as described herein) and/or a pharmaceutically acceptable salt thereof in the treatment of cancer, an autoimmune disease, an inflammatory disease, a metabolic disease, a neurodegenerative disease, obesity or an obesity-related disease in a subject.

Also provided is a compound of formula (I) of the present invention (e.g., a compound of any of the examples as described herein) and/or a pharmaceutically acceptable salt thereof for the treatment of cancer, an autoimmune disease, an inflammatory disease, a metabolic disease, a neurodegenerative disease, obesity or an obesity-related disease in a subject.

Also provided is the use of the compound of formula (I) of the present invention (e.g., a compound of any of the examples as described herein) and/or a pharmaceutically acceptable salt thereof in the manufacture of a medicament for treating cancer, an autoimmune disease, an inflammatory disease, a metabolic disease, a neurodegenerative disease, obesity or an obesity-related disease in a subject.

DETAILED DESCRIPTION OF THE INVENTION

Definitions

As used in the present application, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —O($C_{1-6}$ alkyl) refers to the attachment of $C_{1-6}$ alkyl to the rest of the molecule through an oxygen atom. When the point of attachment for a substituent is well known to the person of ordinary skill in the art ("POSITA"), "-" can be omitted, for example, a halogen substituent.

The term "alkyl" as used herein refers to a straight or branched saturated hydrocarbon radical containing 1-18 carbon atoms, preferably 1-10 carbon atoms, particularly preferably 1-6 carbon atoms, further preferably 1-4 carbon atoms. For example, "$C_{1-6}$ alkyl" refers to an alkyl containing 1-6 carbon atoms. Examples of alkyl include, but are not limited to, methyl ("Me"), ethyl ("Et"), n-propyl ("n-Pr"), i-propyl ("i-Pr"), n-butyl ("n-Bu"), i-butyl ("i-Bu"), s-butyl ("s-Bu") and t-butyl ("t-Bu").

The term "alkylene" as used herein refers to a straight or branched saturated divalent hydrocarbon radical containing 1-18 carbon atoms, preferably 1-10 carbon atoms, particularly preferably 1-6 carbon atoms, further preferably 1-4 carbon atoms. For example, "$C_{1-6}$ alkylene" refers to a straight or branched alkylene containing 1-6 carbon atoms, for example, straight alkylene-$(CH_2)_n$—, wherein n is an integer from 1 to 6, or a branched alkylene, for example, —$CH_2$—$CH(CH_3)$—$CH_2$—, —$CH(CH_3)$—$CH_2$—, and —$CH(CH_3)$—$CH_2$—$CH_2$—, preferably a straight $C_{1-6}$ alkylene, more preferably —$CH_2$— and —$CH_2$—$CH_2$—.

The term "alkenyl" as used herein refers to a straight or branched unsaturated hydrocarbon radical containing one or more, for example 1, 2, or 3 carbon-carbon double bonds (C═C) and 2-10 carbon atoms, preferably 2-6 carbon atoms, more preferably 2-4 carbon atoms. For example, "$C_{2-6}$ alkenyl" refers to an alkenyl containing 2-6 carbon atoms. Examples of alkenyl include, but are not limited to, vinyl, 2-propenyl and 2-butenyl. The point of attachment for the alkenyl can be on or not on the double bonds.

The term "alkynyl" as used herein refers to a straight or branched unsaturated hydrocarbon radical containing one or more, for example 1, 2, or 3, carbon-carbon triple bonds (C≡C) and 2-10 carbon atoms, preferably 2-6 carbon atoms, more preferably 2-4 carbon atoms. For example, "$C_{2-6}$ alkynyl" refers to an alkynyl containing 2-6 carbon atoms. Examples of alkynyl include, but are not limited to, ethynyl, 2-propynyl and 2-butynyl. The point of attachment for the alkynyl can be on or not on the triple bonds.

The term "halogen" or "halo" as used herein refers to fluoro, chloro, bromo, and iodo, preferably fluoro, chloro and bromo, more preferably fluoro and chloro.

The term "haloalkyl" as used herein refers to an alkyl radical, as defined herein, in which one or more, for example 1, 2, 3, 4, or 5, hydrogen atoms are replaced with halogen atoms, and when more than one hydrogen atoms are replaced with halogen atoms, the halogen atoms may be the same or different from each other. In one embodiment, the term "haloalkyl" as used herein refers to an alkyl radical, as defined herein, in which two or more, such as 2, 3, 4, or 5 hydrogen atoms are replaced with halogen atoms, wherein the halogen atoms are identical to each other. In another embodiment, the term "haloalkyl" as used herein refers to an alkyl radical, as defined herein, in which two or more hydrogen atoms, such as 2, 3, 4, or 5 hydrogen atoms are replaced with halogen atoms, wherein the halogen atoms are different from each other. Examples of haloalkyl include, but are not limited to, $-CF_3$, $-CHF_2$, $-CH_2CF_3$, $-CH(CF_3)_2$, and the like.

The term "cycloalkyl" as used herein refers to saturated or partially unsaturated cyclic hydrocarbon radical having 3-12 ring carbon atoms (such as 3-8 ring carbon atoms, 5-7 ring carbon atoms, 4-7 ring carbon atoms, 5-6 ring carbon atoms or 3-6 ring carbon atoms); which may have one or more rings, such as 1, 2, or 3 rings, preferably 1 or 2 rings. For example, "$C_{3-8}$ cycloalkyl" refers to a cycloalkyl containing 3-8 ring carbon atoms. The cycloalkyl may include a fused or bridged ring, or a spirocyclic ring. The rings of the cycloalkyl may be saturated or have one or more, for example, one or two double bonds (i.e. partially unsaturated), but not fully conjugated, and not an aryl as defined herein. Examples of cycloalkyl include, but are not limited to, cyclopropyl, cyclobutyl, cyclopentyl, cyclohexyl, cycloheptyl, cyclooctyl, bicyclo[4.1.0]heptanyl, bicyclo[3.1.1]heptanyl, spiro[3.3]heptanyl, spiro[2.2]pentanyl, cyclopropenyl, cyclobutenyl, cyclopentenyl, cyclopentadienyl, cyclohexenyl, cycloheptenyl, cyclooctenyl and bicyclo[3.1.1]hept-2-ene. In an embodiment of the present invention, the ring of cycloalkyl is saturated.

The term "heterocyclyl" or "heterocycle" as used herein refers to: saturated or partially unsaturated monocyclic, bicyclic or tricyclic radicals having 3-12 ring atoms (such as 3-8 ring atoms, 4-7 ring atoms, 5-7 ring atoms, 4-6 ring atoms, 3-6 ring atoms or 5-6 ring atoms), and containing one or more (such as 1, 2 or 3, preferably 1 or 2) ring heteroatoms independently chosen from N, O and S in the rings, with the remaining ring atoms being carbon. The heterocycle also includes those wherein the N or S heteroatom are optionally oxidized to various oxidation states. The point of attachment of heterocyclyl can be on the N heteroatom or carbon. For example, "3-12 membered heterocyclyl" or "3-12 membered heterocycle" refers to a heterocyclyl having 3-12 ring atoms, and containing at least one heteroatom chosen from N, O and S; "4-6 membered heterocyclyl" or "4-6 membered heterocycle" refers to a heterocyclyl having 4-6 ring atoms, and containing at least one heteroatom chosen from N, O and S; "5-6 membered heterocyclyl" or "5-6 membered heterocycle" refers to a heterocyclyl having 5 or 6 ring atoms, and containing at least one heteroatom chosen from N, O and S. The heterocycle or heterocyclyl may include a fused or bridged ring, or a spirocyclic ring, wherein at least one ring contains at least one ring heteroatom independently chosen from N, O and S, and the point of attachment thereof to the rest of the molecule is located on the ring containing ring heteroatom, and the remaining rings are not "aryl" or "heteroaryl" as defined in the present invention. The rings of the heterocycle or heterocyclyl may be saturated or have one or more, for example, one or two double bonds (i.e. partially unsaturated), but not fully conjugated, and not a heteroaryl as defined herein. In an embodiment of the present invention, the rings of heterocycle or heterocyclyl are saturated. Examples of heterocyclyl include, but are not limited to: 4-6 membered heterocyclyl or 5-6 membered heterocyclyl, for example, oxetanyl, azetidinyl, pyrrolidyl, tetrahydrofuranyl, dioxolanyl, morpholinyl, thiomorpholinyl, piperidyl, piperazinyl, pyrazolidinyl, dihydrooxadiazolyl, and oxaspiro[3.3]heptanyl.

The term "aryl" or "aromatic ring" as used herein refers to carbocyclic hydrocarbon radical of 6 to 14 carbon atoms consisting of one ring or more fused rings, wherein at least one ring is an aromatic ring. Examples of aryl include, but are not limited to: phenyl, naphthyl, 1,2,3,4-tetrahydronaphthyl, indenyl, indanyl, azulenyl, preferably phenyl and naphthyl.

The term "heteroaryl" or "heteroaromatic ring" as used herein refers to: aromatic hydrocarbyl (i.e., 5-12 membered heteroaryl, 5-10 membered heteroaryl, 5-6 membered heteroaryl or 6 membered heteroaryl) having 5-12 ring atoms (such as 5-10 ring atoms, 5-6 ring atoms or 6 ring atoms), and containing one or more (such as 1, 2, 3 or 4, preferably 1, 2 or 3, more preferably 1 or 2) ring heteroatoms independently chosen from N, O and S in the rings, with the remaining ring atoms being carbon atoms; which may have one or more rings, such as 1, 2, or 3 rings, preferably 1 or 2 rings. For example, the heteroaryl includes:

- monocyclic aromatic hydrocarbyl having 5, 6 or 7 ring atoms (preferably 5 or 6 ring atoms, namely, 5-6 membered heteroaryl), and containing one or more, for example 1, 2, 3 or 4, preferably 1, 2 or 3, more preferably 1 or 2 ring heteroatoms independently chosen from N, O and S (preferably N and O) in the ring, with the remaining ring atoms being carbon atoms; and
- bicyclic aromatic hydrocarbyl having 8-12 ring atoms (preferably 9 or 10 ring atoms), and at least one of the rings contains one or more, such as 1, 2, 3 or 4, preferably 1, 2 or 3 ring heteroatoms independently chosen from N, O and S (preferably N), with the remaining ring atoms being carbon atoms, wherein at least one ring is aromatic ring and the point of attachment thereof to the rest of the molecule is located on aromatic ring. For example, bicyclic heteroaryl include a 5-6 membered heteroaryl ring fused with a 5-6 membered cycloalkyl ring.

When the total number of S and O atoms in the heteroaryl group exceeds 1, said S and O heteroatoms are not adjacent to one another.

Heteroaryl also include those in which the N ring atom is in the form of N-oxide, for example N-oxide pyridine.

Examples of heteroaryl include, but are not limited to: 5-6 membered heteroaryl, such as pyridyl, N-oxide pyridyl, pyrazinyl, pyrimidyl, triazinyl (such as 1,3,5-triazinyl), pyrazolyl, imidazolyl, oxazolyl, isoxazolyl, oxadiazolyl (such as 1,2,4-oxadiazolyl, 1,2,5-oxadiazolyl and 1,3,4-oxadiazolyl), thiazolyl, isothiazolyl, thiadiazolyl, tetrazolyl, triazolyl (such as 1,2,3-triazolyl and 1,2,4-triazolyl), thienyl, furanyl, pyranyl, pyrrolyl, and pyridazinyl; and bicyclic heteroaryl, such as benzodioxolyl, benzoxazolyl, benzoisoxazolyl, benzothienyl, benzothiazolyl, benzoisothiazolyl, imidazopyridyl (such as imidazo[1,2-a]pyridyl), imidazopyridazinyl (such as imidazo[1,2-b]pyridazinyl), pyrrolopyridyl (such as 1H-pyrrolo[2,3-b]pyridyl), pyrrolopyrimidyl (such as pyrrolo[3,4-d]pyrimidyl), pyrazolopyridyl (such as 1H-pyrazolo[3,4-b]pyridyl), pyrazolopyrimidyl (such as pyrazolo[1,5-a]pyrimidyl), triazolopyridyl (such as [1,2,4]triazolo[4,3-a]pyridyl and [1,2,4]triazolo[1,5-a]pyridyl), triazolopyridazinyl (such as [1,2,4]triazolo[4,3-b]pyridazinyl), tetrazolopyridyl (such as tetrazolo[1,5-a]pyridyl), benzofuranyl, benzoimidazolinyl, indolyl, indazolyl, purinyl, quinolinyl, isoquinolinyl, and quinazolinyl.

The term “hydroxyl” as used herein refers to —OH group.

The term “oxo” as used herein refers to =O group.

The term “optional” or “optionally” as used herein means that the subsequently described event or circumstance may or may not occur, and the description includes instances wherein the event or circumstance occur and instances in which it does not occur. For example, “optionally substituted alkyl” includes “unsubstituted alkyl” and “substituted alkyl” defined herein. It will be understood by the POSITA, with respect to any group containing one or more substituents, that such groups are not intended to introduce any substitution or substitution patterns that are sterically impractical, chemically incorrect, synthetically non-feasible and/or inherently unstable.

The term “substituted” or “substituted with . . . ”, as used herein, means that one or more hydrogen atoms on the designated atom or group are replaced with one or more substituents chosen from the indicated group of substituents, provided that the designated atom’s normal valence is not exceeded. When a substituent is oxo (i.e., =O), then two hydrogens on a single atom are replaced by the oxo. Combinations of substituents and/or variables are permitted only when they result in chemically correct and stable compounds. A chemically correct and stable compound is meant to imply a compound that is sufficiently robust to survive sufficient isolation from a reaction mixture, and then can be formulated into a formulation having at least practical utility.

Unless otherwise specified, substituents are named into the core structure. For example, it is to be understood that when (cycloalkyl)alkyl is listed as a possible substituent, the point of attachment of this substituent to the core structure is in the alkyl portion.

The term “substituted with one or more substituents” as used herein means that one or more hydrogens on the designated atom or group are independently replaced with one or more substituents chosen from indicated group. In some embodiments, “substituted with one or more substituents” means the designated atom or group is replaced with 1, 2, 3 or 4 substituents independently chosen from designated group.

It will be understood by the POSITA that some of the compounds of formula (I) may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further understood by the POSITA that the present invention includes all the individual stereoisomers (e.g. enantiomers), racemic mixtures or partially resolved mixtures of the compounds of formula (I) and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in “*Topics in Stereochemistry*”, Vol. 6, Wiley Interscience, 1971) and include physical methods such as chromatography using a chiral adsorbent. Individual isomers can be prepared in chiral form from chiral precursors. Alternatively, individual isomers can be separated chemically from a mixture by forming diastereomeric salts with a chiral acid, such as the individual enantiomers of 10-camphorsulfonic acid, camphoric acid, alpha-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively, the racemates can be covalently linked to a chiral compound (auxiliary) to produce diastereomers which can be separated by chromatography or by fractional crystallization after which time the chiral auxiliary is chemically removed to afford the pure enantiomers.

The term “tautomer” as used herein refers to constitutional isomers of compounds generated by rapid movement of an atom in two positions in a molecule. Tautomers readily interconvert into each other, e.g., enol form and ketone form are typical tautomers. For another example, some compounds of the present invention, when $R_2$ is hydrogen, may also exist in the structure of formula (II) as shown in the following figure, namely, the compound of formula (II) may become a tautomer of the compound of formula (I) of the present invention; such tautomer is a compound of the present invention.

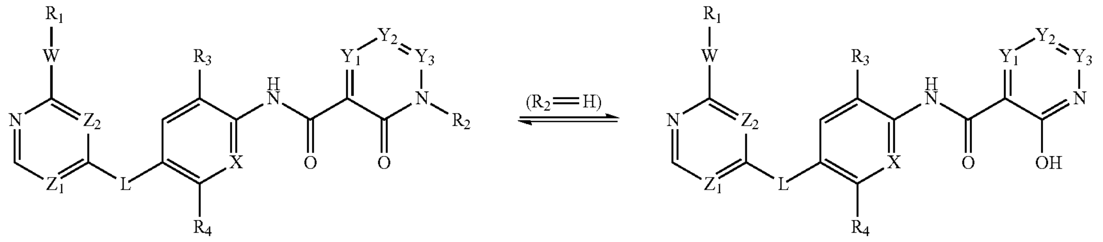

(I) (II)

A "pharmaceutically acceptable salt" is intended to mean a salt of a free acid or base of a compound of formula (I) that is non-toxic, biologically tolerable, or otherwise biologically suitable for administration to the subject. For example, the pharmaceutically acceptable salt is an acid addition salt including such as a salt derived from an inorganic acid and an organic acid. Said inorganic acid includes such as hydrochloric acid, hydrobromic acid, hydroiodic acid, sulfuric acid, phosphoric acid, and nitric acid; said organic acid includes such as p-toluenesulfonic acid, salicylic acid, methanesulfonic acid, oxalic acid, succinic acid, citric acid, malic acid, lactic acid, fumaric acid, and the like. For examples, see, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002.

In addition, if a compound of the present invention herein is obtained as an acid addition salt, the free base can be obtained by basifying a solution of the acid addition salt. Conversely, if the product is a free base, an acid addition salt, particularly a pharmaceutically acceptable acid addition salt, may be produced by dissolving the free base in a suitable solvent and treating the solution with an acid, in accordance with conventional procedures for preparing acid addition salts from base compounds. The POSITA will recognize various synthetic methodologies that may be used without undue experimentation to prepare non-toxic pharmaceutically acceptable acid addition salts or base addition salts.

The term "solvates" means solvent addition forms that contain either stoichiometric or non-stoichiometric amounts of solvent. Some compounds have a tendency to trap a fixed molar ratio of solvent molecules in the solid state, thus forming a solvate. If the solvent is water, the solvate formed is a hydrate, when the solvent is alcohol, the solvate formed is an alcoholate. Hydrates are formed by the combination of one or more molecules of water, with one molecule of the substances in which the water retains its molecular state as $H_2O$, such combination being able to form one or more hydrates, for example, hemihydrate, monohydrate, and dihydrate.

As used herein, the terms "group(s)" and "radical(s)" are synonymous and are intended to indicate functional groups or fragments of molecules attachable to other fragments of molecules.

The term "active ingredient" is used to indicate a chemical substance which has biological activity. In some embodiments, an "active ingredient" is a chemical substance having pharmaceutical utility. In USA, the practical pharmaceutical activity can be determined by appropriate pre-clinical trials, whether in vivo or in vitro. However, the pharmaceutical activity that can sufficiently be accepted by regulatory agencies (such as the US FDA) must have a higher standard than that in pre-clinical trials. Whether such a higher standard of pharmaceutical activity can be successfully obtained is generally not reasonably expected from the results of pre-clinical trials, but it can be established through appropriate and effective randomized, double-blind, and controlled clinical trials in humans.

The terms "treating" or "treatment" of a disease or disorder, in the context of achieving therapeutic benefit, refer to administering one or more pharmaceutical substances, especially the compound of formula (I) or a pharmaceutically acceptable salt thereof described herein to a subject that has the disease or disorder, or has a symptom of a disease or disorder, or has a predisposition toward a disease or disorder, with the purpose to cure, heal, alleviate, relieve, alter, remedy, ameliorate, improve, or affect the disease or disorder, the symptoms of the disease or disorder, or the predisposition toward the disease or disorder. In some embodiments, the disease or disorder is cancer. In some embodiment, the disease or disorder is an autoimmune disease or inflammatory disease.

The terms "treating", "contacting" and "reacting", in the context of a chemical reaction, mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

The term "effective amount" as used herein refers to an amount or dose of the compound of the present invention sufficient to generally bring about a therapeutic benefit in patients in need of treatment for a disease or disorder mediated by CSF-1R activity or at least in part by CSF-1R. Effective amounts or doses of the active ingredient of the present disclosure may be ascertained by methods such as modeling, dose escalation studies or clinical trials, and by taking into consideration factors, e.g., the mode or route of administration or drug delivery, the pharmacokinetics of the agent, the severity and course of the disease or disorder, the subject's previous or ongoing therapy, the subject's health status and response to drugs, and the judgment of the attending physician. In USA, the determination of an effective dose is generally difficult to predict from pre-clinical trials. In fact, the dose is completely unpredictable. After the dose was originally used in a randomized, double-blind, and controllable clinical trial, a new unpredictable dose schedule will be developed.

An exemplary dose is in the range of from about 0.0001 to about 200 mg of active agent per kg of subject's body weight per day, such as from about 0.001 to 100 mg/kg/day, or about 0.01 to 35 mg/kg/day, or about 0.1 to 10 mg/kg daily in single or divided dosage units (e.g., BID, TID, QID). For a 70 kg person, an illustrative range of a suitable dose is from about 0.05 to about 7 g/day, or from about 0.2 to about 5 g/day. Once improvement of the patient's disease or disorder has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

The term "inhibition" or "inhibiting" refers to a decrease in the baseline activity of a biological activity or process. The term "inhibition of CSF-1R activity" is a practical pharmaceutical activity for purposes of this disclosure and refers to a decrease in the activity of CSF-1R as a direct or indirect response to the presence of the compound of formula (I) and/or a pharmaceutically acceptable salt thereof described herein, relative to the activity of CSF-1R in the absence of the compound of formula (I) and/or a pharmaceutically acceptable salt thereof. The decrease in activity may be due to the direct interaction of the compound of formula (I) and/or a pharmaceutically acceptable salt thereof described herein with CSF-1R, or due to the interaction of the compound of formula (I) and/or a pharmaceutically acceptable salt thereof described herein, with one or more other factors that in turn affect the CSF-1R activity. For example, the presence of the compound of formula (I) and/or a pharmaceutically acceptable salt thereof described herein may decrease the CSF-1R activity by directly binding to the CSF-1R, by directly or indirectly influencing another factor, or by directly or indirectly decreasing the amount of CSF-1R present in the cell or organism.

The term "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a human.

In general, the term "about" is used herein to modify a numerical value above or below the stated value by a variance of 20%.

Technical and scientific terms used herein and not specifically defined have the meaning commonly understood by the POSITA to which the present disclosure pertains.

Provided is a compound of formula (I):

(I)

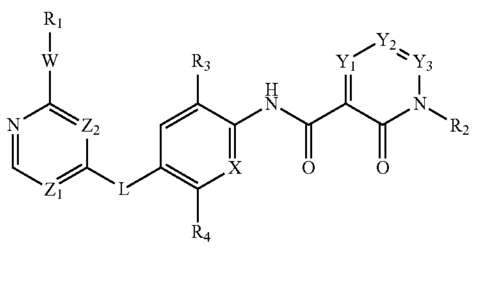

or a pharmaceutically acceptable salt thereof, and/or a deuterate, a solvate, a racemic mixture, an enantiomer, a diastereomer and a tautomer thereof, wherein X is N or $CR_5$;

$Z_1$ and $Z_2$ are each independently N or $CR_6$;

$Y_1$ is N or $CR_7$; $Y_2$ is N or $CR_8$; $Y_3$ is N or $CR_9$;

L is NH, O, S or $CH_2$;

W is absent or NH, O, S or $CH_2$;

$R_1$ is phenyl, 5-12 membered heteroaryl, 4-6 membered heterocyclyl or $C_{3-8}$ cycloalkyl, each of which is optionally substituted with one or more groups chosen from: halogen, —CN, $C_{1-6}$ alkyl, $C_{2-6}$ alkenyl, $C_{2-6}$ alkynyl, $C_{1-6}$ haloalkyl, —($C_{1-6}$ alkylene)$_n$-$NH_2$, —($C_{1-6}$ alkylene)$_n$-NH($C_{1-6}$ alkyl), —($C_{1-6}$ alkylene)$_n$-N($C_{1-6}$ alkyl)$_2$, —($C_{1-6}$ alkylene)$_n$-OH, —($C_{1-6}$ alkylene)$_n$-O—($C_{1-6}$ alkyl) or —($C_{1-6}$ alkylene)$_n$-O—($C_{1-6}$ haloalkyl);

$R_2$ is hydrogen, —CN, $C_{1-6}$ alkyl, $C_{2-6}$ alkenyl, $C_{2-6}$ alkynyl, $C_{1-6}$ haloalkyl, —($C_{1-6}$ alkylene)-$NH_2$, —($C_{1-6}$ alkylene)-NH($C_{1-6}$ alkyl), —($C_{1-6}$ alkylene)-N($C_{1-6}$ alkyl)$_2$, —($C_{1-6}$ alkylene)-O—($C_{1-6}$ alkyl), —($C_{1-6}$ alkylene)-O—($C_{1-6}$ haloalkyl), —($C_{1-6}$ alkylene)-OH, $C_{3-8}$ cycloalkyl or 4-6 membered heterocyclyl;

$R_3$, $R_4$, $R_5$, $R_6$, $R_7$ and $R_8$ are each independently chosen from: hydrogen, halogen, —CN, $C_{1-6}$ alkyl, $C_{1-6}$ haloalkyl, —O($C_{1-6}$ alkyl), —O($C_{1-6}$ haloalkyl) or —OH;

$R_9$ is hydrogen, halogen, —CN, $C_{1-6}$ alkyl, $C_{1-6}$ haloalkyl, —O($C_{1-6}$ alkyl), —O($C_{1-6}$ haloalkyl), —OH, —($C_{1-6}$ alkylene)-OH, —$NH_2$, —NH($C_{1-6}$ alkyl), —N($C_{1-6}$ alkyl)$_2$ or $C_{3-8}$ cycloalkyl;

n is 0 or 1;

or when $Y_3$ is $CR_9$, $R_2$ and $R_9$ together with the N atoms and C atoms to which they are attached form a 5-6 membered heteroaromatic ring or 5-6 membered heterocycle;

or when $Y_2$ is $CR_8$ and $Y_3$ is $CR_9$, $R_8$ and $R_9$ together with the C atoms to which they are attached form a benzene ring;

or

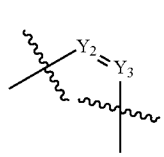

is

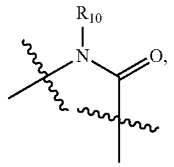

wherein $R_{10}$ is hydrogen or $C_{1-6}$ alkyl;

provided that when X is CH, $Z_1$ is not N.

In some embodiments of the compound of formula (I), X is N.

In some embodiments of the compound of formula (I), X is $CR_5$.

In some embodiments of the compound of formula (I), $R_5$ is hydrogen, halogen, $C_{1-6}$ alkyl or —O($C_{1-6}$ alkyl).

In some embodiments of the compound of formula (I), X is CH.

In some embodiments of the compound of formula (I), $Z_1$ and $Z_2$ are each independently $CR_6$.

In some embodiments of the compound of formula (I), $Z_1$ is N; $Z_2$ is $CR_6$.

In some embodiments of the compound of formula (I), $Z_1$ is $CR_6$; $Z_2$ is N.

In some embodiments of the compound of formula (I), $R_6$ is hydrogen.

In some embodiments of the compound of formula (I), both $Z_1$ and $Z_2$ are CH.

In some embodiments of the compound of formula (I), $Y_1$ is $CR_7$, $Y_2$ is $CR_8$, $Y_3$ is $CR_9$.

In some embodiments of the compound of formula (I), $Y_1$ is $CR_7$, $Y_2$ is N, $Y_3$ is $CR_9$.

In some embodiments of the compound of formula (I), $Y_1$ is N, $Y_2$ is $CR_8$, $Y_3$ is $CR_9$.

In some embodiments of the compound of formula (I), $Y_1$ is $CR_7$, $Y_2$ is $CR_8$, $Y_3$ is N.

In some embodiments of the compound of formula (I), L is O or $CH_2$.

In some embodiments of the compound of formula (I), L is O.

In some embodiments of the compound of formula (I), $R_7$ is chosen from: hydrogen, $C_{1-6}$ alkyl or —O($C_{1-6}$ alkyl).

In some embodiments of the compound of formula (I), $R_7$ is hydrogen.

In some embodiments of the compound of formula (I), $R_8$ is chosen from hydrogen, halogen or $C_{1-6}$ alkyl.

In some embodiments of the compound of formula (I), $R_8$ is chosen from hydrogen, fluoro or methyl.

In some embodiments of the compound of formula (I), $R_9$ is hydrogen, $C_{1-6}$ alkyl, $C_{1-6}$ haloalkyl, —O($C_{1-6}$ alkyl), —$NH_2$, —NH($C_{1-6}$ alkyl), —N($C_{1-6}$ alkyl)$_2$ or $C_{3-6}$ cycloalkyl.

In some embodiments of the compound of formula (I), $R_9$ is hydrogen or methyl.

In some embodiments of the compound of formula (I), $Y_1$ is $CR_7$, $Y_2$ is $CR_8$, $Y_3$ is $CR_9$; $R_7$ and $R_8$ are each independently chosen from: hydrogen, halogen, $C_{1-6}$ alkyl or —O($C_{1-6}$ alkyl); $R_9$ is hydrogen, $C_{1-6}$ alkyl, $C_{1-6}$ haloalkyl, —O($C_{1-6}$ alkyl), —$NH_2$, —NH($C_{1-6}$ alkyl) or —N($C_{1-6}$ alkyl)$_2$.

In some embodiments of the compound of formula (I), $Y_1$ is $CR_7$, $Y_2$ is $CR_8$, $Y_3$ is $CR_9$; $R_7$ is hydrogen or —O($C_{1-6}$ alkyl); $R_8$ is hydrogen, halogen or $C_{1-6}$ alkyl; $R_9$ is hydrogen, $C_{1-6}$ alkyl, $C_{1-6}$ haloalkyl, —O($C_{1-6}$ alkyl), —$NH_2$, —NH($C_{1-6}$ alkyl) or —N($C_{1-6}$ alkyl)$_2$.

In some embodiments of the compound of formula (I), $Y_1$ is $CR_7$, $Y_2$ is $CR_8$, $Y_3$ is $CR_9$; $R_7$ is hydrogen; $R_8$ is hydrogen or halogen; $R_9$ is hydrogen or $C_{1-6}$ alkyl.

In some embodiments of the compound of formula (I), $Y_1$ is $CR_7$, $Y_2$ is $CR_8$, $Y_3$ is $CR_9$; $R_7$ is hydrogen; $R_8$ is hydrogen or fluoro; $R_9$ is hydrogen or methyl.

In some embodiments of the compound of formula (I), $Y_1$ is $CR_7$, $Y_2$ is $CR_8$, $Y_3$ is $CR_9$; $R_7$, $R_8$ and $R_9$ are hydrogen.

In some embodiments of the compound of formula (I), $Y_1$ is $CR_7$, $Y_2$ is N, $Y_3$ is $CR_9$; $R_7$ is hydrogen, $C_{1-6}$ alkyl or —O($C_{1-6}$ alkyl); $R_9$ is hydrogen, $C_{1-6}$ alkyl, $C_{1-6}$ haloalkyl or $C_{3-6}$ cycloalkyl.

In some embodiments of the compound of formula (I), $Y_1$ is $CR_7$, $Y_2$ is N, $Y_3$ is $CR_9$; $R_7$ is hydrogen or $C_{1-6}$ alkyl; $R_9$ is hydrogen, $C_{1-6}$ alkyl or $C_{3-6}$ cycloalkyl.

In some embodiments of the compound of formula (I), $Y_1$ is $CR_7$, $Y_2$ is N, $Y_3$ is $CR_9$; $R_7$ is hydrogen; $R_9$ is hydrogen, $C_{1-6}$ alkyl or $C_{3-6}$ cycloalkyl.

In some embodiments of the compound of formula (I), $Y_1$ is $CR_7$, $Y_2$ is N, $Y_3$ is $CR_9$; $R_7$ is hydrogen; $R_9$ is $C_{1-6}$ alkyl.

In some embodiments of the compound of formula (I), $Y_1$ is $CR_7$, $Y_2$ is N, $Y_3$ is $CR_9$; $R_7$ is hydrogen; $R_9$ is methyl.

In some embodiments of the compound of formula (I), $Y_1$ is $CR_7$, $Y_2$ is N, $Y_3$ is $CR_9$; both $R_7$ and $R_9$ are hydrogen.

In some embodiments of the compound of formula (I), $Y_1$ is N, $Y_2$ is $CR_8$, $Y_3$ is $CR_9$; both $R_8$ and $R_9$ are hydrogen.

In some embodiments of the compound of formula (I), $Y_1$ is $CR_7$, $Y_2$ is $CR_8$, $Y_3$ is N; both $R_7$ and $R_8$ are hydrogen.

In some embodiments of the compound of formula (I), W is absent or NH.

In some embodiments of the compound of formula (I), W is absent.

In some embodiments of the compound of formula (I), W is NH.

In some embodiments of the compound of formula (I), $R_1$ is phenyl, 5-12 membered heteroaryl, 4-6 membered heterocyclyl or $C_{3-8}$ cycloalkyl, each of which is optionally substituted with one or more groups chosen from: halogen, $C_{1-6}$ alkyl, $C_{1-6}$ haloalkyl, —($C_{1-6}$ alkylene)$_n$-$NH_2$, —($C_{1-6}$ alkylene)$_n$-NH($C_{1-6}$ alkyl), —($C_{1-6}$ alkylene)$_n$-N($C_{1-6}$ alkyl)$_2$ or —($C_{1-6}$ alkylene)$_n$-OH.

In some embodiments of the compound of formula (I), $R_1$ is phenyl, 5-10 membered heteroaryl, 4-6 membered heterocyclyl or $C_{3-8}$ cycloalkyl, each of which is optionally substituted with one or more groups chosen from: halogen, $C_{1-6}$ alkyl, $C_{1-6}$ haloalkyl, —($C_{1-6}$ alkylene)$_n$-$NH_2$, —($C_{1-6}$ alkylene)$_n$-NH($C_{1-6}$ alkyl), —($C_{1-6}$ alkylene)$_n$-N($C_{1-6}$ alkyl)$_2$ or —($C_{1-6}$ alkylene)$_n$-OH.

In some embodiments of the compound of formula (I), $R_1$ is phenyl, 5-6 membered monocyclic heteroaryl, 9-10 membered bicyclic heteroaryl, 4-6 membered heterocyclyl or $C_{3-8}$ cycloalkyl, each of which is optionally substituted with one or more groups chosen from: halogen, $C_{1-6}$ alkyl, $C_{1-6}$ haloalkyl, —($C_{1-6}$ alkylene)$_n$-$NH_2$, —($C_{1-6}$ alkylene)$_n$-NH($C_{1-6}$ alkyl), —($C_{1-6}$ alkylene)$_n$-N($C_{1-6}$ alkyl)$_2$ or —($C_{1-6}$ alkylene)$_n$-OH.

In some embodiments of the compound of formula (I), $R_1$ is phenyl, pyrazolyl, pyrrolyl, furanyl, thienyl, pyridyl, thiazolyl, 1,2,3-triazolyl, 1,2,4-triazolyl, imidazolyl, imidazo[1,2-a]pyridyl, piperazinyl or cyclohexenyl, each of which is optionally substituted with one or more groups chosen from: halogen, $C_{1-6}$ alkyl, $C_{1-6}$ haloalkyl, —($C_{1-6}$ alkylene)$_n$-$NH_2$, —($C_{1-6}$ alkylene)$_n$-NH($C_{1-6}$ alkyl), —($C_{1-6}$ alkylene)$_n$-N($C_{1-6}$ alkyl)$_2$ or —($C_{1-6}$ alkylene)$_n$-OH.

In some embodiments of the compound of formula (I), $R_1$ is phenyl, pyrazolyl, pyrrolyl, furanyl, thienyl, pyridyl, thiazolyl, 1,2,3-triazolyl, 1,2,4-triazolyl, imidazolyl, imidazo[1,2-a]pyridyl, piperazinyl or cyclohexenyl, each of which is optionally substituted with one or more groups chosen from: halogen, $C_{1-6}$ alkyl, $C_{1-6}$ haloalkyl, —($C_{1-6}$ alkylene)-$NH_2$, —($C_{1-6}$ alkylene)-NH($C_{1-6}$ alkyl), —($C_{1-6}$ alkylene)-N($C_{1-6}$ alkyl)$_2$ or —($C_{1-6}$ alkylene)-OH.

In some embodiments of the compound of formula (I), $R_1$ is pyrazolyl or pyrrolyl, each of which is optionally substituted with one or more groups chosen from: $C_{1-6}$ alkyl, $C_{1-6}$ haloalkyl, —($C_{1-6}$ alkylene)-$NH_2$, —($C_{1-6}$ alkylene)-NH($C_{1-6}$ alkyl), —($C_{1-6}$ alkylene)-N($C_{1-6}$ alkyl)$_2$ or —($C_{1-6}$ alkylene)-OH.

In some embodiments of the compound of formula (I), $R_1$ is pyrazolyl or pyrrolyl, each of which is optionally substituted with one or more groups chosen from: methyl, ethyl, i-propyl, —$CHF_2$, —$CF_3$, —($CH_2CH_2$)—$NH_2$, —($CH_2CH_2$)—NH($C_{1-6}$ alkyl), —($CH_2CH_2$)—N($C_{1-6}$ alkyl)$_2$ or —($CH_2CH_2$)—OH.

In some embodiments of the compound of formula (I), $R_1$ is pyrazolyl or pyrrolyl, each of which is optionally substituted with one or more $C_{1-6}$ alkyl.

In some embodiments of the compound of formula (I), $R_1$ is pyrazolyl or pyrrolyl, each of which is optionally substituted with one or more methyl.

In some embodiments of the compound of formula (I), $R_1$ is

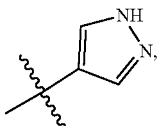

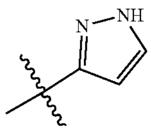

or

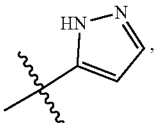

each of which is substituted with one or more methyl.

In some embodiments of the compound of formula (I), $R_1$ is

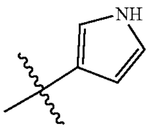 [SMILES: *c1cc[nH]c1]

substituted with one or more methyl.

In some embodiments of the compound of formula (I), $R_1$ is phenyl optionally substituted with one or more halogen.

In some embodiments of the compound of formula (I), $R_1$ is phenyl optionally substituted with one or more F.

In some embodiments of the compound of formula (I), $R_1$ is furanyl, thienyl, pyridyl, thiazolyl, 1,2,3-triazolyl, 1,2,4-triazolyl, imidazolyl, imidazo[1,2-a]pyridyl, piperazinyl or cyclohexenyl, each of which is optionally substituted with one or more $C_{1-6}$ alkyl.

In some embodiments of the compound of formula (I), $R_1$ is furanyl, thienyl, pyridyl, thiazolyl, 1,2,3-triazolyl, 1,2,4-triazolyl, imidazolyl or imidazo[1,2-a]pyridyl, each of which is optionally substituted with one or more methyl.

In some embodiments of the compound of formula (I), $R_1$ is piperazinyl, which is optionally substituted with one or more ethyl.

In some embodiments of the compound of formula (I), W is NH; $R_1$ is pyrazolyl, pyridyl or thiazolyl, each of which is optionally substituted with one or more groups chosen from: halogen, $C_{1-6}$ alkyl, $C_{1-6}$ haloalkyl, —($C_{1-6}$ alkylene)-$NH_2$, —($C_{1-6}$ alkylene)-NH($C_{1-6}$ alkyl), —($C_{1-6}$ alkylene)-N($C_{1-6}$ alkyl)$_2$ or —($C_{1-6}$ alkylene)-OH.

In some embodiments of the compound of formula (I), W is NH; $R_1$ is pyrazolyl, pyridyl or thiazolyl, each of which is optionally substituted with one or more groups chosen from: $C_{1-6}$ alkyl or $C_{1-6}$ haloalkyl.

In some embodiments of the compound of formula (I), W is NH; $R_1$ is pyrazolyl optionally substituted with one or more methyl.

In some embodiments of the compound of formula (I), W is NH; $R_1$ is

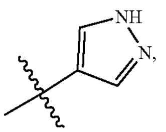

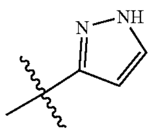

or

-continued

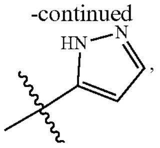

each of which is substituted with one or more methyl.

In some embodiments of the compound of formula (I), W is absent; $R_1$ is pyrazolyl or pyrrolyl, each of which is optionally substituted with one or more methyl.

In some embodiments of the compound of formula (I), W is absent; $R_1$ is

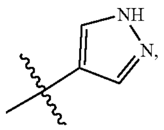

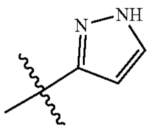

or

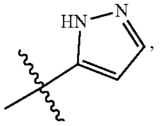

each of which is substituted with one or more methyl.

In some embodiments of the compound of formula (I), W is absent; $R_1$ is

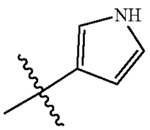 [SMILES: *c1cc[nH]c1]

substituted with one or more methyl.

In some embodiments of the compound of formula (I), $R_2$ is hydrogen, $C_{1-6}$ alkyl, $C_{2-6}$ alkenyl, $C_{1-6}$ haloalkyl, —($C_{1-6}$ alkylene)-N($C_{1-6}$ alkyl)$_2$, —($C_{1-6}$ alkylene)-O—($C_{1-6}$ alkyl), —($C_{1-6}$ alkylene)-OH, $C_{3-6}$ cycloalkyl or 4-6 membered heterocyclyl.

In some embodiments of the compound of formula (I), $R_2$ is hydrogen, $C_{1-6}$ alkyl, $C_{2-6}$ alkenyl, $C_{1-6}$ haloalkyl, —($CH_2CH_2$)—N($C_{1-6}$ alkyl)$_2$, —($CH_2CH_2$)—O—($C_{1-6}$ alkyl), —($CH_2CH_2$)—OH, $C_{3-6}$ cycloalkyl or 4-6 membered heterocyclyl.

In some embodiments of the compound of formula (I), $R_2$ is hydrogen, $C_{1-6}$ alkyl, $C_{2-6}$ alkenyl, $C_{1-6}$ haloalkyl, —($CH_2CH_2$)—N($C_{1-6}$ alkyl)$_2$, —($CH_2CH_2$)—O—($C_{1-6}$ alkyl), —($CH_2CH_2$)—OH, $C_{3-6}$ cycloalkyl or oxetanyl.

In some embodiments of the compound of formula (I), $R_2$ is $C_{1-6}$ alkyl, $C_{2-6}$ alkenyl, —($CH_2CH_2$)—O—($C_{1-6}$ alkyl), —($CH_2CH_2$)—OH, cyclopropyl, cyclobutyl or oxetanyl.

In some embodiments of the compound of formula (I), $R_2$ is $C_{1-6}$ alkyl.

In some embodiments of the compound of formula (I), $R_2$ is methyl, ethyl or i-propyl.

In some embodiments of the compound of formula (I), $R_2$ is methyl.

In some embodiments of the compound of formula (I), $R_2$ is i-propyl.

In some embodiments of the compound of formula (I), $R_3$ and $R_4$ are each independently chosen from: hydrogen, halogen, —CN, $C_{1-6}$ alkyl or —O($C_{1-6}$ alkyl).

In some embodiments of the compound of formula (I), $R_3$ and $R_4$ are each independently chosen from: hydrogen, halogen, —CN, $C_{1-6}$ alkyl or —O($C_{1-6}$ alkyl); and when X is CH, at least one of $R_3$ and $R_4$ is hydrogen.

In some embodiments of the compound of formula (I), $R_3$ is hydrogen, halogen, —CN, $C_{1-6}$ alkyl or —O($C_{1-6}$ alkyl); $R_4$ is hydrogen or $C_{1-6}$ alkyl.

In some embodiments of the compound of formula (I), both $R_3$ and $R_4$ are hydrogen.

In some embodiments of the compound of formula (I), X is CH; $R_3$ and $R_4$ are each independently chosen from: hydrogen, halogen, $C_{1-6}$ alkyl or —O($C_{1-6}$ alkyl), and at least one of $R_3$ and $R_4$ is hydrogen.

In some embodiments of the compound of formula (I), X is CH; $R_3$ is hydrogen, halogen, $C_{1-6}$ alkyl or —O($C_{1-6}$ alkyl); $R_4$ is hydrogen.

In some embodiments of the compound of formula (I), n is 1.

In some embodiments of the compound of formula (I), $Y_3$ is $CR_9$; $R_2$ and $R_9$ together with the N atoms and C atoms to which they are attached form pyridine or pyrrolidine.

In some embodiments of the compound of formula (I), $Y_3$ is $CR_9$; $R_2$ and $R_9$ together with the N atoms and C atoms to which they are attached form pyridine.

In some embodiments of the compound of formula (I), $Y_3$ is $CR_9$; $R_2$ and $R_9$ together with the N atoms and C atoms to which they are attached form pyrrolidine.

In some embodiments of the compound of formula (I),

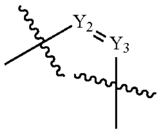

is

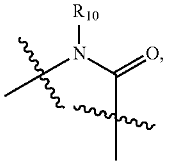

wherein $R_{10}$ is $C_{1-6}$ alkyl.

In some embodiments of the compound of formula (I),

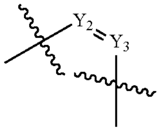

is

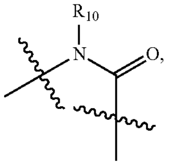

wherein $R_{10}$ is methyl.

In some embodiments of the compound of formula (I), X is $CR_5$; $Z_1$ and $Z_2$ are each independently $CR_6$; $Y_1$ is $CR_7$; $Y_2$ is N or $CR_8$; $Y_3$ is $CR_9$; W is absent; $R_1$ is 5-6 membered heteroaryl optionally substituted with one or more $C_{1-6}$ alkyl; $R_2$ is $C_{1-6}$ alkyl; $R_3$, $R_4$, $R_5$, $R_6$, $R_7$ and $R_8$ are each independently chosen from: hydrogen, halogen, $C_{1-6}$ alkyl or —O($C_{1-6}$ alkyl), and at least one of $R_3$ and $R_4$ is hydrogen; $R_9$ is hydrogen or $C_{1-6}$ alkyl.

In some embodiments of the compound of formula (I), X is CH; both $Z_1$ and $Z_2$ are CH; $Y_1$ is CH; $Y_2$ is N or CH; $Y_3$ is $CR_9$; W is absent; $R_1$ is pyrazolyl optionally substituted with one or more $C_{1-6}$ alkyl; $R_2$ is $C_{1-6}$ alkyl; $R_3$ is hydrogen, halogen, $C_{1-6}$ alkyl or —O($C_{1-6}$ alkyl); $R_4$ is hydrogen; $R_9$ is hydrogen or $C_{1-6}$ alkyl.

In some embodiments of the compound of formula (I), X is N; both $Z_1$ and $Z_2$ are CH; $Y_1$ is CH; $Y_2$ is N or $CR_8$; $Y_3$ is $CR_9$; W is absent; $R_1$ is pyrazolyl or pyrrolyl, which is optionally substituted with one or more $C_{1-6}$ alkyl; $R_2$ is $C_{1-6}$ alkyl; $R_3$ is hydrogen, halogen, $C_{1-6}$ alkyl or —O($C_{1-6}$ alkyl); $R_4$ is hydrogen; $R_8$ is hydrogen or halogen; $R_9$ is hydrogen or $C_{1-6}$ alkyl.

In some embodiments of the compound of formula (I), X is N; both $Z_1$ and $Z_2$ are CH; $Y_1$ is CH; $Y_2$ is N or $CR_8$; $Y_3$ is $CR_9$; W is absent; $R_1$ is pyrazolyl or pyrrolyl, which is substituted with one or more methyl; $R_2$ is methyl or i-propyl; $R_3$ is hydrogen; $R_4$ is hydrogen; $R_8$ is hydrogen or F; $R_9$ is hydrogen or methyl.

In some embodiments of the compound of formula (I), X is N; both $Z_1$ and $Z_2$ are CH; $Y_1$ is CH; $Y_1$ is N or $CR_8$; $Y_3$ is $CR_9$; W is NH; R, is pyrazolyl optionally substituted with one or more $C_{1-6}$ alkyl; $R_2$ is $C_{1-6}$ alkyl; $R_3$ is hydrogen, halogen, $C_{1-6}$ alkyl or —O($C_{1-6}$ alkyl); $R_4$ is hydrogen; $R_8$ is hydrogen or halogen; $R_9$ is hydrogen or $C_{1-6}$ alkyl.

In some embodiments of the compound of formula (I), X is N; both $Z_1$ and $Z_2$ are CH; $Y_1$ is CH; $Y_2$ is N or $CR_8$; $Y_3$ is $CR_9$; W is NH; $R_1$ is pyrazolyl substituted with one or more methyl; $R_2$ is methyl or i-propyl; $R_3$ is hydrogen; $R_4$ is hydrogen; $R_8$ is hydrogen or F; $R_9$ is hydrogen or methyl.

Also provided are compounds of examples chosen from Compounds 1-135, as numbered in the experimental section, and/or pharmaceutically acceptable salts thereof:

| No. | Structural formula |
|---|---|
| 1 | 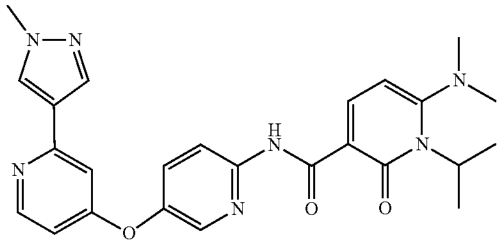 [SMILES: CC(C)n1c(N(C)C)ccc(C(=O)Nc2ccc(Oc3ccnc(-c4cnn(C)c4)c3)cn2)c1=O] |
| 2 | 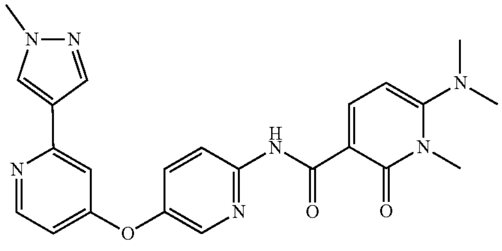 |
| 3 | 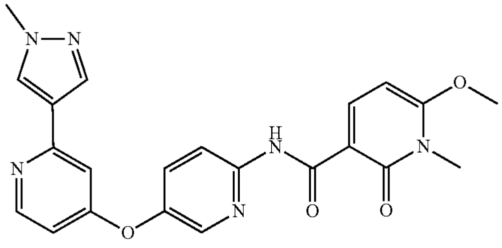 |
| 4 | 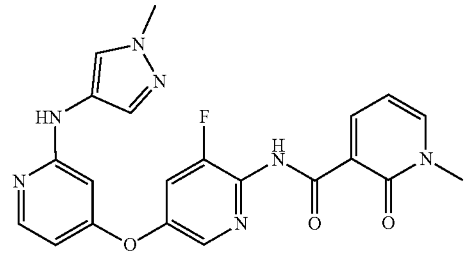 [SMILES: Cn1cc(Nc2cc(Oc3cnc(NC(=O)c4cccn(C)c4=O)c(F)c3)ccn2)cn1] |

-continued
| No. | Structural formula |
|---|---|
| 5 | 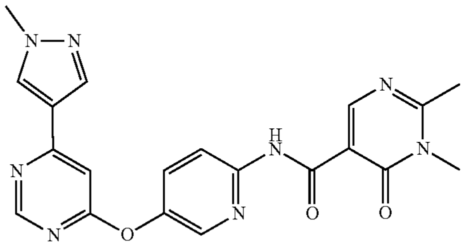 |
| 6 | 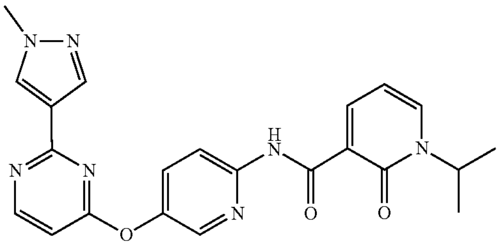 [SMILES: CC(C)n1cccc(C(=O)Nc2ccc(Oc3ccnc(-c4cnn(C)c4)n3)cn2)c1=O] |
| 7 | 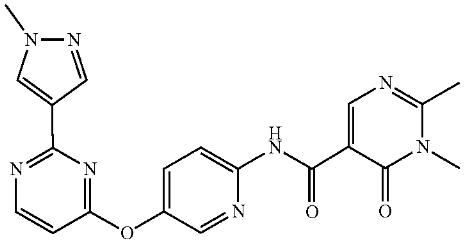 |
| 8 | 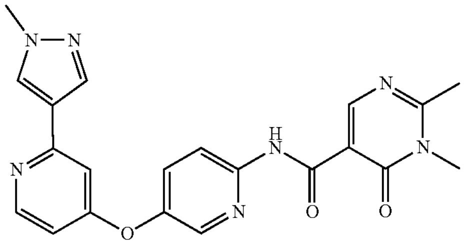 |
| 9 | 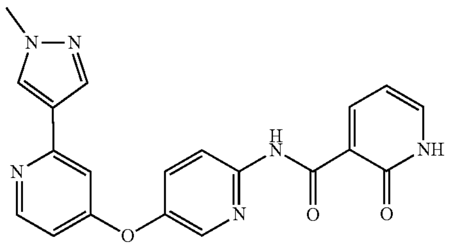 [SMILES: Cn1cc(-c2cc(Oc3ccc(NC(=O)c4ccc[nH]c4=O)nc3)ccn2)cn1] |
| 10 | 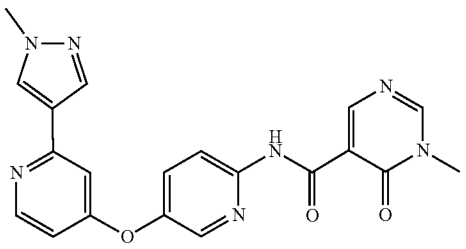 |
| 11 | 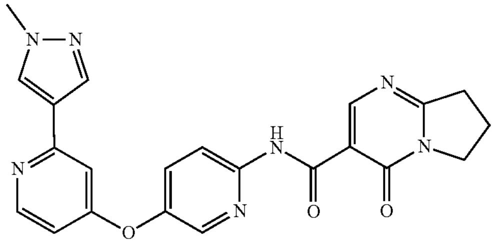 [SMILES: Cn1cc(-c2cc(Oc3ccc(NC(=O)c4cnc5n(c4=O)CCC5)nc3)ccn2)cn1] |
| 12 | 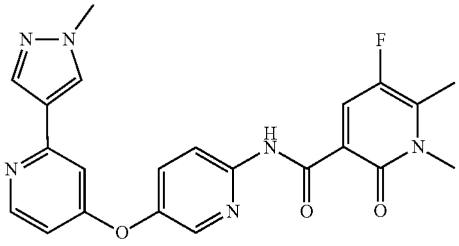 [SMILES: Cc1c(F)cc(C(=O)Nc2ccc(Oc3ccnc(-c4cnn(C)c4)c3)cn2)c(=O)n1C] |
| 13 | 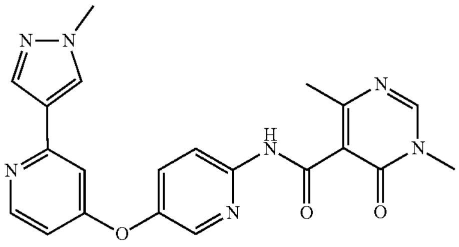 [SMILES: Cc1ncn(C)c(=O)c1C(=O)Nc1ccc(Oc2ccnc(-c3cnn(C)c3)c2)cn1] |
| 14 | 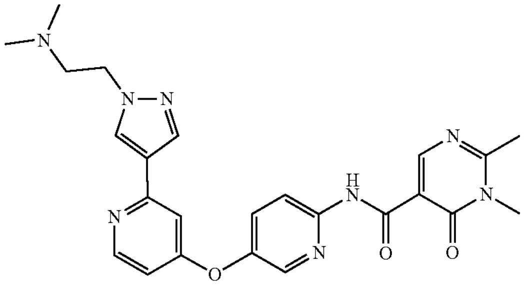 |
| 15 | 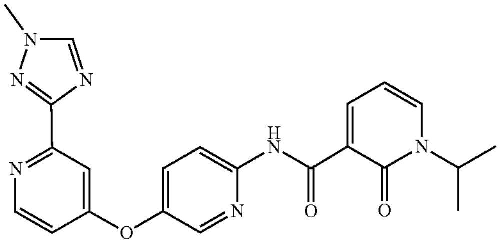 [SMILES: CC(C)n1cccc(C(=O)Nc2ccc(Oc3ccnc(-c4ncn(C)n4)c3)cn2)c1=O] |
| 16 | 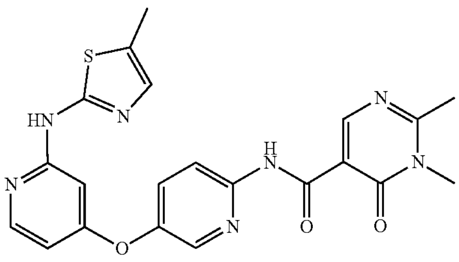 [SMILES: Cc1cnc(Nc2cc(Oc3ccc(NC(=O)c4cnc(C)n(C)c4=O)nc3)ccn2)s1] |

-continued
| No. | Structural formula |
|---|---|
| 17 | 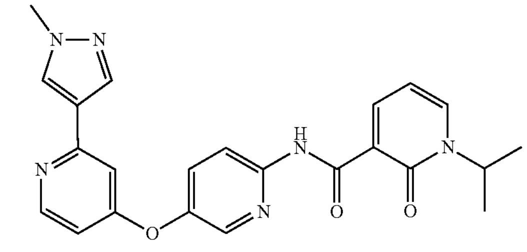 [SMILES: CC(C)n1cccc(C(=O)Nc2ccc(Oc3ccnc(-c4cnn(C)c4)c3)cn2)c1=O] |
| 18 | 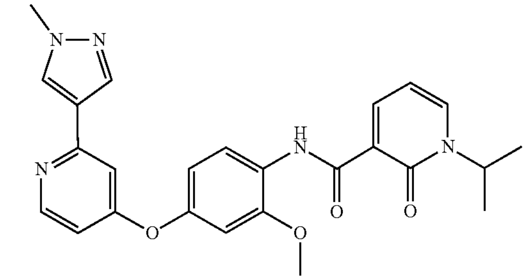 [SMILES: COc1cc(Oc2ccnc(-c3cnn(C)c3)c2)ccc1NC(=O)c1cccn(C(C)C)c1=O] |
| 19 | 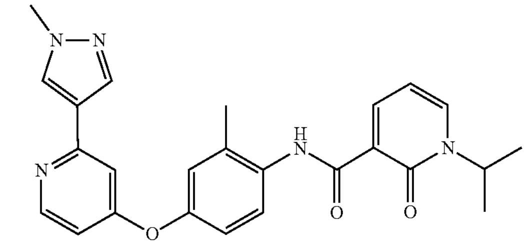 [SMILES: Cc1cc(Oc2ccnc(-c3cnn(C)c3)c2)ccc1NC(=O)c1cccn(C(C)C)c1=O] |
| 20 | 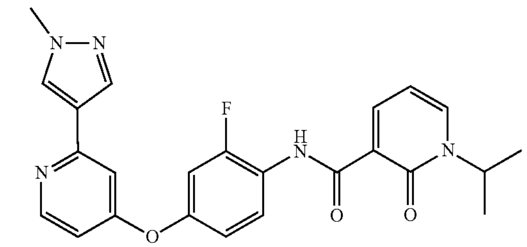 [SMILES: CC(C)n1cccc(C(=O)Nc2ccc(Oc3ccnc(-c4cnn(C)c4)c3)cc2F)c1=O] |
| 21 | 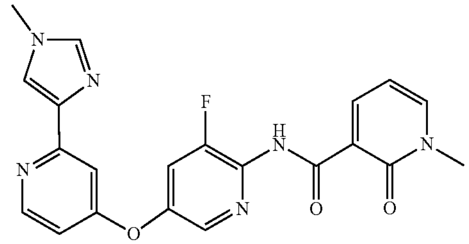 |
| 22 | 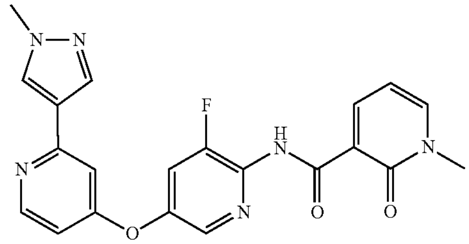 |
-continued
| No. | Structural formula |
|---|---|
| 23 | 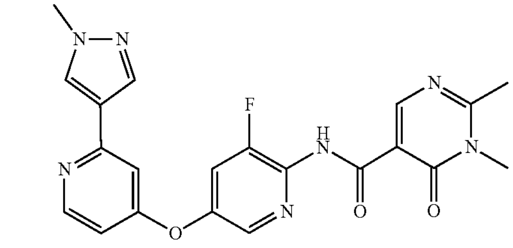 |
| 24 | 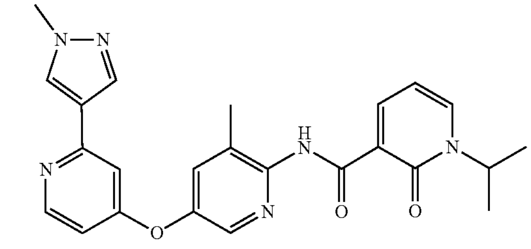 [SMILES: Cc1cc(Oc2ccnc(-c3cnn(C)c3)c2)cnc1NC(=O)c1cccn(C(C)C)c1=O] |
| 25 | 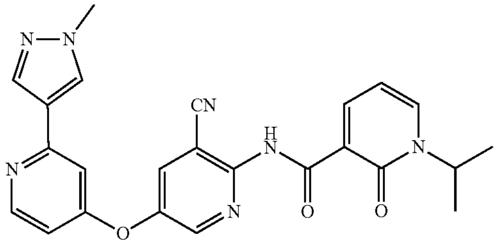 [SMILES: CC(C)n1cccc(C(=O)Nc2ncc(Oc3ccnc(-c4cnn(C)c4)c3)cc2C#N)c1=O] |
| 26 | 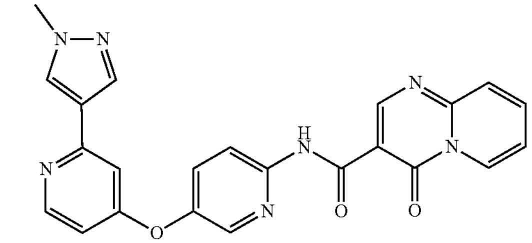 [SMILES: Cn1cc(-c2cc(Oc3ccc(NC(=O)c4cnc5ccccn5c4=O)nc3)ccn2)cn1] |
| 27 | 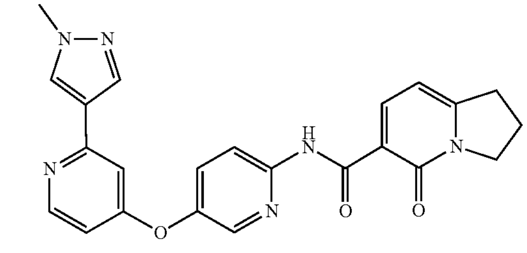 [SMILES: Cn1cc(-c2cc(Oc3ccc(NC(=O)c4ccc5n(c4=O)CCC5)nc3)ccn2)cn1] |
| 28 | 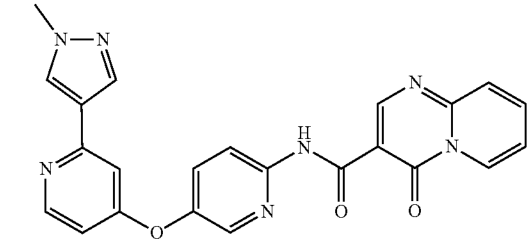 [SMILES: Cn1cc(-c2cc(Oc3ccc(NC(=O)c4cnc5ccccn5c4=O)nc3)ccn2)cn1] |

-continued
| No. | Structural formula |
|---|---|
| 29 | 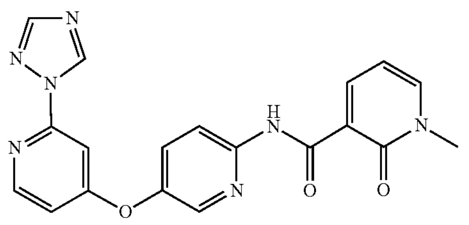 [SMILES: Cn1cccc(C(=O)Nc2ccc(Oc3ccnc(-n4cncn4)c3)cn2)c1=O] |
| 30 | 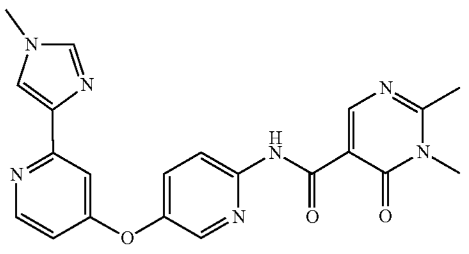 |
| 31 | 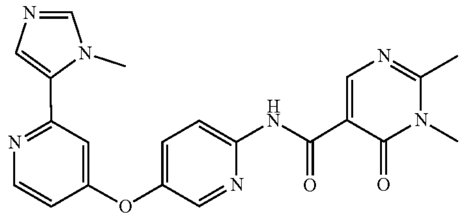 [SMILES: Cc1ncc(C(=O)Nc2ccc(Oc3ccnc(-c4cncn4C)c3)cn2)c(=O)n1C] |
| 32 | 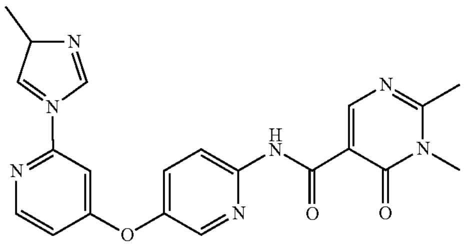 |
| 33 | 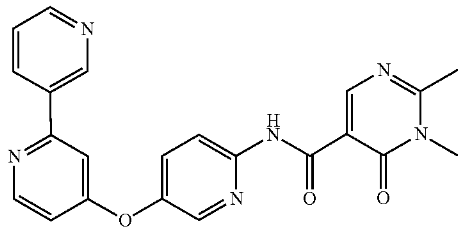 [SMILES: Cc1ncc(C(=O)Nc2ccc(Oc3ccnc(-c4cccnc4)c3)cn2)c(=O)n1C] |
| 34 | 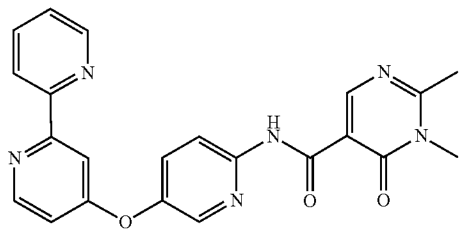 [SMILES: Cc1ncc(C(=O)Nc2ccc(Oc3ccnc(-c4ccccn4)c3)cn2)c(=O)n1C] |
-continued
| No. | Structural formula |
|---|---|
| 35 | 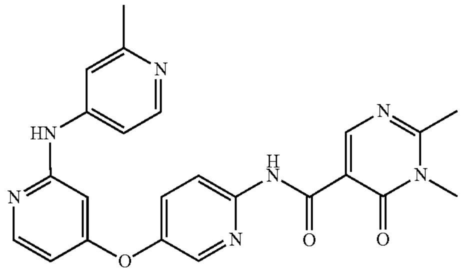 [SMILES: Cc1cc(Nc2cc(Oc3ccc(NC(=O)c4cnc(C)n(C)c4=O)nc3)ccn2)ccn1] |
| 36 | 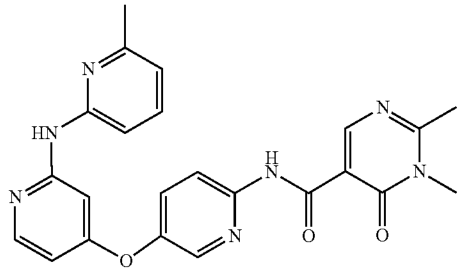 [SMILES: Cc1cccc(Nc2cc(Oc3ccc(NC(=O)c4cnc(C)n(C)c4=O)nc3)ccn2)n1] |
| 37 | 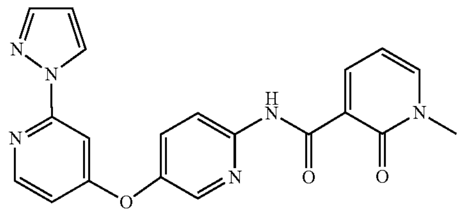 [SMILES: Cn1cccc(C(=O)Nc2ccc(Oc3ccnc(-n4cccn4)c3)cn2)c1=O] |
| 38 | 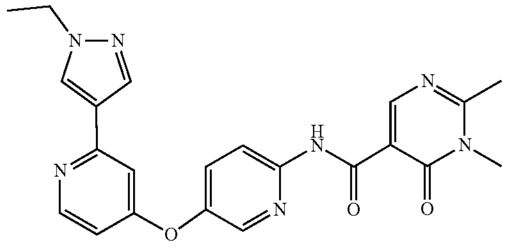 [SMILES: CCn1cc(-c2cc(Oc3ccc(NC(=O)c4cnc(C)n(C)c4=O)nc3)ccn2)cn1] |
| 39 | 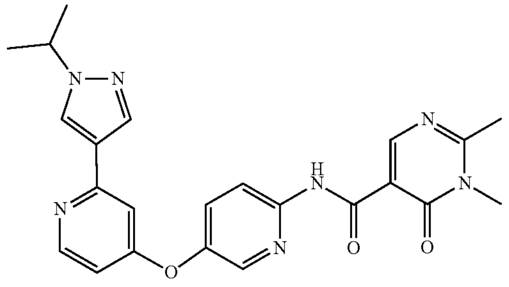 [SMILES: Cc1ncc(C(=O)Nc2ccc(Oc3ccnc(-c4cnn(C(C)C)c4)c3)cn2)c(=O)n1C] |
| 40 | 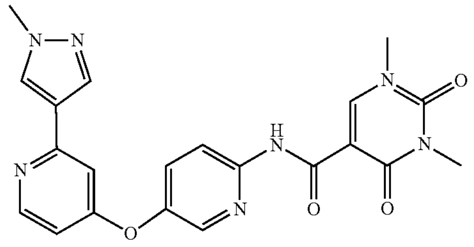 |

-continued
| No. | Structural formula |
|---|---|
| 41 | 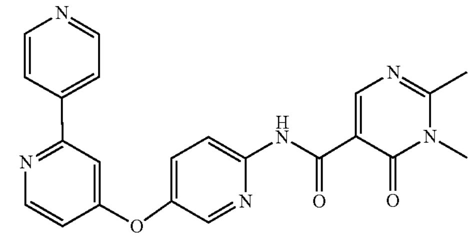 [SMILES: Cc1ncc(C(=O)Nc2ccc(Oc3ccnc(-c4ccncc4)c3)cn2)c(=O)n1C] |
| 42 | 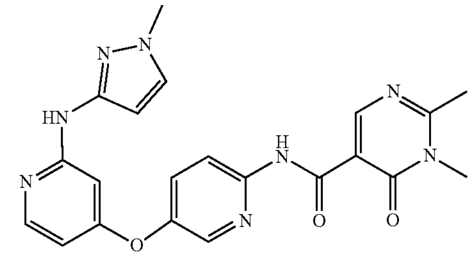 [SMILES: Cc1ncc(C(=O)Nc2ccc(Oc3ccnc(Nc4ccn(C)n4)c3)cn2)c(=O)n1C] |
| 43 | 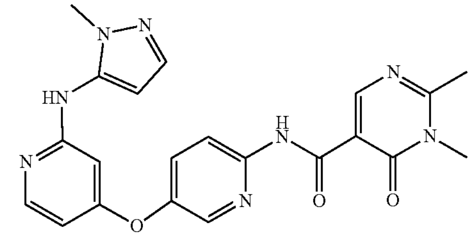 [SMILES: Cc1ncc(C(=O)Nc2ccc(Oc3ccnc(Nc4ccnn4C)c3)cn2)c(=O)n1C] |
| 44 | 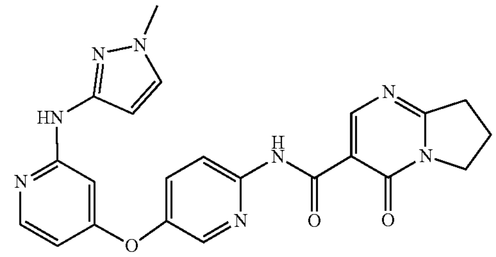 [SMILES: Cn1ccc(Nc2cc(Oc3ccc(NC(=O)c4cnc5n(c4=O)CCC5)nc3)ccn2)n1] |
| 45 | 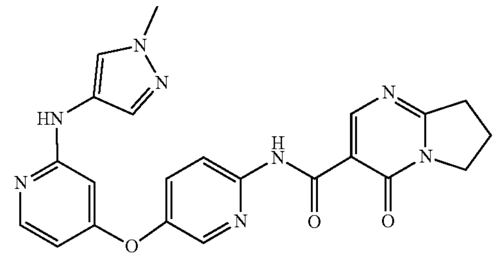 |
| 46 | 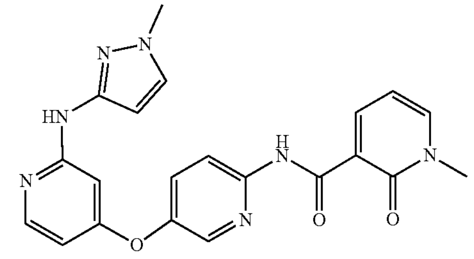 [SMILES: Cn1ccc(Nc2cc(Oc3ccc(NC(=O)c4cccn(C)c4=O)nc3)ccn2)n1] |
-continued
| No. | Structural formula |
|---|---|
| 47 | 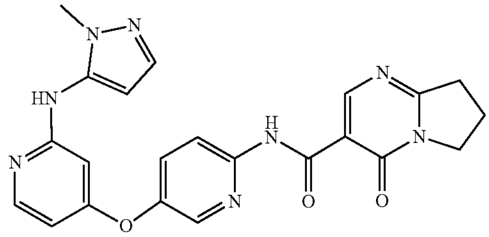 [SMILES: Cn1nccc1Nc1cc(Oc2ccc(NC(=O)c3cnc4n(c3=O)CCC4)nc2)ccn1] |
| 48 | 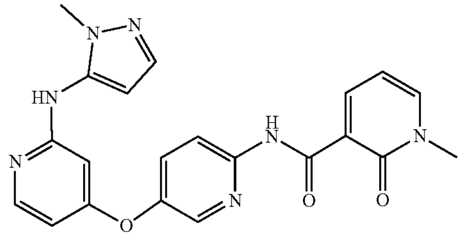 [SMILES: Cn1nccc1Nc1cc(Oc2ccc(NC(=O)c3cccn(C)c3=O)nc2)ccn1] |
| 49 | 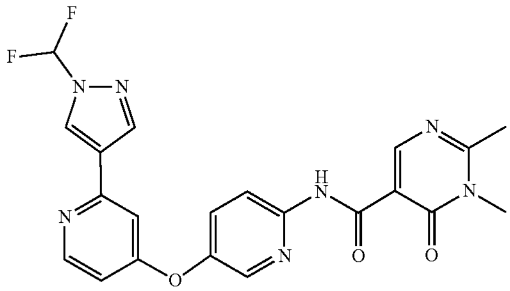 [SMILES: Cc1ncc(C(=O)Nc2ccc(Oc3ccnc(-c4cnn(C(F)F)c4)c3)cn2)c(=O)n1C] |
| 50 | 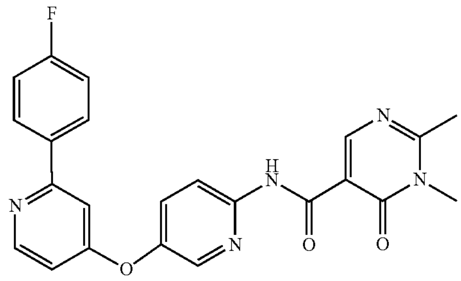 [SMILES: Cc1ncc(C(=O)Nc2ccc(Oc3ccnc(-c4ccc(F)cc4)c3)cn2)c(=O)n1C] |
| 51 | 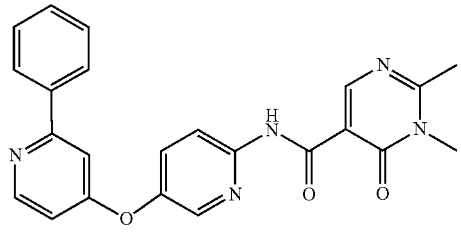 [SMILES: Cc1ncc(C(=O)Nc2ccc(Oc3ccnc(-c4ccccc4)c3)cn2)c(=O)n1C] |
| 52 | 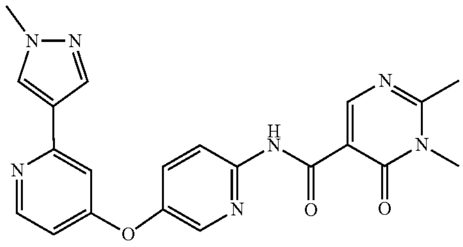 |

-continued
| No. | Structural formula |
|---|---|
| 53 | 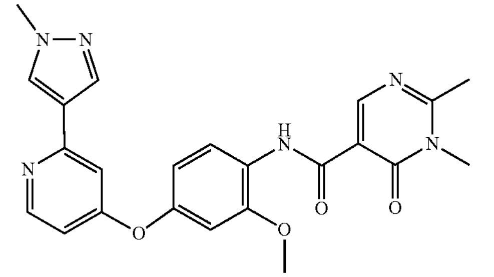 |
| 54 | 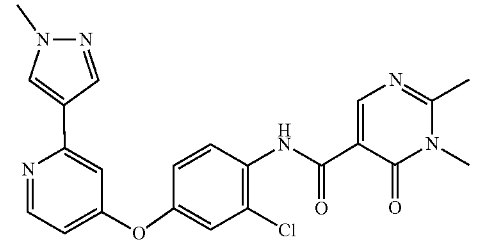 |
| 55 | 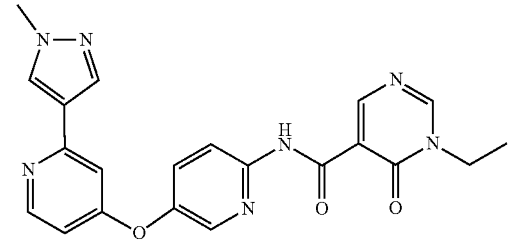 [SMILES: CCn1cncc(C(=O)Nc2ccc(Oc3ccnc(-c4cnn(C)c4)c3)cn2)c1=O] |
| 56 | 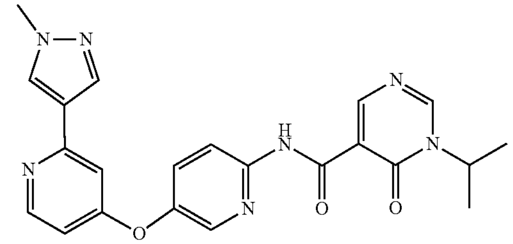 [SMILES: CC(C)n1cncc(C(=O)Nc2ccc(Oc3ccnc(-c4cnn(C)c4)c3)cn2)c1=O] |
| 57 | 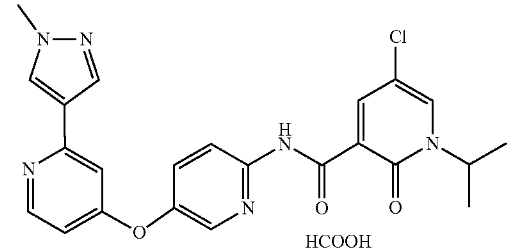 [SMILES: CC(C)n1cc(Cl)cc(C(=O)Nc2ccc(Oc3ccnc(-c4cnn(C)c4)c3)cn2)c1=O ; "HCOOH"] HCOOH |
| 58 | 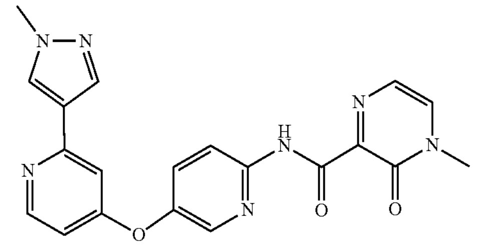 |
-continued
| No. | Structural formula |
|---|---|
| 59 | 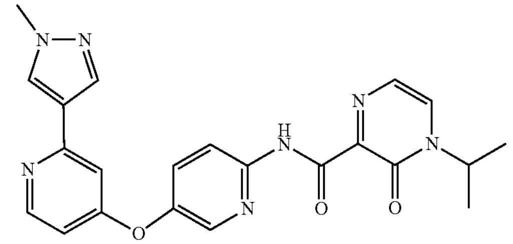 [SMILES: CC(C)n1ccnc(C(=O)Nc2ccc(Oc3ccnc(-c4cnn(C)c4)c3)cn2)c1=O] |
| 60 | 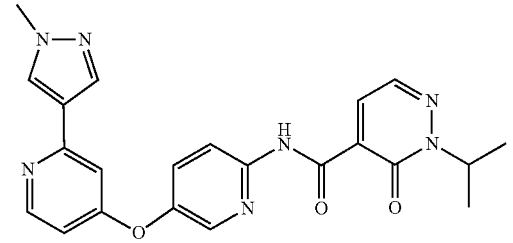 [SMILES: CC(C)n1nccc(C(=O)Nc2ccc(Oc3ccnc(-c4cnn(C)c4)c3)cn2)c1=O] |
| 61 | 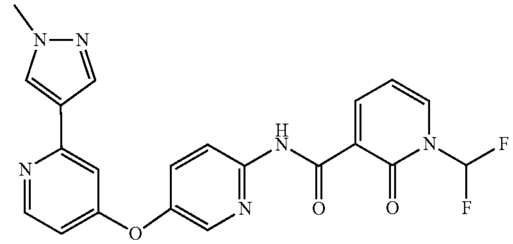 [SMILES: Cn1cc(-c2cc(Oc3ccc(NC(=O)c4cccn(C(F)F)c4=O)nc3)ccn2)cn1] |
| 62 | 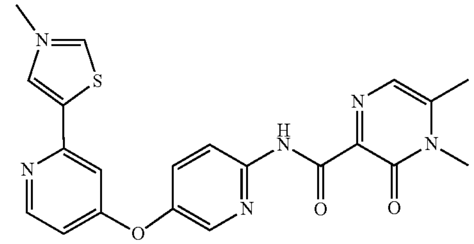 |
| 63 | 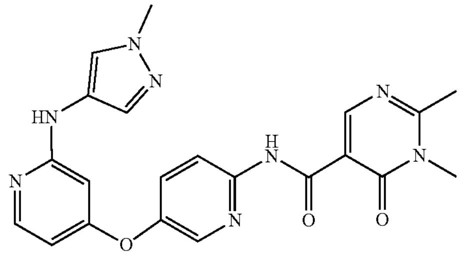 [SMILES: Cc1ncc(C(=O)Nc2ccc(Oc3ccnc(Nc4cnn(C)c4)c3)cn2)c(=O)n1C] |
| 64 | 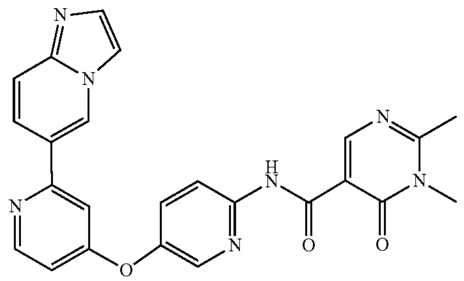 [SMILES: Cc1ncc(C(=O)Nc2ccc(Oc3ccnc(-c4ccc5nccn5c4)c3)cn2)c(=O)n1C] |

-continued
| No. | Structural formula |
| --- | --- |
| 65 | 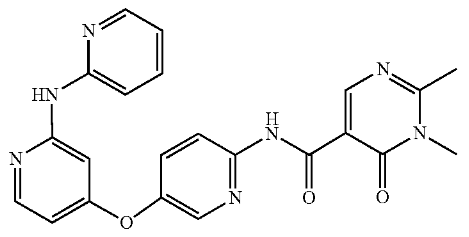 [SMILES: Cc1ncc(C(=O)Nc2ccc(Oc3ccnc(Nc4ccccn4)c3)cn2)c(=O)n1C] |
| 66 | 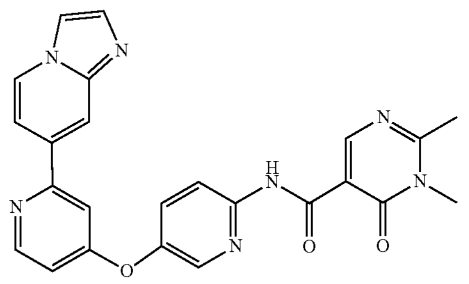 [SMILES: Cc1ncc(C(=O)Nc2ccc(Oc3ccnc(-c4ccn5ccnc5c4)c3)cn2)c(=O)n1C] |
| 67 | 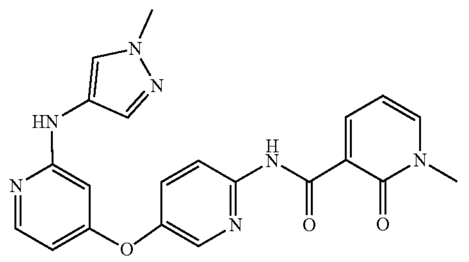 [SMILES: Cn1cc(Nc2cc(Oc3ccc(NC(=O)c4cccn(C)c4=O)nc3)ccn2)cn1] |
| 68 | 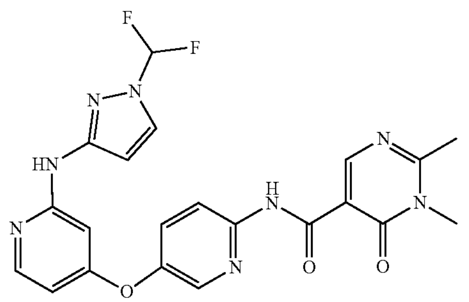 [SMILES: Cc1ncc(C(=O)Nc2ccc(Oc3ccnc(Nc4ccn(C(F)F)n4)c3)cn2)c(=O)n1C] |
| 69 | 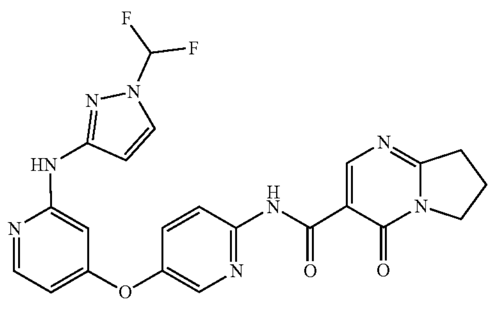 [SMILES: O=C(Nc1ccc(Oc2ccnc(Nc3ccn(C(F)F)n3)c2)cn1)c1cnc2n(c1=O)CCC2] |
-continued
| No. | Structural formula |
| --- | --- |
| 70 | 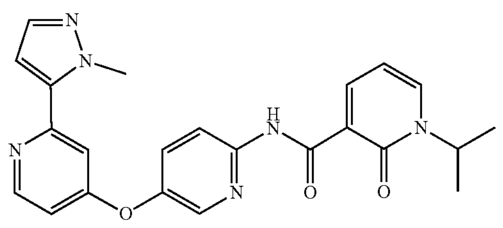 [SMILES: CC(C)n1cccc(C(=O)Nc2ccc(Oc3ccnc(-c4ccnn4C)c3)cn2)c1=O] |
| 71 | 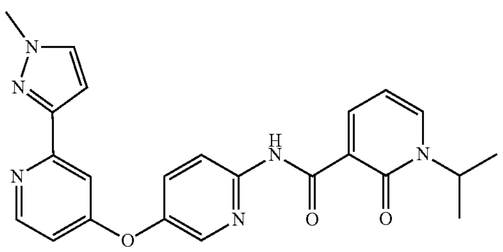 [SMILES: CC(C)n1cccc(C(=O)Nc2ccc(Oc3ccnc(-c4ccn(C)n4)c3)cn2)c1=O] |
| 72 | 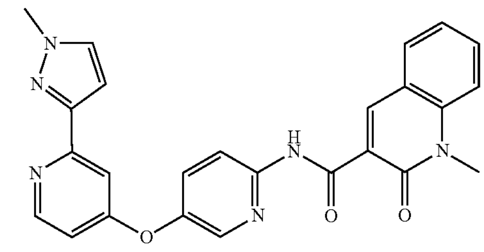 [SMILES: Cn1ccc(-c2cc(Oc3ccc(NC(=O)c4cc5ccccc5n(C)c4=O)nc3)ccn2)n1] |
| 73 | 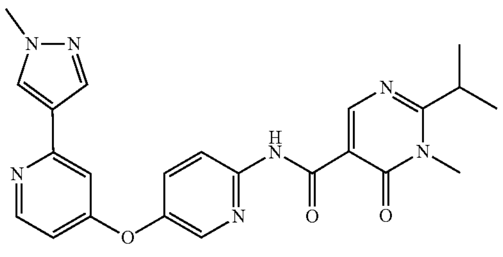 [SMILES: CC(C)c1ncc(C(=O)Nc2ccc(Oc3ccnc(-c4cnn(C)c4)c3)cn2)c(=O)n1C] |
| 74 | 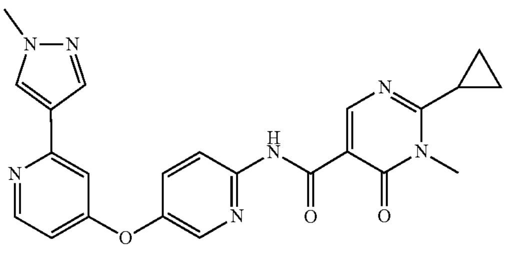 [SMILES: Cn1cc(-c2cc(Oc3ccc(NC(=O)c4cnc(C5CC5)n(C)c4=O)nc3)ccn2)cn1] |
| 75 | 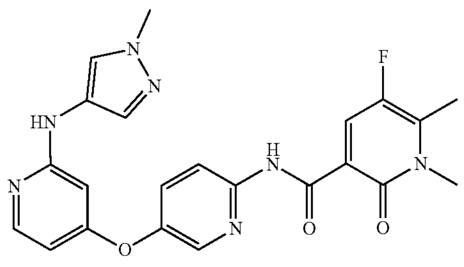 [SMILES: Cc1c(F)cc(C(=O)Nc2ccc(Oc3ccnc(Nc4cnn(C)c4)c3)cn2)c(=O)n1C] |

-continued
| No. | Structural formula |
|---|---|
| 76 | 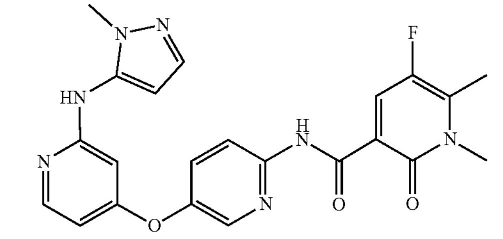 [SMILES: Cc1c(F)cc(C(=O)Nc2ccc(Oc3ccnc(Nc4ccnn4C)c3)cn2)c(=O)n1C] |
| 77 | 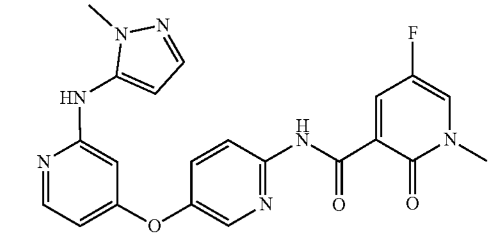 [SMILES: Cn1nccc1Nc1cc(Oc2ccc(NC(=O)c3cc(F)cn(C)c3=O)nc2)ccn1] |
| 78 | 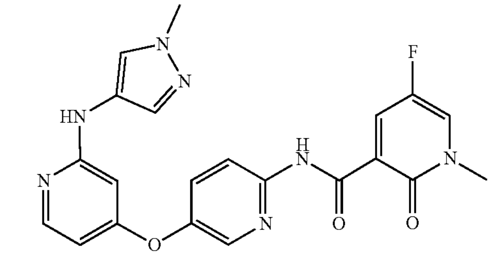 [SMILES: Cn1cc(Nc2cc(Oc3ccc(NC(=O)c4cc(F)cn(C)c4=O)nc3)ccn2)cn1] |
| 79 | 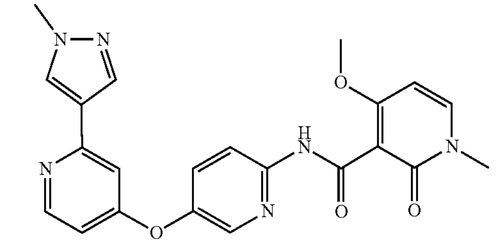 |
| 80 | 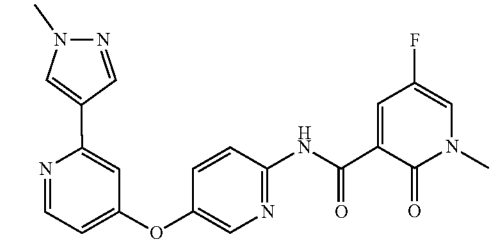 |
| 81 | 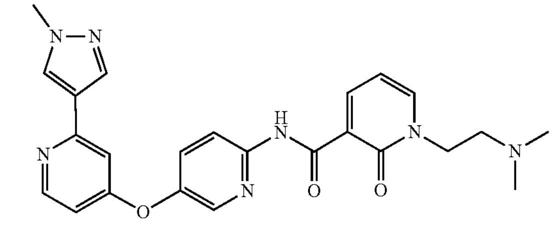 |
| 82 | 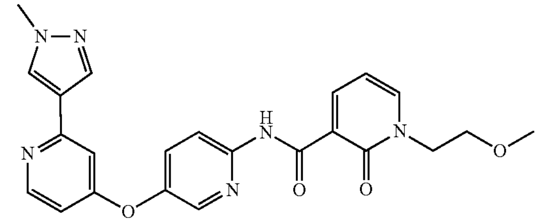 |
| 83 | 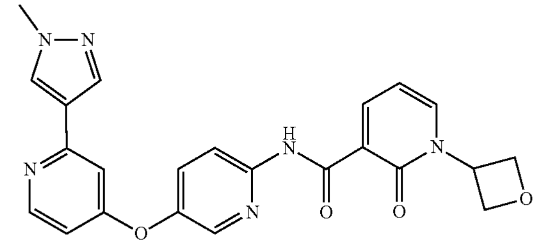 [SMILES: Cn1cc(-c2cc(Oc3ccc(NC(=O)c4cccn(C5COC5)c4=O)nc3)ccn2)cn1] |
| 84 | 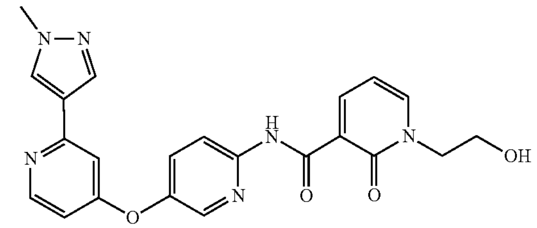 [SMILES: Cn1cc(-c2cc(Oc3ccc(NC(=O)c4cccn(CCO)c4=O)nc3)ccn2)cn1] |
| 85 | 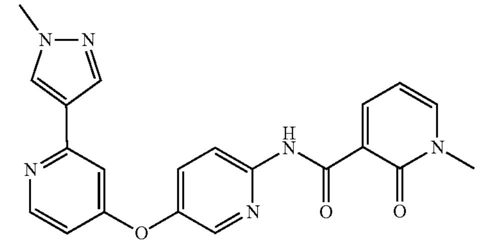 |
| 86 | 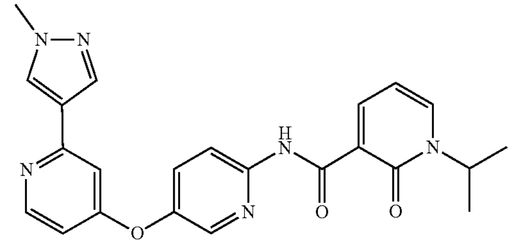 [SMILES: CC(C)n1cccc(C(=O)Nc2ccc(Oc3ccnc(-c4cnn(C)c4)c3)cn2)c1=O] |
| 87 | 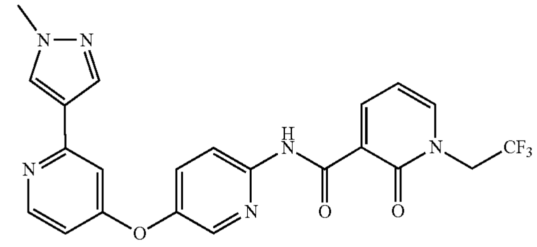 [SMILES: Cn1cc(-c2cc(Oc3ccc(NC(=O)c4cccn(CC(F)(F)F)c4=O)nc3)ccn2)cn1] |

-continued
| No. | Structural formula |
|---|---|
| 88 | 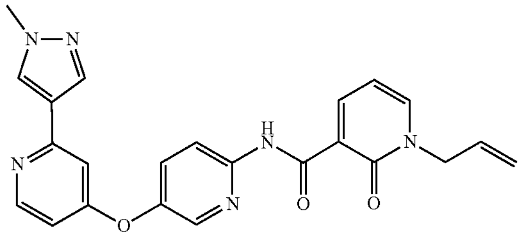 [SMILES: C=CCn1cccc(C(=O)Nc2ccc(Oc3ccnc(-c4cnn(C)c4)c3)cn2)c1=O] |
| 89 | 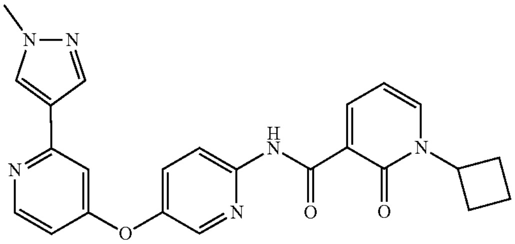 [SMILES: Cn1cc(-c2cc(Oc3ccc(NC(=O)c4cccn(C5CCC5)c4=O)nc3)ccn2)cn1] |
| 90 | 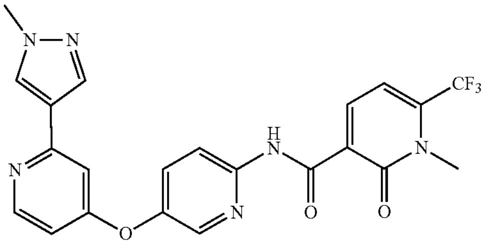 [SMILES: Cn1cc(-c2cc(Oc3ccc(NC(=O)c4ccc(C(F)(F)F)n(C)c4=O)nc3)ccn2)cn1] |
| 91 | 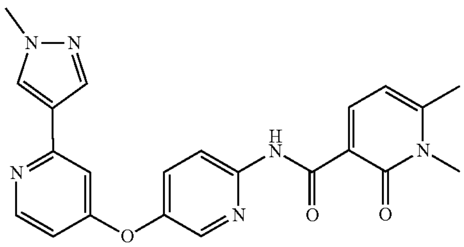 |
| 92 | 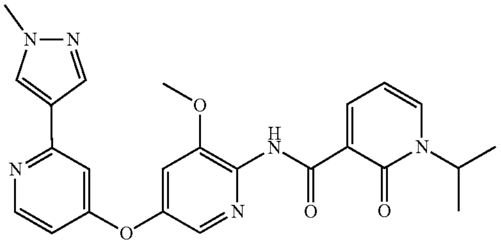 [SMILES: COc1cc(Oc2ccnc(-c3cnn(C)c3)c2)cnc1NC(=O)c1cccn(C(C)C)c1=O] |
| 93 | 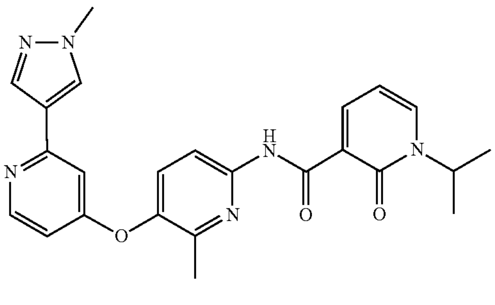 [SMILES: Cc1nc(NC(=O)c2cccn(C(C)C)c2=O)ccc1Oc1ccnc(-c2cnn(C)c2)c1] |
-continued
| No. | Structural formula |
|---|---|
| 94 | 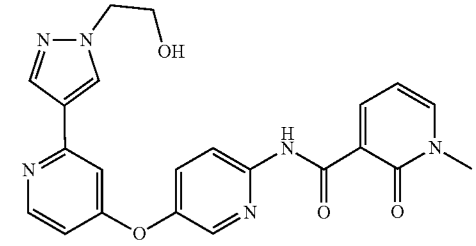 [SMILES: Cn1cccc(C(=O)Nc2ccc(Oc3ccnc(-c4cnn(CCO)c4)c3)cn2)c1=O] |
| 95 | 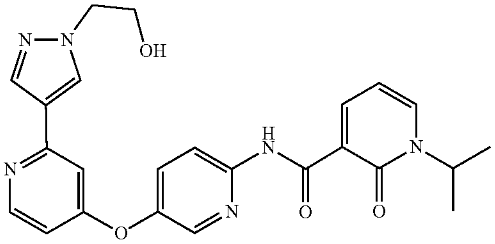 [SMILES: CC(C)n1cccc(C(=O)Nc2ccc(Oc3ccnc(-c4cnn(CCO)c4)c3)cn2)c1=O] |
| 96 | 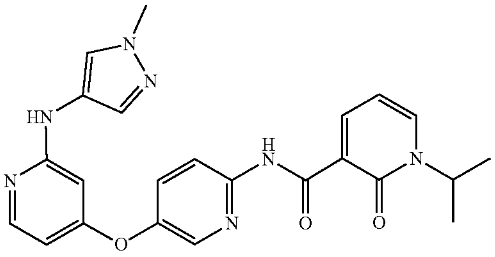 [SMILES: CC(C)n1cccc(C(=O)Nc2ccc(Oc3ccnc(Nc4cnn(C)c4)c3)cn2)c1=O] |
| 97 | 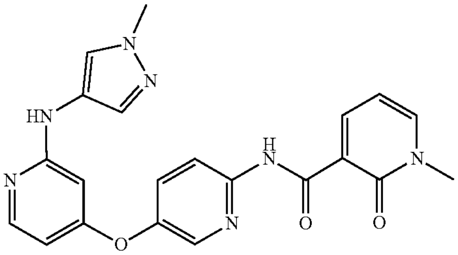 [SMILES: Cn1cc(Nc2cc(Oc3ccc(NC(=O)c4cccn(C)c4=O)nc3)ccn2)cn1] |
| 98 | 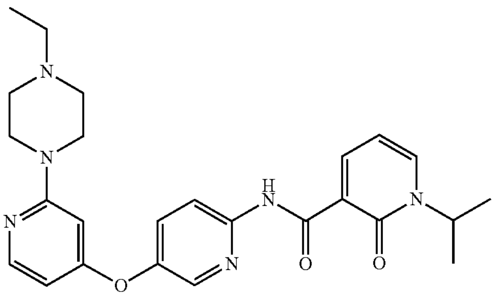 [SMILES: CCN1CCN(c2cc(Oc3ccc(NC(=O)c4cccn(C(C)C)c4=O)nc3)ccn2)CC1] |
| 99 | 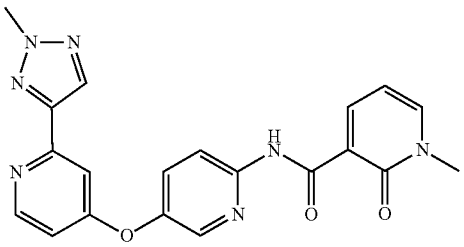 |

-continued
| No. | Structural formula |
|---|---|
| 100 | 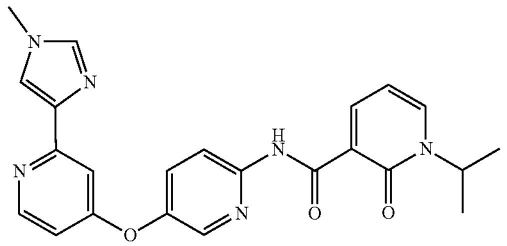 |
| 101 | 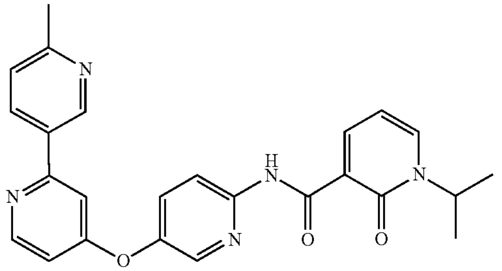 [SMILES: Cc1ccc(-c2cc(Oc3ccc(NC(=O)c4cccn(C(C)C)c4=O)nc3)ccn2)cn1] |
| 102 | 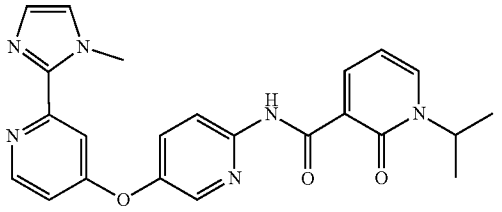 [SMILES: CC(C)n1cccc(C(=O)Nc2ccc(Oc3ccnc(-c4nccn4C)c3)cn2)c1=O] |
| 103 | 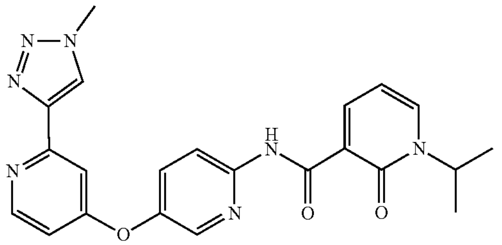 [SMILES: CC(C)n1cccc(C(=O)Nc2ccc(Oc3ccnc(-c4cn(C)nn4)c3)cn2)c1=O] |
| 104 | 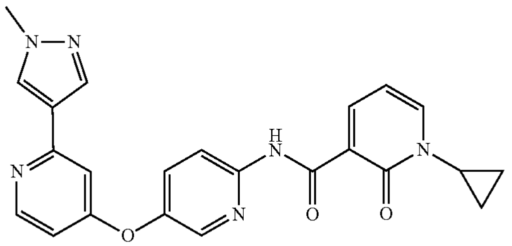 [SMILES: Cn1cc(-c2cc(Oc3ccc(NC(=O)c4cccn(C5CC5)c4=O)nc3)ccn2)cn1] |
| 105 | 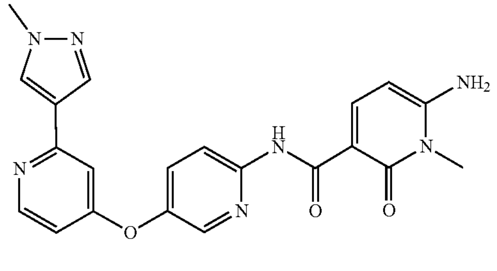 [SMILES: Cn1cc(-c2cc(Oc3ccc(NC(=O)c4ccc(N)n(C)c4=O)nc3)ccn2)cn1] |
-continued
| No. | Structural formula |
|---|---|
| 106 | 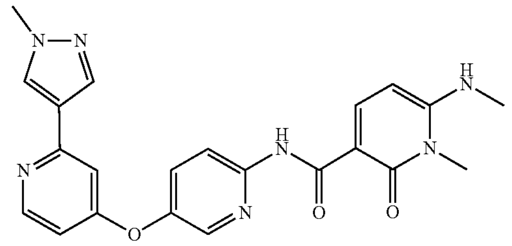 |
| 107 | 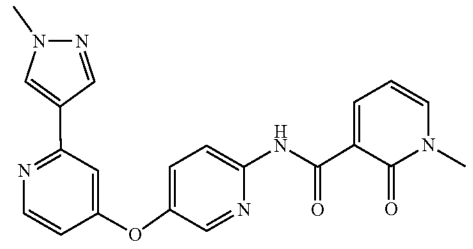 |
| 108 | 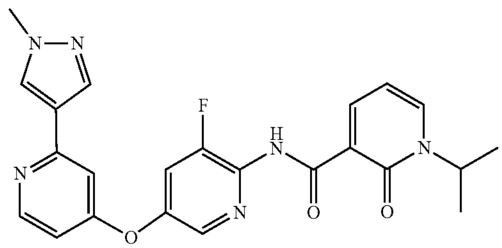 |
| 109 | 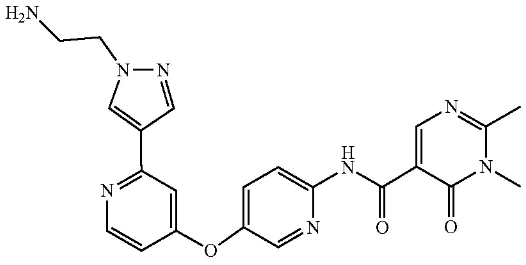 [SMILES: Cc1ncc(C(=O)Nc2ccc(Oc3ccnc(-c4cnn(CCN)c4)c3)cn2)c(=O)n1C] |
| 110 | 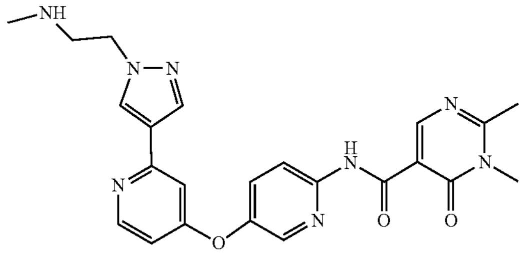 |
| 111 | 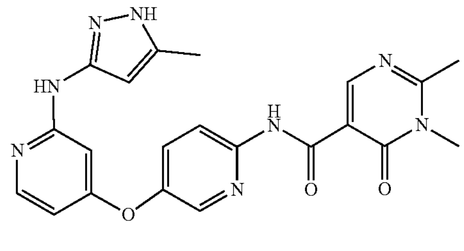 [SMILES: Cc1cc(Nc2cc(Oc3ccc(NC(=O)c4cnc(C)n(C)c4=O)nc3)ccn2)n[nH]1] |

-continued
| No. | Structural formula |
| --- | --- |
| 112 | 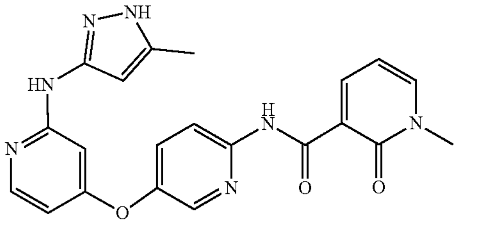 [SMILES: Cc1cc(Nc2cc(Oc3ccc(NC(=O)c4cccn(C)c4=O)nc3)ccn2)n[nH]1] |
| 113 | 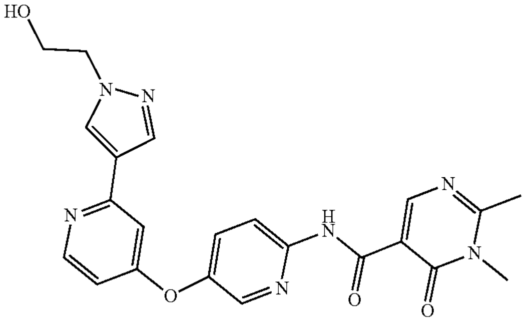 [SMILES: Cc1ncc(C(=O)Nc2ccc(Oc3ccnc(-c4cnn(CCO)c4)c3)cn2)c(=O)n1C] |
| 114 | 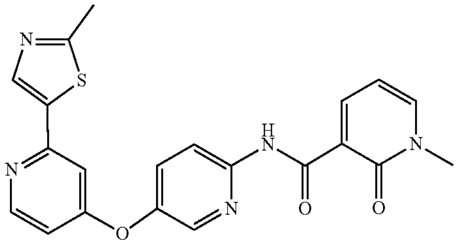 [SMILES: Cc1ncc(-c2cc(Oc3ccc(NC(=O)c4cccn(C)c4=O)nc3)ccn2)s1] |
| 115 | 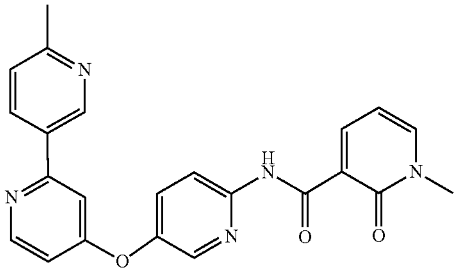 [SMILES: Cc1ccc(-c2cc(Oc3ccc(NC(=O)c4cccn(C)c4=O)nc3)ccn2)cn1] |
| 116 | 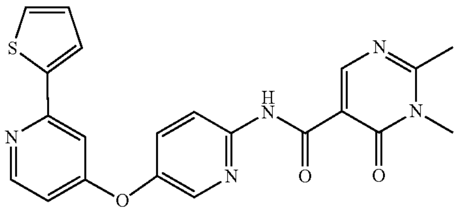 [SMILES: Cc1ncc(C(=O)Nc2ccc(Oc3ccnc(-c4cccs4)c3)cn2)c(=O)n1C] |
| 117 | 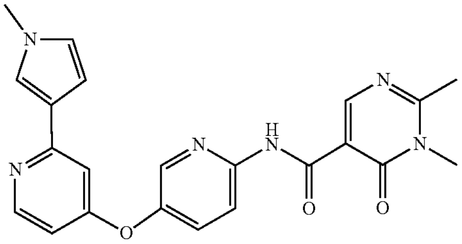 |
-continued
| No. | Structural formula |
| --- | --- |
| 118 | 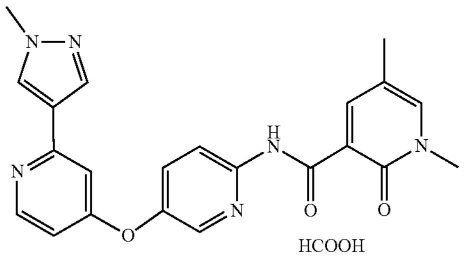 HCOOH |
| 119 | 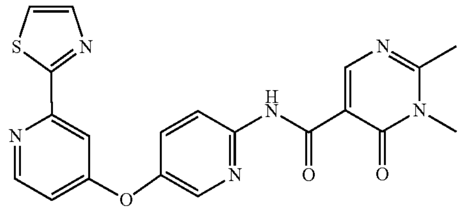 [SMILES: Cc1ncc(C(=O)Nc2ccc(Oc3ccnc(-c4nccs4)c3)cn2)c(=O)n1C] |
| 120 | 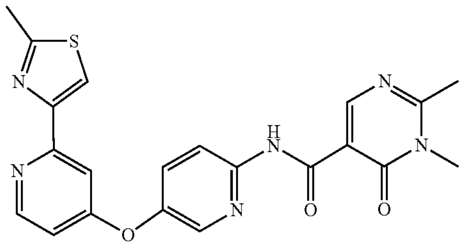 |
| 121 | 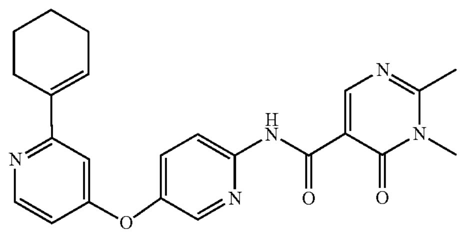 [SMILES: Cc1ncc(C(=O)Nc2ccc(Oc3ccnc(C4=CCCCC4)c3)cn2)c(=O)n1C] |
| 122 | 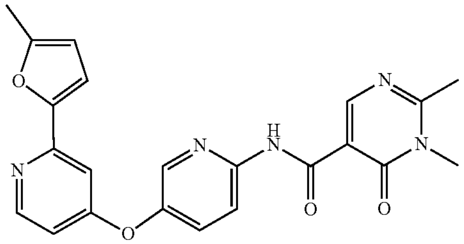 |
| 123 | 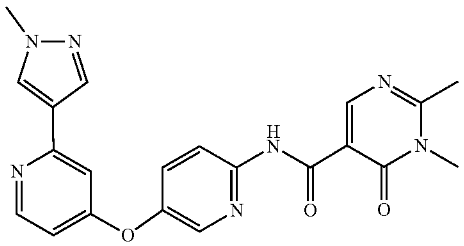 |

-continued
| No. | Structural formula |
|---|---|
| 124 | 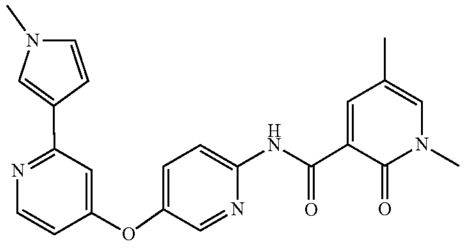 |
| 125 | 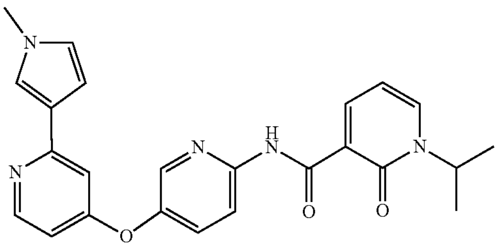 [SMILES: CC(C)n1cccc(C(=O)Nc2ccc(Oc3ccnc(-c4ccn(C)c4)c3)cn2)c1=O] |
| 126 | 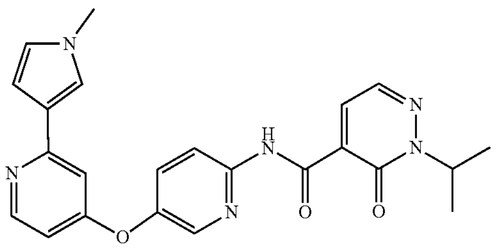 [SMILES: CC(C)n1nccc(C(=O)Nc2ccc(Oc3ccnc(-c4ccn(C)c4)c3)cn2)c1=O] |
| 127 | 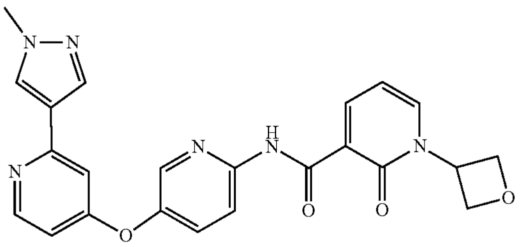 [SMILES: Cn1cc(-c2cc(Oc3ccc(NC(=O)c4cccn(C5COC5)c4=O)nc3)ccn2)cn1] |
| 128 | 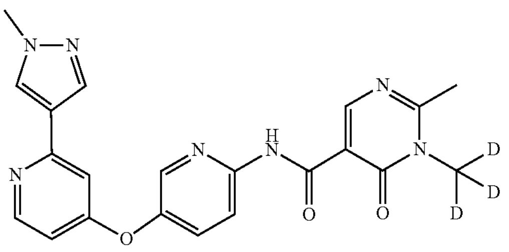 [SMILES: [2H]C([2H])([2H])n1c(C)ncc(C(=O)Nc2ccc(Oc3ccnc(-c4cnn(C)c4)c3)cn2)c1=O] |
| 129 | 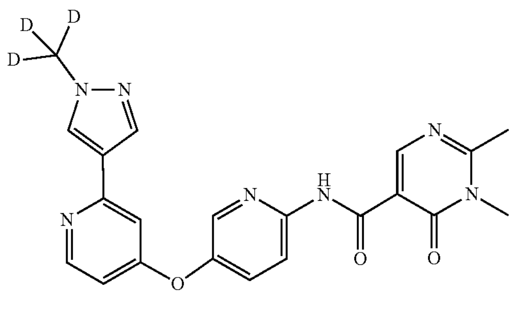 [SMILES: [2H]C([2H])([2H])n1cc(-c2cc(Oc3ccc(NC(=O)c4cnc(C)n(C)c4=O)nc3)ccn2)cn1] |
-continued
| No. | Structural formula |
|---|---|
| 130 | 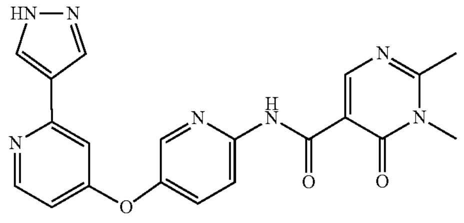 [SMILES: Cc1ncc(C(=O)Nc2ccc(Oc3ccnc(-c4cn[nH]c4)c3)cn2)c(=O)n1C] |
| 131 | 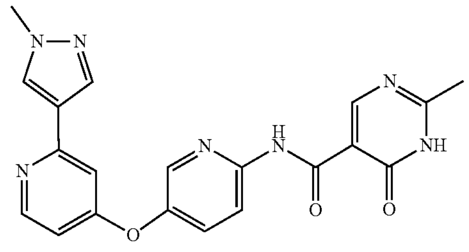 |
| 132 | 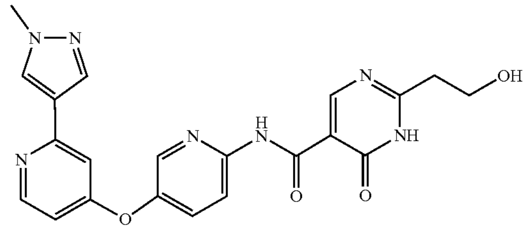 [SMILES: Cn1cc(-c2cc(Oc3ccc(NC(=O)c4cnc(CCO)[nH]c4=O)nc3)ccn2)cn1] |
| 133 | 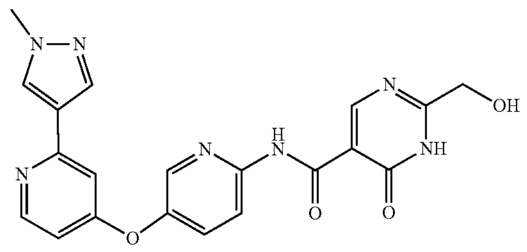 [SMILES: Cn1cc(-c2cc(Oc3ccc(NC(=O)c4cnc(CO)[nH]c4=O)nc3)ccn2)cn1] |
| 134 | 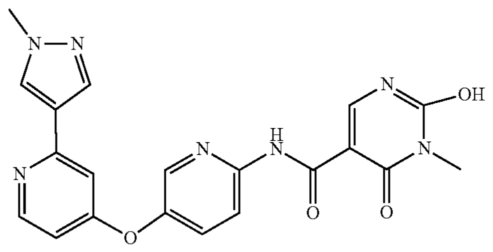 [SMILES: Cn1cc(-c2cc(Oc3ccc(NC(=O)c4cnc(O)n(C)c4=O)nc3)ccn2)cn1] |
| 135 | 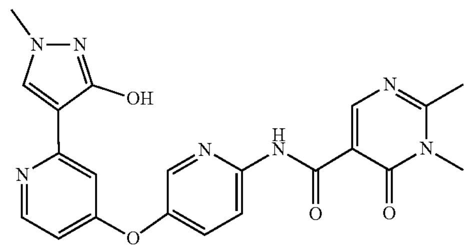 |
In another aspect, also provided is a pharmaceutical composition, comprising the compound of formula (I) (e.g., a compound of any of the examples as described herein) and/or a pharmaceutically acceptable salt thereof, and optionally comprising at least one pharmaceutically acceptable excipient (e.g., a pharmaceutically acceptable carrier).

In another aspect, also provided is a method of in vivo or in vitro inhibiting the activity of CSF-1R, comprising contacting CSF-1R with an effective amount of a compound of formula (I) (e.g., a compound of any of the examples as described herein) and/or a pharmaceutically acceptable salt thereof.

In another aspect, also provided is a method of treating a disease mediated by CSF-1R or at least in part by CSF-1R in a subject, comprising administering to the subject in need thereof an effective amount of a compound of formula (I) (e.g., a compound of any of the examples as described herein) and/or a pharmaceutically acceptable salt thereof.

In another aspect, also provided is a method of treating cancer, an autoimmune disease, an inflammatory disease, a metabolic disease, a neurodegenerative disease, obesity or an obesity-related disease in a subject, comprising administering to the subject in need thereof an effective amount of a compound of formula (I) (e.g., a compound of any of the examples as described herein) and/or a pharmaceutically acceptable salt thereof.

In another aspect, also provided is a method of treating cancer, an autoimmune disease or an inflammatory disease in a subject, comprising administering to the subject in need thereof an effective amount of a compound of formula (I) (e.g., a compound of any of the examples as described herein) and/or a pharmaceutically acceptable salt thereof.

In another aspect, also provided is a method of treating a disease mediated by CSF-1R or at least in part by CSF-1R in a subject, comprising administering to the subject in need thereof an effective amount of a pharmaceutical composition comprising a compound of formula (I) (e.g., a compound of any of the examples as described herein) and/or a pharmaceutically acceptable salt thereof, and at least one pharmaceutically acceptable excipient (e.g., a pharmaceutically acceptable carrier).

In another aspect, also provided is a method of treating cancer, an autoimmune disease, an inflammatory disease, a metabolic disease, a neurodegenerative disease, obesity or an obesity-related disease in a subject, comprising administering to the subject in need thereof an effective amount of a pharmaceutical composition comprising a compound of formula (I) (e.g., a compound of any of the examples as described herein) and/or a pharmaceutically acceptable salt thereof, and at least one pharmaceutically acceptable excipient (e.g., a pharmaceutically acceptable carrier).

In another aspect, also provided is a method of treating cancer, an autoimmune disease or an inflammatory disease in a subject, comprising administering to the subject in need thereof an effective amount of a pharmaceutical composition comprising a compound of formula (I) (e.g., a compound of any of the examples as described herein) and/or a pharmaceutically acceptable salt thereof, and at least one pharmaceutically acceptable excipient (e.g., a pharmaceutically acceptable carrier).

In another aspect, also provided is the use of a compound of formula (I) (e.g., a compound of any of the examples as described herein) and/or a pharmaceutically acceptable salt thereof described herein in the treatment of a disease mediated by CSF-1R or at least in part by CSF-1R in a subject.

In another aspect, also provided is the use of the compound of formula (I) (e.g., a compound of any of the examples as described herein) and/or a pharmaceutically acceptable salt thereof described herein in the treatment of cancer, an autoimmune disease, an inflammatory disease, a metabolic disease, a neurodegenerative disease, obesity or an obesity-related disease in a subject.

In another aspect, also provided is the use of the compound of formula (I) (e.g., a compound of any of the examples as described herein) and/or a pharmaceutically acceptable salt thereof described herein in the treatment of cancer, an autoimmune disease or an inflammatory disease in a subject.

In another aspect, also provided is the use of a compound of formula (I) (e.g., a compound of any of the examples as described herein) and/or a pharmaceutically acceptable salt thereof described herein in the manufacture of a medicament for treating a disease mediated by CSF-1R or at least in part by CSF-1R in a subject.

In another aspect, also provided is the use of the compound of formula (I) (e.g., a compound of any of the examples as described herein) and/or a pharmaceutically acceptable salt thereof described herein in the manufacture of a medicament for treating cancer, an autoimmune disease, an inflammatory disease, a metabolic disease, a neurodegenerative disease, obesity or an obesity-related disease in a subject.

In another aspect, also provided is the use of a compound of formula (I) (e.g., a compound of any of the examples as described herein) and/or a pharmaceutically acceptable salt thereof described herein in the manufacture of a medicament for treating cancer, an autoimmune disease or an inflammatory disease in a subject.

In another aspect, also provided is a combination, comprising a compound of formula (I) (e.g., a compound of any of the examples as described herein) and/or a pharmaceutically acceptable salt thereof, and at least one additional therapeutic agent.

In another aspect, also provided is a method of treating a disease mediated by CSF-1R or at least in part by CSF-1R in a subject, comprising administering to the subject in need thereof an effective amount of a compound of formula (I) (e.g., a compound of any of the examples as described herein) and/or a pharmaceutically acceptable salt thereof, and additional therapeutic agents.

In another aspect, also provided is a method of treating cancer, an autoimmune disease or an inflammatory disease in a subject, comprising administering to the subject in need thereof an effective amount of a compound of formula (I) (e.g., a compound of any of the examples as described herein) and/or a pharmaceutically acceptable salt thereof, and additional therapeutic agents.

In another aspect, also provided is the use of a compound of formula (I) (e.g., a compound of any of the examples as described herein) and/or a pharmaceutically acceptable salt thereof described herein together with additional therapeutic agents in the manufacture of a combined drug for treating a disease mediated by CSF-1R or at least in part by CSF-1R in a subject.

In another aspect, also provided is the use of a compound of formula (I) (e.g., a compound of any of the examples as described herein) and/or a pharmaceutically acceptable salt thereof described herein together with additional therapeutic agents in the manufacture of a combined drug for treating cancer, an autoimmune disease or an inflammatory disease.

In some embodiments, the additional therapeutic agent is an anti-neoplastic agent.

In some embodiments, the anti-neoplastic agent is chosen from a chemotherapeutic agent, an immune checkpoint inhibitor or agonist, and a targeted therapeutic agent.

In some embodiments, the disease mediated by CSF-1R or at least in part by CSF-1R is cancer, an autoimmune disease, an inflammatory disease, a metabolic disease, a neurodegenerative disease, obesity or an obesity-related disease.

In some embodiments, the disease mediated by CSF-1R or at least in part by CSF-1R is cancer, an autoimmune disease or an inflammatory disease.

In some embodiments, the cancer is solid tumor or hematologic malignancy (such as leukemia, lymphoma or myeloma).

In some embodiments, the cancer is chosen from ovarian cancer, lung cancer (including non-small cell lung cancer), brain tumor (including glioblastoma (GBM)), tenosynovial giant cell tumor, gastrointestinal stromal tumor (GIST), gastric cancer, esophageal cancer, colon cancer, colorectal cancer, pancreatic cancer, prostate cancer, breast cancer, cervical cancer, melanoma, mesothelioma, mesothelial carcinoma, renal cancer, liver cancer, thyroid carcinoma, head and neck cancer, urothelial carcinoma, bladder cancer, endometrial cancer, choriocarcinoma, adrenal carcinoma, sarcoma, leukemia, lymphoma or myeloma.

In some embodiments, the cancer is chosen from ovarian cancer, lung cancer (including non-small cell lung cancer), glioblastoma (GBM), tenosynovial giant cell tumor, gastrointestinal stromal tumor (GIST), gastric cancer, esophageal cancer, colon cancer, colorectal cancer, pancreatic cancer, prostate cancer, breast cancer, cervical cancer, melanoma, mesothelioma, mesothelial carcinoma, renal cancer, liver cancer, thyroid carcinoma, head and neck cancer, urothelial carcinoma, bladder cancer, endometrial cancer, choriocarcinoma, adrenal carcinoma, sarcoma, acute myelogenous leukemia (AML) (including recurrent or refractory AML), acute lymphocytic leukemia (ALL), B-cell lymphoma, T-cell lymphoma, diffuse large B-cell lymphoma (DLBCL) or multiple myeloma (MM).

In some embodiments, the autoimmune disease or inflammatory disease is chosen from arthritis (including rheumatoid arthritis and collagen-induced arthritis), osteoarthritis, pigmented villonodular synovitis (PVNS), systemic lupus erythematosus, multiple sclerosis, autoimmune nephritis, Crohn's disease, asthma or chronic obstructive pulmonary disease.

In some embodiments, the metabolic disease is chosen from osteoporosis, diabetes, diabetic ketoacidosis, hyperglycemia and hyperosmolar syndrome, hypoglycemia, gout, protein-energy malnutrition, vitamin A deficiency disease, scurvy, vitamin D deficiency disease, etc.

In some embodiments, the neurodegenerative disease is chosen from Parkinson's disease (PD), multiple system atrophy, Alzheimer's disease (AD), frontotemporal dementia, Huntington's disease (HD), corticobasal degeneration, spinocerebellar ataxia, motor neuron disease (including amyotrophic lateral sclerosis (ALS)), hereditary motor and sensory neuropathy (CMT), etc.

In some embodiments, the obesity-related disease is chosen from diabetes, hypertension, insulin resistance syndrome, dyslipidemia, heart disease, cardiovascular disease (including atherosclerosis, abnormal heart rhythms, arrhythmias, myocardial infarction, congestive heart failure, coronary heart disease, and angina pectoris), cerebral infarction, cerebral hemorrhage, osteoarthritis, metabolic syndrome, non-alcoholic fatty liver disease, non-alcoholic steatohepatitis, and the like.

General Synthetic Methods of the Disclosed Embodiments

The compound of formula (I) and/or a pharmaceutically acceptable salt thereof described herein can be synthesized using commercially available materials, by methods known in the art, or methods disclosed in the patent application. The synthetic routes shown in routes 1-3 illustrate the general synthetic methods of the compounds of the present invention.

Method 1:

Route 1

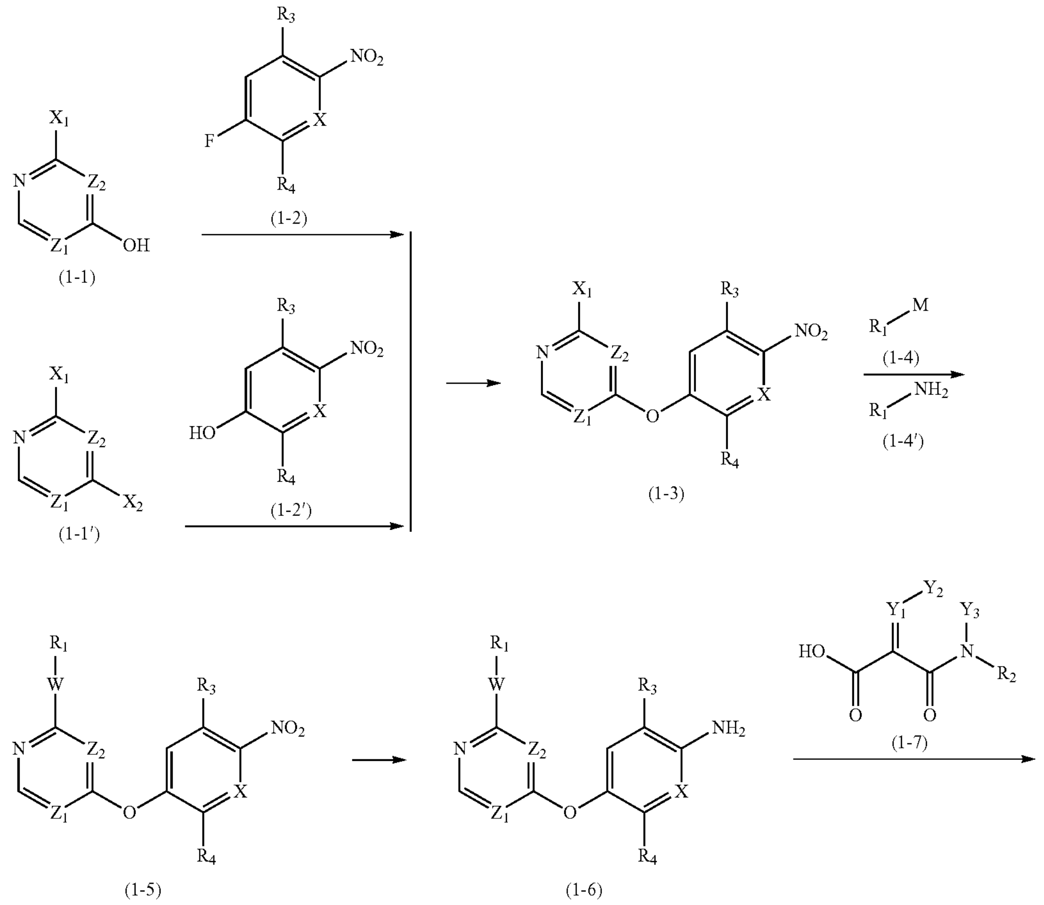

(1-1) (1-2) (1-1') (1-2') (1-3) (1-4) (1-4') (1-5) (1-6) (1-7)

-continued

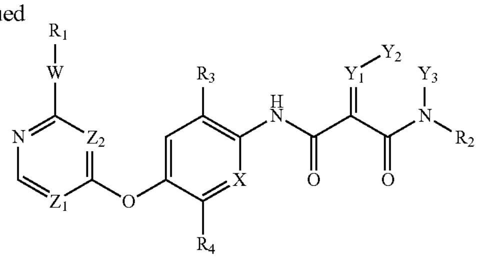

(I)

As shown in route 1, under alkaline conditions (such as, but not limited to potassium carbonate), a compound represented by molecular formula (1-1) is subjected to a substitution reaction with a compound represented by molecular formula (1-2), or the compound represented by molecular formula (1-1') is subjected to a substitution reaction with the compound represented by molecular formula (1-2') to obtain a compound represented by molecular formula (1-3). The compound represented by molecular formula (1-3) is subjected to a coupling reaction with a compound represented by molecular formula (1-4) under the catalysis of a palladium reagent (such as, but not limited to $Pd(dppf)Cl_2$), or is subjected to a substitution reaction with a compound represented by molecular formula (1-4') under the catalysis of a palladium reagent (such as, but not limited to $Pd_2(dba)_3$) and ligand (such as, but not limited to BINAP) to obtain a compound represented by molecular formula (1-5); which is continuously subjected to a reduction reaction to obtain a compound represented by molecular formula (1-6). The compound represented by molecular formula (1-6) is subjected to a condensation reaction with a compound represented by molecular formula (1-7) in the presence of a condensing agent (such as, but not limited to HATU, and the like) to obtain a compound of formula (I), wherein $R_1$, $R_2$, $R_3$, $R_4$, W, X, $Y_1$, $Y_2$, $Y_3$, $Z_1$ and $Z_2$ are as defined herein; M is borate, boronic acid or alkyl tin; $X_1$ is halogen, chosen from Cl and Br; $X_2$ is halogen, chosen from F and Cl.

Method 2:

Route 2

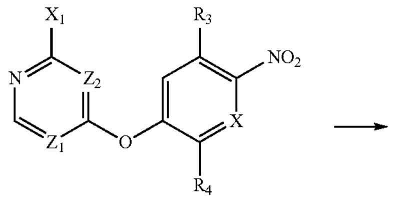

(1-3)

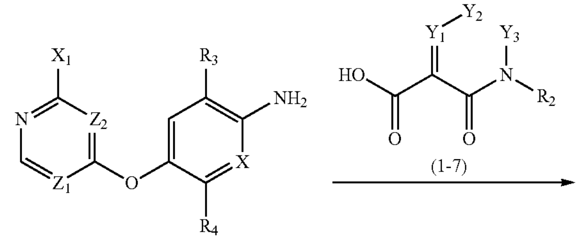

(1-8)

(1-7)

-continued

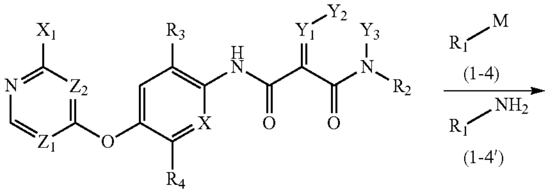

(1-9)

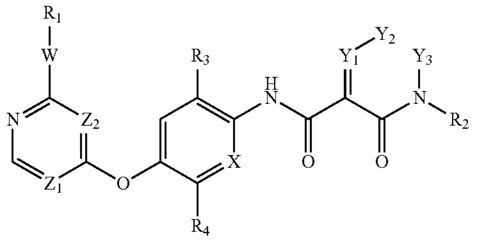

(I)

As shown in route 2, the compound represented by molecular formula (1-3) is subjected to a reduction reaction to obtain a compound represented by molecular formula (1-8), and then which is continuously subjected to a condensation reaction with the compound represented by molecular formula (1-7) in the presence of a condensing agent (such as, but not limited to HATU, and the like) to obtain a compound represented by molecular formula (1-9). The compound represented by molecular formula (1-9) is subjected to a coupling reaction with the compound represented by molecular formula (1-4) under the catalysis of a palladium reagent (such as, but not limited to $Pd(dppf)Cl_2$), or is subjected to a substitution reaction with the compound represented by molecular formula (1-4') under the catalysis of a palladium reagent (such as, but not limited to $Pd_2(dba)_3$) and ligand (such as, but not limited to BINAP) to obtain a compound of formula (I), wherein $R_1$, $R_2$, $R_3$, $R_4$, W, X, $Y_1$, $Y_2$, $Y_3$, $Z_1$ and $Z_2$ are as defined herein; M is borate, boronic acid or alkyl tin; $X_1$ is halogen, chosen from Cl and Br.

Method 3:

Route 3

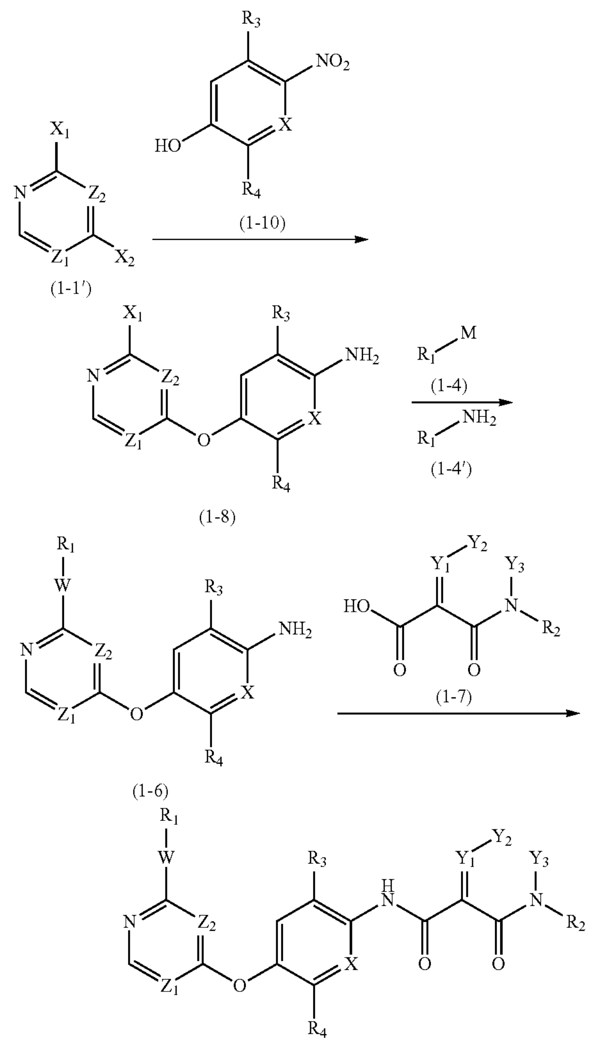

(1-1')
(1-10)
(1-8)
(1-4)
(1-4')
(1-6)
(1-7)
(I)

As shown in route 3, the compound represented by molecular formula (1-1') is subjected to a substitution reaction with a compound represented by molecular formula (1-10) under alkaline conditions (such as, but not limited to cesium carbonate) to obtain a compound represented by molecular formula (1-8). The compound represented by molecular formula (1-8) is subjected to a coupling reaction with the compound represented by molecular formula (1-4) under the catalysis of a palladium reagent (such as, but not limited to Pd(dppf)$Cl_2$), or is subjected to a substitution reaction with the compound represented by molecular formula (1-4') under the catalysis of a palladium reagent (such as, but not limited to $Pd_2(dba)_3$) and ligand (such as, but not limited to BINAP) to obtain a compound represented by molecular formula (1-6). The compound represented by molecular formula (1-6) is subjected to a condensation reaction with the compound represented by molecular formula (1-7) in the presence of a condensing agent (such as, but not limited to HATU, and the like) to obtain a compound of formula (I), wherein $R_1$, $R_2$, $R_3$, $R_4$, W, X, $Y_1$, $Y_2$, $Y_3$, $Z_1$ and $Z_2$ are as defined herein; M is borate, boronic acid or alkyl tin; $X_1$ is halogen, chosen from Cl and Br; $X_2$ is halogen, chosen from F and Cl.

The substituents of the compounds thus obtained can be further modified to provide other desired compounds. Synthetic chemistry transformations are described, for example, in R. Larock, *Comprehensive Organic Transformations*, VCH Publishers (1989); L. Fieser and M. Fieser, *Fieser and Fieser's Reagentsfor Organic Synthesis*, John Wiley and Sons (1994); and L. Paquette, ed., *Encyclopedia ofReagentsfor Organic Synthesis*, John Wiley and Sons (1995) and subsequent editions thereof.

Before use, the compound of formula (I) and/or a pharmaceutically acceptable salt thereof described herein can be purified by column chromatography, high performance liquid chromatography, crystallization or other suitable methods.

Pharmaceutical Compositions and Practical Utility

The compound of formula (I) (e.g., a compound of any of the examples as described herein) and/or a pharmaceutically acceptable salt thereof described herein is used, alone or in combination with one or more additional active ingredients, to formulate pharmaceutical compositions. A pharmaceutical composition comprises: (a) an effective amount of a compound of formula (I) and/or a pharmaceutically acceptable salt thereof described herein and optional additional active ingredients; and (b) a pharmaceutically acceptable excipient (e.g., a pharmaceutically acceptable carrier).

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the compound of formula (I) and/or a pharmaceutically acceptable salt thereof described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are disclosed in Remington's Pharmaceutical Sciences, A. Osol, a standard reference text in the art.

A pharmaceutical composition comprising the compound of formula (I) (e.g., a compound of any of the examples as described herein) and/or a pharmaceutically acceptable salt thereof described herein can be administered in various known manners, such as orally, topically, rectally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A pharmaceutical composition described herein can be prepared in the form of tablet, capsule, sachet, dragee, powder, granule, lozenge, powder for reconstitution, liquid preparation, or suppository. In some embodiments, a pharmaceutical composition comprising the compound of formula (I) and/or a pharmaceutically acceptable salt thereof is formulated for intravenous infusion, topical administration, or oral administration.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In some embodiments, the compound of formula (I) and/or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a tablet. In some embodiments, the compound of formula (I) and/or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a capsule.

A sterile injectable composition (e.g., aqueous or oleaginous suspension) can be formulated according to techniques known in the art using suitable dispersing or wetting agents (for example, Tween 80) and suspending agents. The sterile injectable intermediate medium can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives, and natural pharmaceutically acceptable oils, such as olive oil or castor oil, especially in their polyoxyethylated versions, can be used as injectable intermediate medium. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes, by weight, about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

Suitable in vitro assays can be used to evaluate the practical utility of the compound of formula (I) and/or a pharmaceutically acceptable salt thereof described herein in inhibiting the activity of CSF-1R. The compound of formula (I) and/or a pharmaceutically acceptable salt thereof described herein can further be examined for additional practical utility in treating cancer, an autoimmune disease or an inflammatory disease, and the like by in vivo assays. For example, the compound of formula (I) and/or a pharmaceutically acceptable salt thereof described herein can be administered to an animal (e.g., a mouse model) having cancer and its therapeutic effects can be accessed. If the pre-clinical results are successful, the dosage range and administration route for animals, such as humans, can be projected.

The compound of formula (I) and/or a pharmaceutically acceptable salt thereof described herein can be shown to have sufficient pre-clinical practical utility to merit clinical trials hoped to demonstrate a beneficial therapeutic or prophylactic effect, for example, in subjects with cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and hematologic malignancies. The term "cancer" encompasses diseases of skin, tissues, organs, bone, cartilage, blood, and vessels. The term "cancer" encompasses primary cancer, and further metastatic cancer.

Non-limiting examples of solid tumors include pancreatic cancer; bladder cancer; colorectal cancer; colon cancer; breast cancer, including metastatic breast cancer; prostate cancer, including androgen-dependent and androgen-independent prostate cancer; testicular cancer; renal cancer, including, e.g., metastatic renal cell carcinoma; urothelial carcinoma; liver cancer; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; endometrial cancer; gastrointestinal stromal tumor (GIST); gastric cancer; esophageal cancer; head and neck cancer, including, e.g., squamous cell carcinoma of the head and neck; skin cancer, including, e.g., melanoma and basal carcinoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; sarcoma, including, e.g., Kaposi's sarcoma; adrenal carcinoma; mesothelioma; mesothelial carcinoma; choriocarcinoma; muscle carcinoma; connective tissue carcinoma; tenosynovial giant cell tumor; and thyroid carcinoma.

Non-limiting examples of hematologic malignancies include acute myelogenous leukemia (AML); chronic myelogenous leukemia (CML), including accelerated phase CML and CML blastic phase (CML-BP); acute lymphocytic leukemia (ALL); chronic lymphocytic leukemia (CLL); Hodgkin's lymphoma; non-Hodgkin's lymphoma (NHL); follicular lymphoma; mantle cell lymphoma (MCL); B-cell lymphoma; T cell lymphoma; diffuse large B-cell lymphoma (DLBCL); multiple myeloma (MM); Waldenstrom macroglobulinemia; myelodysplastic syndrome (MDS), including refractory anemia (RA), refractory anemia with ring sideroblasts (RARS), refractory anemia with excess blasts (RAEB) and refractory anemia with excess blasts in transformation (RAEB-T); and myeloproliferative syndrome.

In some embodiments, the solid tumors include ovarian cancer, lung cancer (including non-small cell lung cancer), glioblastoma (GBM), tenosynovial giant cell tumor, gastrointestinal stromal tumor (GIST), gastric cancer, esophageal cancer, colon cancer, colorectal cancer, pancreatic cancer, prostate cancer, breast cancer, cervical cancer, melanoma, mesothelioma, mesothelial carcinoma, renal cancer, liver cancer, thyroid carcinoma, head and neck cancer, urothelial carcinoma, bladder cancer, endometrial cancer, choriocarcinoma, adrenal carcinoma and sarcoma.

In some embodiments, typical hematologic malignancies include leukemia, for example acute lymphocytic leukemia (ALL), acute myelogenous leukemia (AML), chronic lymphocytic leukemia (CLL) and chronic myelogenous leukemia (CML); multiple myeloma (MM); and lymphoma, for example Hodgkin's lymphoma, non-Hodgkin's lymphoma (NHL), mantle cell lymphoma (MCL), follicular lymphoma, B-cell lymphoma, T-cell lymphoma and diffuse large B-cell lymphoma (DLBCL).

The compound of formula (I) and/or a pharmaceutically acceptable salt thereof described herein can be used to achieve a beneficial therapeutic or prophylactic effect, for example, in subjects with cancer.

The compound of formula (I) and/or a pharmaceutically acceptable salt thereof described herein can be used to achieve a beneficial therapeutic or prophylactic effect, for example, in subjects with an autoimmune disease or inflammatory disease.

The term "autoimmune disease" refers to a disease or disorder arising from and/or directed against an individual's own tissues or organs, or a co-segregate or manifestation thereof, or resulting condition therefrom. Examples of autoimmune diseases include, but are not limited to: chronic obstructive pulmonary disease (COPD), allergic rhinitis, lupus erythematosus, myasthenia gravis, multiple sclerosis (MS), rheumatoid arthritis (RA), collagen-induced arthritis, psoriasis, inflammatory bowel disease (including Crohn's disease), asthma, autoimmune nephritis, idiopathic thrombocytopenic purpura (ITP) and myeloproliferative disease, such as myelofibrosis, and post-polycythemia vera/essential thrombocytosis myelofibrosis (post-PV/ET myelofibrosis).

The term "inflammatory disease" or "inflammatory disorder" refers to a pathological state that leads to inflammation, especially due to neutrophil chemotaxis. Non-limiting examples of inflammatory diseases include systemic inflammation and local inflammation, inflammation associated with immunosuppression, organ-graft refection, allergic disease, inflammatory skin disease (including psoriasis and atopic dermatitis); systemic scleroderma and sclerosis; reactions associated with inflammatory bowel diseases (IBD, such as Crohn's disease and ulcerative colitis); ischemia reperfusion injury, including reperfusion injury of tissue caused by surgery, myocardial ischemia, such as myocardial infarction, cardiac arrest, reperfusion after heart operation and abnormal contractile response of coronary vessel after percutaneous transluminal coronary angioplasty, surgical tissue reperfusion injury of stroke and abdominal aortic aneurysm; cerebral edema secondary to stroke; cranial trauma, and hemorrhagic shock; asphyxia; adult respiratory distress syndrome; acute lung injury; Behcet's disease; dermatomyositis; polymyositis; multiple sclerosis (MS); dermatitis; meningitis; encephalitis; uveitis; osteoarthritis; lupus nephritis; autoimmune disease such as rheumatoid arthritis (RA), Sjorgen's syndrome, and vasculitis; diseases involving leukopedesis; central nervous system (CNS) inflammatory disease and multiple organ injury syndrome secondary to septicemia or trauma; alcoholic hepatitis; bacterial pneumonia; antigen-antibody complex mediated disease, including glomerulonephritis; pyaemia; sarcoidosis; immunopathologic responses to tissue/organ transplantation; lung inflammation, including pleurisy, alveolitis, vasculitis, pneumonia, chronic bronchitis, bronchiectasia, diffuse panbronchiolitis, hypersensitivity pneumonitis, idiopathic pulmonary fibrosis (IPF), cystic fibrosis, etc. Preferably indications include, but are not limited to, chronic inflammation, autoimmune diabetes, rheumatoid arthritis (RA), rheumatoid spondylitis, gouty arthritis and other arthrosis conditions, multiple sclerosis (MS), asthma, systemic lupus erythematosus, adult respiratory distress syndrome, Behcet's disease, psoriasis, chronic pulmonary inflammatory disease, graft versus host reaction, Crohn's disease, ulcerative colitis, inflammatory bowel disease (IBD), Alzheimer's disease and pyresis, and any diseases associated with inflammation and related conditions.

The term "metabolic diseases" refers to diseases or disorders caused by metabolic problems, including metabolic disorders and hypermetabolism. Examples of metabolic diseases include, but are not limited to: osteoporosis, diabetes, diabetic ketoacidosis, hyperglycemia and hyperosmolar syndrome, hypoglycemia, gout, protein-energy malnutrition, vitamin A deficiency disease, scurvy, vitamin D deficiency disease, etc.

The term "neurodegenerative diseases" refers to degenerative diseases or disorders of the nervous system caused by neuronal degeneration and apoptosis. Examples of neurodegenerative diseases include, but are not limited to: Parkinson's disease (PD), multiple system atrophy, Alzheimer's disease (AD), frontotemporal dementia, Huntington's disease (HD), corticobasal degeneration, spinocerebellar ataxia, motor neuron disease (including amyotrophic lateral sclerosis (ALS)), hereditary motor and sensory neuropathy (CMT), etc.

The term "obesity-related diseases" refers to diseases or disorders related to, resulted from, or caused by obesity. Examples of obesity-related disease include, but are not limited to: diabetes, hypertension, insulin resistance syndrome, dyslipidemia, heart disease, cardiovascular disease (including atherosclerosis, abnormal heart rhythms, arrhythmias, myocardial infarction, congestive heart failure, coronary heart disease, and angina pectoris), cerebral infarction, cerebral hemorrhage, osteoarthritis, metabolic syndrome, non-alcoholic fatty liver disease, non-alcoholic steatohepatitis, and the like.

In addition, the compound of formula (I) (e.g., a compound of any of the examples as described herein) and/or a pharmaceutically acceptable salt thereof described herein can be administered in combination with additional therapeutic agents, for treating cancer, an autoimmune disease or an inflammatory disease. The additional therapeutic agents may be administered separately with the compound of formula (I) and/or a pharmaceutically acceptable salt thereof described herein or included with such an ingredient in a pharmaceutical composition according to the disclosure, such as a fixed-dose combination drug product. In some embodiments, additional therapeutic agents are those that are known or discovered to be effective in the treatment of diseases mediated by CSF-1R or at least in part by CSF-1R, such as another CSF-1R inhibitor or a compound active against another target associated with the particular disease. The combination may serve to increase efficacy (e.g., by including in the combination a compound potentiating the potency or effectiveness of the compound of formula (I) and/or a pharmaceutically acceptable salt thereof described herein), decrease one or more side effects, or decrease the required dose of the compound of formula (I) and/or a pharmaceutically acceptable salt thereof described herein.

In some embodiments, the compound of formula (I) (e.g., a compound of any of the examples as described herein) and/or a pharmaceutically acceptable salt thereof described herein can be administered in combination with anti-neoplastic agents. The term "anti-neoplastic agent" as used herein refers to any agent that is administered to a subject suffering from cancer for the purposes of treating the cancer, includes, but is not limited to a radiotherapeutic agent, a chemotherapeutic agent, an immune checkpoint inhibitor or agonist, a targeted therapeutic agent, and the like.

In some embodiments, the compound of formula (I) (e.g., a compound of any of the examples as described herein) and/or a pharmaceutically acceptable salt thereof described herein can be administered in combination with immune checkpoint inhibitors or agonists, targeted therapeutic agents or chemotherapeutic agents.

Non-limiting examples of immune checkpoint inhibitors or agonists include PD-1 inhibitors, for example, anti-PD-1 antibodies, such as pembrolizumab, nivolumab and PDR001 (spartalizumab); PD-L1 inhibitors, for example, anti-PD-L1 antibodies, such as atezolizumab, durvalumab, and avelumab; CTLA-4 inhibitors, for example, anti-CTLA-4 antibodies, such as ipilimumab; and BTLA inhibitors, LAG-3 inhibitors, TIM3 inhibitors, TIGIT inhibitors, VISTA inhibitors, OX-40 agonists, and the like.

Non-limiting examples of chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, mitoxantrone, idarubicin, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; nucleoside mimetics (e.g., 5-fluorouracil, capecitabine, gemcitabine, fludarabine, cytarabine, azacitidine, mercaptopurine, thioguanine, pentostatin, and hydroxyurea); paclitaxel, docetaxel, and related analogs; vincristine, vinblastin, and related analogs; thalidomide and related analogs (e.g., CC-5013 and CC-4047).

Non-limiting examples of targeted therapeutic agents include: protein tyrosine kinase inhibitors (such as imatinib mesylate and gefitinib); proteasome inhibitors (such as bortezomib); NF-κB inhibitors, including IκB kinase inhibitors; IDO inhibitors; A2AR inhibitors; BRAF inhibitors (such as dabrafenib); MEK inhibitors (such as trametinib); mTOR inhibitors (such as rapamycin); anti-CD40 antibodies (such as APX005M, RO7009789); antibodies that bind to proteins overexpressed in cancer to down-regulate cell replication, such as anti-CD20 antibodies (such as rituximab, ibritumomab tiuxetan, and tositumomab), anti-Her2 monoclonal antibodies (such as trastuzumab), anti-EGFR antibodies (such as cetuximab) and anti-VEGF antibodies (such as bevacizumab); anti-angiogenic drugs, such as lenalidomide; and other protein or enzyme inhibitors, these proteins or enzymes are known to be upregulated, overexpressed or activated in cancers, and the inhibition of which can down-regulate cell replication.

EXAMPLES

The examples below are intended to be purely exemplary and should not be considered to be limiting in any way. Efforts have been made to ensure the accuracy with respect to numbers used (for example, amounts, temperature, etc.), but the POSITA should understand that some experimental errors and deviations should be accounted for. Unless indicated otherwise, parts are parts by weight, temperature is in degrees Centigrade, and pressure is at or near atmospheric. All MS data were determined by Agilent 6120 or Agilent 1100. All NMR data were generated using a Varian 400 MHz NMR machine. All reagents, except intermediates, used in this invention are commercially available. All compound names except the reagents are generated by Chemdraw 18.0.

If there is any atom with empty valence(s) in any one of the structures disclosed herein, the empty balance(s) is (are) the hydrogen atom(s) which is (are) omitted for convenience purpose.

In the present application, in the case of inconsistency of the name and structure of a compound, when the two of which are both given for the compound, it is subject to the structure of the compound, unless the context shows that the structure of the compound is incorrect and the name is correct.

In the following examples, the abbreviations are used:

| | |
|---|---|
| AcOH | Acetic acid |
| $Ac_2O$ | Acetic anhydride |
| AcOK | Potassium acetate |
| BINAP | (±)-2,2'-bis-(diphenylphosphino)-1,1'-binaphthyl |
| DMF | N,N-dimethylformamide |
| DMSO | Dimethyl sulfoxide |
| DCM | Dichloromethane |
| DMA | N,N-dimethylacetylamide |
| DCE | Dichloroethane |
| DMAP | 4-dimethylaminopyridine |
| EtOH | Ethanol |
| $Et_3N$ | Triethylamine |
| HATU | Hexafluorophosphate O-(7-azobenzotriazole-1-yl)-N,N,N',N'-tetramethyluronium |
| i-PrOH | Isopropyl alcohol |
| MeOH | Methanol |
| MeI | Iodomethane |
| $Me_4$tBuXPhos | 2-di-tert-butyl phosphin-3,4,5,6-tetramethyl-2',4',6'-triisopropyl biphenyl |
| MsCl | Methanesulfonyl chloride |
| NaOMe | Sodium methoxide |
| NBS | N-bromosuccinimide |
| NMP | N-methyl-2-pyrrolidone |
| n-BuLi | N-butyl lithium |
| $Pd(dppf)Cl_2$ | [1,1'-bis(diphenylphosphino) ferrocene]palladium dichloride |
| $Pd(dppf)Cl_2 \bullet CH_2Cl_2$ | [1,1'-bis(diphenylphosphino) ferrocene]palladium dichloride dichloromethane complex |
| $Pd_2(dba)_3$ | Tris(dibenzylidene acetone)dipalladium |

-continued

| | |
|---|---|
| $Pd(PPh_3)_4$ | Tetra(triphenylphosphine)palladium |
| p-TsOH | p-toluenesulfonic acid |
| t-BuOK | Potassium t-butoxide |
| t-BuONa | T ert-butoxysodium |
| TBAF | Tetrabutylammonium fluoride |
| TBSCl | Tert-butyldimethylchlorosilane |
| THF | Tetrahydrofuran |
| TEA | Triethylamine |
| XantPhos | 4,5-bis(diphenylphosphino)-9,9-dimethylxanthene |
| p-TLC | Preparative thin layer chromatography |

Example 1

Preparation of Intermediates

Intermediate 1

5-chloro-1-isopropyl-2-oxo-1,2-dihydropyridine-3-carboxylic acid

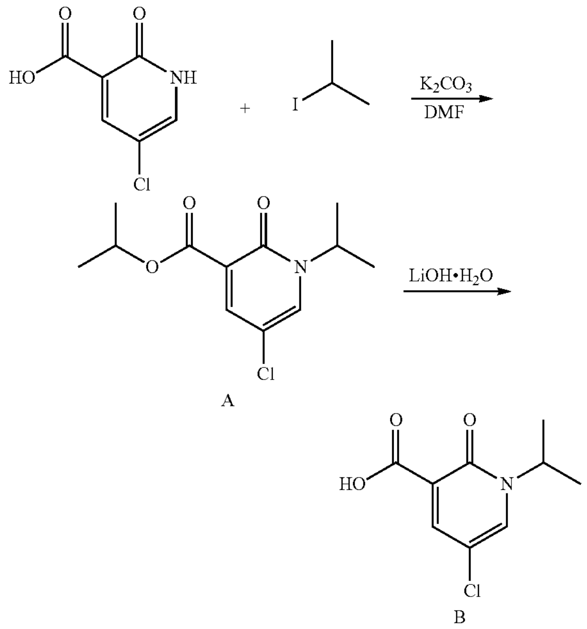

(A) Isopropyl 5-chloro-1-isopropyl-2-oxo-1,2-dihydropyridine-3-carboxylate

Under nitrogen, 5-chloro-2-oxo-1,2-dihydropyridin-3-carboxylic acid (200 mg, 1.15 mmol), 2-iodopropane (784 mg, 4.61 mmol), potassium carbonate (637 mg, 4.61 mmol) and DMF (5 ml) were successively added to a reaction flask, and the mixture was reacted at 80° C. for 5 hours. The reaction solution was concentrated, and the residue was dissolved by adding water (10 ml) and adjusted to pH 2 with 1N HCl solution, and then extracted with dichloromethane (50 ml×3), the organic layers were combined and concentrated, and the residue was purified with flash column chromatography (petroleum ether/ethyl acetate=100:0-0:100, gradient elution), to obtain 110 mg of the title product as a white solid. MS (m/z): 258.1 $[M+H]^+$.

(B) 5-chloro-1-isopropyl-2-oxo-1,2-dihydropyridine-3-carboxylic acid

Isopropyl 5-chloro-1-isopropyl-2-oxo-1,2-dihydropyridine-3-carboxylate (110 mg, 0.43 mmol), lithium hydroxide monohydrate (36 mg, 0.86 mmol), methanol (3 ml) and water (1 ml) were added to a reaction flask, and the mixture was reacted at room temperature for 2 hours. The reaction solution was concentrated, and the residue was dissolved by adding water (2 ml) (adjusting pH to 4 with 1N HCl solution), the precipitated solid was filtered, washed and dried to obtain 74 mg of the title product as a white solid. MS (m/z): 216.0 $[M+H]^+$.

Intermediate 2

4-methyl-3-oxo-3,4-dihydropyrazine-2-carboxylic acid

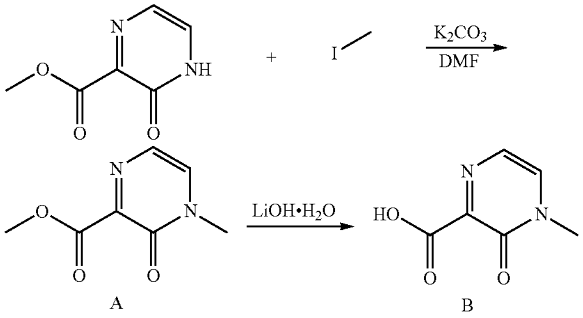

(A) Methyl 4-methyl-3-oxo-3,4-dihydropyrazine-2-carboxylate

Under nitrogen, methyl 3-oxo-3,4-dihydropyrazin-2-carboxylate (250 mg, 1.6 mmol), iodomethane (461 mg, 2.4 mmol), potassium carbonate (448 mg, 3.2 mmol) and DMF (5 ml) were successively added to a reaction flask, and the mixture was reacted at 50° C. for 4 hours. The reaction solution was concentrated, and the residue was dissolved by adding water (10 ml) (adjusting pH to 4 with 1N HCl solution), and then extracted with dichloromethane (50 ml×3), the organic layers were combined and concentrated, the resulting crude product can be directly used in the next step.

(B) 4-methyl-3-oxo-3,4-dihydropyrazine-2-carboxylic acid

Methyl 4-methyl-3-oxo-3,4-dihydropyrazine-2-carboxylate (155 mg, 0.92 mmol), lithium hydroxide monohydrate (77 mg, 1.84 mmol), methanol (4 ml) and water (1 ml) were added to a reaction flask, and the mixture was reacted at room temperature for 2 hours. The reaction solution (adjusting pH to 4 with 1N HCl solution) was concentrated, and the residue was purified with flash column chromatography (water/methanol=100:0-0:100, gradient elution), to obtain 83 mg of the title product as a white solid. MS (m/z): 155.1[M+H]+.

Intermediate 3

4-isopropyl-3-oxo-3,4-dihydropyrazine-2-carboxylic acid

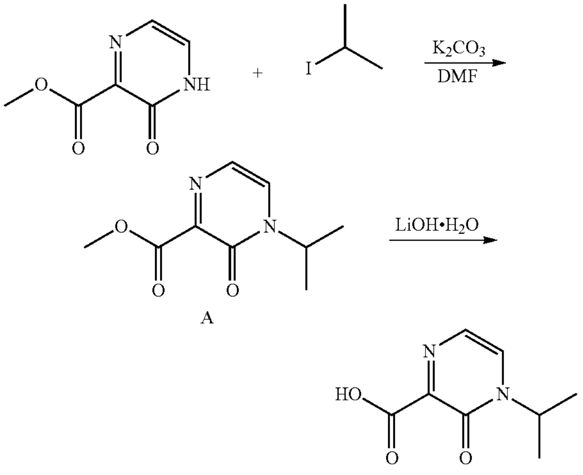

A

B (A) Methyl 4-isopropyl-3-oxo-3,4-dihydropyrazine-2-carboxylate

Under nitrogen, methyl 3-oxo-3,4-dihydropyrazin-2-carboxylate (500 mg, 3.25 mmol), 2-iodopropane (827 mg, 4.87 mmol), potassium carbonate (1.4 g, 9.75 mmol) and DMF (10 ml) were successively added to a reaction flask, and the mixture was reacted at 50° C. for 4 hours. The reaction solution was concentrated, and the residue was dissolved by adding water (50 ml) (adjusting pH to 3 with 1N HCl solution), and then extracted with dichloromethane (50 ml×3), the organic layers were combined and concentrated, and the residue was purified with flash column chromatography (dichloromethane/methanol=100:0-10:1, gradient elution), to obtain 263 mg of the title product as a colorless liquid. MS (m/z): 197.1 [M+H]+.

(B) 4-isopropyl-3-oxo-3,4-dihydropyrazine-2-carboxylic acid

Methyl 4-isopropyl-3-oxo-3,4-dihydropyrazine-2-carboxylate (263 mg, 1.34 mmol), lithium hydroxide monohydrate (113 mg, 2.68 mmol), methanol (3 ml) and water (1 ml) were added to a reaction flask, and the mixture was reacted at room temperature for 2 hours. The reaction solution was concentrated, and the residue was dissolved by adding water (5 ml) (adjusting pH to 4 with 1N HCl solution), the precipitated solid was filtered, washed and dried to obtain 200 mg of the title product as a white solid. MS (m/z): 183.1[M+H]+.

Intermediate 4

2-isopropyl-3-oxo-2,3-dihydropyridazine-4-carboxylic acid

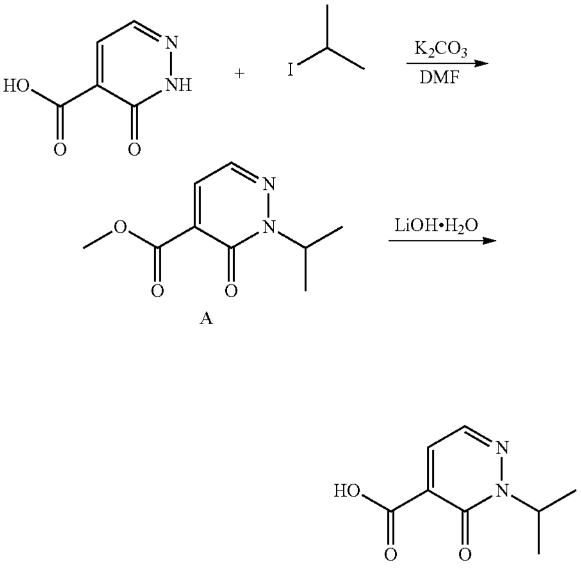

A

B (A) Isopropyl 2-isopropyl-3-oxo-2,3-dihydropyridazine-4-carboxylate

Under nitrogen, 3-oxo-2,3-dihydropyridazin-4-carboxylic acid (500 mg, 3.57 mmol), 2-iodopropane (1.5 g, 8.92 mmol), potassium carbonate (1.5 g, 10.71 mmol) and DMF (10 ml) were successively added to a reaction flask, and the mixture was reacted at 40° C. for 2 hours. The reaction solution was concentrated, and the residue was dissolved by adding water (50 ml) (adjusting pH to 3 with 1N HCl solution), and then extracted with dichloromethane (50 ml×3), the organic layers were combined and concentrated, and the residue was purified with flash column chromatography (petroleum ether/ethyl acetate=100:0-0:100, gradient elution), to obtain 90 mg of the title product as a yellow oil. MS (m/z): 225.1 [M+H]+.

(B) 2-isopropyl-3-oxo-2,3-dihydropyridazine-4-carboxylic acid

Isopropyl 2-isopropyl-3-oxo-2,3-dihydropyridazine-4-carboxylate (90 mg, 0.4 mmol), lithium hydroxide monohydrate (34 mg, 0.8 mmol), methanol (3 ml) and water (1 ml) were added to a reaction flask, and the mixture was reacted at room temperature for 1 hour. The reaction solution (adjusting pH to 4 with 1N HCl solution) was concentrated, and the resulting crude product can be directly used in the next step.

Intermediate 5

1-(difluoromethyl)-2-oxo-1,2-dihydropyridine-3-carboxylic acid

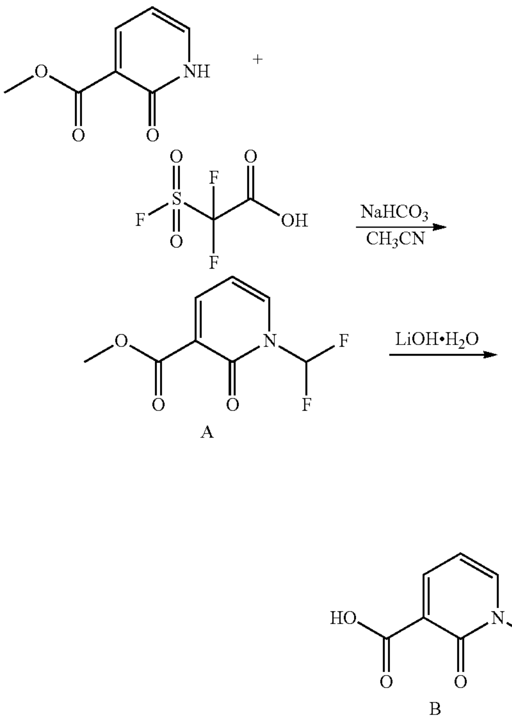

(A) methyl 1-(difluoromethyl)-2-oxo-1,2-dihydropyridine-3-carboxylate

Under nitrogen, methyl 2-oxo-1,2-dihydropyridin-3-carboxylate (153 mg, 1 mmol), 2,2-difluoro-2-(fluorosulfonyl) acetic acid (267 mg, 1.5 mmol), sodium bicarbonate (168 mg, 2 mmol) and acetonitrile (10 ml) were successively added to a reaction flask, and the mixture was refluxed and reacted for 6 hours. The reaction solution was filtered, and the filtrate was concentrated, the residue was purified with flash column chromatography (petroleum ether/ethyl acetate=100:0-0:100, gradient elution), to obtain 146 mg of the title product as a white solid. MS (m/z): 204.1 [M+H]$^+$.

(B) 1-(difluoromethyl)-2-oxo-1,2-dihydropyridine-3-carboxylic acid

Methyl 1-(difluoromethyl)-2-oxo-1,2-dihydropyridine-3-carboxylate (146 mg, 0.72 mmol), lithium hydroxide monohydrate (60 mg, 1.44 mmol), methanol (2 ml) and water (0.5 ml) were added to a reaction flask, and the mixture was reacted at room temperature for 30 minutes. The reaction solution (adjusting pH to 4 with 1N HCl solution) was concentrated, and the residue was purified with flash column chromatography (water/methanol=100:0-0:100, gradient elution), to obtain 84 mg of the title product as a white solid. MS (m/z): 190.1 [M+H]$^+$.

Intermediate 6

4-oxo-4H-pyrido[1,2-a]pyrimidine-3-carboxylic acid

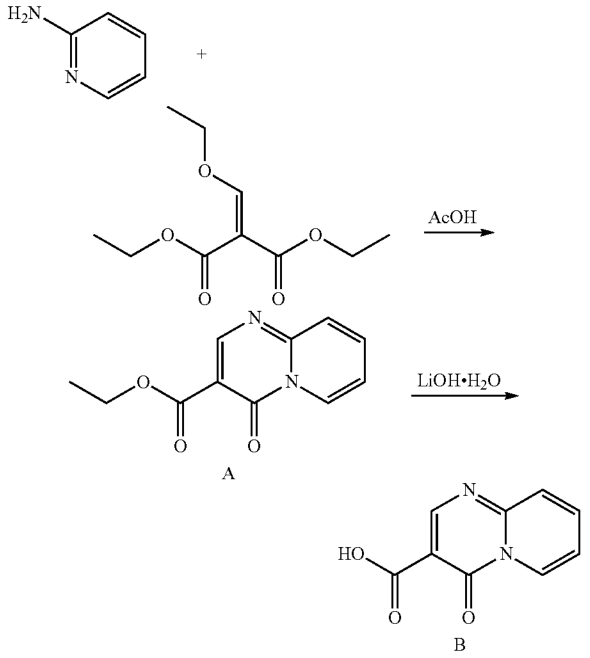

(A) Ethyl 4-oxo-4H-pyrido[1,2-a]pyrimidine-3-carboxylate 2-aminopyridine (500 mg, 5.31 mmol) and 2-(ethoxymethylene)diethyl malonate (1.206 g, 5.58 mmol) were added to a reaction flask, and the mixture was heated to 130° C. and reacted for 40 minutes, and then acetic acid (25 ml) was added, the reaction solution was further heated, refluxed and reacted for 4 hours, and the reaction solution was concentrated to obtain a oil, which was directly used in the next step without purification. MS (m/z): 219.0 [M+H]$^+$.

(B) 4-oxo-4H-pyrido[1,2-a]pyrimidine-3-carboxylic acid

Ethyl 4-oxo-4H-pyrido[1,2-a]pyrimidine-3-carboxylate (1.16 g, 5.32 mmol), lithium hydroxide monohydrate (894 mg, 21.28 mmol), THF (20 ml), MeOH (8 ml) and water (8 ml) were added to a reaction flask, and the mixture was stirred at room temperature overnight (adjusting pH to 3.0 with 1N hydrochloric acid), the white solid was precipitated, filtered, and the solid was dried to obtain 828 mg of the title product. MS (m/z): 191.0 [M+H]$^+$.

Intermediate 7

5-oxo-1,2,3,5-tetrahydroindolizine-6-carboxylic acid

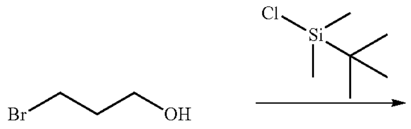

-continued

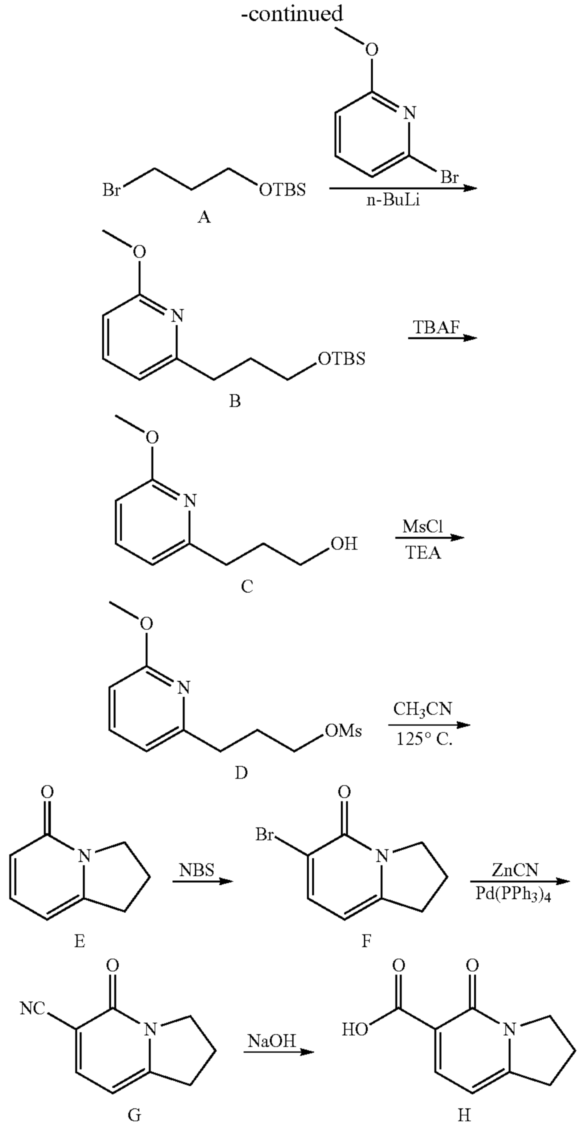

(A) (3-bromopropoxy)(tert-butyl)dimethylsilane 3-bromopropane-1-ol (4.0 g, 28.78 mmol), 1H-imidazole (3.92 g, 57.56 mmol), DCM (150 ml) and TBSCl (4.55 g, 30.22 mmol) were successively added to a reaction flask, and the mixture was stirred at room temperature overnight. The reaction solution was washed with water, the organic phase was dried and concentrated, and the residue was purified with flash column chromatography (petroleum ether/ethyl acetate=100:0-90:10, gradient elution), to obtain 6.5 g of the title product as a colorless liquid.

(B) 2-(3-((tert-butyldimethylsilyl)oxy)propyl)-6-methoxypyridine 2-bromo-6-methoxypyridine (4.83 g, 25.67 mmol) and dried THF (100 ml) were added to a reaction flask, and the reaction solution was cooled to −78° C., under nitrogen, added dropwise 2.4N n-BuLi (11.77 ml, 28.24 mmol), reacted for 30 minutes, and then slowly added dropwise (3-bromopropoxy)(tert-butyl)dimethylsilane (6.5 g, 25.67 mmol), continuously reacted at −78° C. for 1 hour, and then warmed to room temperature, reacted overnight, quenched by adding water, and extracted with ethyl acetate, the organic phase was dried and concentrated to obtain a yellow oil. MS (m/z): 282.2 $[M+H]^+$.

(C) 3-(6-methoxypyridin-2-yl)propan-1-ol

The oil obtained from the above-mentioned step (B) was dissolved in THF (80 ml), the solution was added TBAF trihydrate (16.1 g, 51.34 mmol), stirred at room temperature overnight, and the reaction solution was added ethyl acetate, washed with water, the organic phase was dried and concentrated, and the residue was purified with flash column chromatography (petroleum ether/ethyl acetate=100:0-0:100, gradient elution), to obtain 1.2 g of the title product as a colorless liquid.

(D) 3-(6-methoxypyridin-2-yl)propyl methanesulfonate 3-(6-methoxypyridin-2-yl)propan-1-ol (1.0 g, 5.98 mmol), TEA (1.66 ml, 11.96 mmol) and DCM (50 ml) were added to a reaction flask, and the reaction solution was cooled in an ice bath, and then added dropwise MsCl (822 mg, 7.18 mmol), reacted for half an hour, washed with water, and the organic phase was dried and concentrated, to obtain a colourless liquid. MS (m/z): 246.1 $[M+H]^+$.

(E) 2,3-dihydroindolizin-5(1H)-one 3-(6-methoxypyridin-2-yl)propyl methanesulfonate rude product obtained from the above-mentioned step (D) and acetonitrile (25 ml) were added to a reaction flask, and the reactant was reacted under the microwave at 125° C. for 15 minutes, and then concentrated, the residue was purified with flash column chromatography ($H_2O$/MeOH=100:0-0:100, gradient elution), to obtain 400 mg of the title product as a light yellow oil. MS (m/z): 136.1 $[M+H]^+$.

(F) 6-bromo-2,3-dihydroindolizin-5(1H)-one 2,3-dihydroindolizin-5(1H)-one (300 mg, 2.22 mmol), DMF (5.0 ml) and NBS (435 mg, 2.44 mmol) were added to a reaction flask, and the mixture was stirred at room temperature overnight, the reaction solution was purified with flash column chromatography ($H_2O$/MeOH=100:0-0:100, gradient elution), to obtain 120 mg of a light yellow title product. MS (m/z): 214.0, 216.0 $[M+H]^+$.

$^1$H NMR (400 MHz, DMSO-d6) δ 7.79 (d, J=7.4 Hz, 1H), 6.12 (dt, J=7.4, 1.2 Hz, 1H), 4.06-3.93 (m, 3H), 3.09-2.97 (m, 3H), 2.18-2.01 (m, 3H).

(G) 5-oxo-1,2,3,5-tetrahydroindolizine-6-carbonitrile 6-bromo-2,3-dihydroindolizin-5(1H)-one (120 mg, 0.56 mmol), zinc cyanide (43 mg, 0.365 mmol), $Pd(PPh_3)_4$ (65 mg, 0.0561 mmol) and DMF (5.0 ml) were added to a reaction flask, and the mixture was heated to 100° C. under nitrogen and stirred overnight, the reaction solution was purified with flash column chromatography ($H_2O$/MeOH=100:0-0:100, gradient elution), to obtain 60 mg of a white title product. MS (m/z): 161.1 $[M+H]^+$.

(H) 5-oxo-1,2,3,5-tetrahydroindolizine-6-carboxylic acid 5-oxo-1,2,3,5-tetrahydroindolizine-6-carbonitrile (60 mg, 0.375 mmol) and 2N concentration of sodium hydroxide aqueous solution (1.0 ml, 2.0 mmol) were added to a reaction flask, the mixture was heated to 100° C. and stirred overnight, and then cooled to room temperature (adjusting pH to 3 with 1N concentration of hydrochloric acid), and filtered, to obtain 60 mg of a white title product. MS (m/z): 180.1 $[M+H]^+$.

Intermediate 8

1,3-dimethyl-2,4-dioxo-1,2,3,4-tetrahydropyrimidine-5-carboxylic acid

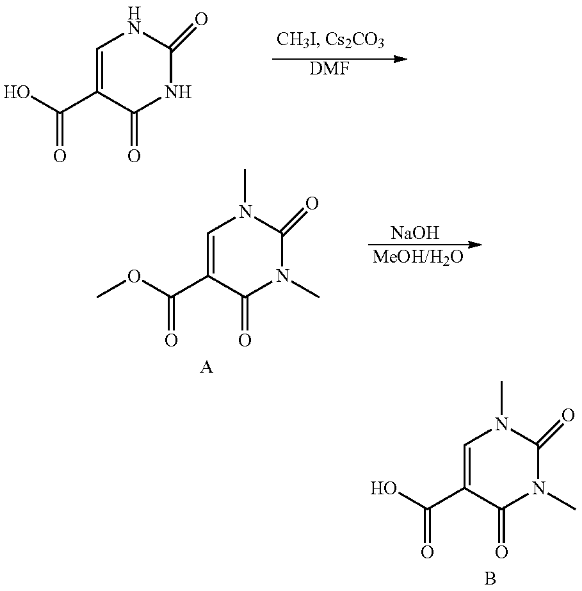

(A) methyl 1,3-dimethyl-2,4-dioxo-1,2,3,4-tetrahydropyrimidine-5-carboxylate In a reaction flask, uracil-5-carboxylic acid (1 g, 6.4 mmol) was dissolved in DMF (15 ml), and $Cs_2CO_3$ (12.5 g, 38.4 mmol) and $CH_3I$ (4.6 g, 32 mmol) were successively added, the reaction solution was reacted at 60° C. for 16 hours. Water was added to the reaction solution, and the reaction solution was extracted with ethyl acetate, washed with saturated brine, and dried with anhydrous sodium sulfate. The reactant was concentrated to obtain 0.8 g of a khaki solid. MS (m/z): 199 $[M+H]^+$.

(B) 1,3-dimethyl-2,4-dioxo-1,2,3,4-tetrahydropyrimidine-5-carboxylic acid

In a reaction flask, methyl 1,3-dimethyl-2,4-dioxo-1,2,3,4-tetrahydropyrimidine-5-carboxylate (500 mg, 2.5 mmol) was dissolved in methanol (6 ml) and water (1.5 ml), and NaOH (200 mg, 5 mmol) was added, the reaction solution was reacted at room temperature for 3 hours. The reaction solution was revolved to remove methanol, and neutralized with 1N hydrochloric acid to pH=3, the solid was precipitated, filtered, dried, to obtain 300 mg of a white solid. MS (m/z): 185 $[M+H]^+$.

Intermediate 9

1-methyl-2-oxo-1,2-dihydroquinoline-3-carboxylic acid

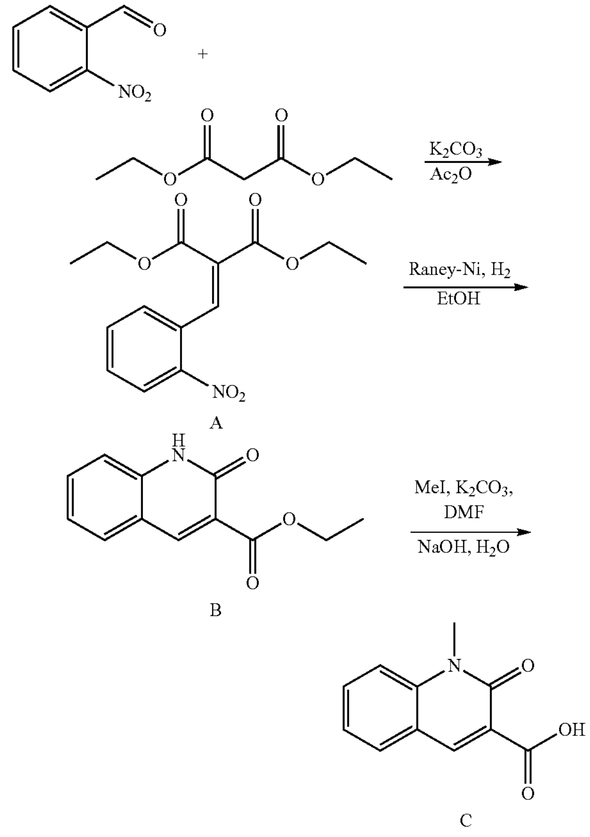

(A) diethyl 2-(2-nitrobenzylidene)malonate

Under nitrogen, 2-nitrobenzene formaldehyde (2.0 g, 13.2 mmol), diethyl malonate (2.0 ml, 13.2 mmol), potassium carbonate (2.74 g, 19.8 mmol) and acetic anhydride (5 ml) were successively added to a reaction flask, and the mixture was heated to 80° C. and stirred for 4 hours. The reaction solution was cooled to room temperature, and then poured into ice water (100 ml), and extracted with ethyl acetate (100 ml). The organic phase was washed with saturated sodium bicarbonate (100 ml) and saturated brine (100 ml), dried with anhydrous sodium sulfate, and then filtered. The filtrate was concentrated, and the residue was purified with flash column chromatography (petroleum ether:ethyl acetate=100:0-0:100, gradient elution), to obtain 3.2 g of the title product as a light yellow solid. MS (m/z): 294.1 $[M+H]^+$.

(B) Ethyl 2-oxo-1,2-dihydroquinoline-3-carboxylate

Diethyl 2-(2-nitrobenzylidene)malonate (3.2 g, 10.9 mmol), ethanol (50 ml) and Raney-Ni (1.0 g) were successively added to a reaction flask, after replacing hydrogen with hydrogen balloon, the reaction solution was stirred under normal pressure at room temperature overnight. Dichloromethane (30 ml) and methanol (30 ml) were added, and then the reaction solution was filtered, the filtrate was concentrated to obtain 2.87 g of the title product as a brown solid. MS (m/z): 218.1 [M+H]$^+$.

(C) 1-methyl-2-oxo-1,2-dihydroquinoline-3-carboxylic acid

Ethyl 2-oxo-1,2-dihydroquinoline-3-carboxylate (500 mg, 2.3 mmol), iodomethane (430 μl, 6.9 mmol), potassium carbonate (636 mg, 4.6 mmol) and DMF (5 ml) were successively added to a reaction flask, and the mixture was stirred at room temperature overnight. Sodium hydroxide aqueous solution (2N, 4 ml) was added dropwise, and the reaction solution was stirred at room temperature for 4 hours. Water (100 ml) was added, and the pH was adjusted to 4 with concentrated hydrochloric acid. The reaction solution was filtered, and the solid was washed with water and dried, to obtain 350 mg of the title product as a white solid. MS (m/z): 204.1 [M+H]$^+$.

Intermediate 10

5-fluoro-1-methyl-2-oxo-1,2-dihydropyridine-3-carboxylic acid

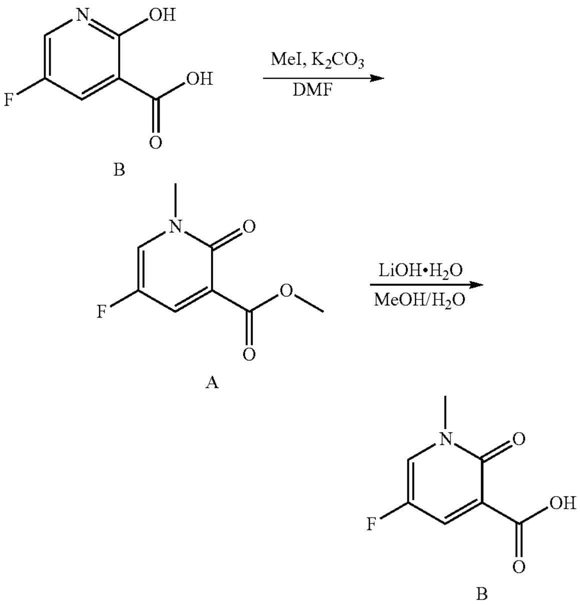

(A) Methyl 5-fluoro-1-methyl-2-oxo-1,2-dihydropyridine-3-carboxylate

Under nitrogen, 5-fluoro-2-hydroxynicotinic acid (720 mg, 4.6 mmol), iodomethane (860 μl, 13.8 mmol), potassium carbonate (2.74 g, 19.8 mmol) and DMF (10 ml) were successively added to a reaction flask, and the mixture was heated to 50° C. and stirred overnight. The reaction solution was cooled to room temperature, and purified with flash column chromatography (water (0.5% formic acid):methanol=100:0-0:100, gradient elution), to obtain 750 mg of the title product as a light yellow solid. MS (m/z): 186.1 [M+H]$^+$.

(B) 5-fluoro-1-methyl-2-oxo-1,2-dihydropyridine-3-carboxylic acid

Methyl 5-fluoro-1-methyl-2-oxo-1,2-dihydropyridine-3-carboxylate (750 mg, 4.05 mmol), lithium hydroxide monohydrate (340 mg, 9.1 mmol) and methanol/water (15 ml/5 ml) were successively added to a reaction flask, and the mixture was stirred at room temperature for 2 hours. The reaction solution was concentrated, and then added water (40 ml) (adjusting pH to 4 with hydrochloric acid aqueous solution (2N)) and filtered. The solid was dried to obtain 600 mg of a white title product. MS (m/z): 172.0 [M+H]$^+$.

Intermediate 11

2-isopropyl-1-methyl-6-oxo-1,6-dihydropyrimidine-5-carboxylic acid

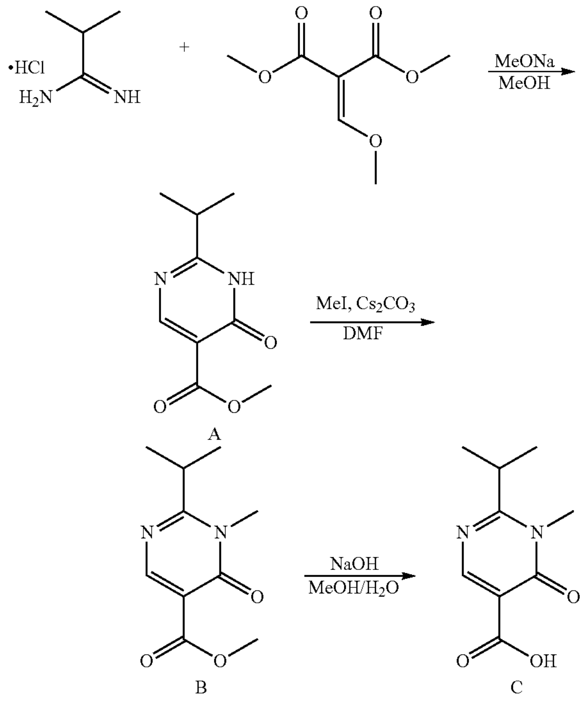

(A) Methyl 2-isopropyl-6-oxo-1,6-dihydropyrimidine-5-carboxylate

Under nitrogen, isopropamidine hydrochloride (1.23 g, 10 mmol), anhydrous methanol (20 ml) and sodium methoxide (504 mg, 10 mmol) were successively added to a reaction flask, and the mixture was stirred for half an hour, and then 2-(methoxymethylene)dimethyl malonate (1.74 g, 10 mmol) and sodium methoxide (504 mg, 10 mmol) were successively added in an ice bath, the reaction solution was warmed slowly to room temperature and then stirred overnight. The reaction solution was concentrated, after stirring the sample with silica gel, which was purified with flash column chromatography (dichloromethane:methanol=100:0-90:10, gradient elution), to obtain 700 mg of the title product as a light yellow solid. MS (m/z): 197.1 [M+H]$^+$.

(B) Methyl 2-isopropyl-1-methyl-6-oxo-1,6-dihydropyrimidine-5-carboxylate

Under nitrogen, methyl 2-isopropyl-6-oxo-1,6-dihydropyrimidine-5-carboxylate (700 mg, 3.6 mmol), iodomethane (436 μl, 7 mmol), cesium carbonate (2.28 g, 7 mmol) and DMF (10 ml) were successively added to a reaction flask, and the mixture was heated to 80° C. and stirred overnight. The reaction solution was cooled to room temperature, and purified with flash column chromatography (water (0.5% formic acid):methanol=100:0-0:100, gradient elution), to obtain 250 mg of the title product as a white solid. MS (m/z): 211.1 $[M+H]^+$.

(C) 2-isopropyl-1-methyl-6-oxo-1,6-dihydropyrimidine-5-carboxylic acid

Methyl 2-isopropyl-1-methyl-6-oxo-1,6-dihydropyrimidine-5-carboxylate (250 mg, 1.2 mmol), sodium hydroxide (96 mg, 2 mmol) and methanol/water (10 ml/2 ml) were successively added to a reaction flask, and the mixture was stirred at room temperature for 2 hours. Adjusting pH to 4 with 2N hydrochloric acid aqueous solution, and the reaction solution was concentrated. The residue was purified with flash column chromatography (water (0.5% formic acid):methanol=100:0-0:100, gradient elution), to obtain 180 mg of a white title product. MS (m/z): 197.1 $[M+H]^+$.

Intermediate 12

2-cyclopropyl-1-methyl-6-oxo-1,6-dihydropyrimidine-5-carboxylic acid

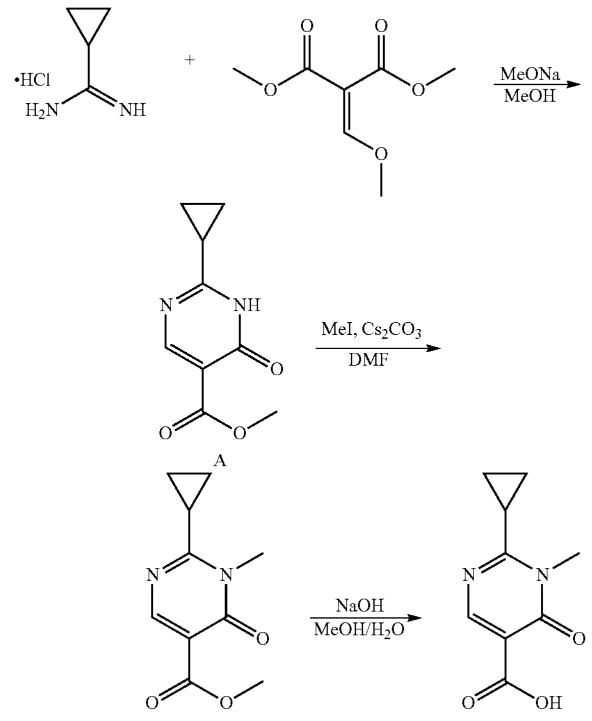

A B C (A) methyl 2-cyclopropyl-6-oxo-1,6-dihydropyrimidine-5-carboxylate

The title compound was prepared with cyclopropamidine hydrochloride and corresponding reagents with reference to the preparation processes of intermediate 11(A). MS (m/z): 195.1 $[M+H]^+$.

(B) Methyl 2-cyclopropyl-1-methyl-6-oxo-1,6-dihydropyrimidine-5-carboxylate

The title compound was prepared with corresponding intermediates and reagents with reference to the preparation processes of intermediate 11(B). MS (m/z): 209.1 $[M+H]^+$.

(C) 2-cyclopropyl-1-methyl-6-oxo-1,6-dihydropyrimidine-5-carboxylic acid

Methyl 2-cyclopropyl-1-methyl-6-oxo-1,6-dihydropyrimidine-5-carboxylate (750 mg, 3.6 mmol), sodium hydroxide (288 mg, 7.2 mmol) and methanol/water (20 ml/4 ml) were successively added to a reaction flask, and the mixture was stirred at room temperature for 2 hours. The reaction solution was concentrated, and then added water (40 ml) (adjusting pH to 4 with hydrochloric acid aqueous solution (2N)) and filtered. The solid was dried to obtain 450 mg of a yellow title product. MS (m/z): 195.1 $[M+H]^+$.

Intermediate 13

5-fluoro-1,6-dimethyl-2-oxo-1,2-dihydropyridine-3-carboxylic acid

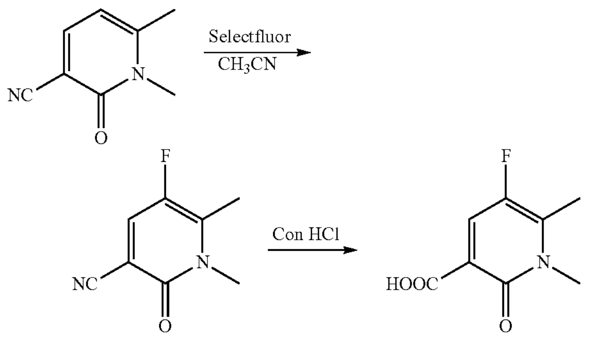

A B (A) 5-fluoro-1,6-dimethyl-2-oxo-1,2-dihydropyridine-3-carbonitrile 1,6-dimethyl-2-oxo-1,2-dihydropyridin-3-carbonitrile (500 mg, 3.38 mmol), fluorine reagent Selectfluor (1.19 g, 3.38 mmol) and acetonitrile (10 ml) were successively added to a reaction flask, and the mixture was reacted under nitrogen at room temperature for hours. The reaction solution was concentrated and purified with flash column chromatography (petroleum ether/ethyl acetate=100:0-0:100, gradient elution), to obtain 133 mg of the title product as a white solid. MS (m/z): 166.7$[M+H]^+$.

(B) 5-fluoro-1,6-dimethyl-2-oxo-1,2-dihydropyridine-3-carboxylic acid 5-fluoro-1,6-dimethyl-2-oxo-1,2-dihydropyridine-3-carbonitrile (133 g, 0.80 mmol) and concentrated hydrochloric acid (2 ml) were successively added to a reaction flask, and the mixture was refluxed and reacted for 3 hours. The reaction solution was purified with flash column chromatography (water/methanol=100:0-0:100, gradient elution), to obtain 60 mg of the title product as a white solid. MS (m/z): 186.0[M+H]$^+$.

Intermediate 14

1-methyl-6-oxo-1,6-dihydropyrimidine-5-carboxylic acid

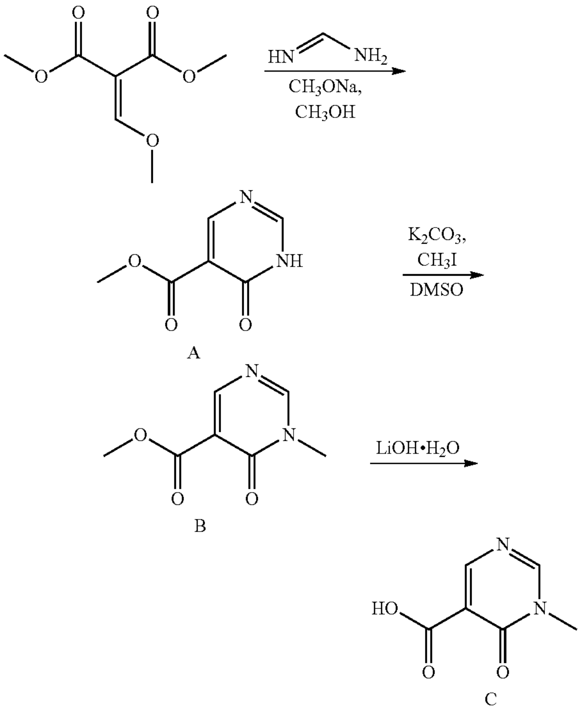

(A) methyl 6-oxo-1,6-dihydropyrimidine-5-carboxylate 2-(methoxymethylene) dimethyl malonate (0.87 g, 5.0 mmol), formamidine (0.22 g, 5.0 mmol), sodium methoxide (0.27 g, 5.0 mmol) and anhydrous methanol (10 ml) were successively added to a reaction flask, and the mixture was refluxed and reacted under nitrogen for 7 hours. The reaction solution was concentrated and purified with flash column chromatography (petroleum ether/ethyl acetate=100:0-0: 100, gradient elution), to obtain 0.51 g of the title product as a white solid. MS (m/z): 155.1[M+H]$^+$.

(B) methyl 1-methyl-6-oxo-1,6-dihydropyrimidine-5-carboxylate

Methyl 6-oxo-1,6-dihydropyrimidine-5-carboxylate (0.51 g, 3.31 mmol), iodomethane (0.94 g, 6.62 mmol), potassium carbonate (0.69 g, 4.97 mmol) and DMSO (10 ml) were successively added to a reaction flask, and the mixture was reacted at 50° C. for 1 hour. The reaction solution was purified with flash column chromatography (water/methanol=100:0-0:100, gradient elution), to obtain 0.44 g of the title product as a yellow solid. MS (m/z): 169.1[M+H]$^+$.

(C) 1-methyl-6-oxo-1,6-dihydropyrimidine-5-carboxylic acid

Methyl 1-methyl-6-oxo-1,6-dihydropyrimidine-5-carboxylate (0.44 g, 2.61 mmol), lithium hydroxide monohydrate (0.22 g, 5.22 mmol), methanol (10 ml) and water (2 ml) were successively added to a reaction flask, and the mixture was reacted at 50° C. for 1 hour. The reaction solution (adjusting pH to 3-4) was extracted with ethyl acetate, concentrated to obtain rude product, which was purified with flash column chromatography (water/methanol=100:0-0:100, gradient elution), to obtain 0.37 g of the title product as a white solid. MS (m/z): 155.1 [M+H]$^+$.

The following intermediates were prepared with corresponding intermediates and reagents with reference to the preparation processes of intermediate 14 under suitable conditions recognized by the POSITA.

| Intermediate | Structural formula | MS (M + H)$^+$ |
|---|---|---|
| 15 | 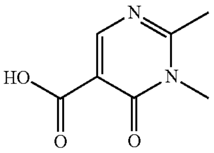 | 169.1 |
| 16 | 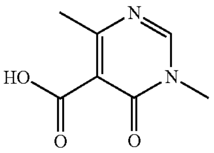 | 169.1 |

Intermediate 17

(2-methyl-2H-1,2,3-triazol-4-yl)boronic acid

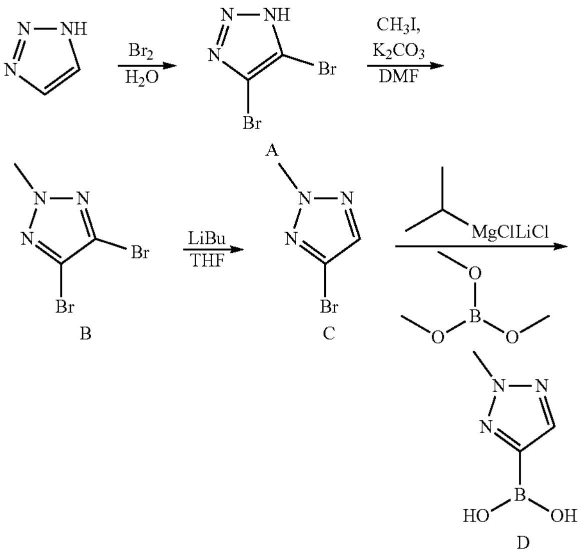

(A) 4,5-dibromo-1H-1,2,3-triazole 1H-1,2,3-triazole (10.0 g, 145 mmol) and water (150 ml) were added to a reaction flask, and the reaction solution was cooled in an ice bath, and then slowly added dropwise liquid bromine (10 ml), after the dropwise addition was completed, the reaction solution was warmed to room temperature and stirred overnight, the reaction mixture was filtered, the solid obtained was washed with water, and dried, to obtain 18.9 g of the title product.

(B) 4,5-dibromo-2-methyl-2H-1,2,3-triazole 4,5-dibromo-1H-1,2,3-triazole (18.9 g, 83.3 mmol), $K_2CO_3$ (23.04 g, 166.7 mmol) and DMF (150 ml) were added to a reaction flask, and the mixture was cooled to minus 10° C., and then slowly added dropwise iodomethane (23.67 g, 166.7 mmol), after the dropwise addition was completed, the reaction solution was slowly warmed to room temperature and stirred overnight, added 500 ml of water, extracted with ethyl acetate three times, the organic phase was washed with saturated brine, dried, and concentrated, the residue was purified with flash column chromatography (petroleum ether/ethyl acetate=100:0-0:100, gradient elution), to obtain 9.2 g of a product 4,5-dibromo-2-methyl-2H-1,2,3-triazole as a white solid. $^1H$ NMR (400 MHz, $CDCl_3$) δ 4.16 (s, 3H). And isomer 4,5-dibromo-1-methyl-1H-1,2,3-triazole 4.66 g. MS (m/z): 239.9, 241.9, 243.9 $[M+H]^+$. $^1H$ NMR (400 MHz, $CDCl_3$) δ 4.06 (s, 3H).

(C) 4-bromo-2-methyl-2H-1,2,3-triazole 4,5-dibromo-2-methyl-2H-1,2,3-triazole (9.2 g, 38.19 mmol) and THF (150 ml) were added to a reaction flask, the reaction solution was cooled to minus 78° C., and then slowly added dropwise 2.5N N-butyl lithium (19.0 ml, 45.83 mmol), after the dropwise addition was completed, the reaction solution was continuously stirred for one hour, quenched by adding 50 ml of water, and extracted with ethyl acetate three times, the organic phase was washed with saturated brine, dried, and concentrated, the residue was purified with flash column chromatography (petroleum ether/ethyl acetate=100:0-0:100, gradient elution), to obtain 2.5 g of a liquid title product. MS (m/z): 162.0, 164.0 $[M+H]^+$.

(D) (2-methyl-2H-1,2,3-triazol-4-yl)boronic acid 4-bromo-2-methyl-2H-1,2,3-triazole (2.5 g, 15.43 mmol) and THF (50 ml) were added to a reaction flask, under nitrogen, 1.3N isopropyl magnesium chloride lithium chloride (14.2 ml, 18.52 mmol) was added dropwise, after the dropwise addition was completed, the reaction solution was continuously stirred for 2 hours, and then the reaction solution was cooled to minus 20° C., added trimethyl borate, continuously stirred for 1.5 hours, warmed to room temperature, quenched with water, and extracted with ethyl acetate, the organic phase was washed with saturated brine, dried, and concentrated, to obtain 1.02 g of the title product as a white solid. MS (m/z): 128.1 $[M+H]^+$.

Intermediate 18

5-((2-(1-methyl-1H-pyrazol-4-yl)pyridin-4-yl)oxy)pyridin-2-amine

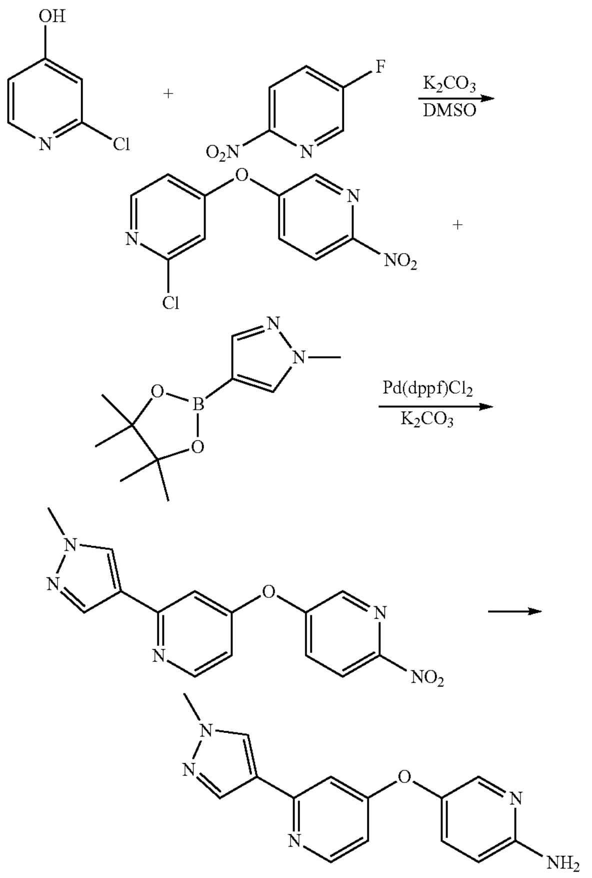

(A) 2-chloro-4-((6-nitropyridin-3-yl)oxy)pyridine 2-chloro-4-hydroxyl pyridine (12.9 g, 0.1 mol), 5-fluoro-2-nitropyridine (14.2 g, 0.1 mol) and potassium carbonate (27.6 g, 0.2 mol) were dissolved in DMSO (130 ml), and the mixture was heated at 80° C. for 2 days. The reaction was cooled to room temperature, and the mixture was diluted with water (100 ml) and ethyl acetate (200 ml). The organic phase was separated, and the aqueous phase was extracted with ethyl acetate. The organic phases were combined, concentrated to obtain crude product, which was purified with flash column chromatography (petroleum ether/ethyl acetate=1:1, elution), to obtain 10.8 g of the title product. MS (m/z): 251.9 $[M+H]^+$.

(B) 2-(1-methyl-1H-pyrazol-4-yl)-4-((6-nitropyridin-3-yl)oxy)pyridine 2-chloro-4-((6-nitropyridin-3-yl)oxy)pyridine (10.8 g, 42.9 mmol), 1-methyl-4-(4,4,5,5-tetramethyl-1,3,2-dioxaborolan-2-yl)-1H-pyrazole (10.7 g, 52.0 mmol), Pd(dppf)$Cl_2$ (3.14 g, 4.3 mmol) and $K_2CO_3$ (11.9 g, 86.0 mmol) were dissolved in the mixed solution of 1,4-dioxane (110 ml) and water (11 ml), under nitrogen, the mixture was heated to 80° C. and stirred for 5 hours. The reaction was cooled to room temperature, quenched with water, and concentrated to obtain crude product, which was purified with flash column chromatography (petroleum ether/ethyl acetate=100:0-0:100 and dichloromethane/methanol=100:0-90:10, gradient elution), to obtain 8.2 g of the title product. MS (m/z): 298.0 [M+H]$^+$.

(C) 5-((2-(1-methyl-1H-pyrazol-4-yl)pyridin-4-yl)oxy)pyridin-2-amine 2-(1-methyl-1H-pyrazol-4-yl)-4-((6-nitropyridin-3-yl)oxy)pyridine (4.8 g, 16.1 mmol) and palladium carbon (1.0 g) were dissolved in methanol (50 ml), under hydrogen, the reaction solution was stirred at room temperature for 15 hours. The reactant was filtered to remove palladium carbon, and the liquid was concentrated to obtain crude product, which was purified with flash column chromatography (water/methanol=100:0-0:100, gradient elution), to obtain 3.6 g of the title product. MS (m/z): 268.0 [M+H]$^+$.

The following intermediates were prepared with corresponding intermediates and reagents with reference to the preparation processes of intermediate 18 under suitable conditions recognized by the POSITA.

| Intermediate | Structural formula | MS (M + H)$^+$ |
|---|---|---|
| 19 | 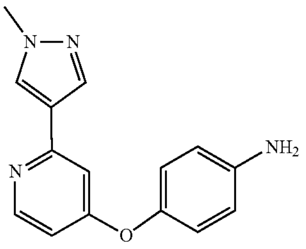 [SMILES: Cn1cc(-c2cc(Oc3ccc(N)cc3)ccn2)cn1] | 267.1 |
| 20 | 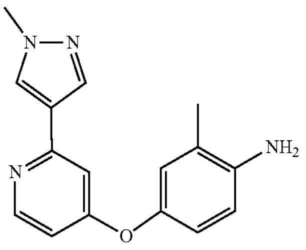 [SMILES: Cc1cc(Oc2ccnc(-c3cnn(C)c3)c2)ccc1N] | 281.1 |
| 21 | 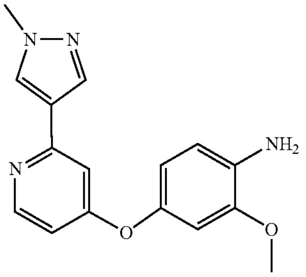 | 297.1 |
| 22 | 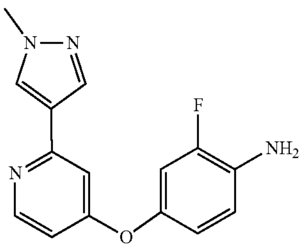 [SMILES: Cn1cc(-c2cc(Oc3ccc(N)c(F)c3)ccn2)cn1] | 285.0 |

-continued

| Intermediate | Structural formula | MS (M + H)$^+$ |
|---|---|---|
| 23 | 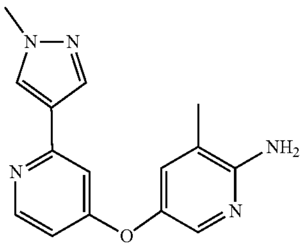 [SMILES: Cc1cc(Oc2ccnc(-c3cnn(C)c3)c2)cnc1N] | 282.1 |

Intermediate 24

5-((2-(2-Methylthiazol-5-yl)pyridin-4-yl)oxy)pyridin-2-amine

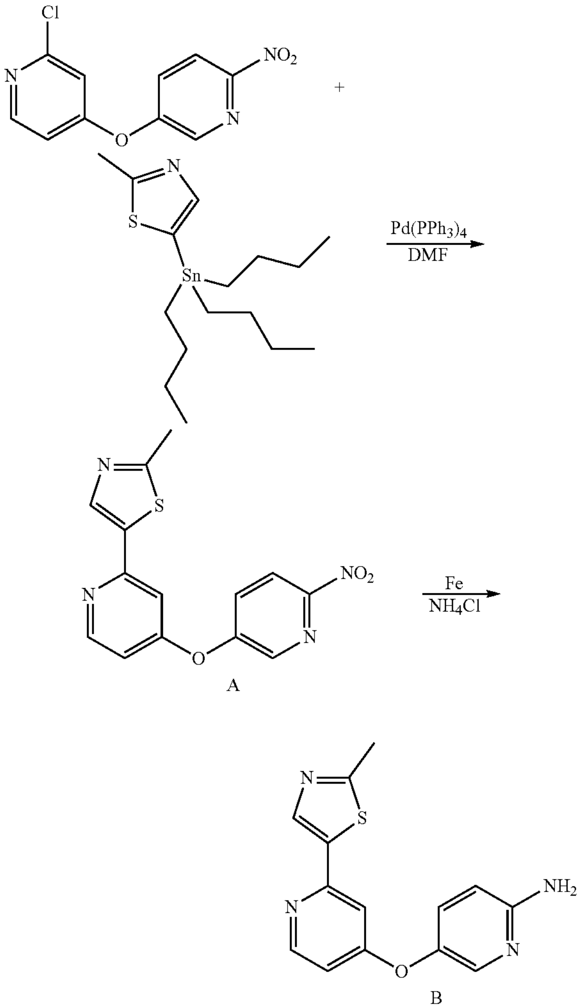

(A) 2-methyl-5-(4-((6-nitropyridin-3-yl)oxy)pyridin-2-yl)thiazole

Under nitrogen, 2-chloro-4-((6-nitropyridin-3-yl)oxy) pyridine (200 mg, 0.79 mmol), 2-methyl-5-(tributylstannyl) thiazole (339 mg, 0.87 mmol), $Pd(PPh_3)_4$ (46 mg, 0.04 mmol) and DMF (5 ml) were successively added to a reaction flask, and the mixture was reacted at 100° C. overnight. The reaction solution was purified with flash column chromatography (water/methanol=100:0-0:100, gradient elution), to obtain 120 mg of a solid title product. MS (m/z): 315.1 $[M+H]^+$.

(B) 5-((2-(2-methylthiazol-5-yl)pyridin-4-yl)oxy) pyridin-2-amine

Under nitrogen, 2-methyl-5-(4-((6-nitropyridin-3-yl)oxy) pyridin-2-yl)thiazole (120 mg, 0.38 mmol), ammonium chloride (102 mg, 1.91 mmol), iron powder (85 mg, 1.52 mmol), ethanol (20 ml) and water (5 ml) were successively added to a reaction flask, and the mixture was reacted at 90° C. for 3 hours. The reaction solution was filtered, and the filtrate was concentrated, the residue was purified with flash column chromatography (water/methanol=100:0-0:100, gradient elution), to obtain 88 mg of a solid title product. MS (m/z): 285.1 $[M+H]^+$.

The following intermediates were prepared with corresponding intermediates and reagents with reference to the preparation processes of intermediate 24 under suitable conditions recognized by the POSITA.

-continued

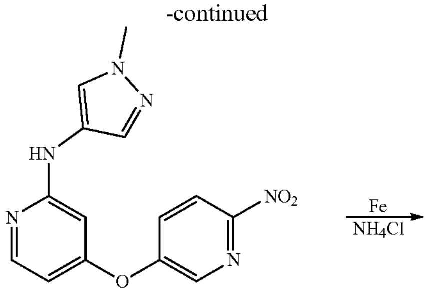

A

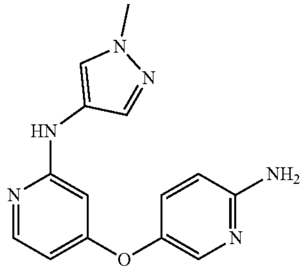

B

| Intermediate | Structural formula | Intermediate | Structural formula | MS (M + H)$^+$ |
|---|---|---|---|---|
| 25 | 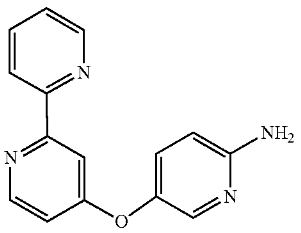 [SMILES: Nc1ccc(Oc2ccnc(-c3ccccn3)c2)cn1] | 54 | 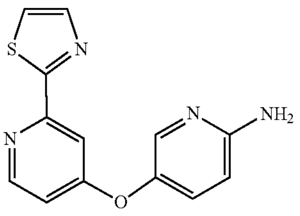 [SMILES: Nc1ccc(Oc2ccnc(-c3nccs3)c2)cn1] | 271.0 |

Intermediate 26

4-((6-aminopyridin-3-yl)oxy)-N-(1-methyl-1H-pyrazol-4-yl)pyridin-2-amine

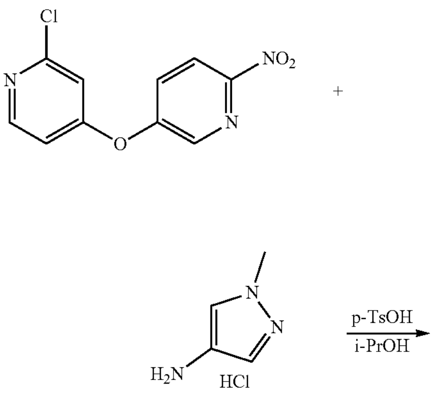

(A) N-(1-methyl-1H-pyrazol-4-yl)-4-((6-nitropyridin-3-yl)oxy)pyridin-2-amine

Under nitrogen, 2-chloro-4-((6-nitropyridin-3-yl)oxy) pyridine (150 mg, 0.6 mmol), 1-methyl-1H-pyrazol-4-amine hydrochloride salt (96 mg, 0.72 mmol), p-toluenesulfonic acid monohydrate (103 mg, 0.6 mmol) and isopropyl alcohol (5 ml) were successively added to a reaction flask, and the mixture was reacted at 150° C. for 16 hours. The reaction solution was concentrated, and the residue was purified with flash column chromatography (water/methanol=100:0-0:100, gradient elution), to obtain 90 mg of the title product as a brown solid. MS (m/z): 313.1 $[M+H]^+$.

(B) 4-((6-aminopyridin-3-yl)oxy)-N-(1-methyl-1H-pyrazol-4-yl)pyridin-2-amine

The title compound was prepared with corresponding intermediates and reagents with reference to the preparation processes of intermediate 24(B). MS (m/z): 283.1 $[M+H]^+$.

Intermediate 27

4-((6-aminopyridin-3-yl)oxy)-N-(pyridin-2-yl)pyridin-2-amine

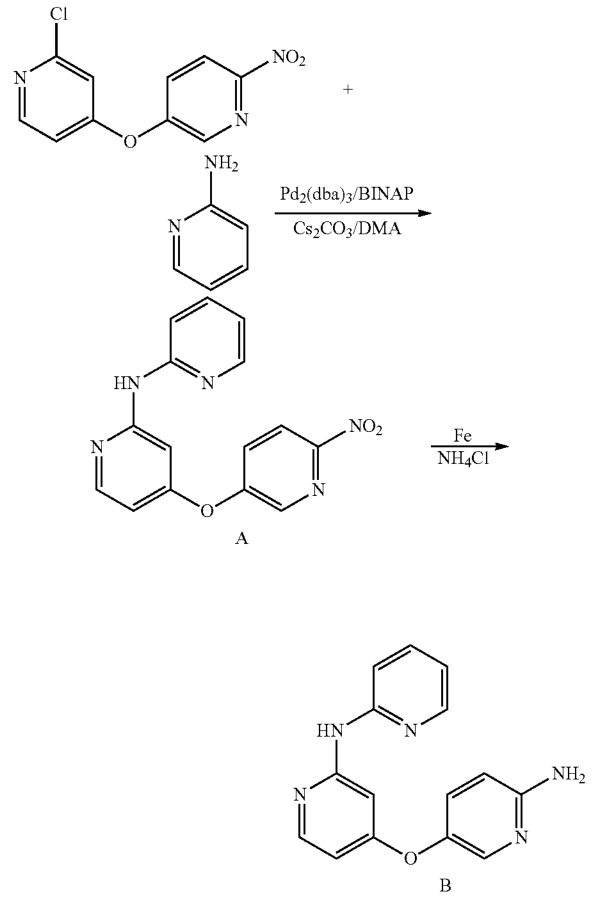

(A) 4-((6-nitropyridin-3-yl)oxy)-N-(pyridin-2-yl)pyridin-2-amine

Under nitrogen, 2-chloro-4-((6-nitropyridin-3-yl)oxy)pyridine (300 mg, 1.2 mmol), 2-aminopyridine (123 mg, 1.3 mmol), BINAP (150 mg, 0.24 mmol), $Pd_2(dba)_3$ (69 mg, 0.12 mmol), cesium carbonate (782 mg, 2.4 mmol) and DMA (5 ml) were successively added to a reaction flask, and the mixture was reacted at 145° C. microwave for 10 minutes. The reaction solution was filtered, and the filtrate was concentrated, the residue was purified with flash column chromatography (water/methanol=100:0-0:100, gradient elution), to obtain 210 mg of the title product as a brown solid. MS (m/z): 310.1 $[M+H]^+$.

(B) 4-((6-aminopyridin-3-yl)oxy)-N-(pyridin-2-yl)pyridin-2-amine

The title compound was prepared with corresponding intermediates and reagents with reference to the preparation processes of intermediate 24(B). MS (m/z): 280.1 $[M+H]^+$.

Intermediate 28

5-((2-(imidazo[1,2-a]pyridin-7-yl)pyridin-4-yl)oxy)pyridin-2-amine

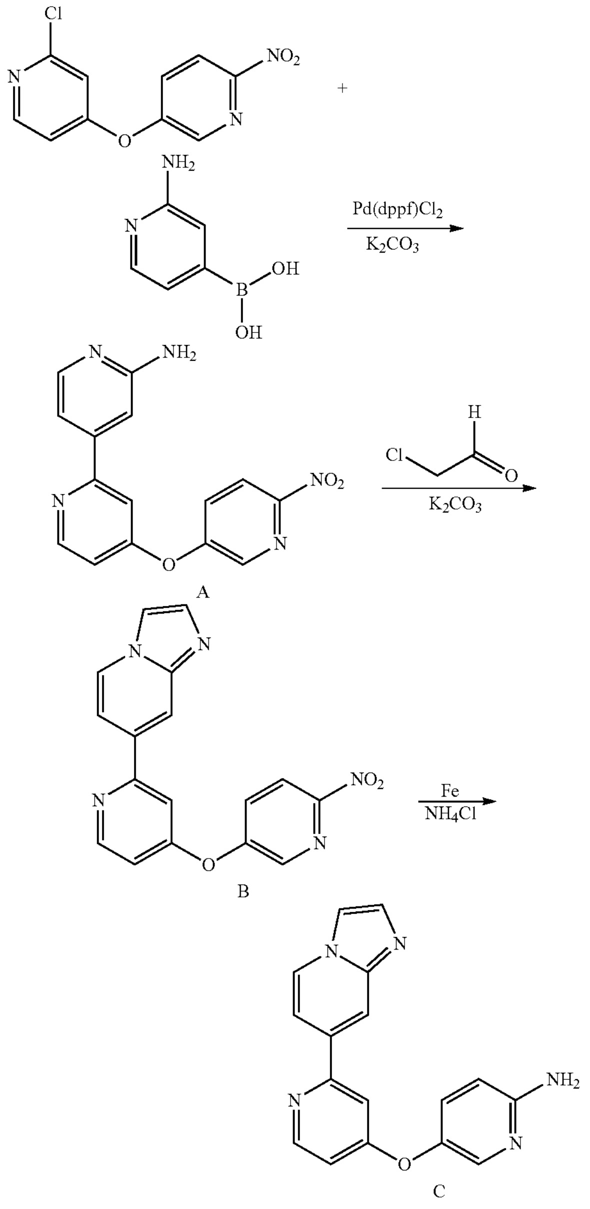

(A) 4-((6-nitropyridin-3-yl)oxy)-[2,4'-bipyridin]-2'-amine

Under nitrogen, 2-chloro-4-((6-nitropyridin-3-yl)oxy)pyridine (300 mg, 1.2 mmol), (2-aminopyridin-4-yl)boronic acid (197 mg, 1.4 mmol), $Pd(dppf)Cl_2$ (98 mg, 0.12 mmol), 2M potassium carbonate solution (1.5 ml) and 1,4-dioxane (6 ml) were successively added to a reaction flask, and the mixture was reacted at 90° C. overnight. The reaction solution was concentrated, and the residue was purified with flash column chromatography (water/methanol=100:0-0:

100, gradient elution), to obtain 187 mg of the title product as a yellow solid. MS (m/z): 310.1 $[M+H]^+$.

(B) 7-(4-((6-nitropyridin-3-yl)oxy)pyridin-2-yl)imidazo[1,2-a]pyridine

Under nitrogen, 4-((6-nitropyridin-3-yl)oxy)-[2,4'-bipyridin]-2'-amine (187 mg, 0.61 mmol), 40% chloroacetaldehyde aqueous solution (1 ml), potassium carbonate (84 mg, 0.61 mmol) and ethanol (5 ml) were successively added to a reaction flask, and the mixture was refluxed and reacted overnight. The reaction solution was concentrated, and the residue was purified with flash column chromatography (water/methanol=100:0-0:100, gradient elution), to obtain 130 mg of the title product as a yellow solid. MS (m/z): 334.0 $[M+H]^+$.

(C) 5-((2-(imidazo[1,2-a]pyridin-7-yl)pyridin-4-yl)oxy)pyridin-2-amine

The title compound was prepared with corresponding intermediates and reagents with reference to the preparation processes of intermediate 24(B). MS (m/z): 304.1 $[M+H]^+$.

Intermediate 29

4-((6-aminopyridin-3-yl)oxy)-N-(1-(difluoromethyl)-1H-pyrazol-3-yl)pyridin-2-amine

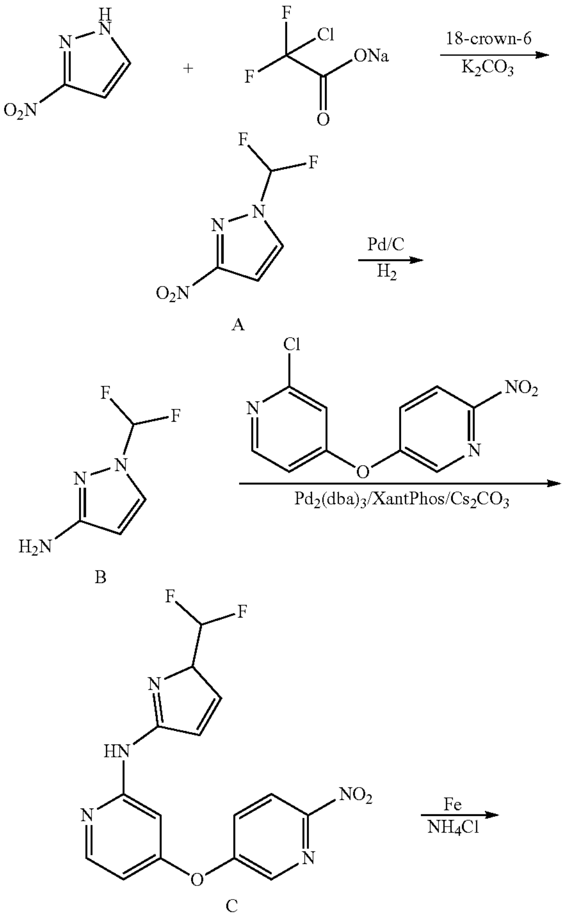

-continued

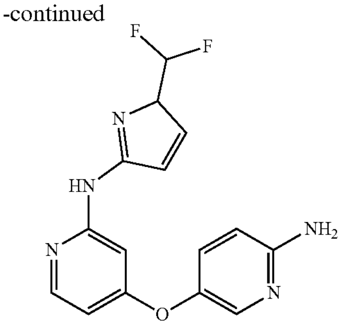

D (A) 1-(difluoromethyl)-3-nitro-1H-pyrazole

Under nitrogen, 3-nitro-1H-pyrazole (5 g, 44.2 mmol), 2-chloro-2,2-sodium difluoroacetate (8.1 g, 53.0 mmol), potassium carbonate (9.2 g, 66.3 mmol), 18-crown-6 (2.3 g, 8.8 mmol) and acetonitrile (20 ml) were successively added to a reaction flask, and the mixture was refluxed and reacted overnight. The reaction solution was filtered, and the filtrate was concentrated, the residue was dissolved by adding water (200 ml), and extracted with ethyl acetate (100 ml×3), the organic layers were combined and concentrated, the residue was purified with flash column chromatography (petroleum ether/ethyl acetate=100:0-0:100, gradient elution), to obtain 5 g of the title product as a yellow oil. MS (m/z): 164.1 $[M+H]^+$.

(B) 1-(difluoromethyl)-1H-pyrazol-3-amine 1-(difluoromethyl)-3-nitro-1H-pyrazole (5 g, 30.7 mmol), Pd/C (500 mg) and methanol (15 ml) were successively added to a reaction flask, and the mixture was reacted under hydrogen at room temperature overnight. The reaction solution was filtered, and the filtrate was concentrated to obtain 4 g of a crude product as a yellow oil. MS (m/z): 134.0 $[M+H]^+$.

(C) N-(1-(difluoromethyl)-1H-pyrazol-3-yl)-4-((6-nitropyridin-3-yl)oxy)pyridin-2-amine Under nitrogen, 2-chloro-4-((6-nitropyridin-3-yl)oxy)pyridine (500 mg, 2.59 mmol), 1-(difluoromethyl)-1H-pyrazol-3-amine (345 mg, 1.3 mmol), XantPhos (231 mg, 0.40 mmol), $Pd_2(dba)_3$ (183 mg, 0.20 mmol), cesium carbonate (1.3 g, 3.88 mmol) and 1,4-dioxane (10 ml) were successively added to a reaction flask, and the mixture was reacted at 100° C. overnight. The reaction solution was concentrated, and the residue was purified with flash column chromatography (water/methanol=100:0-0:100, gradient elution), to obtain 600 mg of a solid title product. MS (m/z): 349.0 $[M+H]^+$.

(D) 4-((6-aminopyridin-3-yl)oxy)-N-(1-(difluoromethyl)-1H-pyrazol-3-yl)pyridin-2-amine The title compound was prepared with corresponding intermediates and reagents with reference to the preparation processes of intermediate 24(B). MS (m/z): 319.0 $[M+H]^+$.

Intermediate 30

5-((2-(1-methyl-1H-imidazol-4-yl)pyridin-4-yl)oxy)pyridin-2-amine

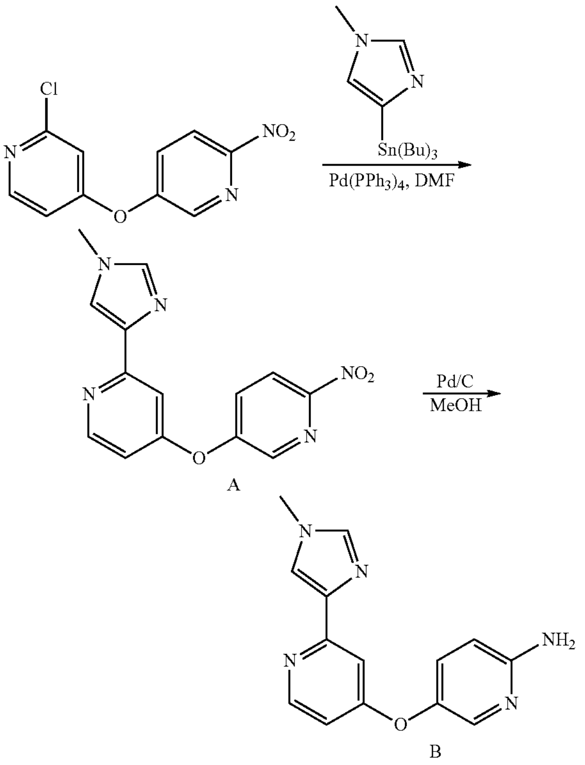

(A) 2-(1-methyl-1H-imidazol-4-yl)-4-((6-nitropyridin-3-yl)oxy)pyridine 2-chloro-4-((6-nitropyridin-3-yl)oxy)pyridine (300 mg, 1.19 mmol), 1-methyl-4-(tributylstannyl)-1H-imidazole (663 mg, 1.79 mmol), $Pd(PPh_3)_4$ (137 mg, 0.119 mmol) and DMF (5.0 ml) were added to a reaction flask, under nitrogen, the mixture was heated to 100° C. and stirred for 3 hours, after cooling, the reaction solution was purified with flash column chromatography ($H_2O$/MeOH=100:0-0:100, gradient elution), to obtain 220 mg of the title product as a white solid. MS (m/z): 298.1 $[M+H]^+$.

(B) 5-((2-(1-methyl-1H-imidazol-4-yl)pyridin-4-yl)oxy)pyridin-2-amine 2-(1-methyl-1H-imidazol-4-yl)-4-((6-nitropyridin-3-yl)oxy)pyridine (220 mg, 0.74 mmol), Pd/C (30 mg) and methanol (15.0 ml) were added to a reaction flask, and the mixture was stirred under hydrogen pressure overnight, and filtered, the filtrate was concentrated to obtain 152 mg of the title product as a yellow oil. MS (m/z): 268.1 $[M+H]^+$.

The following intermediates were prepared with corresponding intermediates and reagents with reference to the preparation processes of intermediate 30 under suitable conditions recognized by the POSITA.

| Intermediate | Structural formula | MS $(M + H)^+$ |
|---|---|---|
| 31 | 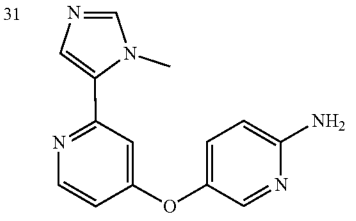 | 268.1 |

Intermediate 32

5-((2-(1H-1,2,4-triazol-1-yl)pyridin-4-yl)oxy)pyridin-2-amine

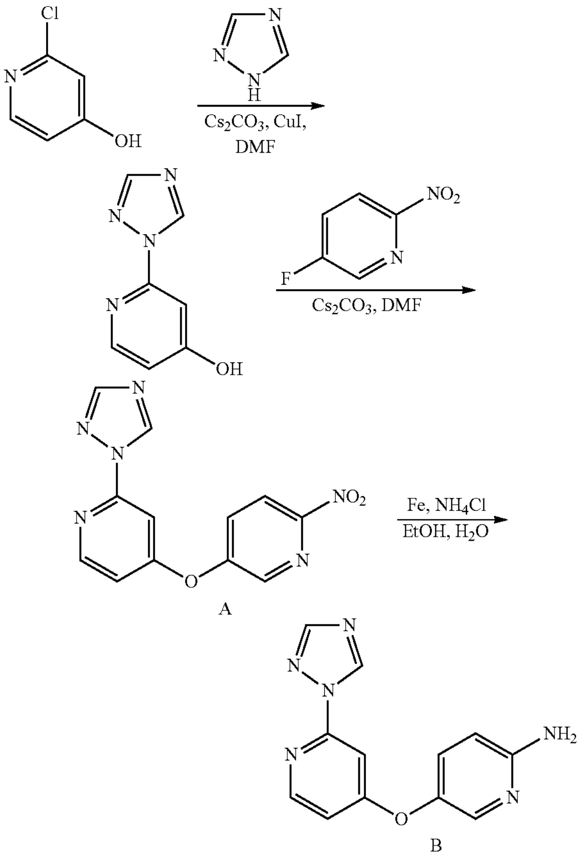

(A) 4-((6-nitropyridin-3-yl)oxy)-2-(1H-1,2,4-triazol-1-yl)pyridine 2-chloropyridin-4-ol (500 mg, 3.86 mmol), 1H-1,2,4-triazole (400 mg, 5.79 mmol), $Cs_2CO_3$ (4.71 mg, 14.48 mmol), CuI (73 mg, 0.386 mmol) and DMF (20.0 ml) were added to a sealed tube, and under nitrogen, the mixture was heated to 130° C. and stirred for 2 days, after cooling, 5-fluoro-2-nitropyridine (1.1 g, 7.72 mmol) was added, the reaction solution was heated to 100° C. and stirred overnight, and filtered, the filtrate was purified with flash column chromatography ($H_2O$/MeOH=100:0-0:100, gradient elution), to obtain 396 mg of the title product as a light yellow solid. MS (m/z): 285.1 $[M+H]^+$.

(B) 5-((2-(1H-1,2,4-triazol-1-yl)pyridin-4-yl)oxy)pyridin-2-amine

The title compound was prepared with corresponding intermediates and reagents with reference to the preparation processes of intermediate 24(B). MS (m/z): 255.1 $[M+H]^+$.

Intermediate 33

5-((2-(4-methyl-1H-imidazol-1-yl)pyridin-4-yl)oxy)pyridin-2-amine

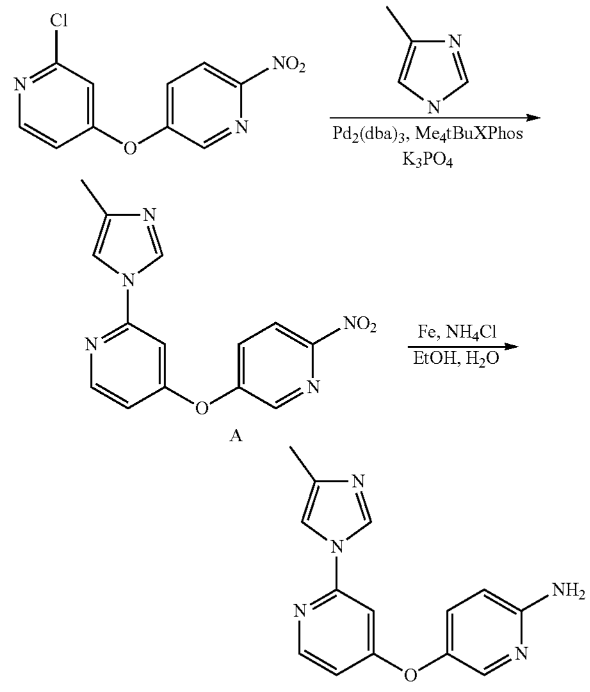

(A) 2-(4-methyl-1H-imidazol-1-yl)-4-((6-nitropyridin-3-yl)oxy)pyridine 2-chloro-4-((6-nitropyridin-3-yl)oxy)pyridine (500 mg, 2.0 mmol), 4-methyl-1H-imidazole (490 mg, 5.97 mmol), $Pd_2(dba)_3$ (36.5 mg, 0.04 mmol), $Me_4tBuXPhos$ (38 mg, 0.08 mmol), $K_3PO_4$ (845 mg, 3.98 mmol), dioxane (4.0 ml) and toluene (20.0 ml) were added to a sealed tube, and under nitrogen, the mixture was heated to 120° C. and stirred overnight, the reaction solution was concentrated, and the residue was purified with flash column chromatography ($H_2O$/MeOH=100:0-0:100, gradient elution), to obtain 280 mg of the title product as a light yellow solid. MS (m/z): 298.1 $[M+H]^+$.

(B) 5-((2-(4-methyl-1H-imidazol-1-yl)pyridin-4-yl)oxy)pyridin-2-amine

The title compound was prepared with corresponding intermediates and reagents with reference to the preparation processes of intermediate 24(B). MS (m/z): 268.1$[M+H]^+$.

Intermediate 34

5-([2,3'-bipyridin]-4-yloxy)pyridin-2-amine

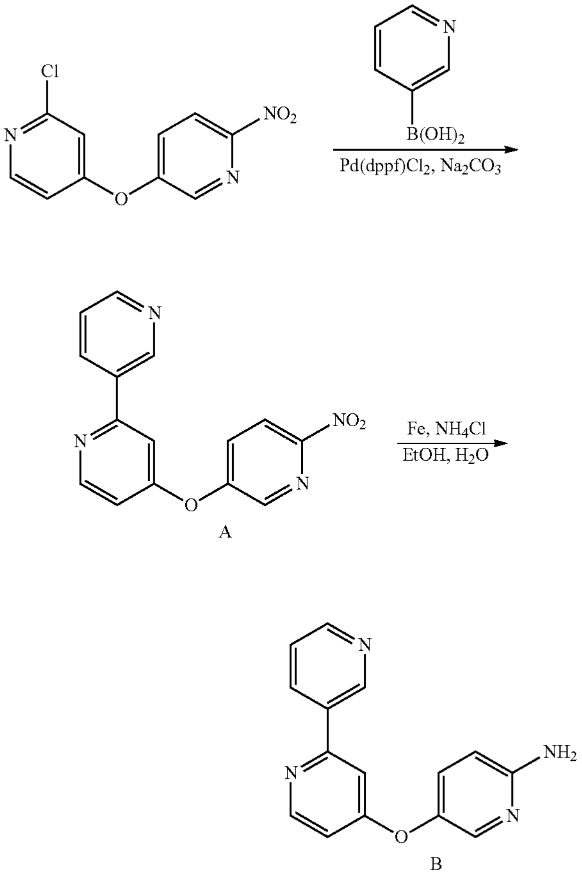

(A) 4-((6-nitropyridin-3-yl)oxy)-2,3'-bipyridine 2-chloro-4-((6-nitropyridin-3-yl)oxy)pyridine (500 mg, 0.2 mmol), pyridin-3-yl boronic acid (367 mg, 0.3 mmol), $Na_2CO_3$ (640 mg, 6.0 mmol), $Pd(dppf)Cl_2{\cdot}CH_2Cl_2$ (163 mg, 0.02 mmol), dioxane (25.0 ml) and water (3.0 ml) were added to a reaction flask, and the mixture was heated to 100° C. and stirred overnight, after cooling, the reaction solution was concentrated, and the residue was purified with flash column chromatography ($H_2O$/MeOH=100:0-0:100, gradient elution), to obtain 441 mg of the title product as a yellow solid. MS (m/z): 295.0 $[M+H]^+$.

(B) 5-([2,3'-bipyridin]-4-yloxy)pyridin-2-amine

The title compound was prepared with corresponding intermediates and reagents with reference to the preparation processes of intermediate 24(B). MS (m/z): 265.1 $[M+H]^+$.

The following intermediates were prepared with corresponding intermediates and reagents with reference to the preparation processes of intermediate 34 under suitable conditions recognized by the POSITA.

| Inter-mediate | Structural formula | MS (M + H)+ |
|---|---|---|
| 55 | 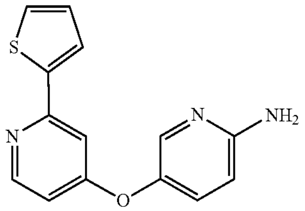 [SMILES: Nc1ccc(Oc2ccnc(-c3cccs3)c2)cn1] | 270.0 |
| 56 | 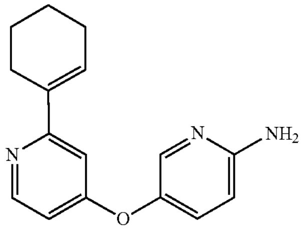 [SMILES: Nc1ccc(Oc2ccnc(C3=CCCCC3)c2)cn1] | 268.1 |
| 57 | 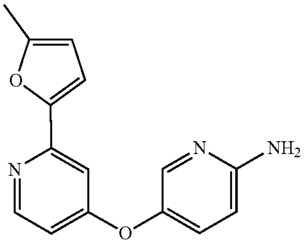 [SMILES: Cc1ccc(-c2cc(Oc3ccc(N)nc3)ccn2)o1] | 268.1 |

Intermediate 35

4-((6-aminopyridin-3-yl)oxy)-N-(6-methylpyridin-2-yl)pyridin-2-amine

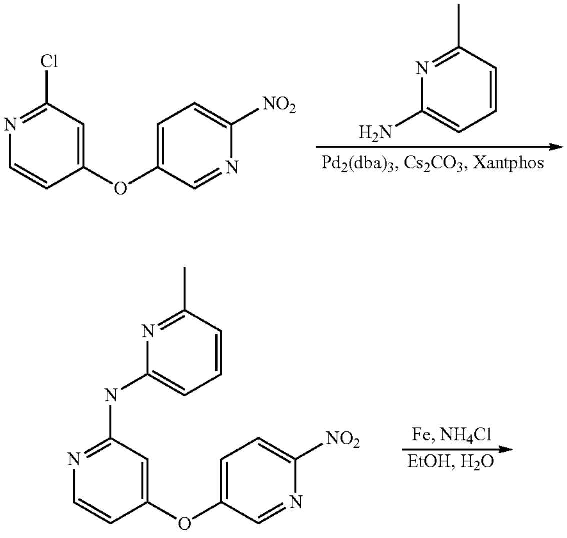

A

-continued

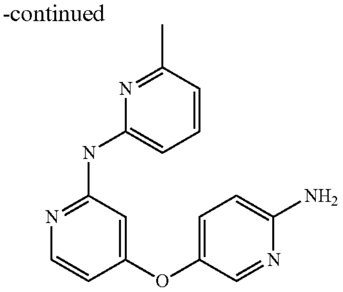

B (A) 6-methyl-N-(4-((6-nitropyridin-3-yl)oxy)pyridin-2-yl)pyridin-2-amine 2-chloro-4-((6-nitropyridin-3-yl)oxy)pyridine (500 mg, 2.0 mmol), 6-methylpyridin-2-amine (432 mg, 4.0 mmol), $Pd_2(dba)_3$ (183 mg, 0.2 mmol), Xantphos (231 mg, 0.4 mmol), $Cs_2CO_3$ (1.63 g, 5.0 mmol) and dioxane (50.0 ml) were added to a sealed tube, and under nitrogen, the mixture was heated to 100° C. and stirred for 4 hours, the reaction solution was concentrated, and the residue was purified with flash column chromatography ($H_2O$/MeOH=100:0-0:100, gradient elution), to obtain 550 mg of a product as a light yellow solid. MS (m/z): 324.1 $[M+H]^+$.

(B) 4-((6-aminopyridin-3-yl)oxy)-N-(6-methylpyridin-2-yl)pyridin-2-amine

The title compound was prepared with corresponding intermediates and reagents with reference to the preparation processes of intermediate 24(B). MS (m/z): 294.1 $[M+H]^+$.

Intermediate 36

5-((2-(1H-pyrazol-1-yl)pyridin-4-yl)oxy)pyridin-2-amine

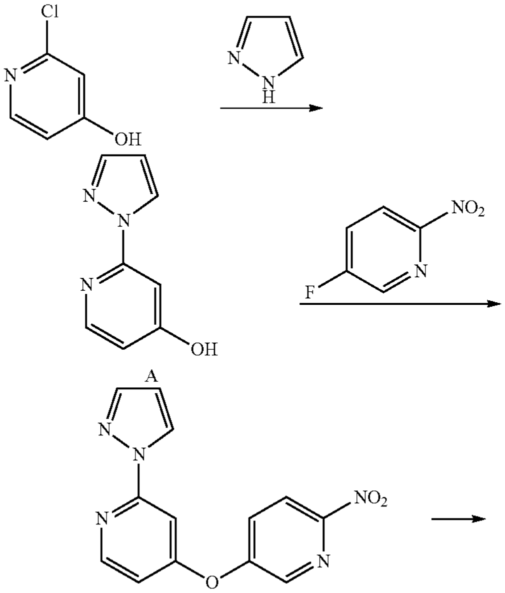

A

B

-continued

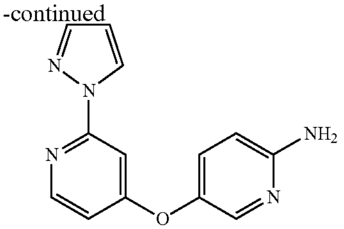

C (A) 2-(1H-pyrazol-1-yl)pyridin-4-ol 2-chloro-4-hydroxyl pyridine (500 mg, 3.9 mmol), pyrazole (527 mg, 7.8 mmol), $Cs_2CO_3$ (2.5 g, 7.8 mmol), CuI (76 mg, 0.4 mmol) and DMF (10 ml) were successively added to a sealed tube, and the mixture was reacted at 130° C. for 12 hours. The reaction solution was concentrated, and the residue was purified with flash column chromatography (petroleum ether/ethyl acetate=100:0-50:50, gradient elution), to obtain 300 mg of the title product as a yellow solid. MS (m/z): 162 $[M+H]^+$.

(B) 4-((6-nitropyridin-3-yl)oxy)-2-(1H-pyrazol-1-yl)pyridine 2-(1H-pyrazol-1-yl)pyridin-4-ol (250 mg, 1.6 mmol), 5-fluoro-2-nitropyridine (220 mg, 1.6 mmol), $K_2CO_3$ (321 mg, 2.4 mmol) and DMF (10 ml) were successively added to a reaction flask, and the mixture was reacted at 100° C. for 12 hours. Water was added to the reaction solution, and the reaction solution was extracted with ethyl acetate, washed with saturated brine, and dried with anhydrous sodium sulfate. The reactant was concentrated to obtain 250 mg of a light yellow solid. MS (m/z): 284 $[M+H]^+$.

(C) 5-((2-(1H-pyrazol-1-yl)pyridin-4-yl)oxy)pyridin-2-amine

The title compound was prepared with corresponding intermediates and reagents with reference to the preparation processes of intermediate 24(B). MS (m/z): 254 $[M+H]^+$.

Intermediate 37

5-((2-(1-ethyl-1H-pyrazol-4-yl)pyridin-4-yl)oxy)pyridin-2-amine

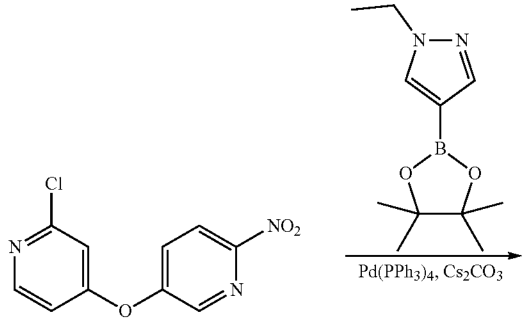

-continued

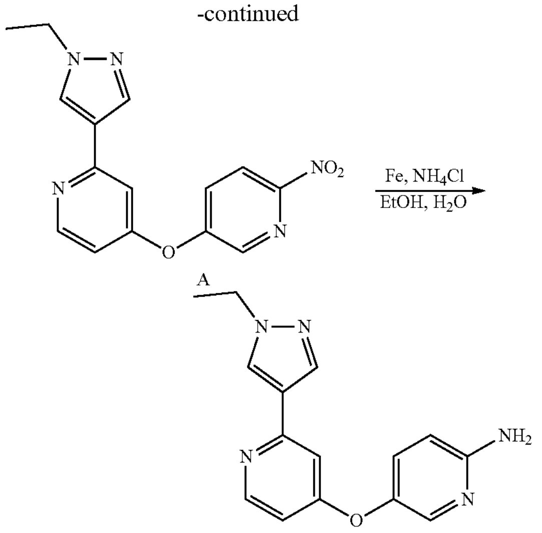

A

B (A) 2-(1-ethyl-1H-pyrazol-4-yl)-4-((6-nitropyridin-3-yl)oxy)pyridine

Under nitrogen, 2-chloro-4-((6-nitropyridin-3-yl)oxy)pyridine (300 mg, 1.2 mmol), 1-ethyl-4-(4,4,5,5-tetramethyl-1,3,2-dioxaborolan-2-yl)-1H-pyrazole (398 mg, 1.8 mmol), $Pd(PPh_3)_4$ (138 mg, 0.12 mmol), $Cs_2CO_3$ (779 mg, 2.4 mmol), dioxane (8 ml) and water (2 ml) were successively added to a reaction flask, and the mixture was reacted at 100° C. for 3 hours. The reaction solution was concentrated, and the residue was purified with flash column chromatography (petroleum ether/ethyl acetate=100:0-50:50, gradient elution), to obtain 300 mg of the title product as a yellow solid. MS (m/z): 312 $[M+H]^+$.

(B) 5-((2-(1-ethyl-1H-pyrazol-4-yl)pyridin-4-yl)oxy)pyridin-2-amine

The title compound was prepared with corresponding intermediates and reagents with reference to the preparation processes of intermediate 24(B). MS (m/z): 282 $[M+H]^+$.

The following intermediates were prepared with corresponding intermediates and reagents with reference to the preparation processes of intermediate 37 under suitable conditions recognized by the POSITA.

| Intermediate | Structural formula | MS $(M + H)^+$ |
| --- | --- | --- |
| 38 | 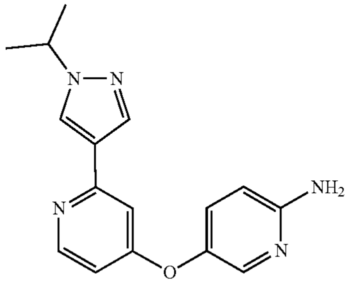 [SMILES: CC(C)n1cc(-c2cc(Oc3ccc(N)nc3)ccn2)cn1] | 296 |

Intermediate 39

5-([2,4'-bipyridin]-4-yloxy)pyridin-2-amine

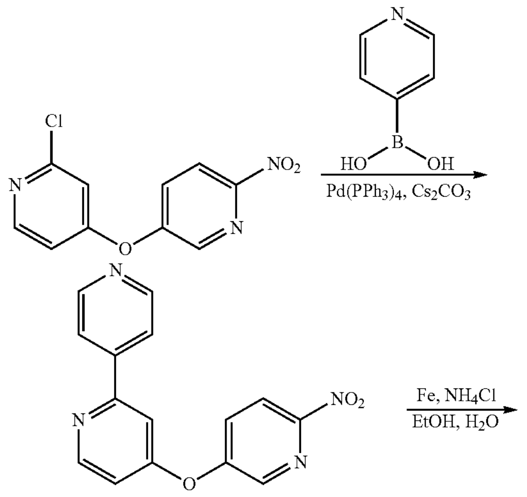

A

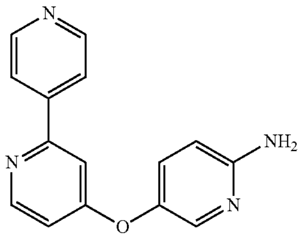

B (A) 4-((6-nitropyridin-3-yl)oxy)-2,4'-bipyridine

Under nitrogen, 2-chloro-4-((6-nitropyridin-3-yl)oxy) pyridine (300 mg, 1.2 mmol), 4-pyridine boronic acid (220 mg, 1.8 mmol), $Pd(PPh_3)_4$ (138 mg, 0.12 mmol), $Cs_2CO_3$ (779 mg, 2.4 mmol), dioxane (8 ml) and water (2 ml) were successively added to a reaction flask, and the mixture was reacted at 100° C. for 3 hours. The reaction solution was concentrated, and the residue was purified with flash column chromatography (petroleum ether/ethyl acetate=100:0-0: 100, gradient elution), to obtain 300 mg of the title product as a yellow solid. MS (m/z): 295 $[M+H]^+$.

(B) 5-([2,4'-bipyridin]-4-yloxy)pyridin-2-amine

The title compound was prepared with corresponding intermediates and reagents with reference to the preparation processes of intermediate 24(B). MS (m/z): 265 $[M+H]^+$.

The following intermediates were prepared with corresponding intermediates and reagents with reference to the preparation processes of intermediate 39 under suitable conditions recognized by the POSITA.

| Inter-mediate | Structural formula | MS $(M + H)^+$ |
|---|---|---|
| 40 | 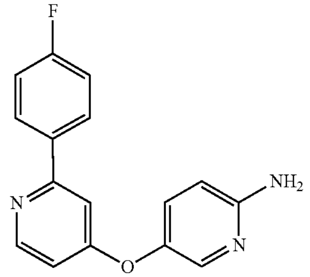 [SMILES: Nc1ccc(Oc2ccnc(-c3ccc(F)cc3)c2)cn1] | 282 |
| 41 | 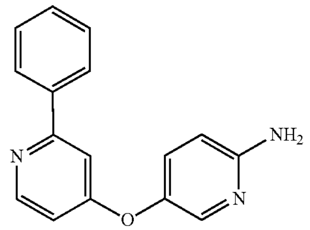 [SMILES: Nc1ccc(Oc2ccnc(-c3ccccc3)c2)cn1] | 264 |

Intermediate 42

4-((6-aminopyridin-3-yl)oxy)-N-(1-methyl-1H-pyrazol-3-yj)pyridin-2-amine

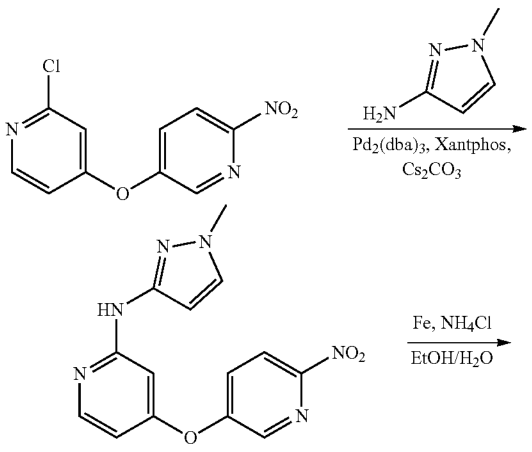

A

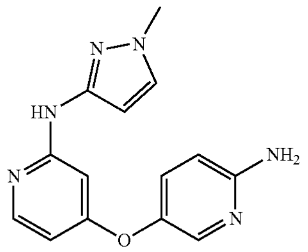

B (A) N-(1-methyl-1H-pyrazol-3-yl)-4-((6-nitropyridin-3-yl)oxy)pyridin-2-amine

Under nitrogen, 2-chloro-4-((6-nitropyridin-3-yl)oxy) pyridine (400 mg, 1.6 mmol), 1-methyl-1H-pyrazol-3-amine (309 mg, 3.2 mmol), $Pd_2(dba)_3$ (145 mg, 0.16 mmol), Xantphos (184 mg, 0.32 mmol), $Cs_2CO_3$ (779 mg, 2.4 mmol) and dioxane (10 ml) were successively added to a reaction flask, and the mixture was reacted at 100° C. for 16 hours. The reaction solution was concentrated, and the residue was purified with flash column chromatography (petroleum ether/ethyl acetate=100:0-0:100, gradient elution), to obtain 200 mg of the title product as a yellow solid. MS (m/z): 313 $[M+H]^+$.

(B) 4-((6-aminopyridin-3-yl)oxy)-N-(1-methyl-1H-pyrazol-3-yl)pyridin-2-amine The title compound was prepared with corresponding intermediates and reagents with reference to the preparation processes of intermediate 24(B). MS (m/z): 283 $[M+H]^+$.

The following intermediates were prepared with corresponding intermediates and reagents with reference to the preparation processes of intermediate 42 under suitable conditions recognized by the POSITA.

| Intermediate | Structural formula | MS $(M + H)^+$ |
|---|---|---|
| 43 | 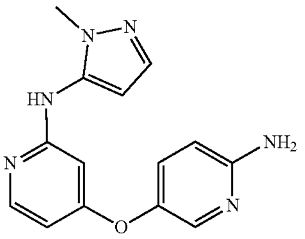 [SMILES: Cn1nccc1Nc1cc(Oc2ccc(N)nc2)ccn1] | 283 |
| 44 | 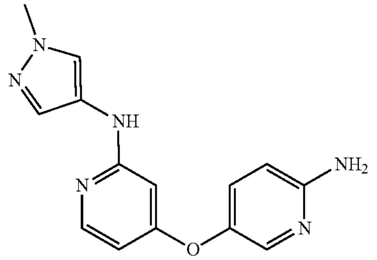 [SMILES: Cn1cc(Nc2cc(Oc3ccc(N)nc3)ccn2)cn1] | 283 |

Intermediate 45

5-((2-(1-(difluoromethyl)-1H-pyrazol-4-yl)pyridin-4-yl)oxy)pyridin-2-amine

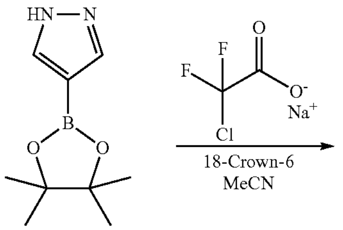

-continued

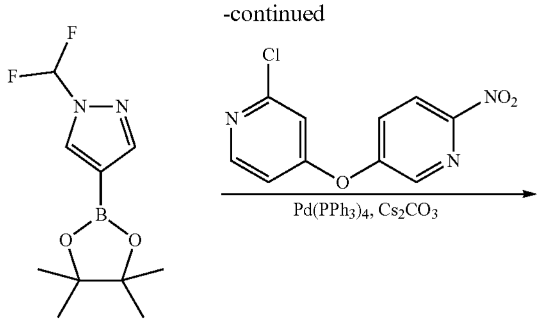

A

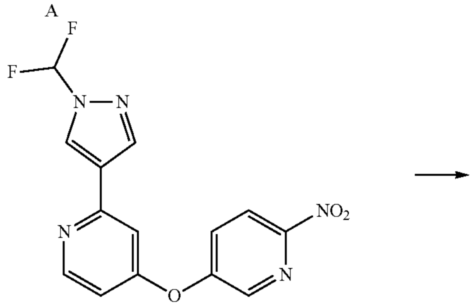

B

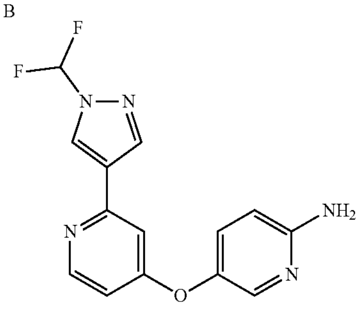

C

(A) 1-(difluoromethyl)-4-(4,4,5,5-tetramethyl-1,3,2-dioxaborolan-2-yl)-1H-pyrazole 4-(4,4,5,5-tetramethyl-1,3,2-dioxaborolan-2-yl)-1H-pyrazole (1 g, 5.1 mmol), 2-chloro-2,2-sodium difluoroacetate (0.94 g, 6.2 mmol), 18-crown-6 (0.27 g, 1.02 mmol) and acetonitrile (20 ml) were successively added to a reaction flask, and the mixture was reacted at 85° C. for 20 hours. Water was added to the reaction solution, and the reaction solution was extracted with ethyl acetate, washed with saturated brine, and dried with anhydrous sodium sulfate. The reactant was concentrated to obtain 900 mg of a crude product, which was directly used in the next step. MS (m/z): 245 $[M+H]^+$.

(B) 2-(1-(difluoromethyl)-1H-pyrazol-4-yl)-4-((6-nitropyridin-3-yl)oxy)pyridine The title compound was prepared with corresponding intermediates and reagents with reference to the preparation processes of intermediate 37(A). MS (m/z): 334 $[M+H]^+$.

(C) 5-((2-(1-(difluoromethyl)-1H-pyrazol-4-yl)pyridin-4-yl)oxy)pyridin-2-amine The title compound was prepared with corresponding intermediates and reagents with reference to the preparation processes of intermediate 24(B). MS (m/z): 304 $[M+H]^+$.

Intermediate 46

2-chloro-4-((2-(1-methyl-1H-pyrazol-4-yl)pyridin-4-yl)oxy)aniline

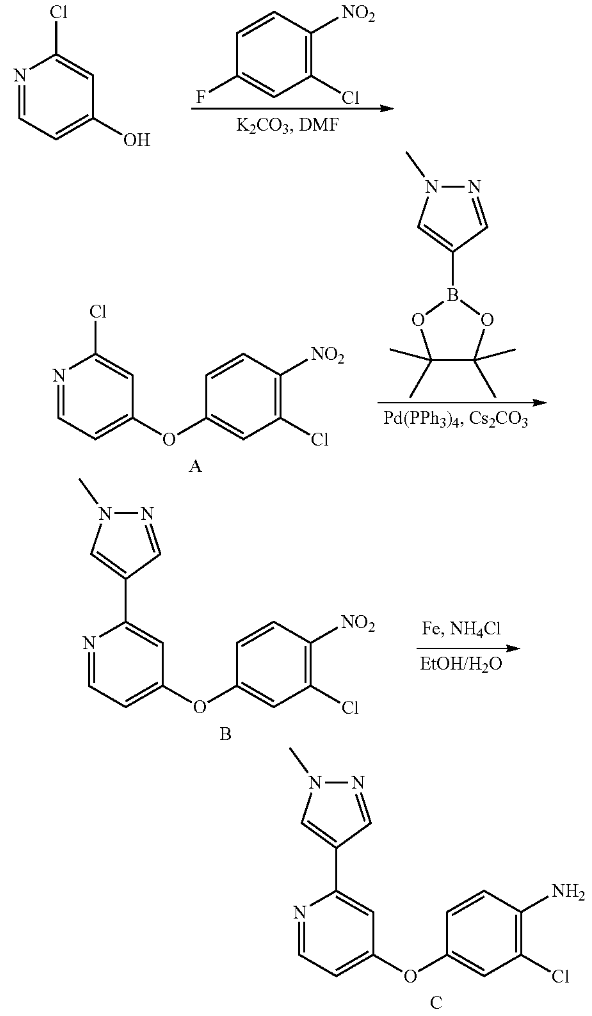

(A) 2-chloro-4-(3-chloro-4-nitrophenoxy)pyridine 2-chloro-4-hydroxyl pyridine (294 mg, 2.28 mmol), 2-chloro-4-fluoro-1-nitrobenzene (400 mg, 2.28 mmol), $K_2CO_3$ (473 mg, 3.42 mmol) and DMF (8 ml) were successively added to a reaction flask, and the mixture was reacted at 80° C. for 4 hours. Water was added to the reaction solution, and the reaction solution was extracted with ethyl acetate, washed with saturated brine, and dried with anhydrous sodium sulfate. The reactant was concentrated to obtain 500 mg of the title product as a yellow solid. MS (m/z): 285 $[M+H]^+$.

(B) 4-(3-chloro-4-nitrophenoxy)-2-(1-methyl-1H-pyrazol-4-yl)pyridine

The title compound was prepared with corresponding intermediates and reagents with reference to the preparation processes of intermediate 37(A). MS (m/z): 331 $[M+H]^+$.

(C) 2-chloro-4-((2-(1-methyl-1H-pyrazol-4-yl)pyridin-4-yl)oxy)aniline

The title compound was prepared with corresponding intermediates and reagents with reference to the preparation processes of intermediate 24(B). MS (m/z): 301 $[M+H]^+$.

Intermediate 47

5-((2-(1-(2-(dimethylamino)ethyl)-1H-pyrazol-4-yl)pyridin-4-yl)oxy)pyridin-2-amine

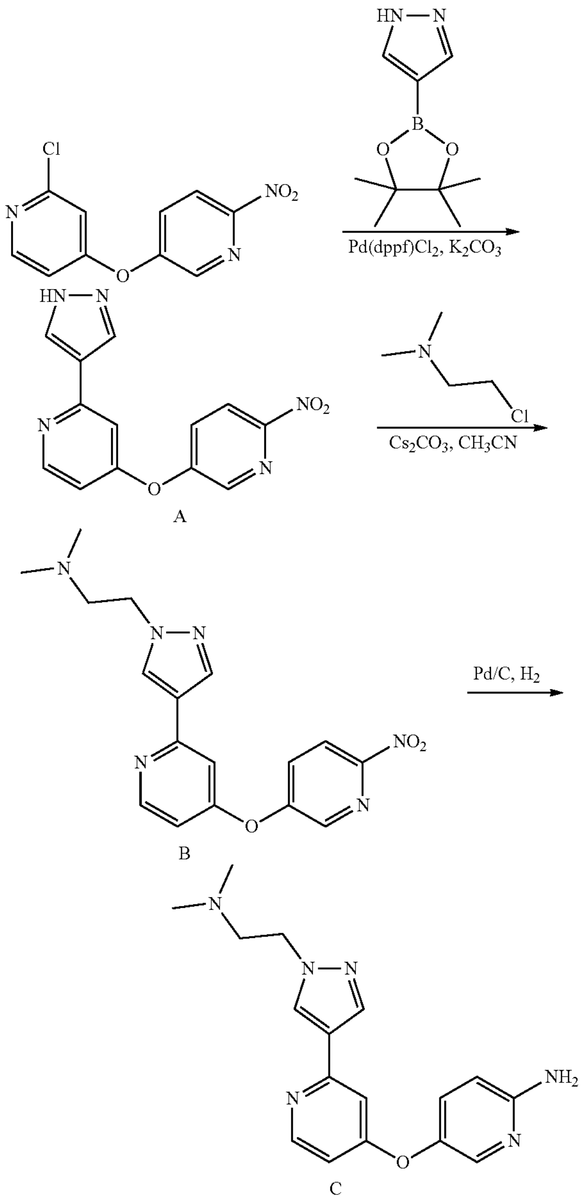

(A) 4-((6-nitropyridin-3-yl)oxy)-2-(1H-pyrazol-4-yl)pyridine 2-chloro-4-((6-nitropyridin-3-yl)oxy)pyridine (1.0 g, 4.0 mmol), 4-(4,4,5,5-tetramethyl-1,3,2-dioxaborolan-2-yl)-1H-pyrazole (1.55 g, 8.0 mmol), $Pd(dppf)Cl_2$ (0.29 g, 0.4 mmol) and $K_2CO_3$ (0.83 g, 6.0 mmol) were dissolved in the mixed solution of 1,4-dioxane (16 ml) and water (4 ml), and under nitrogen, the mixture was heated to 80° C. and reacted overnight. The reaction solution was concentrated to obtain a crude product, which was purified with flash column chromatography (dichloromethane/methanol=100:0-90:10, gradient elution), to obtain 0.57 g of the title product. MS (m/z): 284.1[M+H]+.

(B) N,N-dimethyl-2-(4-(4-((6-nitropyridin-3-yl)oxy)pyridin-2-yl)-1H-pyrazol-1-yl)ethan-1-amine 4-((6-nitropyridin-3-yl)oxy)-2-(1H-pyrazol-4-yl)pyridine (100 mg, 0.35 mmol), 2-chloro-N,N-dimethylethyl-1-amine (72 mg, 0.70 mmol) and cesium carbonate (170 mg, 0.52 mmol) were dissolved in acetonitrile (10 ml), and the mixture was stirred at 80° C. for hours. The reactant was concentrated to obtain a crude product, which was purified with flash column chromatography (water/methanol=100:0-0:100, gradient elution), to obtain 88 mg of the title product. MS (m/z): 355.1 [M+H]+.

(C) 5-((2-(1-(2-(dimethylamino)ethyl)-1H-pyrazol-4-yl)pyridin-4-yl)oxy)pyridin-2-amine N,N-dimethyl-2-(4-(4-((6-nitropyridin-3-yl)oxy)pyridin-2-yl)-1H-pyrazol-1-yl)ethan-1-amine (88 mg, 0.25 mmol) and palladium carbon (10 mg) were dissolved in methanol (10 ml), and the mixture was stirred under hydrogen at room temperature for 5 hours. The reaction solution was filtered to remove palladium carbon, and the liquid was concentrated to obtain 67 mg of a crude product of title compound. MS (m/z): 325.2 [M+H]+.

Intermediate 48

5-((2-(1-methyl-1H-1,2,4-triazol-3-yl)pyridin-4-yl)oxy)pyridin-2-amine

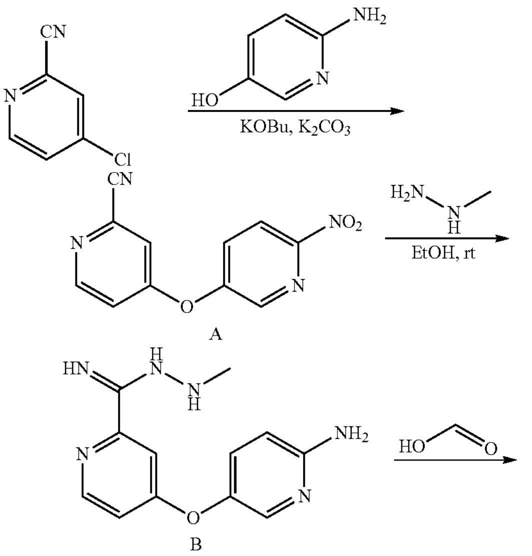

A
B

-continued

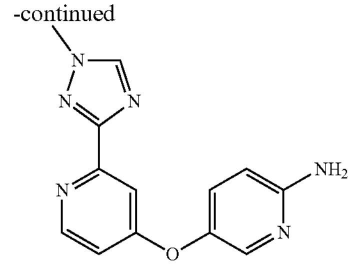
C (A) 4-((6-aminopyridin-3-yl)oxy)picolinonitrile 4-chloropyridine carbonitrile (1.38 g, 10.0 mmol), 6-aminopyridin-3-ol (1.1 g, 10.0 mmol), potassium t-butoxide (1.12 g, 10.0 mmol) and potassium carbonate (1.38 g, 10.0 mmol) were dissolved in DMSO (20 ml), and the mixture was stirred at 80° C. for 15 hours. The reaction solution was quenched with saturated ammonium chloride solution, extracted with ethyl acetate, and concentrated, to obtain a crude product, which was purified with flash column chromatography (water/methanol=100:0-0:100, gradient elution), to obtain 1.12 g of the title product. MS (m/z): 213.0[M+H]+.

(B) 4-((6-aminopyridin-3-yl)oxy)-N'-methylpicolinimidohydrazide 4-((6-aminopyridin-3-yl)oxy)picolinonitrile (1.12 g, 5.28 mmol) and methyl hydrazine (1.21 g, 26.4 mmol) were dissolved in ethanol (20 ml), and the mixture was reacted at room temperature for 15 hours. The reaction solution was concentrated to obtain a crude product, which was purified with flash column chromatography (water/methanol=100:0-0:100, gradient elution), to obtain 430 mg of the title product. MS (m/z): 259.1[M+H]+.

(C) 5-((2-(1-methyl-1H-1,2,4-triazol-3-yl)pyridin-4-yl)oxy)pyridin-2-amine 4-((6-aminopyridin-3-yl)oxy)-N'-methylpicolinimidohydrazide (258 mg, 1.0 mmol) was dissolved in formic acid (5 ml), and the mixture was refluxed and reacted for 4 hours. The reaction solution was concentrated to obtain a crude product, which was purified with flash column chromatography (water/methanol=100:0-0:100, gradient elution), to obtain 88 mg of the title product. MS (m/z): 269.1[M+H]+.

Intermediate 49

N-(4-((6-aminopyridin-3-yl)oxy)pyridin-2-yl)-5-methylthiazol-2-amine

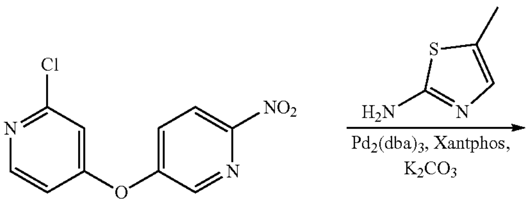

-continued

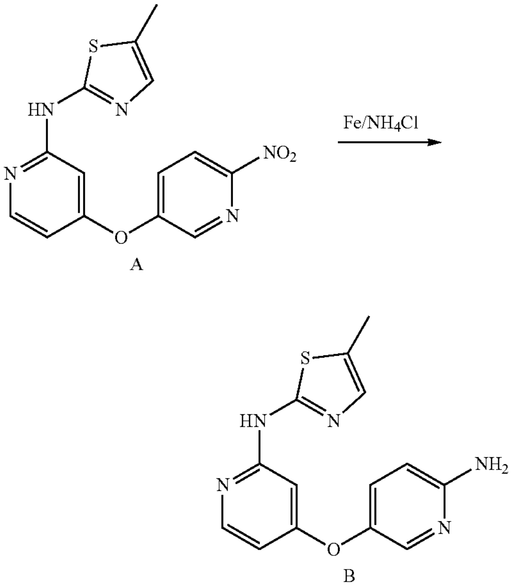

A

B (A) 5-methyl-N-(4-((6-nitropyridin-3-yl)oxy)pyridin-2-yl)thiazol-2-amine 2-chloro-4-((6-nitropyridin-3-yl)oxy)pyridine (300 mg, 1.20 mmol), 5-methylthiazol-2-amine (200 mg, 1.80 mmol), $Pd_2(dba)_3$ (100 mg, 0.12 mmol), Xantphos (60 mg, 0.12 mmol) and potassium carbonate (331 mg, 2.40 mmol) were dissolved in dioxane (15 ml), and the mixture was stirred and reacted at 90° C. for 6 hours. The reaction solution was concentrated to obtain a crude product, which was purified with flash column chromatography (dichloromethane/methanol=100:0-90:10, gradient elution), to obtain 370 mg of the title product. MS (m/z): 330.1 $[M+H]^+$.

(B) N-(4-((6-aminopyridin-3-yl)oxy)pyridin-2-yl)-5-methylthiazol-2-amine

The title compound was prepared with corresponding intermediates and reagents with reference to the preparation processes of intermediate 24(B). MS (m/z): 300.0$[M+H]^+$.

Intermediate 50

3-fluoro-5-((2-(1-methyl-1H-imidazol-4-yl)pyridin-4-yl)oxy)pyridin-2-amine

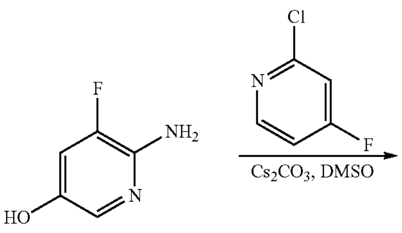

-continued

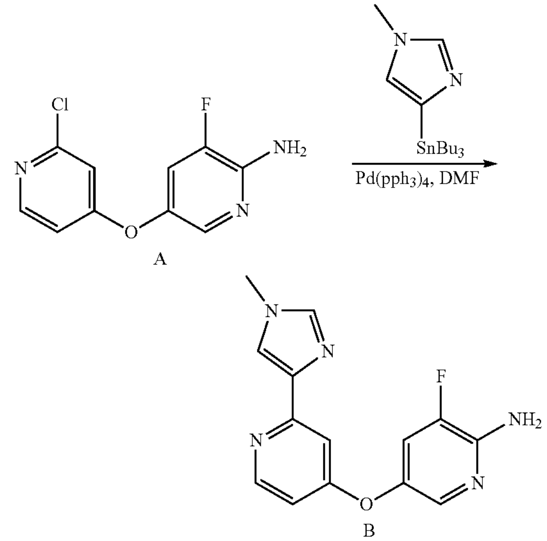

A

B (A) 5-((2-chloropyridin-4-yl)oxy)-3-fluoropyridin-2-amine 6-amino-5-fluoropyridin-3-ol (1.70 g, 13.3 mmol), 2-chloro-4-fluoropyridine (1.74 g, 13.3 mmol) and cesium carbonate (6.50 g, 20.0 mmol) were dissolved in DMSO (50 ml), and the mixture was stirred and reacted at 90° C. for 2 hours. The reactant was concentrated to obtain a crude product, which was purified with flash column chromatography (water/methanol=100:0-0:100, gradient elution), to obtain 1.41 g of the title product. MS (m/z): 240.1$[M+H]^+$.

(B) 3-fluoro-5-((2-(1-methyl-1H-imidazol-4-yl)pyridin-4-yl)oxy)pyridin-2-amine

The title compound was prepared with corresponding intermediates and reagents with reference to the preparation processes of intermediate 30(A). MS (m/z): 286.0$[M+H]^+$.

Intermediate 51

3-fluoro-5-((2-(1-methyl-1H-pyrazol-4-yl)pyridin-4-yl)oxy)pyridin-2-amine

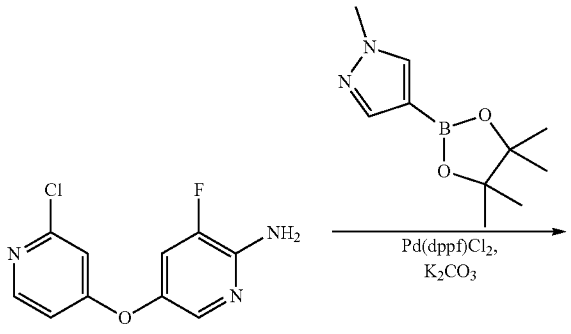

-continued

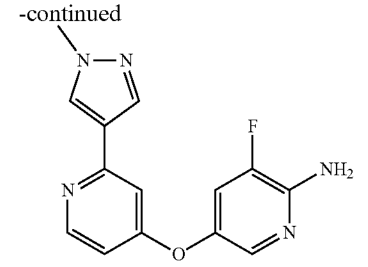

The title compound was prepared with 5-((2-chloropyridin-4-yl)oxy)-3-fluoropyridin-2-amine and corresponding reagents with reference to the preparation processes of intermediate 18(B). MS (m/z): 286.0[M+H]$^+$.

Intermediate 52

2-amino-5-((2-(1-methyl-1H-pyrazol-4-yl)pyridin-4-yl)oxy)nicotinonitrile

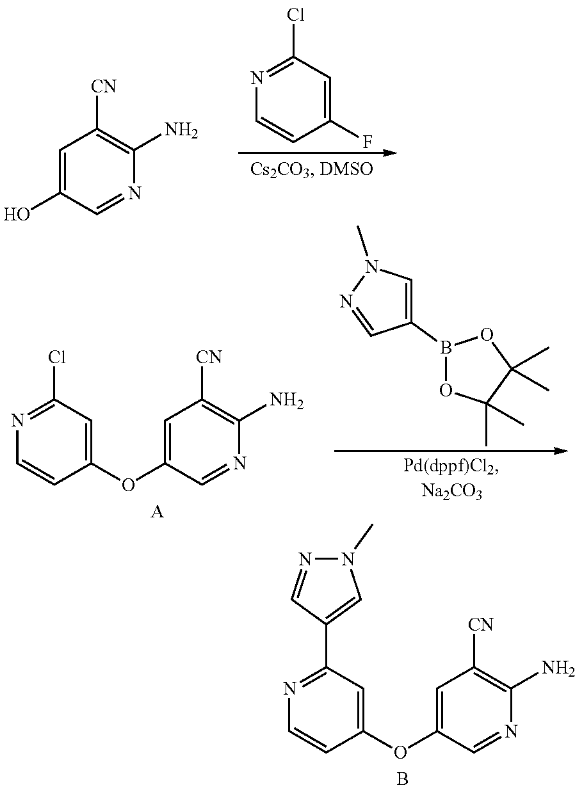

A

B (A) 2-amino-5-((2-chloropyridin-4-yl)oxy)nicotinonitrile

The title compound was prepared with 6-amino-5-cyanopyridin-3-ol and corresponding reagents with reference to the preparation processes of intermediate 50(A). MS (m/z): 247.1[M+H]$^+$.

(B) 2-amino-5-((2-(1-methyl-1H-pyrazol-4-yl)pyridin-4-yl)oxy)nicotinonitrile 2-amino-5-((2-chloropyridin-4-yl)oxy)nicotinonitrile (150 mg, 0.61 mmol), 1-methyl-4-(4,4,5,5-tetramethyl-1,3,2-dioxaborolan-2-yl)-1H-pyrazole (253 mg, 1.22 mmol), $Pd(dppf)Cl_2$ (43 mg, 0.06 mmol) and sodium carbonate (95 mg, 0.92 mmol) were dissolved in dioxane (5 ml) and water (1 ml), and the mixture was reacted under nitrogen at 80° C. for 5 hours. The reactant was concentrated to obtain a crude product, which was purified with flash column chromatography (water/methanol=100:0-0:100, gradient elution), to obtain 93 mg of the title product. MS (m/z): 293.0 [M+H]$^+$.

Intermediate 53

5-((2-(2-methylthiazol-4-yl)pyridin-4-yl)oxy)pyridin-2-amine

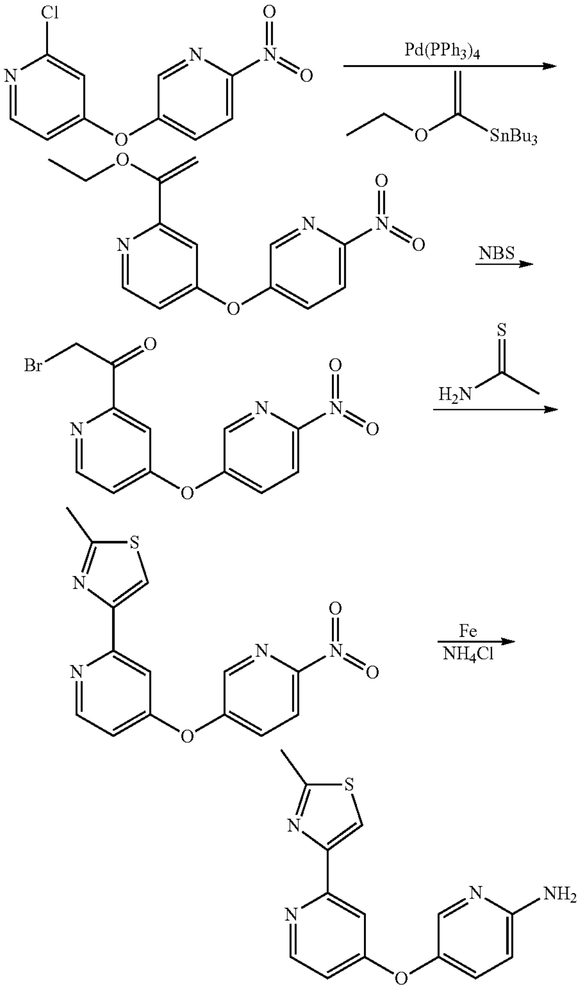

(A) 2-(1-ethoxyvinyl)-4-((6-nitropyridin-3-yl)oxy)pyridine

Under nitrogen, 2-chloro-4-((6-nitropyridin-3-yl)oxy)pyridine (252 mg, 1.0 mmol), tributyl(1-ethoxyvinyl)stannane (722 mg, 2.0 mmol) and $Pd(PPh_3)_4$ (58 mg, 0.05 mmol) were dissolved in 10 ml DMF, and the reaction solution was heated at 100° C. for 15 hours. The reaction solution was cooled to room temperature, and 20 ml of water and 50 ml of ethyl acetate were added. The reaction solution was extracted, and concentrated, a crude product was purified with flash column chromatography (petroleum ether/ethyl acetate=100:0-0:100, gradient elution), to obtain the title product (162 mg) as a yellow solid. MS (m/z): 288.0[M+H]$^+$.

(B) 2-bromo-1-(4-((6-nitropyridin-3-yl)oxy)pyridin-2-yl)ethan-1-one

In a reaction flask, 2-(1-ethoxyvinyl)-4-((6-nitropyridin-3-yl)oxy)pyridine (162 mg, 0.564 mmol) and NBS (100 mg, 0.564 mmol) were dissolved in the mixed solvent of tetrahydrofuran (10 ml) and water (1 ml), and the reaction solution was stirred at room temperature for 1 hour. The reaction solution was concentrated, and then a crude product was purified with flash column chromatography (water/methanol=100:0-0:100, gradient elution), to obtain the title product (136 mg) as a yellow solid. MS (m/z): 338.0[M+H]$^+$.

(C) 2-methyl-4-(4-((6-nitropyridin-3-yl)oxy)pyridin-2-yl)thiazole

In a reaction flask, 2-bromo-1-(4-((6-nitropyridin-3-yl)oxy)pyridin-2-yl)ethan-1-one (136 mg, 0.402 mmol) and thioacetamide (151 mg, 2.01 mmol) were dissolved in 5 ml of ethanol, and the reaction solution was heated and refluxed for 1 hour. The reaction solution was concentrated, and then a crude product was purified with flash column chromatography (water/methanol=100:0-0:100, gradient elution), to obtain the title product (98 mg) as a yellow solid. MS (m/z): 315.0[M+H]$^+$.

(D) 5-((2-(2-methylthiazol-4-yl)pyridin-4-yl)oxy)pyridin-2-amine

The title compound was prepared with corresponding intermediates and reagents with reference to the preparation processes of intermediate 24(B). MS (m/z): 285.0 [M+H]$^+$.

Example 2

Preparation of Compound 1-135

Compound 1

6-(dimethylamino)-1-isopropyl-N-(5-((2-(1-methyl-1H-pyrazol-4-yl)pyridin-4-yl)oxy)pyridin-2-yl)-2-oxo-1,2-dihydropyridine-3-carboxamide

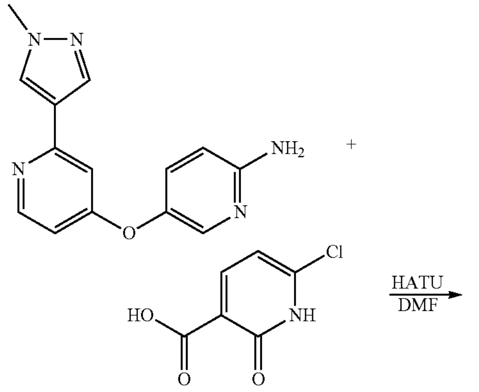

-continued

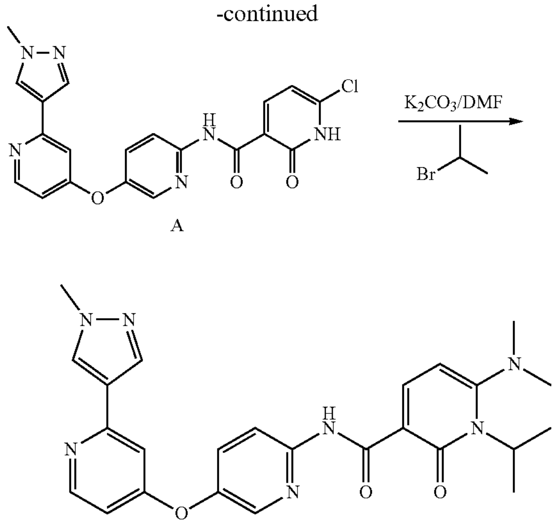

A

B (A) 6-chloro-N-(5-((2-(1-methyl-1H-pyrazol-4-yl)pyridin-4-yl)oxy)pyridin-2-yl)-2-oxo-1,2-dihydropyridine-3-carboxamide Under nitrogen, 5-((2-(1-methyl-1H-pyrazol-4-yl)pyridin-4-yl)oxy)pyridin-2-amine (500 mg, 1.87 mmol), 6-chloro-2-oxo-1,2-dihydropyridin-3-carboxylic acid (487 mg, 2.81 mmol), HATU (1.07 g, 2.81 mmol) and DMF (5 ml) were successively added to a reaction flask, and then TEA (0.76 ml, 5.61 mmol) was added, the mixture was reacted at room temperature overnight. The reaction solution was purified with flash column chromatography (water/methanol=100:0-0:100, gradient elution), to obtain 320 mg of the title product as a brown solid. MS (m/z): 423.1 [M+H]$^+$.

(B) 6-(dimethylamino)-1-isopropyl-N-(5-((2-(1-methyl-1H-pyrazol-4-yl)pyridin-4-yl)oxy)pyridin-2-yl)-2-oxo-1,2-dihydropyridine-3-carboxamide Under nitrogen, 6-chloro-N-(5-((2-(1-methyl-1H-pyrazol-4-yl)pyridin-4-yl)oxy)pyridin-2-yl)-2-oxo-1,2-dihydropyridine-3-carboxamide (70 mg, 0.17 mmol), 2-bromopropane (41 mg, 0.33 mmol), potassium carbonate (69 mg, 0.50 mmol) and DMF (3 ml) were added to a reaction flask, and the mixture was reacted at 80° C. overnight. The reaction solution was purified with flash column chromatography (water/methanol=100:0-0:100, gradient elution) and p-TLC plate (dichloromethane/methanol=15:1), to obtain 12 mg of the title product as a yellow solid. MS (m/z): 474.2 [M+H]$^+$.

$^1$H NMR (400 MHz, DMSO-d6) δ 10.48 (s, 1H), 8.36 (d, J=3.1 Hz, 1H), 8.35 (s, 1H), 8.27 (d, J=2.9 Hz, 1H), 8.25 (s, 1H), 8.12 (d, J=8.7 Hz, 1H), 7.95 (s, 1H), 7.72 (dd, J=9.0, 2.9 Hz, 1H), 7.22 (d, J=2.4 Hz, 1H), 6.70 (dd, J=5.7, 2.3 Hz, 1H), 6.36 (d, J=8.8 Hz, 1H), 5.53-5.41 (m, 1H), 3.82 (s, 3H), 3.09 (s, 6H), 1.44 (d, J=6.2 Hz, 6H).

The following compounds were prepared with corresponding intermediates and reagents with reference to the preparation processes of compound 1 under suitable conditions recognized by the POSITA.

| Compound | Structural formula | MS (M + H)$^+$ | $^1$HNMR |
|---|---|---|---|
| 118 | 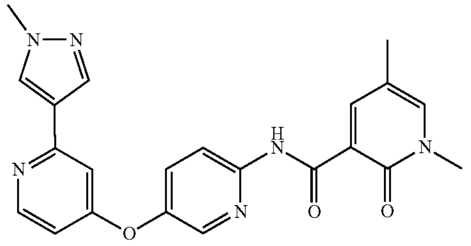 | 417.1 | 1H NMR (400 MHz, DMSO-d6) δ 12.76 (s, 1H), 8.37 (d, J = 3.3 Hz, 1H), 8.36 (s, 1H), 8.34 (d, J = 2.6 Hz, 1H), 8.28 (d, J = 2.9 Hz, 1H), 8.26 (s, 1H), 8.12 (s, 1H), 8.01 (d, J = 1.9 Hz, 1H), 7.96 (s, 1H), 7.74 (dd, J = 9.0, 2.9 Hz, 1H), 7.24 (d, J = 2.4 Hz, 1H), 6.71 (dd, J = 5.7, 2.4 Hz, 1H), 3.83 (s, 3H), 3.57 (s, 3H), 2.14 (s, 3H). |
| 124 | 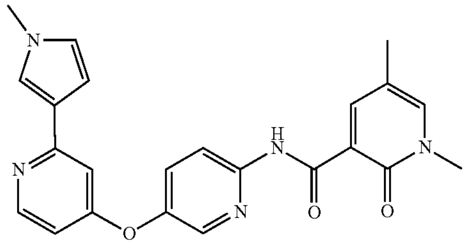 | 416.1 | 1H NMR (400 MHz, DMSO-d6) δ 12.75 (s, 1H), 8.37 (s, 1H), 8.35-8.33 (m, 1H), 8.30 (d, J = 5.7 Hz, 1H), 8.27 (d, J = 2.9 Hz, 1H), 8.01 (d, J = 2.3 Hz, 1H), 7.72 (dd, J = 9.0, 2.9 Hz, 1H), 7.35-7.34 (m, 1H), 7.08 (d, J = 2.4 Hz, 1H), 6.71-6.69 (m, 1H), 6.61 (dd, J = 5.6, 2.2 Hz, 1H), 6.52-6.47 (m, 1H), 3.60 (s, 3H), 3.58 (s, 3H), 2.14 (s, 3H). |

Compound 2

6-(dimethylamino)-1-methyl-N-(5-((2-(1-methyl-1H-pyrazol-4-yl)pyridin-4-yl)oxy)pyridin-2-yl)-2-oxo-1,2-dihydropyridine-3-carboxamide

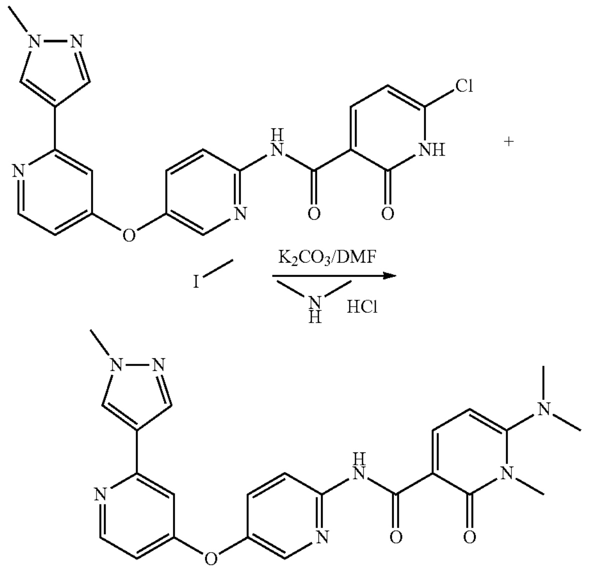

Under nitrogen, 6-chloro-N-(5-((2-(1-methyl-1H-pyrazol-4-yl)pyridin-4-yl)oxy)pyridin-2-yl)-2-oxo-1,2-dihydropyridine-3-carboxamide (100 mg, 0.24 mmol), iodomethane (30 μl, 0.47 mmol), potassium carbonate (100 mg, 0.72 mmol) and DMF (4 ml) were added to a reaction flask, and the mixture was reacted at 80° C. overnight. And then dimethylamine hydrochloride (38 mg, 0.47 mmol) was added, and the mixture was reacted at room temperature overnight, the reaction solution was purified with flash column chromatography (water/methanol=100:0-0:100, gradient elution) and p-TLC plate (dichloromethane/methanol=15:1), to obtain 16 mg of the title product as a light yellow solid. MS (m/z): 446.2[M+H]$^+$.

$^1$H NMR (400 MHz, DMSO-d6) δ 12.48 (s, 1H), 8.36 (dd, J=7.4, 4.3 Hz, 2H), 8.29 (d, J=8.5 Hz, 1H), 8.25 (m, 2H), 7.95 (d, J=0.6 Hz, 1H), 7.71 (dd, J=9.0, 2.9 Hz, 1H), 7.22 (d, J=2.4 Hz, 1H), 6.70 (dd, J=5.7, 2.4 Hz, 1H), 6.16 (d, J=8.6 Hz, 1H), 3.82 (s, 3H), 3.49 (s, 3H), 2.87 (s, 6H).

Compound 3

6-methoxy-1-methyl-N-(5-((2-(1-methyl-1H-pyrazol-4-yl)pyridin-4-yl)oxy)pyridin-2-yl)-2-oxo-1,2-dihydropyridine-3-carboxamide

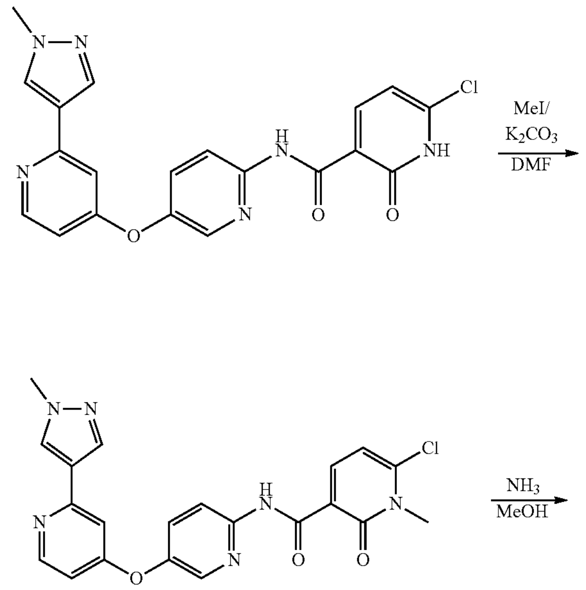

A

-continued

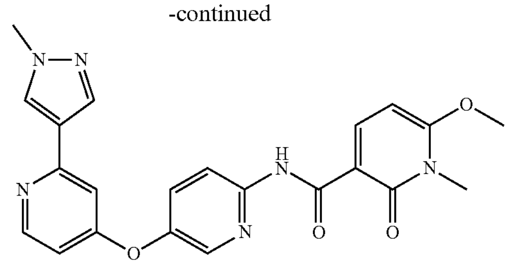

B (A) 6-chloro-1-methyl-N-(5-((2-(1-methyl-1H-pyrazol-4-yl)pyridin-4-yl)oxy)pyridin-2-yl)-2-oxo-1,2-dihydropyridine-3-carboxamide Under nitrogen, 6-chloro-N-(5-((2-(1-methyl-1H-pyrazol-4-yl)pyridin-4-yl)oxy)pyridin-2-yl)-2-oxo-1,2-dihydropyridine-3-carboxamide (320 mg, 0.76 mmol), iodomethane (71 μl, 1.14 mmol), potassium carbonate (540 mg, 1.42 mmol) and DMF (5 ml) were added to a reaction flask, and the mixture was reacted at 80° C. overnight. The reaction solution was purified with flash column chromatography (water/methanol=100:0-0:100, gradient elution), to obtain 130 mg of the title product as a brown solid. MS (m/z): 437.1 $[M+H]^+$.

(B) 6-methoxy-1-methyl-N-(5-((2-(1-methyl-1H-pyrazol-4-yl)pyridin-4-yl)oxy)pyridin-2-yl)-2-oxo-1,2-dihydropyridine-3-carboxamide Under nitrogen, 6-chloro-1-methyl-N-(5-((2-(1-methyl-1H-pyrazol-4-yl)pyridin-4-yl)oxy)pyridin-2-yl)-2-oxo-1,2-dihydropyridine-3-carboxamide (30 mg, 0.07 mmol) and 7M ammonia methanol solution (3 ml) were added to a reaction flask, the tube was sealed and the mixture was reacted at 80° C. for 2 h. And then the reaction solution was concentrated, the residue was purified with flash column chromatography (water/methanol=100:0-0:100, gradient elution) and p-TLC plate (dichloromethane/methanol=15:1), to obtain 3 mg of the title product as a yellow solid. MS (m/z): 433.2 $[M+H]^+$.

$^1$H NMR (400 MHz, DMSO-d6) δ 12.39 (s, 1H), 8.46 (d, J=8.6 Hz, 1H), 8.38-8.33 (m, 2H), 8.29-8.20 (m, 2H), 7.95 (d, J=0.5 Hz, 1H), 7.72 (dd, J=9.0, 2.9 Hz, 1H), 7.23 (d, J=2.3 Hz, 1H), 6.70 (dd, J=5.7, 2.4 Hz, 1H), 6.25 (d, J=8.7 Hz, 1H), 4.04 (s, 3H), 3.82 (s, 3H), 3.45 (s, 3H).

Compound 4

N-(3-fluoro-5-((2-((1-methyl-1H-pyrazol-4-yl)amino)pyridin-4-yl)oxy)pyridin-2-yl)-1-methyl-2-oxo-1,2-dihydropyridine-3-carboxamide

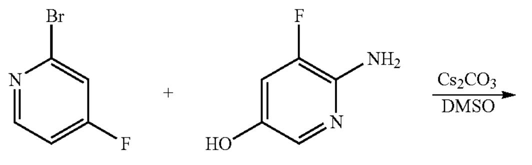

-continued

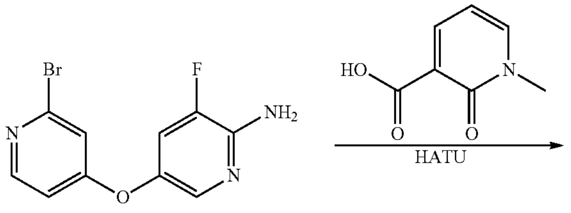

A

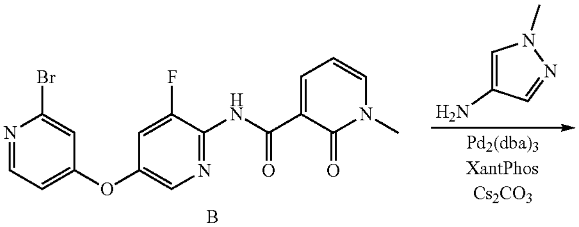

B

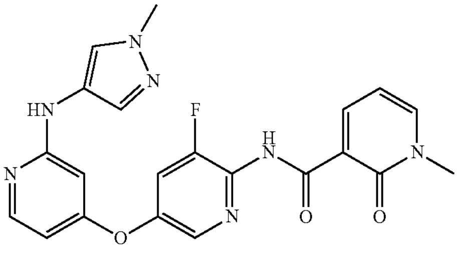

C (A) 5-((2-bromopyridin-4-yl)oxy)-3-fluoropyridin-2-amine

Under nitrogen, 6-amino-5-fluoropyridin-3-ol (1.28 g, 10 mmol), 2-bromo-4-fluoropyridine (1.76 g, 10 mmol), cesium carbonate (4.9 g, 15 mmol) and DMSO (10 ml) were successively added to a reaction flask, and the mixture was reacted at 80° C. for 2 hours. The reaction solution was cooled to room temperature, added to water (100 ml) under stirring, and extracted with ethyl acetate (100 ml×3), the organic layers were combined and concentrated, and the residue was purified with flash column chromatography (water/methanol=100:0-0:100, gradient elution), to obtain 2.7 g of the title product as a yellow solid. MS (m/z): 285.9 $[M+H]^+$.

(B) N-(5-((2-bromopyridin-4-yl)oxy)-3-fluoropyridin-2-yl)-1-methyl-2-oxo-1,2-dihydropyridine-3-carboxamide 5-((2-bromopyridin-4-yl)oxy)-3-fluoropyridin-2-amine (200 mg, 0.70 mmol), 1-methyl-2-oxo-1,2-dihydropyridin-3-carboxylic acid (118 mg, 0.77 mmol), HATU (322 mg, 0.85 mmol), TEA (148 μl, 1.05 mmol) and DMF (6 ml) were successively added to a reaction flask, and the mixture was reacted at 45° C. overnight. The reaction solution was purified with flash column chromatography (water/methanol=100:0-0:100, gradient elution), to obtain 133 mg of the title product as a brown solid. MS (m/z): 419.0 $[M+H]^+$.

(C) N-(3-fluoro-5-((2-((1-methyl-1H-pyrazol-4-yl)amino)pyridin-4-yl)oxy)pyridin-2-yl)-1-methyl-2-oxo-1,2-dihydropyridine-3-carboxamide Under nitrogen, N-(5-((2-bromopyridin-4-yl)oxy)-3-fluoropyridin-2-yl)-1-methyl-2-oxo-1,2-dihydropyridine-3-carboxamide (133 mg, 0.32 mmol), 1-methyl-1H-pyrazol-4-amine (37 mg, 0.38 mmol), XantPhos (37 mg, 0.064 mmol), $Pd_2(dba)_3$ (29 mg, 0.032 mmol), cesium carbonate (261 mg, 0.8 mmol) and 1,4-dioxane (10 ml) were successively added to a reaction flask, and the mixture was reacted at 100° C. overnight. The reaction solution was concentrated, and the residue was purified with flash column chromatography (water/methanol=100:0-0:100, gradient elution) and p-TLC plate (dichloromethane/methanol/formic acid=10:1:0.1), to obtain 15 mg of the title product as a yellow solid. MS (m/z): 436.1$[M+H]^+$.

$^1$H NMR (400 MHz, DMSO-d6) δ 12.22 (s, 1H), 8.83 (s, 1H), 8.46 (dd, J=7.3, 2.1 Hz, 1H), 8.25 (d, J=2.3 Hz, 1H), 8.21 (dd, J=6.5, 2.1 Hz, 1H), 8.16 (s, 2H), 8.05 (d, J=5.8 Hz, 1H), 7.94 (dd, J=10.5, 2.4 Hz, 1H), 7.90 (s, 1H), 7.35 (s, 1H), 6.66-6.58 (m, 1H), 6.39 (dd, J=5.8, 2.2 Hz, 1H), 6.12 (d, J=2.1 Hz, 1H), 3.78 (s, 3H), 3.65 (s, 3H).

Compound 5

1,2-dimethyl-N-(5-((6-(1-methyl-1H-pyrazol-4-yl)pyrimidin-4-yl)oxy)pyridin-2-yl)-6-oxo-1,6-dihydropyrimidine-5-carboxamide

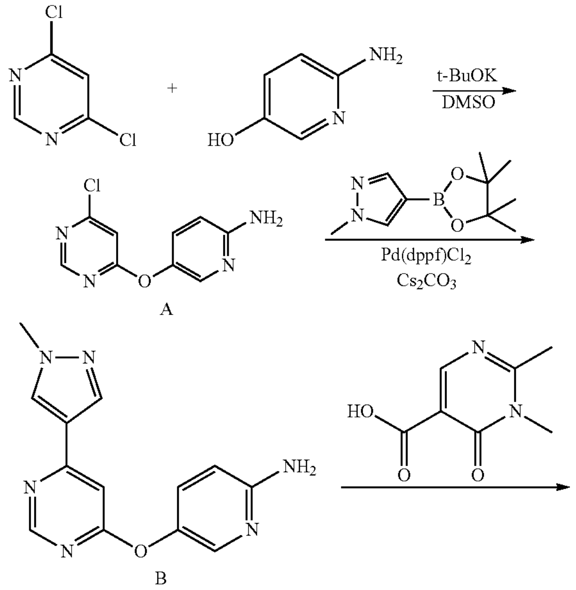

-continued

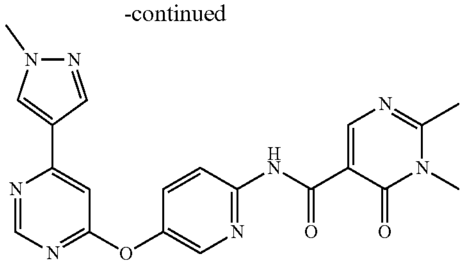

C (A) 5-((6-chloropyrimidin-4-yl)oxy)pyridin-2-amine

Under nitrogen, 4,6-dichloropyrimidine (530 mg, 3.56 mmol), 6-aminopyridin-3-ol (390 mg, 3.56 mmol), potassium t-butoxide (800 mg, 7.12 mmol) and DMSO (18 ml) were successively added to a reaction flask, and the mixture was reacted at 100° C. overnight. The reaction solution was purified with flash column chromatography (water/methanol=100:0-0:100, gradient elution), to obtain a solid title product 494 mg. MS (m/z): 233.0 $[M+H]^+$.

(B) 5-((6-(1-methyl-1H-pyrazol-4-yl)pyrimidin-4-yl)oxy)pyridin-2-amine

Under nitrogen, 5-((6-chloropyrimidin-4-yl)oxy)pyridin-2-amine (300 mg, 1.35 mmol), 1-methyl-4-(4,4,5,5-tetramethyl-1,3,2-dioxaborolan-2-yl)-1H-pyrazole (336 mg, 1.62 mmol), $Pd(dppf)Cl_2$ (110 mg, 0.135 mmol), cesium carbonate (660 mg, 2.03 mmol), water (2 ml) and 1,4-dioxane (8 ml) were successively added to a reaction flask, and the mixture was reacted at 50° C. overnight. The reaction solution was concentrated, and the residue was purified with flash column chromatography (water/methanol=100:0-0:100, gradient elution), to obtain 160 mg of a solid title product. MS (m/z): 269.1 $[M+H]^+$.

(C) 1,2-dimethyl-N-(5-((6-(1-methyl-1H-pyrazol-4-yl)pyrimidin-4-yl)oxy)pyridin-2-yl)-6-oxo-1,6-dihydropyrimidine-5-carboxamide The title compound was prepared with corresponding intermediates and reagents with reference to the preparation processes of compound 1(A). MS (m/z): 419.1 $[M+H]^+$.

$^1$H NMR (400 MHz, DMSO-d6) δ 11.85 (s, 1H), 8.76 (s, 1H), 8.65 (d, J=0.7 Hz, 1H), 8.49 (s, 1H), 8.38-8.27 (m, 2H), 8.18 (s, 1H), 7.82 (dd, J=8.9, 2.8 Hz, 1H), 7.46 (d, J=0.7 Hz, 1H), 3.91 (s, 3H), 3.60 (s, 3H), 2.65 (s, 3H).

Compound 6

1-isopropyl-N-(5-((2-(1-methyl-1H-pyrazol-4-yl)pyrimidin-4-yl)oxy)pyridin-2-yl)-2-oxo-1,2-dihydro-pyridine-3-carboxamide

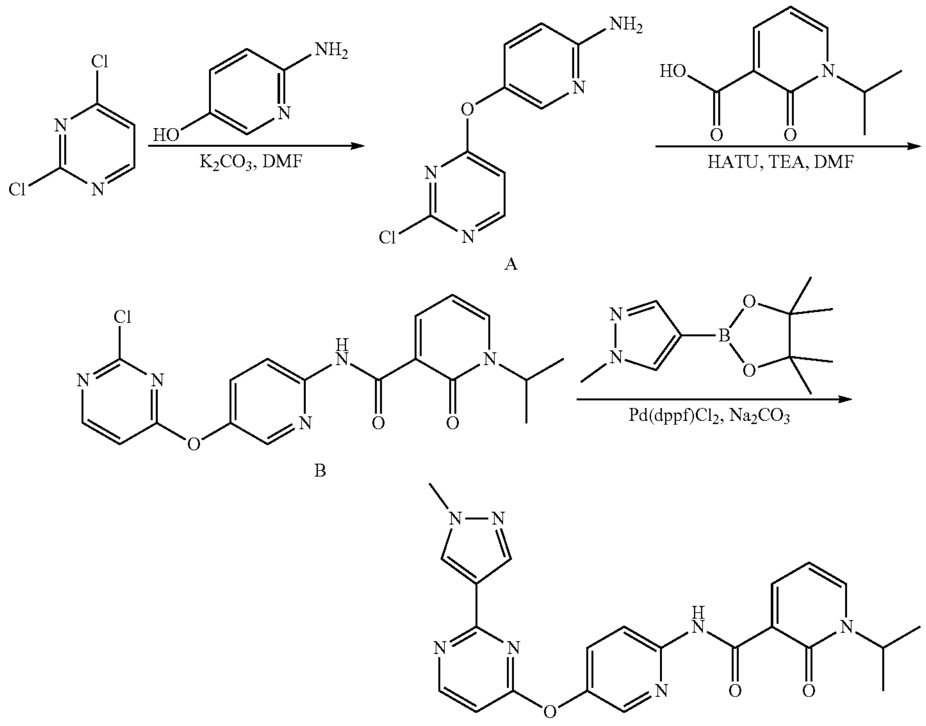

C (A) 5-((2-chloropyrimidin-4-yl)oxy)pyridin-2-amine 2,4-dichloropyrimidine (1.49 g, 10.0 mmol), 6-amino-pyridin-3-ol (1.1 g, 10.0 mmol), $K_2CO_3$ (3.45 g, 25.0 mmol) and DMF (15.0 ml) were added to a reaction flask, and the mixture was heated to 100° C. and stirred for 4 hours, after cooling, the reaction solution was filtered, and the filtrate was purified with flash column chromatography ($H_2O$/MeOH 20=100:0-0:100, gradient elution), to obtain 1.3 g of the title product as a light yellow solid. MS (m/z): 223.0, 225.0 [M+H]$^+$.

(B) N-(5-((2-chloropyrimidin-4-yl)oxy)pyridin-2-yl)-1-isopropyl-2-oxo-1,2-dihydropyridine-3-carboxamide The title compound was prepared with corresponding intermediates and reagents with reference to the preparation processes of compound 1(A). MS (m/z): 386.0, 388.0 [M+H]$^+$.

(C) 1-isopropyl-N-(5-((2-(1-methyl-1H-pyrazol-4-yl)pyrimidin-4-yl)oxy)pyridin-2-yl)-2-oxo-1,2-dihydropyridine-3-carboxamide N-(5-((2-chloropyrimidin-4-yl)oxy)pyridin-2-yl)-1-isopropyl-2-oxo-1,2-dihydropyridine-3-carboxamide (100 mg, 0.26 mmol), 1-methyl-4-(4,4,5,5-tetramethyl-1,3,2-dioxaborolan-2-yl)-1H-pyrazole (65 mg, 0.311 mmol), $Na_2CO_3$ (83 mg, 0.78 mmol), Pd(dppf)$Cl_2$—$CH_2Cl_2$ (22 mg, 0.026 mmol), dioxane (25.0 ml) and water (3.0 ml) were added to a reaction flask, and the mixture was heated to 100° C. and stirred overnight, after cooling, the reaction solution was purified with flash column chromatography ($H_2O$/MeOH=100:0-0:100, gradient elution), to obtain 40 mg of the title product as a white solid. MS (m/z): 432.2 [M+H]$^+$.

$^1$H NMR (400 MHz, DMSO-d6) δ 12.70 (s, 1H), 8.70-8.56 (m, 1H), 8.55-8.44 (m, 1H), 8.44-8.31 (m, 2H), 8.24 (s, 1H), 8.11 (s, 1H), 7.93-7.72 (m, 2H), 7.00-6.82 (m, 1H), 6.79-6.56 (m, 1H), 5.35-5.11 (m, 1H), 3.83 (s, 3H), 1.37 (d, J=5.3 Hz, 6H).

Compound 7

1,2-dimethyl-N-(5-((2-(1-methyl-1H-pyrazol-4-yl)pyrimidin-4-yl)oxy)pyridin-2-yl)-6-oxo-1,6-dihydro-pyrimidine-5-carboxamide

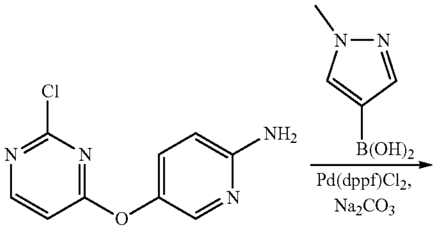

-continued

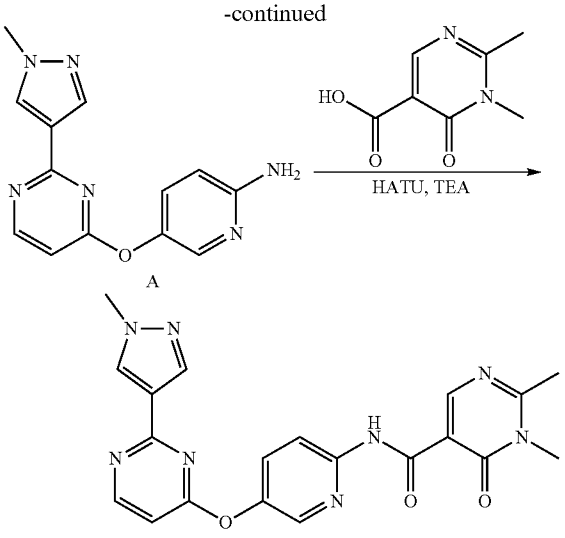

A

B (A) 5-((2-(1-methyl-1H-pyrazol-4-yl)pyrimidin-4-yl)oxy)pyridin-2-amine 5-((2-chloropyrimidin-4-yl)oxy)pyridin-2-amine (1.9 g, 8.56 mmol), (1-methyl-1H-pyrazol-4-yl)boronic acid (1.18 g, 9.41 mmol), $Na_2CO_3$ (2.72 g, 25.68 mmol), Pd(dppf)$Cl_2$—$CH_2Cl_2$ (1.05 g, 1.284 mmol), dioxane (25.0 ml) and water (3.0 ml) were added to a reaction flask, and the mixture was heated to 100° C. and stirred for 4 hours, after cooling, the reaction solution was concentrated, and purified with flash column chromatography ($H_2O$/MeOH=100:0-0:100, gradient elution), to obtain 1.72 g of the title product as a yellow solid. MS (m/z): 269.1 $[M+H]^+$.

(B) 1,2-dimethyl-N-(5-((2-(1-methyl-1H-pyrazol-4-yl)pyrimidin-4-yl)oxy)pyridin-2-yl)-6-oxo-1,6-dihydropyrimidine-5-carboxamide The title compound was prepared with corresponding intermediates and reagents with reference to the preparation processes of compound 1(A). MS (m/z): 419.1 $[M+H]^+$.

$^1$H NMR (400 MHz, DMSO-d6) δ 11.85 (s, 1H), 8.75 (s, 1H), 8.62 (d, J=6.2 Hz, 1H), 8.40-8.31 (m, 2H), 8.11 (s, 1H), 7.89-7.76 (m, 1H), 7.81 (s, 1H), 6.90 (d, J=5.3 Hz, 1H), 3.83 (s, 3H), 3.58 (s, 3H), 2.64 (s, 3H).

Compound 8

1,2-dimethyl-N-(5-((2-(1-methyl-1H-pyrazol-4-yl)pyridin-4-yl)oxy)pyridin-2-yl)-6-oxo-1,6-dihydropyrimidine-5-carboxamide

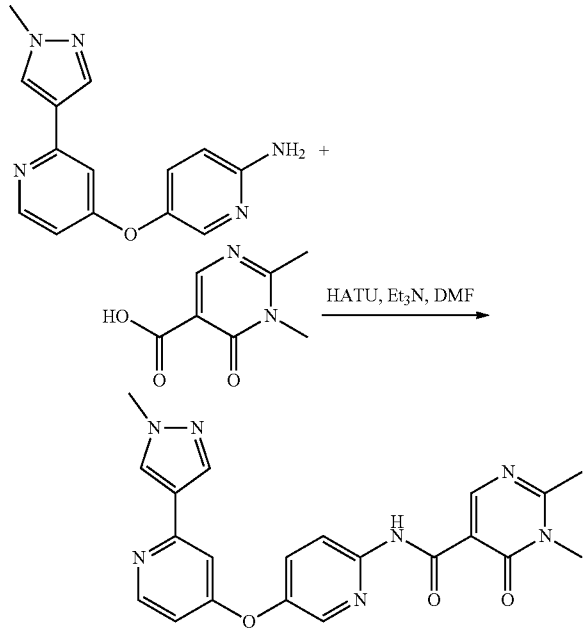

5-((2-(1-methyl-1H-pyrazol-4-yl)pyridin-4-yl)oxy)pyridin-2-amine (158 mg, 0.59 mmol), 1,2-dimethyl-6-oxo-1,6-dihydropyrimidine-5-carboxylic acid (100 mg, 0.59 mmol), HATU (224 mg, 0.59 mmol), triethylamine (178 mg, 1.77 mmol) and DMF (5 ml) were successively added to a reaction flask, and the mixture was heated to 40° C. and reacted for 15 hours. The reaction solution was purified with flash column chromatography (water/methanol=100:0-0:100, gradient elution), to obtain 22 mg of a product as a light yellow solid. MS (m/z): 418.1$[M+H]^+$.

$^1$H NMR (400 MHz, DMSO-d6) δ 11.85 (s, 1H), 8.73 (s, 1H), 8.36 (d, J=5.7 Hz, 1H), 8.33 (d, J=9.0 Hz, 1H), 8.29 (d, J=2.6 Hz, 1H), 8.25 (s, 1H), 7.95 (s, 1H), 7.76 (dd, J=9.0, 2.6 Hz, 1H), 7.23 (d, J=1.9 Hz, 1H), 6.71 (dd, J=5.5, 2.2 Hz, 1H), 3.83 (s, 3H), 3.57 (s, 3H), 2.62 (s, 3H).

The following compounds were prepared with corresponding intermediates and reagents with reference to the preparation processes of compound 8 under suitable conditions recognized by the POSITA.

| Compound | Structural formula | MS $(M+H)^+$ | $^1$HNMR |
|---|---|---|---|
| 116 | 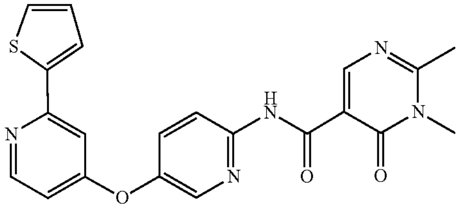 [SMILES: Cc1ncc(C(=O)Nc2ccc(Oc3ccnc(-c4cccs4)c3)cn2)c(=O)n1C] | 420.1 | 1H NMR (400 MHz, DMSO-d6) δ 11.86 (s, 1H), 8.73 (s, 1H), 8.39 (d, J = 5.7 Hz, 1H), 8.34 (d, J = 9.3 Hz, 1H), 8.32 (d, J = 2.8 Hz, 1H), 7.83-7.79 (m, 2H), 7.65-7.59 (m, 1H), 7.55 (d, J = 2.2 Hz, 1H), 7.4-7.071 (m, 1H), 6.81 (dd, J = 5.7, 2.4 Hz, 1H), 3.57 (s, 3H), 2.63 (s, 3H). |

-continued

| Compound | Structural formula | MS $(M+H)^+$ | $^1$HNMR |
|---|---|---|---|
| 119 | 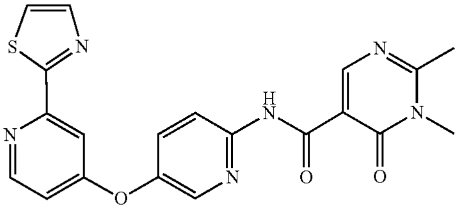 | 421.1 | 1H NMR (400 MHz, DMSO-d6) δ 11.88 (s, 1H), 8.73 (s, 1H), 8.52 (d, J = 5.7 Hz, 1H), 8.43-8.29 (m, 2H), 7.91 (d, J = 3.1 Hz, 1H), 7.89-7.81 (m, 2H), 7.51 (d, J = 2.3 Hz, 1H), 7.12 (dd, J = 5.6, 2.4 Hz, 1H), 3.57 (s, 3H), 2.63 (s, 3H). |

Compound 9

N-(5-((2-(1-methyl-1H-pyrazol-4-yl)pyridin-4-yl)oxy)pyridin-2-yl)-2-oxo-1,2-dihydropyridine-3-carboxamide

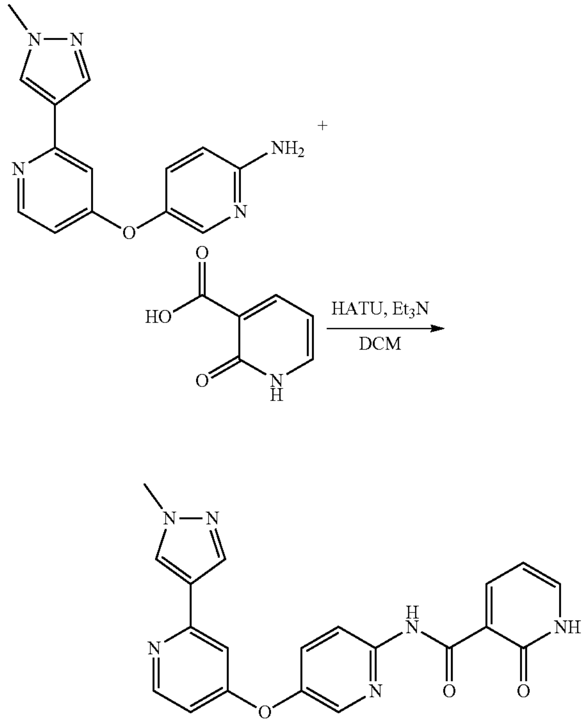

Under nitrogen, 5-((2-(1-methyl-1H-pyrazol-4-yl)pyridin-4-yl)oxy)pyridin-2-amine (100 mg, 0.37 mmol), 2-hydroxynicotinic acid (78 mg, 0.56 mmol), HATU (213 mg, 0.56 mmol), dichloromethane (20 ml) and TEA (155 μl, 1.1 mmol) were successively added to a reaction flask, and the mixture was stirred at room temperature overnight, added water (5 ml), and then concentrated. The residue was purified with flash column chromatography (water (0.5% formic acid):methanol=100:0-0:100, gradient elution) and p-TLC plate, to obtain 45 mg of the title product as a white solid. MS (m/z): 389.2 $[M+H]^+$.

$^1$H NMR (400 MHz, DMSO-d6) δ 12.86 (s, 1H), 12.69 (s, 1H), 8.52 (dd, J=7.2, 2.2 Hz, 1H), 8.40 (d, J=2.6 Hz, 1H), 8.38 (s, 1H), 8.31 (d, J=2.9 Hz, 1H), 8.28 (s, 1H), 7.98 (s, 1H), 7.86 (dd, J=6.2, 2.2 Hz, 1H), 7.77 (dd, J=9.0, 2.9 Hz, 1H), 7.26 (d, J=2.4 Hz, 1H), 6.74 (dd, J=5.7, 2.4 Hz, 1H), 6.60 (dd, J=7.1, 6.3 Hz, 1H), 3.85 (s, 3H).

The following compounds were prepared with corresponding intermediates and reagents with reference to the preparation processes of compound 9 under suitable conditions recognized by the POSITA.

| Compound | Structural formula | MS $(M + H)^+$ | $^1$H NMR |
|---|---|---|---|
| 10 | 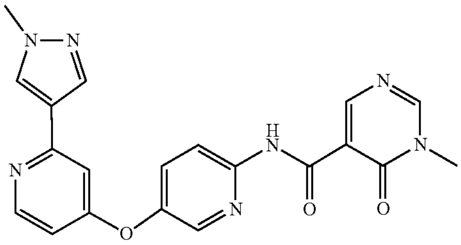 | 404.2 | $^1$H NMR (400 MHz, DMSO-d6) δ 11.81 (s, 1H), 8.82 (s, 2H), 8.42-8.18 (m, 4H), 7.96 (s, 1H), 7.79-7.75 (m, 1H), 7.24 (s, 1H), 6.73-6.71 (m, 1H), 3.83 (s, 3H), 3.56 (s, 3H). |

-continued

| Compound | Structural formula | MS (M + H)$^+$ | $^1$H NMR |
|---|---|---|---|
| 11 | 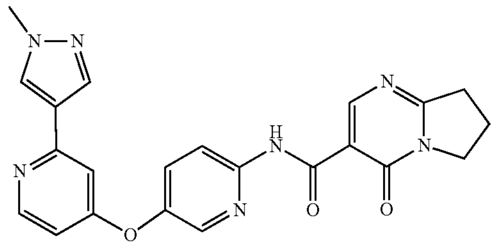 [SMILES: Cn1cc(-c2cc(Oc3ccc(NC(=O)c4cnc5n(c4=O)CCC5)nc3)ccn2)cn1] | 430.2 | $^1$H NMR (400 MHz, DMSO-d6) δ 11.76 (s, 1H), 8.81 (s, 1H), 8.43-8.17 (m, 4H), 7.96 (s, 1H), 7.76 (d, J = 8.4 Hz, 1H), 7.24 (s, 1H), 6.73 (s, 1H), 4.16 (t, J = 6.9 Hz, 2H), 3.83 (s, 3H), 3.18 (t, J = 7.6 Hz, 2H), 2.33-2.11 (m, 2H). |
| 12 | 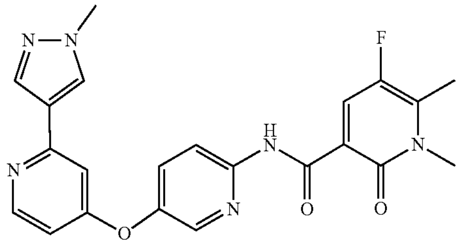 [SMILES: Cc1c(F)cc(C(=O)Nc2ccc(Oc3ccnc(-c4cnn(C)c4)c3)cn2)c(=O)n1C] | 435.1 | 1H NMR (400 MHz, CD3OD) δ 8.45 (dd, J = 9.0, 4.0 Hz, 2H), 8.37 (d, J = 5.8 Hz, 1H), 8.24 (d, J = 2.8 Hz, 1H), 7.99 (s, 1H), 7.91 (s, 1H), 7.61 (dd, J = 9.0, 2.8 Hz, 1H), 7.54 (s, 1H), 7.10 (d, J = 2.3 Hz, 1H), 6.76 (dd, J = 5.8, 2.4 Hz, 1H), 3.96 (s, 3H), 3.72 (s, 3H), 2.54 (d, J = 2.9 Hz, 3H). |
| 13 | 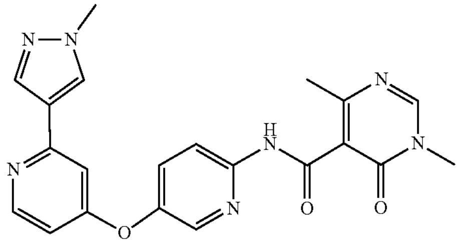 [SMILES: Cc1ncn(C)c(=O)c1C(=O)Nc1ccc(Oc2ccnc(-c3cnn(C)c3)c2)cn1] | 418.1 | $^1$H NMR (400 MHz, DMSO-d6) δ 11.47 (s, 1H), 8.55 (s, 1H), 8.39 (d, J = 5.7 Hz, 1H), 8.36-8.21 (m, 3H), 7.99 (s, 1H), 7.76 (dd, J = 9.0, 2.7 Hz, 1H), 7.27 (d, J = 1.9 Hz, 1H), 6.75 (dd, J = 5.6, 2.1 Hz, 1H), 3.86 (s, 3H), 3.48 (s, 3H), 2.44 (s, 3H). |
| 14 | 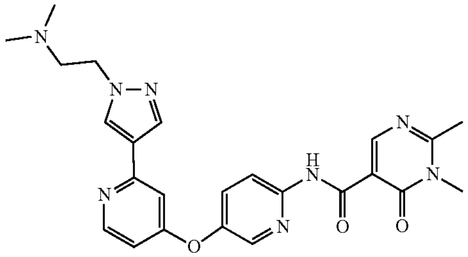 | 475.2 | $^1$H NMR (400 MHz, DMSO-d6) δ 11.85 (s, 1H), 8.74 (s, 1H), 8.43-8.26 (m, 4H), 7.97 (s, 1H), 7.78-7.74 (m, 1H), 7.25 (s, 1H), 6.73-6.70 (m, 1H), 4.19-4.16 (m, 2H), 3.57 (s, 3H), 2.65-2.61 (m, 5H), 2.13 (s, 6H). |
| 15 | 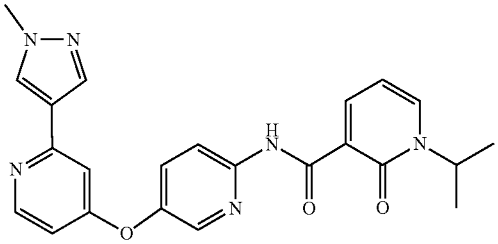 [SMILES: CC(C)n1cccc(C(=O)Nc2ccc(Oc3ccnc(-c4cnn(C)c4)c3)cn2)c1=O] | 432.2 | $^1$H NMR (400 MHz, DMSO-d6) δ 12.71 (s, 1H), 8.61-8.43 (m, 3H), 8.38-8.34 (m, 2H), 8.24-8.21 (m, 1H), 7.86-7.74 (m, 1H), 7.44 (s, 1H), 7.05 (s, 1H), 6.68-6.64 (m, 1H), 5.26-5.10 (m, 1H), 3.89 (s, 3H), 1.36 (d, J = 6.7 Hz, 6H). |
| 16 | 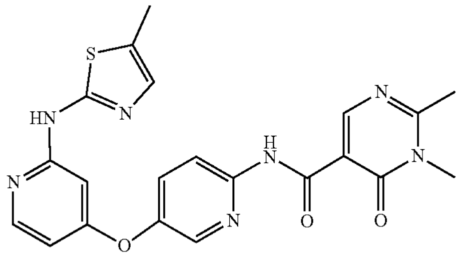 [SMILES: Cc1cnc(Nc2cc(Oc3ccc(NC(=O)c4cnc(C)n(C)c4=O)nc3)ccn2)s1] | 450.1 | $^1$H NMR (400 MHz, DMSO-d6) δ 11.88 (s, 1H), 10.83 (s, 1H), 8.76 (s, 1H), 8.37 (d, J = 9.0 Hz, 1H), 8.32 (d, J = 2.6 Hz, 1H), 8.17 (d, J = 5.8 Hz, 1H), 7.81 (dd, J = 9.0, 2.7 Hz, 1H), 6.99 (s, 1H), 6.63-6.56 (m, 1H), 6.53 (s, 1H), 3.60 (s, 3H), 2.66 (s, 3H), 2.31 (s, 3H). |

-continued

| Compound | Structural formula | MS (M + H)+ | ¹H NMR |
|---|---|---|---|
| 17 | 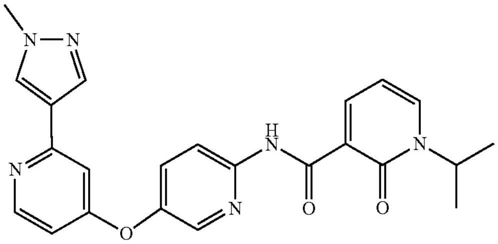 [SMILES: CC(C)n1cccc(C(=O)Nc2ccc(Oc3ccnc(-c4cnn(C)c4)c3)cn2)c1=O] | 430.2 | 1H NMR (400 MHz, DMSO-d6) δ 12.27 (s, 1H), 8.42 (d, J = 7.1 Hz, 1H), 8.33 (d, J = 5.7 Hz, 1H), 8.26-8.15 (m, 2H), 7.92 (s, 1H), 7.78 (d, J = 8.8 Hz, 2H), 7.19-7.15 (m, 3H), 6.75-6.56 (m, 2H), 5.24-5.19 (m, 1H), 3.82 (s, 3H), 1.35 (d, J = 6.8 Hz, 6H). |
| 18 | 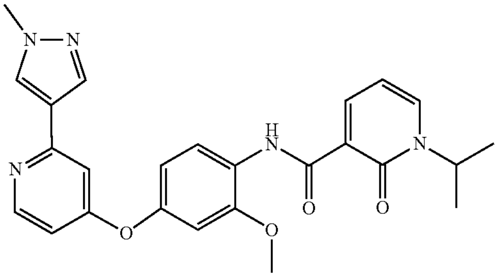 [SMILES: COc1cc(Oc2ccnc(-c3cnn(C)c3)c2)ccc1NC(=O)c1cccn(C(C)C)c1=O] | 460.0 | 1H NMR (400 MHz, DMSO-d6) δ 12.38 (s, 1H), 8.54 (d, J = 8.8 Hz, 1H), 8.42 (dd, J = 7.2, 1.5 Hz, 1H), 8.33 (d, J = 5.7 Hz, 1H), 8.22 (s, 1H), 8.16 (dd, J = 6.7, 1.6 Hz, 1H), 7.93 (s, 1H), 7.19 (d, J = 2.2 Hz, 1H), 6.96 (d, J = 2.3 Hz, 1H), 6.74 (dd, J = 8.8, 2.3 Hz, 1H), 6.67-6.55 (m, 2H), 5.30-5.20 (m, 1H), 3.84 (d, J = 16.8 Hz, 6H), 1.33 (d, J = 6.8 Hz, 6H). |
| 19 | 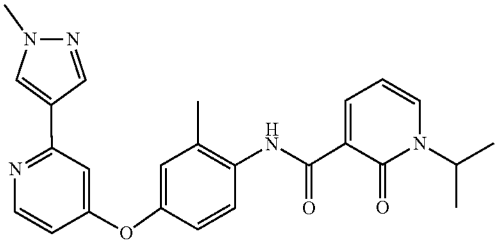 | 444.0 | 1H NMR (400 MHz, DMSO-d6) δ 12.18 (s, 1H), 8.45 (d, J = 6.8 Hz, 1H), 8.38 (d, J = 8.8 Hz, 1H), 8.33 (d, J = 5.7 Hz, 1H), 8.22 (s, 1H), 8.20 (d, J = 6.5 Hz, 1H), 7.94 (s, 1H), 7.20 (s, 1H), 7.10 (s, 1H), 7.02 (dd, J = 8.8, 2.0 Hz, 1H), 6.66 (m, 1H), 6.61 (dd, J = 5.3, 1.7 Hz, 1H), 5.26 (m, 1H), 3.83 (s, 3H), 2.34 (s, 3H), 1.35 (d, J = 6.8 Hz, 6H). |
| 20 | 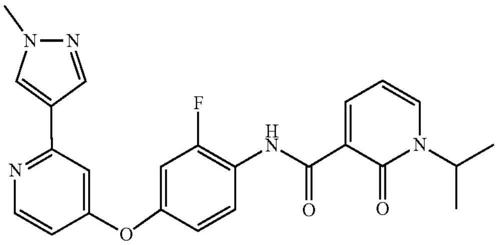 [SMILES: CC(C)n1cccc(C(=O)Nc2ccc(Oc3ccnc(-c4cnn(C)c4)c3)cc2F)c1=O] | 448.2 | 1H NMR (400 MHz, a mixture of CD3OD and $CDC1_3$) δ 8.56-8.45 (m, 2H), 8.31 (d, J = 5.6 Hz, 1H), 8.02 (s, 1H), 7.97 (dd, J = 6.7, 2.0 Hz, 1H), 7.90 (s, 1H), 7.13 (d, J = 2.2 Hz, 1H), 7.03 (dd, J = 11.2, 2.6 Hz, 1H), 6.96 (d, J = 8.8 Hz, 1H), 6.74 (dd, J = 5.8, 2.3 Hz, 1H), 6.64 (m, 1H), 5.34 (m, 1H), 3.90 (s, 3H), 1.43 (d, J = 6.8 Hz, 6H). |
| 21 | 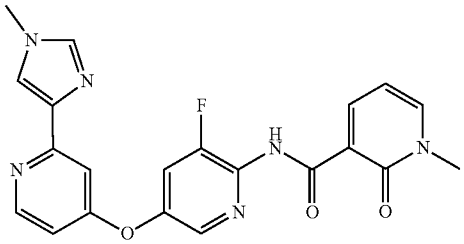 | 421.0 | 1H NMR (400 MHz, DMSO-d6) δ 12.24 (s, 1H), 8.43 (dd, J = 7.3, 2.1 Hz, 1H), 8.39 (d, J = 5.6 Hz, 1H), 8.28 (d, J = 2.4 Hz, 1H), 8.19 (dd, J = 6.5, 2.1 Hz, 1H), 7.99 (dd, J = 10.4, 2.4 Hz, 1H), 7.70 (s, 1H), 7.62 (s, 1H), 7.31 (s, 1H), 6.87 (dd, J = 5.5, 2.3 Hz, 1H), 6.63-6.56 (m, 1H), 3.67 (s, 3H), 3.62 (s, 3H). |
| 22 | 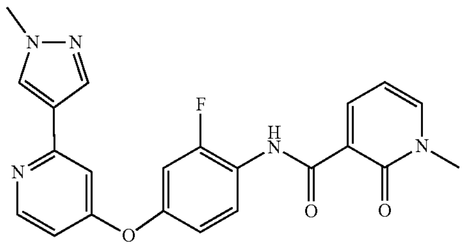 | 421.1 | 1H NMR (400 MHz, DMSO-d6) δ 12.25 (s, 1H), 8.43 (dd, J = 7.3, 2.1 Hz, 1H), 8.40 (d, J = 5.7 Hz, 1H), 8.27 (s, 1H), 8.24 (d, J = 2.3 Hz, 1H), 8.18 (dd, J = 6.5, 2.0 Hz, 1H), 7.98 (s, 1H), 7.93 (dd, J = 10.5, 2.3 Hz, 1H), 7.32 (d, J = 2.2 Hz, 1H), 6.80 (dd, J = 5.7, 2.3 Hz, 1H), 6.60 (m, 1H), 3.83 (s, 3H), 3.62 (s, 3H). |

-continued

| Compound | Structural formula | MS (M + H)+ | 1H NMR |
|---|---|---|---|
| 23 | 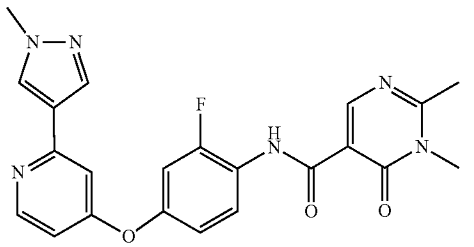 | 436.1 | 1H NMR (400 MHz, DMSO-d6) δ 11.40 (s, 1H), 8.69 (s, 1H), 8.41 (d, J = 5.7 Hz, 1H), 8.28 (s, 1H), 8.26 (d, J = 2.3 Hz, 1H), 7.98 (s, 1H), 7.94 (dd, J = 10.4, 2.3 Hz, 1H), 7.32 (d, J = 2.1 Hz, 1H), 6.81 (dd, J = 5.7, 2.3 Hz, 1H), 3.85 (s, 3H), 3.58 (s, 3H), 2.63 (s, 3H). |
| 24 | 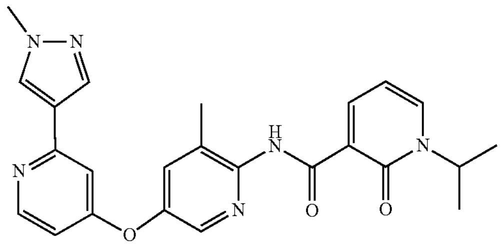 [SMILES: Cc1cc(Oc2ccnc(-c3cnn(C)c3)c2)cnc1NC(=O)c1cccn(C(C)C)c1=O] | 445.2 | 1H NMR (400 MHz, DMSO-d6) δ 12.08 (s, 1H), 8.42 (d, J = 7.1 Hz, 1H), 8.38 (d, J = 5.6 Hz, 1H), 8.26 (s, 1H), 8.22-8.17 (m, 2H), 7.97 (s, 1H), 7.64 (s, 1H), 7.29 (d, J = 1.6 Hz, 1H), 6.70 (d, J = 3.5 Hz, 1H), 6.64 rn, 1H), 5.23 (m, 1H), 3.84 (s, 3H), 2.25 (s, 3H), 1.36 (d, J = 6.7 Hz, 6H). |
| 25 | 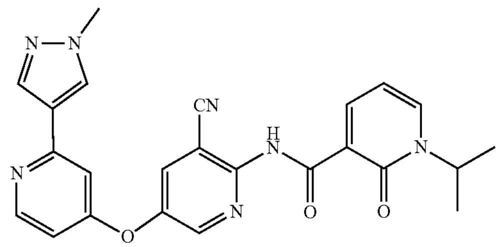 [SMILES: CC(C)n1cccc(C(=O)Nc2ncc(Oc3ccnc(-c4cnn(C)c4)c3)cc2C#N)c1=O] | 456.1 | 1H NMR (400 MHz, DMSO-d6) δ 12.66 (s, 1H), 8.67 (s, 1H), 8.49-8.45 (m, 1H), 8.42-8.39 (m, 2H), 8.28 (s, 2H), 7.99 (s, 1H), 7.33 (s, 1H), 6.84-6.81 (m, 1H), 6.70-6.66 (m, 1H), 5.31-5.16 (m, 1H), 3.84 (s, 3H), 1.37 (d, J = 6.6 Hz, 6H). |
| 26 | 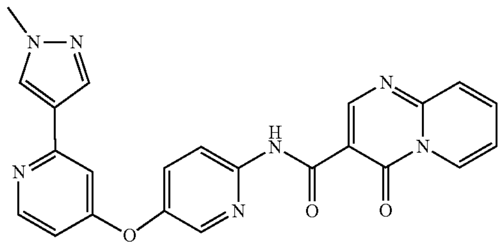 [SMILES: Cn1cc(-c2cc(Oc3ccc(NC(=O)c4cnc5ccccn5c4=O)nc3)ccn2)cn1] | 440.2 | $^{1}$H NMR (400 MHz, DMSO-d6) δ 11.66 (s, 1H), 9.25 (d, J = 6.9 Hz, 1H), 9.13 (s, 1H), 8.44-8.34 (m, 2H), 8.30-8.21 (m, 3H), 7.98-7.89 (m, 2H), 7.76 (dd, J = 8.9, 2.7 Hz, 1H), 7.65 (m, 1H), 7.23 (d, J = 2.1 Hz, 1H), 6.71 (dd, J = 5.6, 2.3 Hz, 1H), 3.82 (s, 3H). |
| 27 | 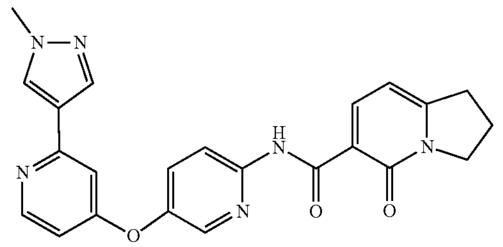 [SMILES: Cn1cc(-c2cc(Oc3ccc(NC(=O)c4ccc5n(c4=O)CCC5)nc3)ccn2)cn1] | 429.2 | $^{1}$H NMR (400 MHz, DMSO-d6) δ 12.56 (s, 1H), 8.43 (d, J = 7.5 Hz, 1H), 8.38 (d, J = 3.5 Hz, 1H), 8.36 (s, 1H), 8.28 (d, J = 2.9 Hz, 1H), 8.25 (s, 1H), 7.96 (s, 1H), 7.73 (dd, J = 9.0, 2.8 Hz, 1H), 7.23 (d, J = 2.4 Hz, 1H), 6.71 (dd, J = 5.7, 2.4 Hz, 1H), 6.58 (d, J = 7.5 Hz, 1H), 4.16 (t, J = 7.3 Hz, 2H), 3.83 (s, 3H), 3.21 (t, J = 7.8 Hz, 2H), 2.26-2.11 (m, 2H). |
| 28 | 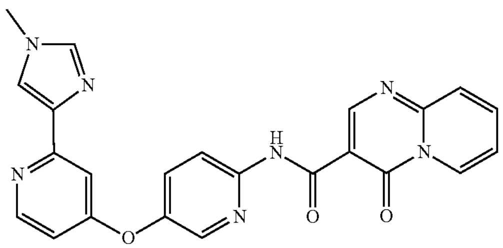 [SMILES: Cn1cnc(-c2cc(Oc3ccc(NC(=O)c4cnc5ccccn5c4=O)nc3)ccn2)c1] | 440.0 | $^{1}$H NMR (400 MHz, DMSO-d6) δ 11.69 (s, 1H), 9.27 (d, J = 7.0 Hz, 1H), 9.15 (s, 1H), 8.40 (d, J = 9.0 Hz, 1H), 8.37 (d, J = 5.7 Hz, 1H), 8.33 (d, J = 2.8 Hz, 1H), 8.29-8.22 (m, 1H), 7.95 (d, J = 8.8 Hz, 1H), 7.81 (dd, J = 9.0, 2.9 Hz, 1H), 7.71-7.63 (m, 2H), 7.58 (s, 1H), 7.26 (d, J = 2.5 Hz, 1H), 6.82 (dd, J = 5.6, 2.6 Hz, 1H), 3.66 (s, 3H). |

-continued

| Compound | Structural formula | MS (M + H)+ | ¹H NMR |
|---|---|---|---|
| 29 | 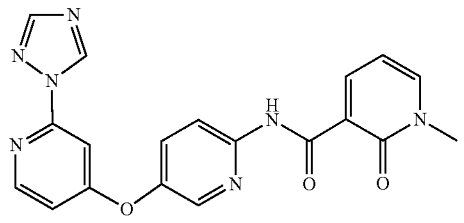 [SMILES: Cn1cccc(C(=O)Nc2ccc(Oc3ccnc(-n4cncn4)c3)cn2)c1=O] | 390.1 | ¹H NMR (400 MHz, DMSO-d6) δ 12.67 (s, 1H), 9.35 (s, 1H), 8.48 (dd, J = 7.4, 2.2 Hz, 1H), 8.42 (d, J = 5.8 Hz, 1H), 8.39 (d, J = 9.0 Hz, 1H), 8.36 (d, J = 2.9 Hz, 1H), 8.23 (s, 1H), 8.18 (dd, J = 6.5, 2.2 Hz, 1H), 7.84 (dd, J = 9.0, 2.9 Hz, 1H), 7.27 (d, J = 2.4 Hz, 1H), 7.09 (dd, J = 5.8, 2.4 Hz, 1H), 6.68-6.54 (m, 1H), 3.62 (s, 3H). |
| 30 | 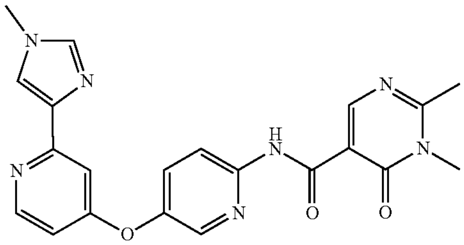 | 418.2 | ¹H NMR (400 MHz, DMSO-d6) δ 11.87 (s, 1H), 8.74 (s, 1H), 8.44-8.26 (m, 3H), 7.86-7.76 (m, 1H), 7.68 (s, 1H), 7.59 (s, 1H), 7.26 (s, 1H), 6.90-6.75 (m, 1H), 3.67 (s, 3H), 3.58 (s, 3H), 2.63 (s, 3H). |
| 31 | 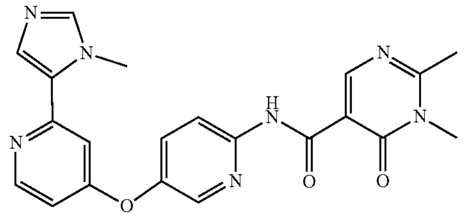 [SMILES: Cc1ncc(C(=O)Nc2ccc(Oc3ccnc(-c4cncn4C)c3)cn2)c(=O)n1C] | 418.2 | ¹H NMR (400 MHz, DMSO-d6) δ 11.85 (s, 1H), 8.73 (s, 1H), 8.47 (d, J = 5.6 Hz, 1H), 8.40-8.26 (m, 2H), 7.78 (dd, J = 8.9, 2.5 Hz, 1H), 7.72 (s, 1H), 7.48 (s, 1H), 7.35 (d, J = 1.8 Hz, 1H), 6.86-6.75 (m, 1H), 3.91 (s, 3H), 3.57 (s, 3H), 2.63 (s, 3H). |
| 32 | 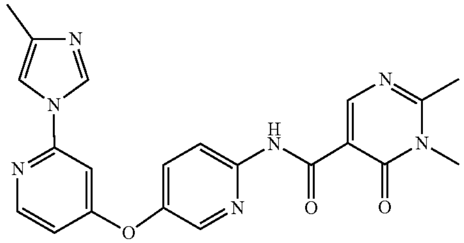 | 418.2 | ¹H NMR (400 MHz, DMSO-d6) δ 11.86 (s, 1H), 8.74 (s, 1H), 8.46-8.26 (m, 4H), 7.80 (d, J = 7.2 Hz, 1H), 7.64 (s, 1H), 7.40 (s, 1H), 6.86 (d, J = 4.1 Hz, 1H), 3.58 (s, 3H), 2.63 (s, 3H), 2.13 (s, 3H). |
| 33 | 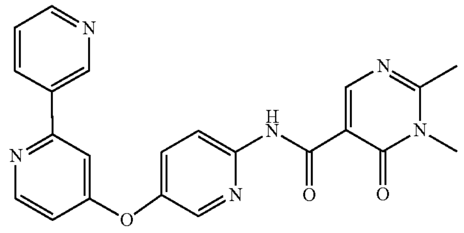 [SMILES: Cc1ncc(C(=O)Nc2ccc(Oc3ccnc(-c4cccnc4)c3)cn2)c(=O)n1C] | 415.1 | ¹H NMR (400 MHz, DMSO-d6) δ 11.86 (s, 1H), 9.23 (dd, J = 2.3, 0.7 Hz, 1H), 8.74 (s, 1H), 8.62 (dd, J = 4.8, 1.6 Hz, 1H), 8.58 (d, J = 5.7 Hz, 1H), 8.42-8.37 (m, 1H), 8.35 (m, 2H), 7.81 (dd, J = 9.0, 3.0 Hz, 1H), 7.70 (d, J = 2.4 Hz, 1H), 7.48 (m, 1H), 6.95 (dd, J = 5.7, 2.4 Hz, 1H), 3.58 (s, 3H), 2.63 (s, 3H). |
| 34 | 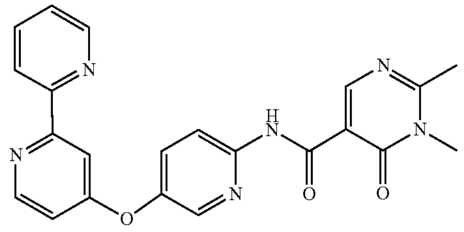 [SMILES: Cc1ncc(C(=O)Nc2ccc(Oc3ccnc(-c4ccccn4)c3)cn2)c(=O)n1C] | 415.1 | ¹H NMR (400 MHz, DMSO-d6) δ 12.04-11.95 (br, 1H), 8.92-8.81 (m, 1H), 8.76-8.64 (m, 2H), 8.77-8.62 (m, 3H), 8.10-7.99 (m, 1H), 7.99-7.86 (m, 2H), 7.61-7.46 (m, 1H), 7.32-7.15 (m, 1H), 3.76-3.63 (m, 3H), 2.79-2.68 (m, 3H). |

-continued

| Compound | Structural formula | MS (M + H)$^+$ | $^1$H NMR |
| --- | --- | --- | --- |
| 35 | 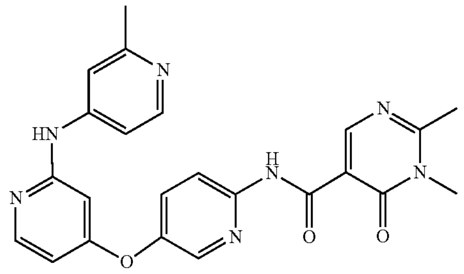 [SMILES: Cc1cc(Nc2cc(Oc3ccc(NC(=O)c4cnc(C)n(C)c4=O)nc3)ccn2)ccn1] | 444.1 | $^1$H NMR (400 MHz, DMSO-d6) δ 11.89 (s, 1H), 9.43 (s, 1H), 8.77 (s, 1H), 8.38 (d, J = 9.0 Hz, 1H), 8.34 (d, J = 2.7 Hz, 1H), 8.19 (d, J = 5.8 Hz, 1H), 8.15 (d, J = 5.7 Hz, 1H), 7.83 (dd, J = 9.0, 2.9 Hz, 1H), 7.49 (s, 1H), 7.43 (dd, J = 5.7, 1.8 Hz, 1H), 6.63 (dd, J = 5.8, 2.2 Hz, 1H), 6.33 (d, J = 2.1 Hz, 1H), 3.61 (s, 3H), 2.66 (s, 3H), 2.36 (s, 3H). |
| 36 | 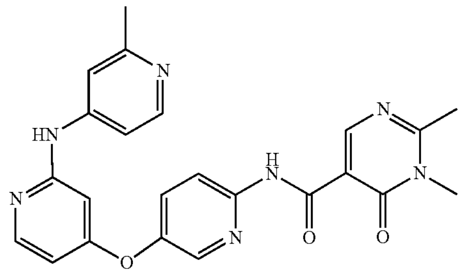 [SMILES: Cc1cc(Nc2cc(Oc3ccc(NC(=O)c4cnc(C)n(C)c4=O)nc3)ccn2)ccn1] | 444.1 | $^1$H NMR (400 MHz, DMSO-d6) δ 11.88 (s, 1H), 9.64 (s, 1H), 8.77 (s, 1H), 8.38 (d, J = 9.0 Hz, 1H), 8.33 (d, J = 2.8 Hz, 1H), 8.12 (d, J = 5.7 Hz, 1H), 7.82 (dd, J = 9.0, 2.8 Hz, 1H), 7.64 (d, J = 2.2 Hz, 1H), 7.49 (m, 1H), 7.28 (d, J = 8.3 Hz, 1H), 6.66 (d, J = 7.3 Hz, 1H), 6.58 (dd, J = 5.7, 2.3 Hz, 1H), 3.60 (s, 3H), 2.66 (s, 3H), 2.16 (s, 3H). |
| 37 | 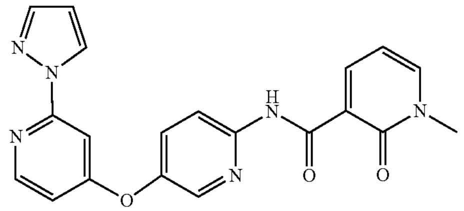 [SMILES: Cn1cccc(C(=O)Nc2ccc(Oc3ccnc(-n4cccn4)c3)cn2)c1=O] | 389.0 | $^1$H NMR (400 MHz, DMSO-d6) δ 12.67 (s, 1H), 8.58 (d, J = 2.6 Hz, 1H), 8.48 (dd, J = 7.3, 2.1 Hz, 1H), 8.40 (d, J = 9.0 Hz, 1H), 8.37-8.35 (m, 2H), 8.18 (dd, J = 6.5, 2.2 Hz, 1H), 7.84 (dd, J = 9.0, 2.9 Hz, 1H), 7.74 (d, J = 1.5 Hz, 1H), 7.30 (d, J = 2.4 Hz, 1H), 6.99 (dd, J = 5.8, 2.4 Hz, 1H), 6.62-6.59 (m, 1H), 6.55-6.53 (m, 1H), 3.62 (s, 3H). |
| 38 | 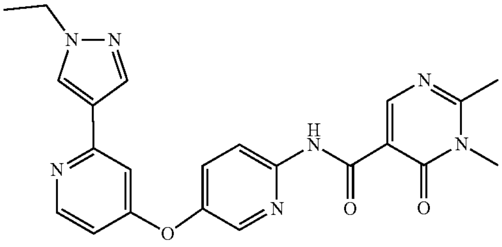 [SMILES: CCn1cc(-c2cc(Oc3ccc(NC(=O)c4cnc(C)n(C)c4=O)nc3)ccn2)cn1] | 432.1 | 1H NMR (400 MHz, DMSO-d6) δ 11.85 (s, 1H), 8.74 (s, 1H), 8.38 (d, J = 5.7 Hz, 1H), 8.34 (d, J = 9.2 Hz, 1H), 8.31-8.29 (m, 2H), 7.97 (s, 1H), 7.77 (dd, J = 9.0, 2.9 Hz, 1H), 7.25 (d, J = 2.4 Hz, 1H), 6.73 (dd, J = 5.7, 2.4 Hz, 1H), 4.12 (q, J = 12 Hz, 8 Hz, 2H), 3.58 (s, 3H), 2.63 (s, 3H), 1.36 (t, J = 12 Hz, 3H). |
| 39 | 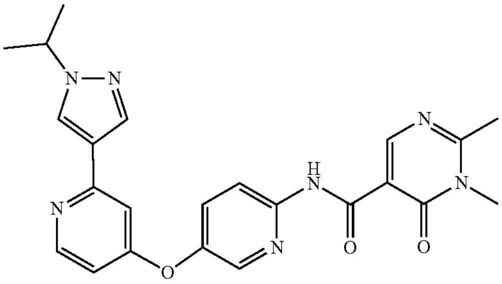 [SMILES: Cc1ncc(C(=O)Nc2ccc(Oc3ccnc(-c4cnn(C(C)C)c4)c3)cn2)c(=O)n1C] | 446.1 | $^1$H NMR (400 MHz, DMSO-d6) δ 11.85 (s, 1H), 8.74 (s, 1H), 8.38 (d, J = 5.7 Hz, 1H), 8.35-8.33 (m, 2H), 8.30 (d, J = 2.8 Hz, 1H), 7.97 (s, 1H), 7.76 (dd, J = 9.0, 2.9 Hz, 1H), 7.28 (d, J = 2.4 Hz, 1H), 6.72 (dd, J = 5.7, 2.4 Hz, 1H), 4.48 (dd, J = 13.3, 6.7 Hz, 1H), 3.58 (s, 3H), 2.63 (s, 3H), 1.42 (s, 3H), 1.40 (s, 3H). |
| 40 | 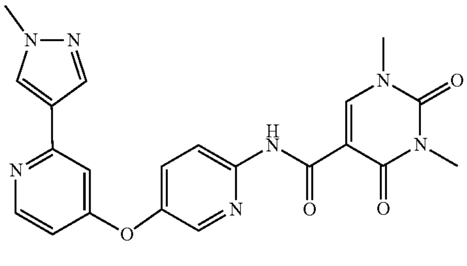 [SMILES: Cn1cc(-c2cc(Oc3ccc(NC(=O)c4cn(C)c(=O)n(C)c4=O)nc3)ccn2)cn1] | 434.0 | $^1$H NMR (400 MHz, DMSO-d6) δ 11.56 (s, 1H), 8.78 (s, 1H), 8.38-8.36 (m, 1H), 8.33-8.28 (m, J = 2H), 8.25 (s, 1H), 7.96 (s, 1H), 7.78-7.74 (m, 1H), 7.24 (s, 1H), 6.73-6.71 (m, 1H), 3.84 (s, 3H), 3.49 (s, 3H), 3.26 (s, 3H). |

-continued

| Compound | Structural formula | MS (M + H)$^+$ | $^{1}$H NMR |
|---|---|---|---|
| 41 | 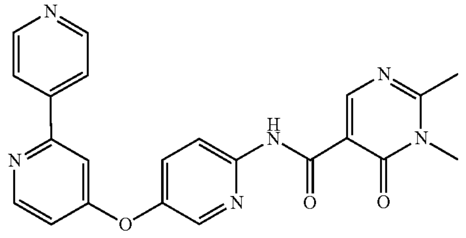 [SMILES: Cc1ncc(C(=O)Nc2ccc(Oc3ccnc(-c4ccncc4)c3)cn2)c(=O)n1C] | 415.0 | $^{1}$H NMR (400 MHz, DMSO-d6) δ 11.87 (s, 1H), 8.74 (s, 1H), 8.67-8.66 (m, 2H), 8.61 (d, J = 5.6 Hz, 1H), 8.38-8.32 (m, 2H), 8.03- 8.02 (m, 2H), 7.82 (dd, J = 8.9, 3.0 Hz, 1H), 7.76 (d, J = 2.3 Hz, 1H), 7.02 (dd, J = 5.6, 2.4 Hz, 1H), 3.58 (s, 3H), 2.63 (s, 3H). |
| 42 | 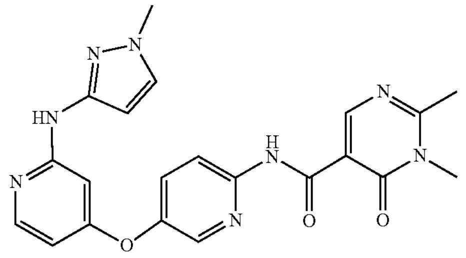 [SMILES: Cc1ncc(C(=O)Nc2ccc(Oc3ccnc(Nc4ccn(C)n4)c3)cn2)c(=O)n1C] | 433.0 | $^{1}$H NMR (400 MHz, DMSO-d6) δ 11.84 (s, 1H), 9.19 (s, 1H), 8.75 (s, 1H), 8.34 (d, J = 9.0 Hz, 1H), 8.27 (d, J = 2.9 Hz, 1H), 8.01 (d, J = 5.8 Hz, 1H), 7.75 (dd, J = 9.0, 2.9 Hz, 1H), 7.45 (d, J = 2.2 Hz, 1H), 6.90 (d, J = 2.2 Hz, 1H), 6.33 (dd, J = 5.7, 2.3 Hz, 1H), 6.17 (d, J = 2.2 Hz, 1H), 3.65 (s, 3H), 3.59 (s, 3H), 2.64 (s, 3H). |
| 43 | 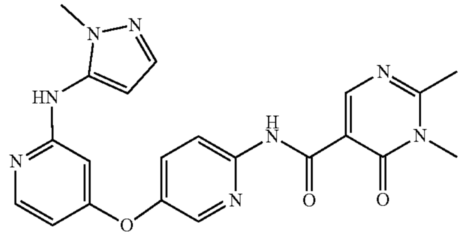 [SMILES: Cc1ncc(C(=O)Nc2ccc(Oc3ccnc(Nc4ccnn4C)c3)cn2)c(=O)n1C] | 433.1 | $^{1}$H NMR (400 MHz, DMSO-d6) δ 11.85 (s, 1H), 8.74 (s, 1H), 8.73 (s, 1H), 8.34 (d, J = 9.0 Hz, 1H), 8.29 (d, J = 3.5 Hz, 1H), 8.01 (d, J = 5.8 Hz, 1H), 7.77 (dd, J = 6.7, 3.3 Hz, 1H), 7.26 (d, J = 1.9 Hz, 1H), 6.46 (dd, J = 5.8, 2.3 Hz, 1H), 6.19-6.18 (m, 2H), 3.60 (s, 3H), 3.58 (s, 3H), 2.63 (s, 3H). |
| 44 | 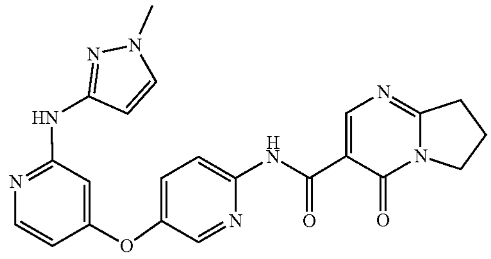 [SMILES: Cn1ccc(Nc2cc(Oc3ccc(NC(=O)c4cnc5n(c4=O)CCC5)nc3)ccn2)n1] | 445.1 | $^{1}$H NMR (400 MHz, DMSO-d6) δ 11.79 (s, 1H), 8.82 (s, 1H), 8.37-8.35 (m, 1H), 8.32 (d, J = 2.9 Hz, 1H), 8.11 (s, 1H), 8.08 (d, J = 9.0 Hz, 1H), 7.81 (dd, J = 9.0, 2.9 Hz, 1H), 7.57 (s, 1H), 6.74 (s, 1H), 6.57 (s, 1H), 6.10 (d, J = 2.2 Hz, 1H), 4.15 (t, J = 6.6 Hz, 2H), 3.72 (s, 3H), 3.18 (t, J = 6.6 Hz, 2H), 2.25-2.19 (m, 2H). |
| 45 | 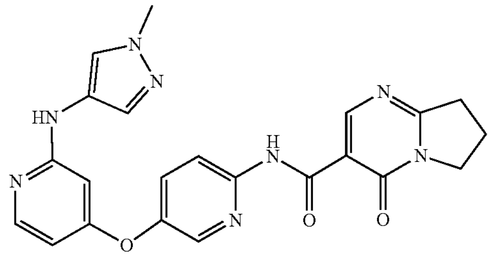 | 445.1 | $^{1}$H NMR (400 MHz, DMSO-d6) δ 11.78 (s, 1H), 8.84 (s, 1H), 8.76 (s, 1H), 8.35 (d, J = 9.0 Hz, 1H), 8.29 (d, J = 2.8 Hz, 1H), 8.03 (d, J = 5.8 Hz, 1H), 7.89 (s, 1H), 7.77 (dd, J = 9.0, 2.9 Hz, 1H), 7.33 (s, 1H), 6.34 (dd, J = 5.8, 2.2 Hz, 1H), 6.05 (d, J = 2.1 Hz, 1H), 4.18 (t, J = 8.0 Hz, 2H), 3.78 (s, 3H), 3.21 (t, J = 8.0 Hz, 2H), 2.29-2.20 (m, 2H). |
| 46 | 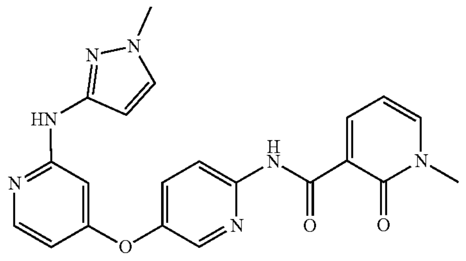 [SMILES: Cn1ccc(Nc2cc(Oc3ccc(NC(=O)c4cccn(C)c4=O)nc3)ccn2)n1] | 418.1 | $^{1}$H NMR (400 MHz, DMSO-d6) δ 12.64 (s, 1H), 9.21 (s, 1H), 8.50 (dd, J = 7.3, 2.1 Hz, 1H), 8.38 (d, J = 9.0 Hz, 1H), 8.28 (d, J = 2.8 Hz, 1H), 8.20 (dd, J = 6.5, 2.0 Hz, 1H), 8.02 (d, J = 5.8 Hz, 1H), 7.75 (dd, J = 9.0, 2.9 Hz, 1H), 7.47 (d, J = 2.1 Hz, 1H), 6.91 (d, J = 1.7 Hz, 1H), 6.64-6.61 (m, 1H), 6.35 (dd, J = 5.8, 2.3 Hz, 1H), 6.19 (d, J = 2.0 Hz, 1H), 3.66 (s, 3H), 3.64 (s, 3H). |

-continued

| Compound | Structural formula | MS (M + H)+ | $^1$H NMR |
|---|---|---|---|
| 47 | 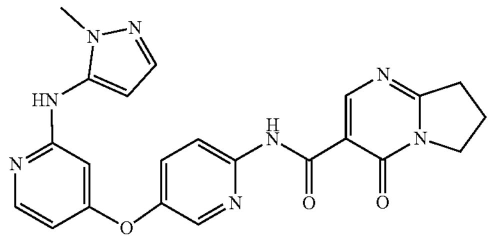 [SMILES: Cn1nccc1Nc1cc(Oc2ccc(NC(=O)c3cnc4n(c3=O)CCC4)nc2)ccn1] | 445.1 | $^1$H NMR (400 MHz, DMSO-d6) δ 11.79 (s, 1H), 8.83 (s, 1H), 8.76 (s, 1H), 8.36 (d, J = 9.0 Hz, 1H), 8.31 (d, J = 2.8 Hz, 1H), 8.03 (d, J = 5.8 Hz, 1H), 7.80 (dd, J = 9.0, 2.9 Hz, 1H), 7.28 (d, J = 1.8 Hz, 1H), 6.48 (dd, J = 5.8, 2.2 Hz, 1H), 6.22-6.20 (m, 2H), 4.17 (t, J = 8.0 Hz, 2H), 3.62 (s, 3H), 3.21 (t, J = 8.0 Hz, 2H), 2.28-2.20 (m, 2H). |
| 48 | 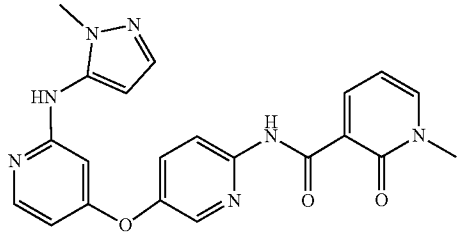 [SMILES: Cn1nccc1Nc1cc(Oc2ccc(NC(=O)c3cccn(C)c3=O)nc2)ccn1] | 418.1 | $^1$H NMR (400 MHz, DMSO-d6) δ 12.65 (s, 1H), 8.75 (s, 1H), 8.50 (dd, J = 7.4, 2.1 Hz, 1H), 8.39 (d, J = 9.0 Hz, 1H), 8.30 (d, J = 2.8 Hz, 1H), 8.20 (dd, J = 6.5, 2.1 Hz, 1H), 8.03 (d, J = 5.8 Hz, 1H), 7.78 (dd, J = 9.0, 2.9 Hz, 1H), 7.28 (d, J = 1.8 Hz, 1H), 6.64-6.61 (m, 1H), 6.48 (dd, J = 5.8, 2.2 Hz, 1H), 6.21-6.20 (m, 2H), 3.64 (s, 3H), 3.62 (s, 3H). |
| 49 | 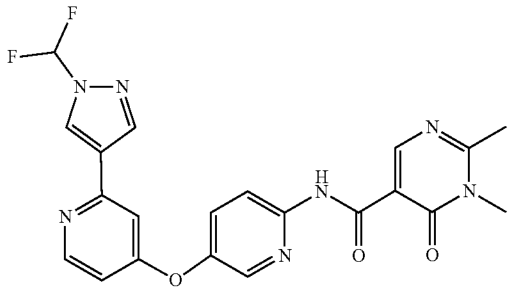 [SMILES: Cc1ncc(C(=O)Nc2ccc(Oc3ccnc(-c4cnn(C(F)F)c4)c3)cn2)c(=O)n1C] | 454.1 | $^1$H NMR (400 MHz, DMSO-d6) δ 11.88 (s, 1H), 8.85 (s, 1H), 8.76 (s, 1H), 8.47 (d, J = 5.7 Hz, 1H), 8.39-8.36 (m, 2H), 8.34 (d, J = 2.8 Hz, 1H), 7.99 (s, 0.25H), 7.83 (s, 0.5H), 7.81 (dd, J = 9.0, 2.9 Hz, 1H), 7.69 (s, 0.25H), 7.48 (d, J = 2.3 Hz, 1H), 6.87 (dd, J = 5.7, 2.4 Hz, 1H), 3.60 (s, 3H), 2.66 (s, 3H). |
| 50 | 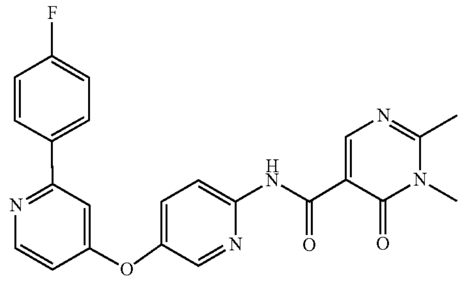 [SMILES: Cc1ncc(C(=O)Nc2ccc(Oc3ccnc(-c4ccc(F)cc4)c3)cn2)c(=O)n1C] | 432.1 | $^1$H NMR (400 MHz, DMSO-d6) δ 11.88 (s, 1H), 8.76 (s, 1H), 8.56 (d, J = 5.6 Hz, 1H), 8.39-8.35 (m, 2H), 8.14-8.10 (m, 2H), 7.83 (dd, J = 9.0, 2.9 Hz, 1H), 7.58 (d, J = 2.2 Hz, 1H), 7.32-7.27 (m, 2H), 6.92 (dd, J = 5.6, 2.3 Hz, 1H), 3.60 (s, 3H), 2.66 (s, 3H). |
| 51 | 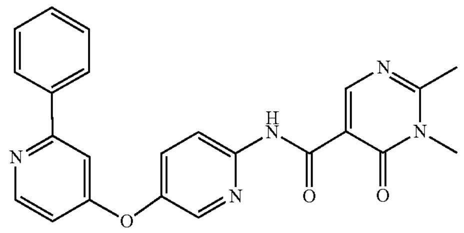 [SMILES: Cc1ncc(C(=O)Nc2ccc(Oc3ccnc(-c4ccccc4)c3)cn2)c(=O)n1C] | 414.1 | $^1$H NMR (400 MHz, DMSO-d6) δ 11.88 (s, 1H), 8.76 (s, 1H), 8.57 (d, J = 5.6 Hz, 1H), 8.39-8.36 (m, 2H), 8.07-8.04 (m, 2H), 7.83 (dd, J = 9.0, 2.9 Hz, 1H), 7.57 (d, J = 2.3 Hz, 1H), 7.50-7.43 (m, 3H), 6.93 (dd, J = 5.6, 2.4 Hz, 1H), 3.60 (s, 3H), 2.65 (s, 3H). |
| 52 | 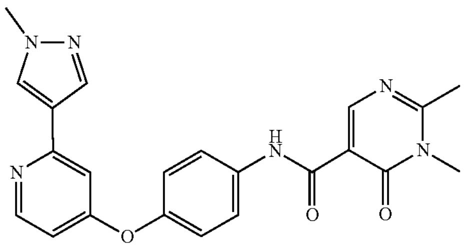 | 417.1 | $^1$H NMR (400 MHz, DMSO-d6) δ 11.39 (s, 1H), 8.69 (s, 1H), 8.36 (d, J = 5.8 Hz, 1H), 8.25 (s, 1H), 7.96 (s, 1H), 7.81-7.78 (m, 2H), 7.23 (d, J = 2.1 Hz, 1H), 7.21-7.18 (m, 2H), 6.66 (dd, J = 5.7, 2.1 Hz, 1H), 3.84 (s, 3H), 3.58 (s, 3H), 2.63 (s, 3H). |

-continued

| Compound | Structural formula | MS (M + H)+ | $^1$H NMR |
| --- | --- | --- | --- |
| 53 | 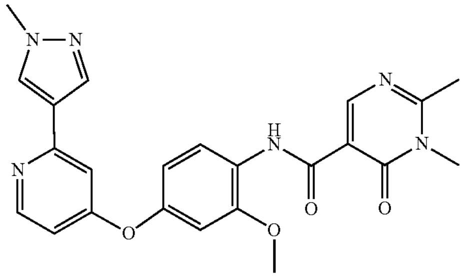 | 447.1 | 1H NMR (400 MHz, DMSO-d6) δ 11.64 (s, 1H), 8.70 (s, 1H), 8.51 (d, J = 8.8 Hz, 1H), 8.35 (d, J = 5.7 Hz, 1H), 8.24 (s, 1H), 7.94 (s, 1H), 7.21 (d, J = 2.4 Hz, 1H), 6.99 (d, J = 2.5 Hz, 1H), 6.77 (dd, J = 8.8, 2.5 Hz, 1H), 6.66 (dd, J = 5.5, 2.2 Hz, 1H), 3.88 (s, 3H), 3.84 (s, 3H), 3.57 (s, 3H), 2.62 (s, 3H). |
| 54 | 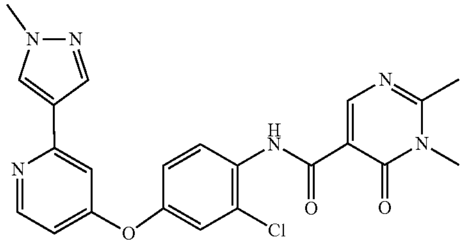 | 451.1 | 1H NMR (400 MHz, DMSO-d6) δ 11.86 (s, 1H), 8.74 (s, 1H), 8.60 (d, J = 9.1 Hz, 1H), 8.37 (d, J = 5.7 Hz, 1H), 8.26 (s, 1H), 7.96 (s, 1H), 7.48 (d, J = 5.7 Hz, 1H), 7.25-7.22 (m , 2H), 6.70 (dd, J = 5.7, 2.1 Hz, 1H), 3.84 (s, 3H), 3.58 (s, 3H), 2.63 (s, 3H). |
| 55 | 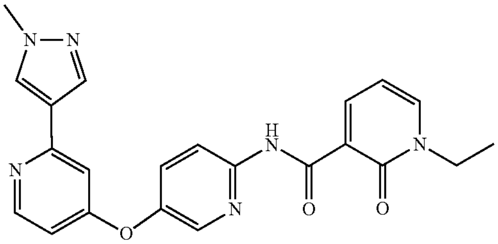 [SMILES: CCn1cccc(C(=O)Nc2ccc(Oc3ccnc(-c4cnn(C)c4)c3)cn2)c1=O] | 417.2 | 1H NMR (400 MHz, DMSO-d6) δ 12.66 (s, 1H), 8.47 (dd, J = 7.3, 2.2 Hz, 1H), 8.37 (s, 1H), 8.36-8.34 (m, 1H), 8.28 (dd, J = 2.9, 0.6 Hz, 1H), 8.25 (s, 1H), 8.21-8.16 (m, 1H), 7.95 (d, J = 0.7 Hz, 1H), 7.74 (dd, J = 9.0, 3.0 Hz, 1H), 7.27-7.21 (m, 1H), 6.71 (dd, J = 5.7, 2.4 Hz, 1H), 6.62 (dd, J = 7.3, 6.5 Hz, 1H), 4.10 (q, J = 7.1 Hz, 2H), 3.82 (s, 3H), 1.29 (t, J = 7.1 Hz, 3H). |
| 56 | 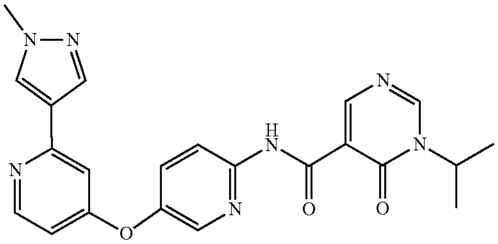 [SMILES: CC(C)n1cncc(C(=O)Nc2ccc(Oc3ccnc(-c4cnn(C)c4)c3)cn2)c1=O] | 432.2 | 1H NMR (400 MHz, DMSO-d6) δ 11.85 (s, 1H), 8.90 (s, 1H), 8.82 (s, 1H), 8.37 (d, J = 5.7 Hz, 1H), 8.33 (d, J = 9.0 Hz, 1H), 8.30 (d, J = 2.9 Hz, 1H), 8.25 (s, 1H), 7.95 (s, 1H), 7.77 (dd, J = 9.0, 2.9 Hz, 1H), 7.24 (d, J = 2.4 Hz, 1H), 6.71 (dd, J = 5.7, 2.3 Hz, 1H), 5.06-4.95 (m, 1H), 3.83 (s, 3H), 1.44 (d, J = 6.8 Hz, 6H). |
| 57 | 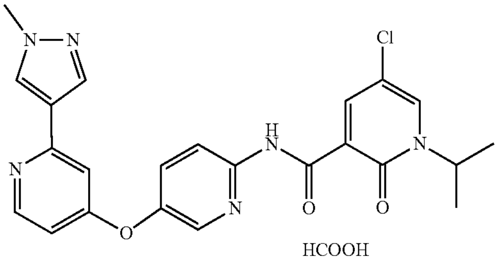 [SMILES: CC(C)n1cc(Cl)cc(C(=O)Nc2ccc(Oc3ccnc(-c4cnn(C)c4)c3)cn2)c1=O ; "HCOOH"] HCOOH | 465.1 | 1H NMR (400 MHz, DMSO-d6) δ 12.52 (s, 1H), 8.44 (d, J = 2.9, 1H), 8.38-8.32 (m, 2H), 8.29 (d, J = 2.9 Hz, 1H), 8.24 (s, 1H), 8.11 (s, 1H), 7.95 (s, 1H), 7.75 (dd, J = 9.0, 2.9 Hz, 1H), 7.23 (d, J = 2.4 Hz, 1H), 6.70 (dd, J = 5.6, 2.3 Hz, 1H), 5.25-5.06 (m, 1H), 3.82 (s, 3H), 1.37 (d, J = 6.8 Hz, 6H). |
| 58 | 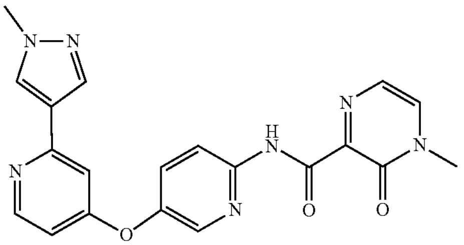 | 401.1 | 1H NMR (400 MHz, DMSO-d6) δ 12.18 (s, 1H), 8.38-8.33 (m, 2H), 8.31 (d, J = 2.7 Hz, 1H), 8.26 (s, 1H), 8.10 (d, J = 3.9 Hz, 1H), 7.96 (s, 1H), 7.77 (dd, J = 9.0, 2.9 Hz, 1H), 7.70 (d, J = 3.9 Hz, 1H), 7.24 (d, J = 2.4 Hz, 1H), 6.72 (dd, J = 5.7, 2.4 Hz, 1H), 3.83 (s, 3H), 3.59 (s, 3H). |

-continued

| Compound | Structural formula | MS (M + H)+ | ¹H NMR |
|---|---|---|---|
| 59 | 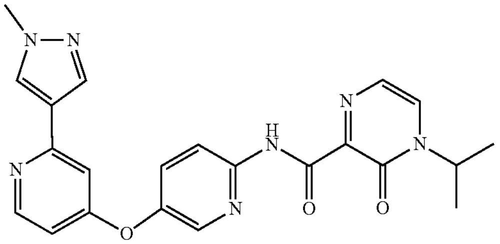 [SMILES: CC(C)n1ccnc(C(=O)Nc2ccc(Oc3ccnc(-c4cnn(C)c4)c3)cn2)c1=O] | 432.1 | 1H NMR (400 MHz, DMSO-d6) δ 10.91 (s, 1H), 8.38-8.34 (m, 2H), 8.33-8.26 (s, 2H), 8.26 (s, 1H), 8.24 (d, J = 2.6 Hz, 1H), 7.96 (s, 1H), 7.76 (dd, J = 9.0, 2.8 Hz, 1H), 7.26 (d, J = 2.3 Hz, 1H), 6.78-6.62 (m, 1H), 5.31 (m, 1H), 3.83 (s, 3H), 1.32 (d, J = 6.1 Hz, 6H). |
| 60 | 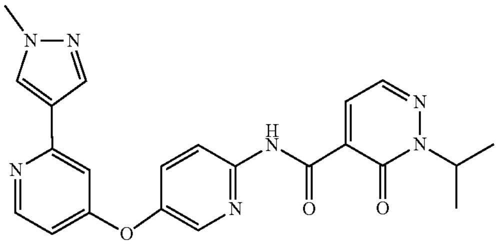 [SMILES: CC(C)n1nccc(C(=O)Nc2ccc(Oc3ccnc(-c4cnn(C)c4)c3)cn2)c1=O] | 432.2 | 1H NMR (400 MHz, DMSO-d6) δ 12.33 (s, 1H), 8.37 (d, J = 5.7 Hz, 1H), 8.34 (d, J = 6.7 Hz, 1H), 8.33 (s, 1H), 8.31 (d, J = 4.2 Hz, 1H), 8.25 (s, 1H), 8.21 (d, J = 4.2 Hz, 1H), 7.96 (s, 1H), 7.79 (dd, J = 8.9, 3.0 HZ, 1H), 7.25 (d, J = 2.4 Hz, 1H), 6.72 (dd, J = 5.7, 2.4 Hz, 1H), 5.3-5.24 (m, 1H), 3.83 (s, 3H), 1.33 (d, J = 6.6 Hz, 6H). |
| 61 | 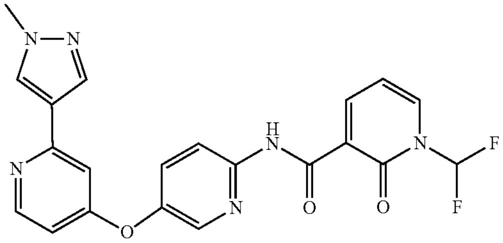 [SMILES: Cn1cc(-c2cc(Oc3ccc(NC(=O)c4cccn(C(F)F)c4=O)nc3)ccn2)cn1] | 439.1 | 1H NMR (400 MHz, DMSO-d6) δ 11.03 (s, 1H), 8.40-8.35 (m, 2H), 8.33-8.28 (m, 2H), 8.27 (s, 1H), 8.14 (dd, J = 7.5, 1.9 Hz, 1H), 7.97 (s, 1H), 7.89 (s, 0.25H), 7.77 (dd, J = 9.0, 3.0 Hz, 1H), 7.71 (s, 0.5H), 7.53 (s, 0.25H), 7.39 (dd, J = 7.4, 5.0 Hz, 1H), 7.27 (d, J = 2.4 Hz, 1H), 6.73 (dd, J = 5.7, 2.4 Hz, 1H), 3.84 (s, 3H). |
| 62 | 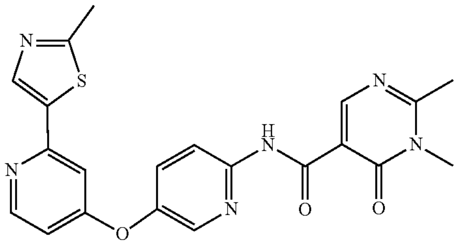 [SMILES: Cc1ncc(-c2cc(Oc3ccc(NC(=O)c4cnc(C)n(C)c4=O)nc3)ccn2)s1] | 435.1 | 1H NMR (400 MHz, DMSO-d6) δ 11.88 (s, 1H), 8.76 (s, 1H), 8.43 (d, J = 5.8 Hz, 1H), 8.37 (d, J = 9.0 Hz, 1H), 8.34 (d, J = 2.9 Hz, 2H), 7.81 (dd, J = 9.0, 2.9 Hz, 1H), 7.64 (d, J = 2.4 Hz, 1H), 6.86 (dd, J = 5.8, 2.4 Hz, 1H), 3.60 (s, 3H), 2.67 (s, 3H), 2.65 (s, 3H). |
| 63 | 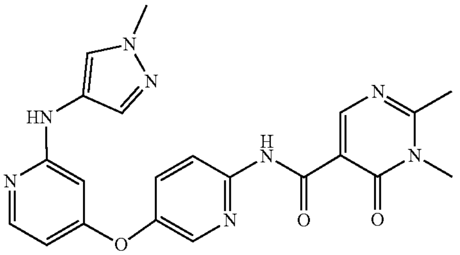 [SMILES: Cc1ncc(C(=O)Nc2ccc(Oc3ccnc(Nc4cnn(C)c4)c3)cn2)c(=O)n1C] | 433.1 | 1H NMR (400 MHz, DMSO-d6) δ 11.86 (s, 1H), 8.76 (s, 1H), 8.74 (s, 1H), 8.35 (d, J = 8.9 Hz, 1H), 8.29 (d, J = 2.9 Hz, 1H), 8.02 (d, J = 5.8 Hz, 1H), 7.88 (s, 1H), 7.77 (dd, J = 9.0, 2.9 Hz, 1H), 7.32 (d, J = 0.6 Hz, 1H), 6.34 (dd, J = 5.8, 2.3 Hz, 1H), 6.04 (d, J = 2.2 Hz, 1H), 3.77 (s, 3H), 3.60 (s, 3H), 2.65 (s, 3H). |
| 64 | 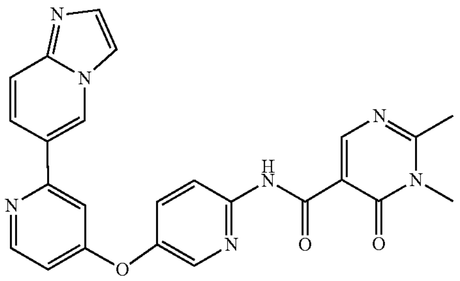 [SMILES: Cc1ncc(C(=O)Nc2ccc(Oc3ccnc(-c4ccc5nccn5c4)c3)cn2)c(=O)n1C] | 454.2 | 1H NMR (400 MHz, DMSO-d6) δ 11.89 (s, 1H), 9.33 (s, 1H), 8.76 (s, 1H), 8.57 (d, J = 5.7 Hz, 1H), 8.44-8.33 (m, 2H), 8.03 (s, 1H), 7.93 (dd, J = 9.5, 1.6 Hz, 1H), 7.84 (dd, J = 9.0, 2.9 Hz, 1H), 7.63 (dd, J = 6.7, 4.5 Hz, 3H), 6.96 (dd, J = 5.6, 2.3 Hz, 1H), 3.60 (s, 3H), 2.66 (s, 3H). |

-continued

| Compound | Structural formula | MS (M + H)+ | $^1$H NMR |
|---|---|---|---|
| 65 | 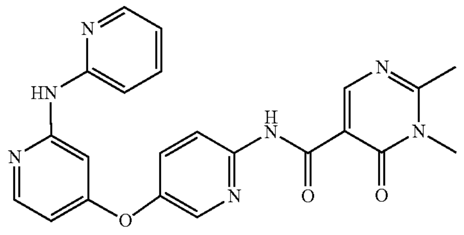 [SMILES: Cc1ncc(C(=O)Nc2ccc(Oc3ccnc(Nc4ccccn4)c3)cn2)c(=O)n1C] | 430.1 | 1H NMR (400 MHz, DMSO-d6) δ 11.86 (s, 1H), 9.67 (s, 1H), 8.76 (s, 1H), 8.36 (d, J = 9.0 Hz, 1H), 8.31 (d, J = 2.9 Hz, 1H), 8.18-8.08 (m, 2H), 7.78 (dd, J = 9.0, 2.9 Hz, 1H), 7.73-7.57 (m, 2H), 7.42 (d, J = 2.3 Hz, 1H), 6.87-6.78 (m, 1H), 6.50 (dd, J = 5.8, 2.3 Hz, 1H), 3.60 (s, 3H), 2.65 (s, 3H). |
| 66 | 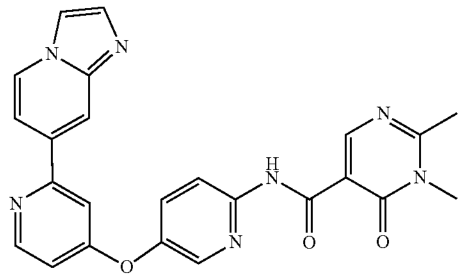 [SMILES: Cc1ncc(C(=O)Nc2ccc(Oc3ccnc(-c4ccn5ccnc5c4)c3)cn2)c(=O)n1C] | 454.1 | 1H NMR (400 MHz, DMSO-d6) δ 11.89 (s, 1H), 8.76 (s, 1H), 8.63-8.57 (m, 2H), 8.37 (dd, J = 6.9, 6.3 Hz, 2H), 8.32 (s, 1H), 8.01 (s, 1H), 7.86-7.80 (m, 2H), 7.67 (dd, J = 7.2, 1.8 Hz, 1H), 7.65 (d, J = 1.1 Hz, 1H), 6.95 (dd, J = 5.6, 2.3 Hz, 1H), 3.60 (s, 3H), 2.65 (s, 3H). |
| 67 | 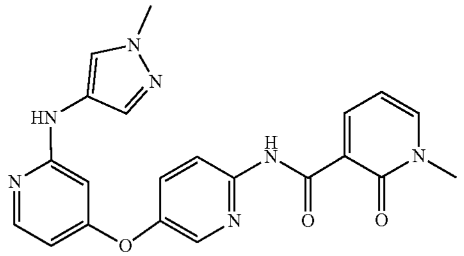 [SMILES: Cn1cc(Nc2cc(Oc3ccc(NC(=O)c4cccn(C)c4=O)nc3)ccn2)cn1] | 418.1 | 1H NMR (400 MHz, DMSO-d6) δ 12.65 (s, 1H), 8.75 (s, 1H), 8.50 (dd, J = 7.3, 2.1 Hz, 1H), 8.38 (d, J = 9.0 Hz, 1H), 8.28 (d, J = 2.8 Hz, 1H), 8.20 (dd, J = 6.5, 2.1 Hz, 1H), 8.02 (d, J = 5.8 Hz, 1H), 7.88 (s, 1H), 7.75 (dd, J = 9.0, 2.9 Hz, 1H), 7.32 (s, 1H), 6.70-6.56 (m, 1H), 6.34 (dd, J = 5.8, 2.2 Hz, 1H), 6.04 (d, J = 2.1 Hz, 1H), 3.77 (s, 3H), 3.64 (s, 3H). |
| 68 | 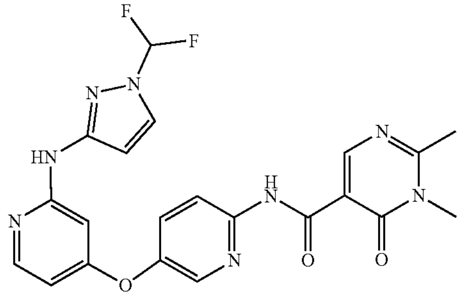 [SMILES: Cc1ncc(C(=O)Nc2ccc(Oc3ccnc(Nc4ccn(C(F)F)n4)c3)cn2)c(=O)n1C] | 469.1 | 1H NMR (400 MHz, DMSO-d6) δ 11.86 (s, 1H), 9.68 (s, 1H), 8.76 (s, 1H), 8.35 (d, J = 9.0 Hz, 1H), 8.30 (d, J = 2.8 Hz, 1H), 8.09 (d, J = 5.8 Hz, 1H), 8.00 (d, J = 2.7 Hz, 1H), 7.78 (dd, J = 9.0, 2.9 Hz, 1H), 7.50 (t, J = 59.3 Hz, 1H), 6.98 (d, J = 2.0 Hz, 1H), 6.57 (d, J = 2.7 Hz, 1H), 6.44 (dd, J = 5.8, 2.2 Hz, 1H), 3.60 (s, 3H), 2.65 (s, 3H). |
| 69 | 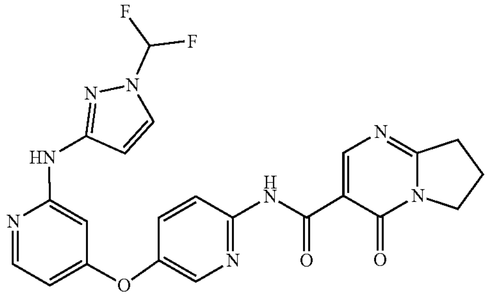 [SMILES: O=C(Nc1ccc(Oc2ccnc(Nc3ccn(C(F)F)n3)c2)cn1)c1cnc2n(c1=O)CCC2] | 481.1 | 1H NMR (400 MHz, DMSO-d6) δ 11.78 (s, 1H), 9.68 (s, 1H), 8.84 (s, 1H), 8.35 (d, J = 9.0 Hz, 1H), 8.30 (d, J = 2.8 Hz, 1H), 8.09 (d, J = 5.8 Hz, 1H), 8.00 (d, J = 2.7 Hz, 1H), 7.78 (dd, J = 9.0, 2.9 Hz, 1H), 7.58 (t, J = 59.3 Hz, 1H), 6.98 (d, J = 2.1 Hz, 1H), 6.57 (d, J = 2.7 Hz, 1H), 6.44 (dd, J = 5.8, 2.3 Hz, 1H), 4.25-4.12 (m, 2H), 3.23-3.13 (m, 2H), 2.28-2.17 (m, 2H). |

-continued

| Compound | Structural formula | MS (M + H)+ | 1H NMR |
|---|---|---|---|
| 70 | 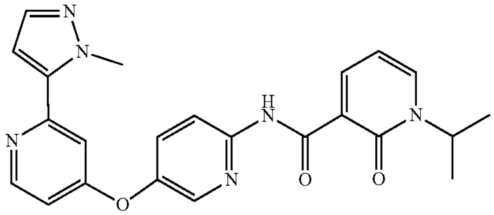 [SMILES: CC(C)n1cccc(C(=O)Nc2ccc(Oc3ccnc(-c4ccnn4C)c3)cn2)c1=O] | 431.2 | 1H NMR (400 MHz, DMSO-d6) δ 12.69 (s, 1H), 8.53 (d, J = 5.7 Hz, 1H), 8.46 (dd, J = 7.3, 2.1 Hz, 1H), 8.36 (d, J = 9.1 Hz, 1H), 8.31 (d, J = 2.8 Hz, 1H), 8.22 (dd, J = 6.7, 2.1 Hz, 1H), 7.77 (dd, J = 9.0, 2.9 Hz, 1H), 7.43 (d, J = 2.0 Hz, 1H), 7.39 (d, J = 2.4 Hz, 1H), 6.90 (dd, J = 5.7, 2.5 Hz, 1H), 6.76 (d, J = 2.0 Hz, 1H), 6.65 (m, 1H), 5.31-5.10 (m, 1H), 4.09 (s, 3H), 1.35 (d, J = 6.8 Hz, 6H). |
| 71 | 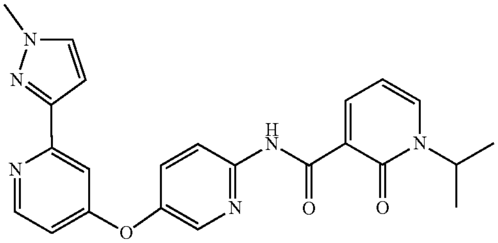 [SMILES: CC(C)n1cccc(C(=O)Nc2ccc(Oc3ccnc(-c4ccn(C)n4)c3)cn2)c1=O] | 431.2 | 1H NMR (400 MHz, DMSO-d6) δ 12.71 (s, 1H), 8.48-8.45 (m, 1H), 8.44 (d, J = 5.8 Hz, 1H), 8.38 (d, J = 9.0 Hz, 1H), 8.32 (d, J = 2.9 Hz, 1H), 8.22 (dd, J = 6.7, 1.9 Hz, 1H), 7.78 (dd, J = 9.0, 2.9 Hz, 1H), 7.72 (d, J = 2.2 Hz, 1H), 7.26 (d, J = 2.6 Hz, 1H), 6.98-6.91 (m, 1H), 6.75 (dd, J = 2.2, 0.5 Hz, 1H), 6.66 (m, 1H), 5.21 (m, 1H), 3.82 (s, 3H), 1.36 (d, J = 6.8 Hz, 6H). |
| 72 | 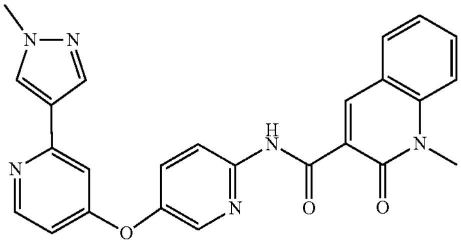 [SMILES: Cn1cc(-c2cc(Oc3ccc(NC(=O)c4cc5ccccc5n(C)c4=O)nc3)ccn2)cn1] | 453.2 | 1H NMR (400 MHz, DMSO-d6) δ 12.68 (s, 1H), 9.08 (s, 1H), 8.44 (d, J = 9.0 Hz, 1H), 8.40 (d, J = 5.7 Hz, 1H), 8.35 (d, J = 2.9 Hz, 1H), 8.29 (s, 1H), 8.12 (d, J = 7.9 Hz, 1H), 7.99 (s, J = 4.2 Hz, 1H), 7.88-7.79 (m, 2H), 7.74 (d, J = 8.6 Hz, 1H), 7.48-7.42 (m, 1H), 7.27 (d, J = 2.4 Hz, 1H), 6.76 (dd, J = 5.7, 2.4 Hz, 1H), 3.86 (s, 3H), 3.82 (s, 3H). |
| 73 | 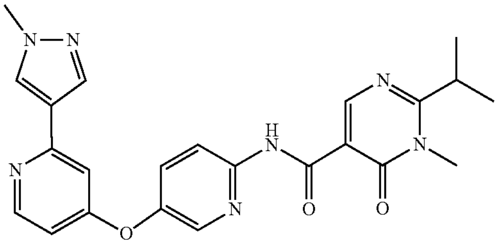 [SMILES: CC(C)c1ncc(C(=O)Nc2ccc(Oc3ccnc(-c4cnn(C)c4)c3)cn2)c(=O)n1C] | 446.1 | 1H NMR (400 MHz, DMSO-d6) δ 11.88 (s, 1H), 8.84 (s, 1H), 8.39 (d, J = 5.7 Hz, 1H), 8.37 (d, J = 9.0 Hz, 1H), 8.32 (d, J = 2.9 Hz, 1H), 8.28 (s, 1H), 7.98 (s, 1H), 7.79 (dd, J = 9.0, 2.9 Hz, 1H), 7.27 (d, J = 2.4 Hz, 1H), 6.75 (dd, J = 5.7, 2.4 Hz, 1H), 3.86 (s, 3H), 3.67 (s, 3H), 3.43-3.34 (m, 1H), 1.27 (d, J = 6.6 Hz, 6H). |
| 74 | 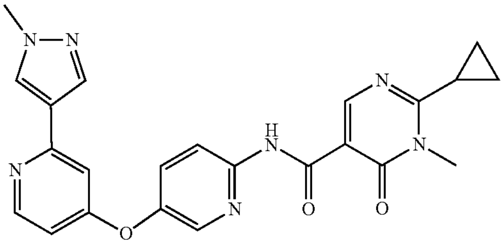 [SMILES: Cn1cc(-c2cc(Oc3ccc(NC(=O)c4cnc(C5CC5)n(C)c4=O)nc3)ccn2)cn1] | 444.1 | 1H NMR (400 MHz, DMSO-d6) δ 11.86 (s, 1H), 8.72 (s, 1H), 8.39 (d, J = 5.7 Hz, 1H), 8.36 (d, J = 9.0 Hz, 1H), 8.31 (d, J = 2.9 Hz, 1H), 8.27 (s, 1H), 7.98 (s, 1H), 7.78 (dd, J = 9.0, 2.9 Hz, 1H), 7.26 (d, J = 2.4 Hz, 1H), 6.74 (dd, J = 5.7, 2.0 Hz, 1H), 3.85 (s, 3H), 3.77 (s, 3H), 2.41-2.33 (m, 1H), 1.25-1.20 (m, 4H). |
| 75 | 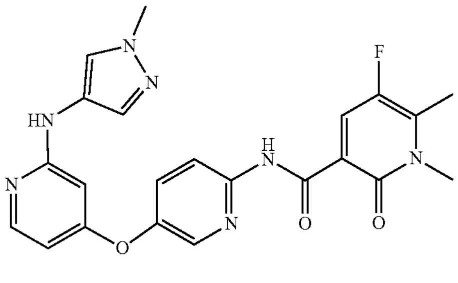 [SMILES: Cc1c(F)cc(C(=O)Nc2ccc(Oc3ccnc(Nc4cnn(C)c4)c3)cn2)c(=O)n1C] | 450.1 | 1H NMR (400 MHz, DMSO-d6) δ 12.67 (s, 1H), 8.75 (s, 1H), 8.45-8.33 (m, 2H), 8.29 (d, J = 2.8 Hz, 1H), 8.02 (d, J = 5.8 Hz, 1H), 7.88 (s, 1H), 7.76 (dd, J = 9.0, 2.9 Hz, 1H), 7.32 (s, 1H), 6.34 (dd, J = 5.8, 2.2 Hz, 1H), 6.04 (d, J = 2.1 Hz, 1H), 3.77 (s, 3H), 3.64 (s, 3H), 2.48 (s, 3H). |

-continued

| Compound | Structural formula | MS $(M + H)^+$ | $^1H$ NMR |
|---|---|---|---|
| 76 | 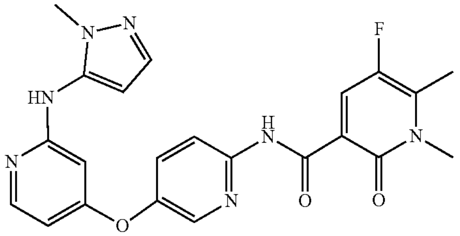 [SMILES: Cc1c(F)cc(C(=O)Nc2ccc(Oc3ccnc(Nc4ccnn4C)c3)cn2)c(=O)n1C] | 450.1 | 1H NMR (400 MHz, DMSO-d6) δ 12.67 (s, 1H), 8.75 (s, 1H), 8.44-8.35 (m, 2H), 8.31 (d, J = 2.8 Hz, 1H), 8.03 (d, J = 5.8 Hz, 1H), 7.79 (dd, J = 9.0, 2.9 Hz, 1H), 7.28 (d, J = 1.8 Hz, 1H), 6.48 (dd, J = 5.8, 2.2 Hz, 1H), 6.26-6.17 (m, 2H), 3.63 (s, 3H), 3.62 (s, 3H), 2.48 (s, 3H). |
| 77 | 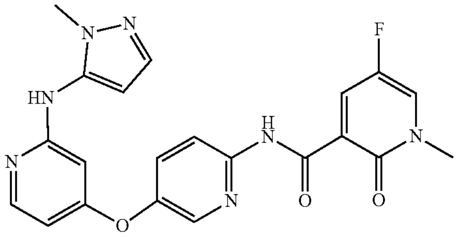 [SMILES: Cn1nccc1Nc1cc(Oc2ccc(NC(=O)c3cc(F)cn(C)c3=O)nc2)ccn1] | 436.1 | 1H NMR (400 MHz, DMSO-d6) δ 12.66 (s, 1H), 8.75 (s, 1H), 8.56-8.50 (m, 1H), 8.49-8.42 (m, 1H), 8.38 (d, J = 9.0 Hz, 1H), 8.32 (d, J = 2.7 Hz, 1H), 8.03 (d, J = 5.8 Hz, 1H), 7.79 (dd, J = 9.0, 2.9 Hz, 1H), 7.28 (d, J = 1.8 Hz, 1H), 6.48 (dd, J = 5.8, 2.2 Hz, 1H), 6.29-6.12 (m, 2H), 3.62 (s, J = 1.4 Hz, 3H), 3.62 (s, 3H). |
| 78 | 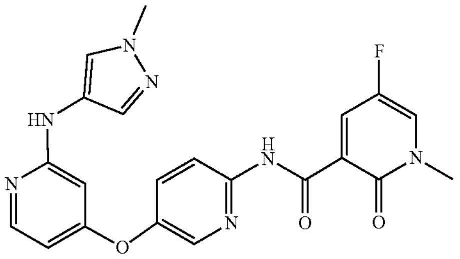 [SMILES: Cn1cc(Nc2cc(Oc3ccc(NC(=O)c4cc(F)cn(C)c4=O)nc3)ccn2)cn1] | 436.1 | $^1H$ NMR (400 MHz, DMSO-d6) δ 12.65 (s, 1H), 8.75 (s, 1H), 8.54-8.49 (m, 1H), 8.49-8.42 (m, 1H), 8.36 (d, J = 9.0 Hz, 1H), 8.29 (d, J = 2.8 Hz, 1H), 8.02 (d, J = 5.8 Hz, 1H), 7.88 (s, 1H), 7.77 (dd, J = 9.0, 2.9 Hz, 1H), 7.32 (s, 1H), 6.34 (dd, J = 5.8, 2.2 Hz, 1H), 6.04 (d, J = 2.1 Hz, 1H), 3.77 (s, 3H), 3.62 (s, 3H). |

Compound 79

4-methoxy-1-methyl-N-(5-((2-(1-methyl-1H-pyrazol-4-yl)pyridin-4-yl)oxy)pyridin-2-yl)-2-oxo-1,2-dihydropyridine-3-carboxamide

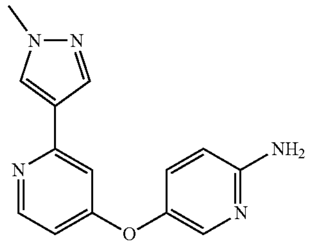

+

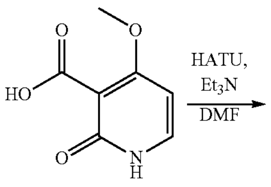

-continued

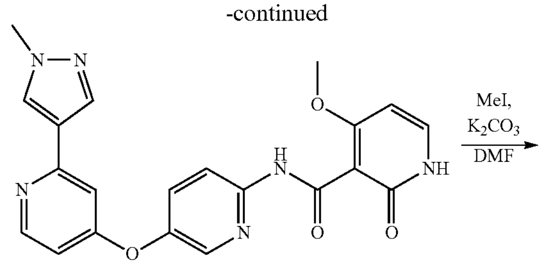

A

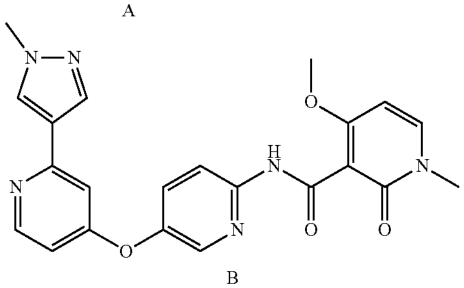

B (A) 4-methoxy-N-(5-((2-(1-methyl-1H-pyrazol-4-yl)pyridin-4-yl)oxy)pyridin-2-yl)-2-oxo-1,2-dihydropyridine-3-carboxamide Under nitrogen, 5-((2-(1-methyl-1H-pyrazol-4-yl)pyridin-4-yl)oxy)pyridin-2-amine (100 mg, 0.37 mmol), 2-hydroxyl-4-methoxynicotinic acid (76 mg, 0.45 mmol), HATU (213 mg, 0.56 mmol), DMF (5 ml) and TEA (155 μl, 1.1 mmol) were successively added to a reaction flask, and the mixture was heated to 40° C. and stirred overnight. The reaction solution was purified with flash column chromatography (water (0.5% formic acid):methanol=100:0-0:100, gradient elution), to obtain 80 mg of the title product as a white solid. MS (m/z): 419.2 [M+H]$^+$.

(B) 4-methoxy-1-methyl-N-(5-((2-(1-methyl-1H-pyrazol-4-yl)pyridin-4-yl)oxy)pyridin-2-yl)-2-oxo-1,2-dihydropyridine-3-carboxamide Under nitrogen, 4-methoxy-N-(5-((2-(1-methyl-1H-pyrazol-4-yl)pyridin-4-yl)oxy)pyridin-2-yl)-2-oxo-1,2-dihydropyridine-3-carboxamide (80 mg, 0.2 mmol), iodomethane (74 mg, 0.52 mmol), potassium carbonate (72 mg, 0.52 mmol) and DMF (5 ml) were successively added to a reaction flask, and the mixture was stirred at room temperature for 1 hour and completely reacted. The reaction solution was purified with flash column chromatography (water (0.5% formic acid):methanol=100:0-0:100, gradient elution) and p-TLC plate, to obtain 60 mg of the title product as a white solid. MS (m/z): 433.2 [M+H]$^+$.

$^1$H NMR (400 MHz, DMSO-d6) δ 11.33 (s, 1H), 8.38 (d, J=5.7 Hz, 1H), 8.31 (d, J=9.0 Hz, 1H), 8.28 (s, 1H), 8.26 (d, J=2.9 Hz, 1H), 7.98 (s, 1H), 7.93 (d, J=7.7 Hz, 1H), 7.72 (dd, J=9.0, 2.9 Hz, 1H), 7.25 (d, J=2.4 Hz, 1H), 6.73 (dd, J=5.7, 2.4 Hz, 1H), 6.42 (d, J=7.8 Hz, 1H), 3.86 (s, 3H), 3.85 (s, 3H), 3.45 (s, 3H).

The following compounds were prepared with corresponding intermediates and reagents with reference to the preparation processes of compound 79 under suitable conditions recognized by the POSITA.

-continued

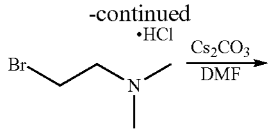

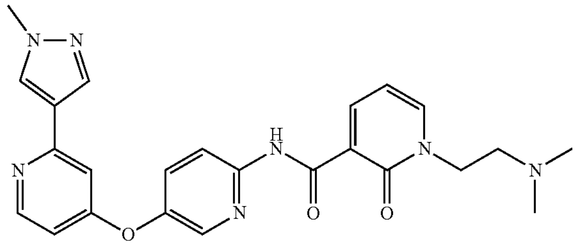

Under nitrogen, N-(5-((2-(1-methyl-1H-pyrazol-4-yl)pyridin-4-yl)oxy)pyridin-2-yl)-2-oxo-1,2-dihydropyridine-3-carboxamide (80 mg, 0.21 mmol), 2-bromo-N,N-dimethy-

| Compound | Structural formula | MS (M + H)$^+$ | $^1$HNMR |
|---|---|---|---|
| 80 | 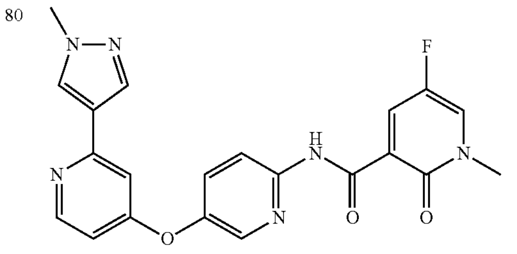 | 421.2 | $^1$H NMR (400 MHz, DMSO-d6) δ 12.67 (s, 1H), 8.56-8.50 (m, 1H), 8.46 (dd, J = 8.1, 3.5 Hz, 1H), 8.42-8.36 (m, 2H), 8.33 (d, J = 2.8 Hz, 1H), 8.28 (s, 1H), 7.98 (d, J = 0.5 Hz, 1H), 7.79 (dd, J = 9.0, 2.9 Hz, 1H), 7.27 (d, J = 2.4 Hz, 1H), 6.74 (dd, J = 5.7, 2.4 Hz, 1H), 3.86 (s, 3H), 3.63 (s, 3H). |

Compound 81

1-(2-(dimethylamino)ethyl)-N-(5-((2-(1-methyl-1H-pyrazol-4-yl)pyridin-4-yl)oxy)pyridin-2-yl)-2-oxo-1,2-dihydropyridine-3-carboxamide

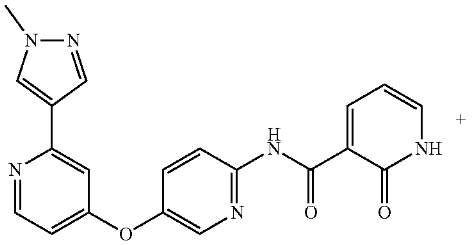

lethyl-1-amine hydrochloride salt (144 mg, 0.63 mmol), cesium carbonate (267 mg, 0.82 mmol) and DMF (5 ml) were successively added to a reaction flask, and the mixture was heated to 80° C. and stirred overnight. The reaction solution was cooled to room temperature, and then purified with flash column chromatography (water (0.5% ammonia): methanol=100:0-0:100, gradient elution), to obtain 50 mg of the title product as a white solid. MS (m/z): 460.2 [M+H]$^+$.

$^1$H NMR (400 MHz, DMSO-d6) δ 12.66 (s, 1H), 8.50 (dd, J=7.4, 2.2 Hz, 1H), 8.40 (s, 1H), 8.38 (d, J=3.7 Hz, 1H), 8.31 (d, J=2.8 Hz, 1H), 8.28 (s, 1H), 8.13 (dd, J=6.5, 2.2 Hz, 1H), 7.98 (d, J=0.5 Hz, 1H), 7.77 (dd, J=9.0, 2.9 Hz, 1H), 7.26 (d, J=2.4 Hz, 1H), 6.74 (dd, J=5.7, 2.4 Hz, 1H), 6.66-6.59 (m, 1H), 4.19 (t, J=6.1 Hz, 2H), 3.85 (s, 3H), 2.59 (t, J=6.1 Hz, 2H), 2.20 (s, 6H).

The following compounds were prepared with corresponding intermediates and reagents with reference to the preparation processes of compound 81 under suitable conditions recognized by the POSITA.

| Compound | Structural formula | MS $(M + H)^+$ | $^1$HNMR |
|---|---|---|---|
| 82 | 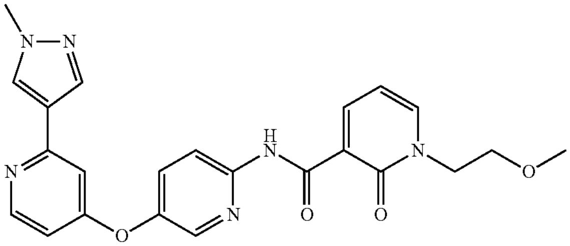 | 447.2 | $^1$H NMR (400 MHz, DMSO-d6) δ 12.61 (s, 1H), 8.52 (dd, J = 7.4, 2.2 Hz, 1H), 8.40 (s, 1H), 8.38 (d, J = 3.1 Hz, 1H), 8.31 (d, J = 2.9 Hz, 1H), 8.28 (s, 1H), 8.10 (dd, J = 6.5, 2.2 Hz, 1H), 7.98 (d, J = 0.5 Hz, 1H), 7.78 (dd, J = 9.0, 2.9 Hz, 1H), 7.26 (d, J = 2.4 Hz, 1H), 6.74 (dd, J = 5.7, 2.4 Hz, 1H), 6.67-6.60 (m, 1H), 4.29 (t, J = 5.1 Hz, 2H), 3.86 (s, 3H), 3.68 (t, J = 5.2 Hz, 2H), 3.26 (s, 3H). |
| 83 | 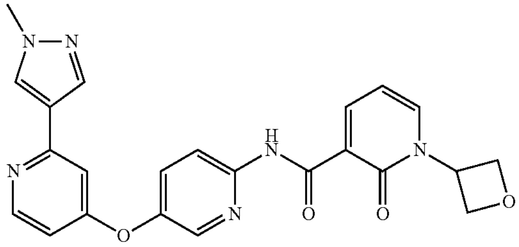 [SMILES: Cn1cc(-c2cc(Oc3ccc(NC(=O)c4cccn(C5COC5)c4=O)nc3)ccn2)cn1] | 445.2 | $^1$H NMR (400 MHz, DMSO-d6) δ 12.45 (s, 1H), 8.54 (dd, J = 7.4, 2.0 Hz, 1H), 8.43-8.35 (m, 2H), 8.30 (d, J = 2.9 Hz, 1H), 8.28 (s, 1H), 8.21 (dd, J = 6.7, 2.0 Hz, 1H), 7.98 (s, 1H), 7.78 (dd, J = 9.0, 2.9 Hz, 1H), 7.26 (d, J = 2.4 Hz, 1H), 6.77-6.69 (m, 2H), 5.68 - 5.54 (m, 1H), 4.94 (t, J = 7.5 Hz, 2H), 4.84 (t, J = 7.2 Hz, 2H), 3.85 (s, 3H). |
| 84 | 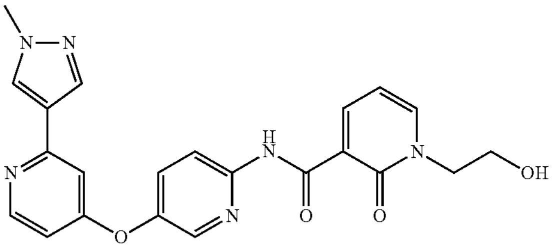 [SMILES: Cn1cc(-c2cc(Oc3ccc(NC(=O)c4cccn(CCO)c4=O)nc3)ccn2)cn1] | 433.2 | $^1$H NMR (400 MHz, DMSO-d6) δ 12.66 (s, 1H), 8.52 (dd, J = 7.4, 2.2 Hz, 1H), 8.40 (d, J = 2.1 Hz, 1H), 8.39 (s, 1H), 8.31 (d, J = 2.9 Hz, 1H), 8.28 (s, 1H), 8.08 (dd, J = 6.5, 2.2 Hz, 1H), 7.98 (s, 1H), 7.77 (dd, J = 9.0, 2.9 Hz, 1H), 7.26 (d, J = 2.4 Hz, 1H), 6.74 (dd, J = 5.7, 2.4 Hz, 1H), 6.66-6.59 (m, 1H), 5.15-4.86 (m, 1H), 4.16 (t, J = 5.2 Hz, 2H), 3.86 (s, 3H), 3.73 (t, J = 5.2 Hz, 2H). |
| 85 | 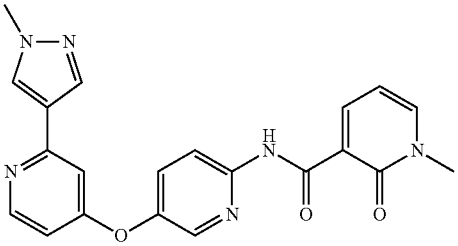 | 403.2 | 1H NMR (400 MHz, DMSO-d6) δ 12.66 (s, 1H), 8.50 (dd, J = 7.4, 2.2 Hz, 1H), 8.40 (d, J = 2.6 Hz, 1H), 8.39 (s, 1H), 8.31 (d, J = 2.9 Hz, 1H), 8.28 (s, 1H), 8.21 (dd, J = 6.5, 2.2 Hz, 1H), 7.99 (d, J = 4.0 Hz, 1H), 7.77 (dd, J = 9.0, 2.9 Hz, 1H), 7.27 (d, J = 2.4 Hz, 1H), 6.74 (dd, J = 5.7, 2.4 Hz, 1H), 6.66-6.59 (m, 1H), 3.86 (s, 3H), 3.64 (s, 3H). |
| 86 | 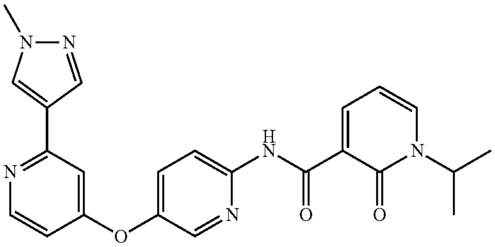 [SMILES: CC(C)n1cccc(C(=O)Nc2ccc(Oc3ccnc(-c4cnn(C)c4)c3)cn2)c1=O] | 431.2 | 1H NMR (400 MHz, DMSO-d6) δ 12.69 (s, 1H), 8.56-8.13 (m, 6H), 7.96 (s, 1H), 7.76-7.74 (m, 1H), 7.24 (s, 1H), 6.69-6.66 (m, 2H), 5.23-5.18 (m, 1H), 3.83 (s, 3H), 1.36 (s, 6H). |
| 87 | 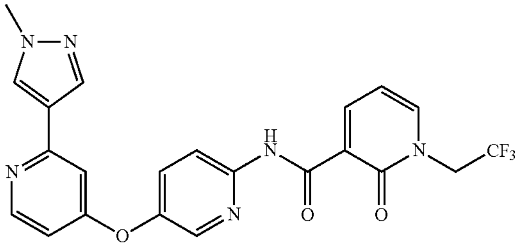 [SMILES: Cn1cc(-c2cc(Oc3ccc(NC(=O)c4cccn(CC(F)(F)F)c4=O)nc3)ccn2)cn1] | 471.2 | 1H NMR (400 MHz, DMSO-d6) δ 12.25 (s, 1H), 8.56 (dd, J = 7.2, 1.6 Hz, 1H), 8.37-8.33 (m, 2H), 8.28 (d, J = 2.8 Hz, 1H), 8.24 (s, 1H), 8.15 (d, J = 6.4 Hz, 1H), 7.95 (s, 1H), 7.74 (dd, J = 9.0, 2.8 Hz, 1H), 7.22 (d, J = 2.2 Hz, 1H), 6.79-6.65 (m, 2H), 5.08 (q, J = 8.9 Hz, 2H), 3.82 (s, 3H). |

-continued

| Compound | Structural formula | MS (M + H)$^+$ | $^1$HNMR |
| --- | --- | --- | --- |
| 88 | 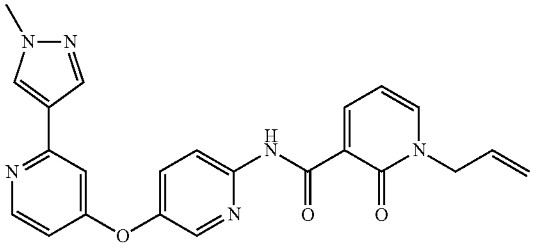 [SMILES: C=CCn1cccc(C(=O)Nc2ccc(Oc3ccnc(-c4cnn(C)c4)c3)cn2)c1=O] | 429.2 | 1H NMR (400 MHz, DMSO-d6) δ 12.57 (s, 1H), 8.51-8.48 (m, 1H), 8.42-8.30 (m, 2H), 8.30-8.18 (m, 2H), 8.13-8.10 (m, 1H), 7.95 (s, 1H), 7.75-7.71 (m, 1H), 7.22 (s, 1H), 6.74-6.55 (m, 2H), 6.15-5.85 (m, 1H), 5.19-5.14 (m, 2H), 4.72-4.68 (m, 2H), 3.82 (s, 3H). |
| 89 | 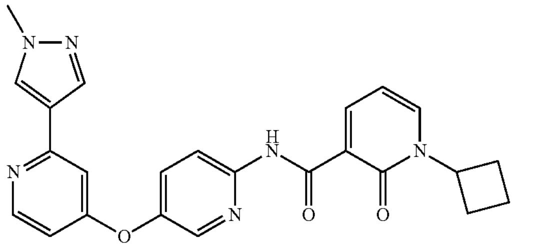 [SMILES: Cn1cc(-c2cc(Oc3ccc(NC(=O)c4cccn(C5CCC5)c4=O)nc3)ccn2)cn1] | 443.1 | 1H NMR (400 MHz, DMSO-d6) δ 12.60 (s, 1H), 8.48-8.45 (m, 1H), 8.37-8.33 (m, 2H), 8.31-8.23 (m, 2H), 8.20-8.17 (m, 1H), 7.96 (s, 1H), 7.75-7.72 (m, 1H), 7.26-7.23 (m, 1H), 6.73-6.70 (m, 1H), 6.65-6.61 (m, 1H), 5.02-4.98 (m, 1H), 3.82 (s, 3H), 2.43-2.38 (m, 2H), 2.34-2.22 (m, 2H), 1.81-1.77 (m, 2H). |
| 90 | 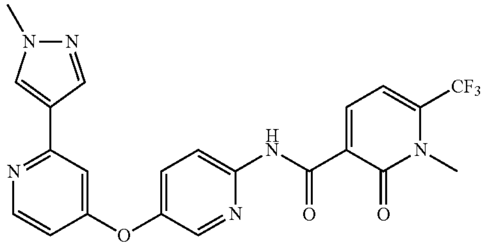 [SMILES: Cn1cc(-c2cc(Oc3ccc(NC(=O)c4ccc(C(F)(F)F)n(C)c4=O)nc3)ccn2)cn1] | 471.1 | 1H NMR (400 MHz, DMSO-d6) δ 12.34 (s, 1H), 8.57-8.54 (m, 1H), 8.43-8.16 (m, 4H), 7.97 (s, 1H), 7.80-7.77 (m, 1H), 7.26-7.22 (m, 2H), 6.75-6.70 (m, 1H), 3.84 (s, 3H), 3.65 (s, 3H). |
| 91 | 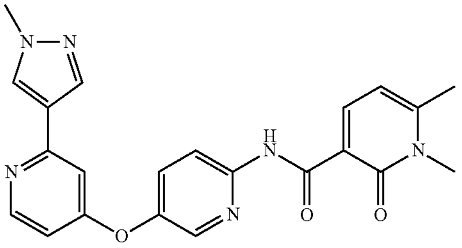 | 417.1 | 1H NMR (400 MHz, DMSO-d6) δ 12.64 (s, 1H), 8.38-8.34 (m, 3H), 8.27 (d, J = 2.5 Hz, 1H), 8.25 (s, 1H), 7.95 (s, 1H), 7.73 (dd, J = 8.8, 2.6 Hz, 1H), 7.23 (s, 1H), 6.71 (d, J = 3.4 Hz, 1H), 6.55 (d, J = 7.6 Hz, 1H), 3.83 (s, 3H), 3.58 (s, 3H), 2.49 (s, 3H). |

Compound 92

1-isopropyl-N-(3-methoxy-5-((2-(1-methyl-1H-pyrazol-4-yl)pyridin-4-yl)oxy)pyridin-2-yl)-2-oxo-1,2-dihydropyridine-3-carboxamide

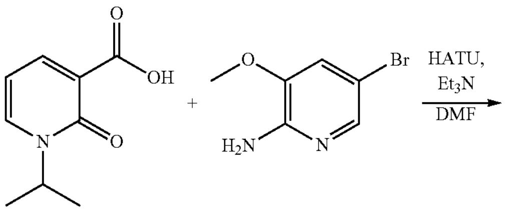

-continued

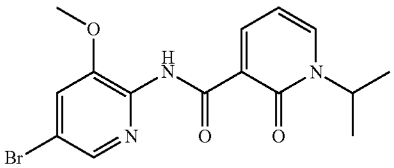

A

+

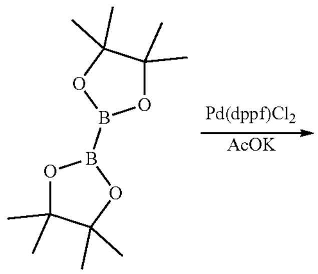

-continued

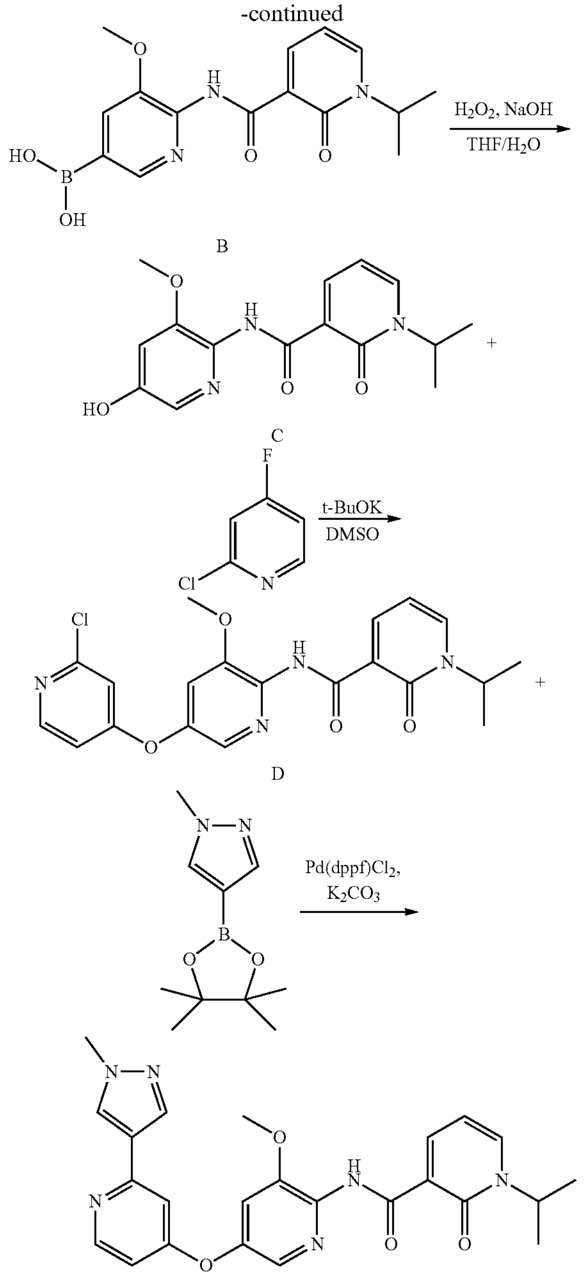

B

C

D

E (A) N-(5-bromo-3-methoxypyridin-2-yl)-1-isopropyl-2-oxo-1,2-dihydropyridine-3-carboxamide The title compound was prepared with corresponding intermediates and reagents with reference to the preparation processes of compound 79(A). MS (m/z): 366.0 $[M+H]^+$.

(B) (6-(1-isopropyl-2-oxo-1,2-dihydropyridine-3-carboxamido)-5-methoxypyridin-3-yl)boronic acid Under nitrogen, N-(5-bromo-3-methoxypyridin-2-yl)-1-isopropyl-2-oxo-1,2-dihydropyridine-3-carboxamide (360 mg, 1.0 mmol), pinacol borate (508 mg, 2 mmol), potassium acetate (294 mg, 3 mmol), dioxane (10 ml) and $Pd(dppf)Cl_2$ (73 mg, 0.1 mmol) were successively added to a reaction flask, and the mixture was refluxed and stirred overnight. The reaction solution was cooled to room temperature and then concentrated, the residue was purified with flash column chromatography (water (0.5% formic acid):methanol=100:0-0:100, gradient elution), to obtain 330 mg of the title product as a white solid. MS (m/z): 332.1 $[M+H]^+$.

(C) N-(5-hydroxy-3-methoxypyridin-2-yl)-1-isopropyl-2-oxo-1,2-dihydropyridine-3-carboxamide Under nitrogen, (6-(1-isopropyl-2-oxo-1,2-dihydropyridine-3-carboxamido)-5-methoxypyridin-3-yl)boronic acid (330 mg, 1.0 mmol) and tetrahydrofuran (20 ml) were successively added to a reaction flask, and 1N sodium hydroxide aqueous solution (2 ml) and 30% hydrogen peroxide (567 mg, 5 mmol) were successively added dropwise, and the mixture was stirred at room temperature for half an hour. After adjusting pH to 4 with 1N hydrochloric acid aqueous solution, saturated sodium thiosulfate aqueous solution (1 ml) was added dropwise, and the reaction solution was concentrated. The residue was purified with flash column chromatography (water (0.5% formic acid):methanol=100:0-0:100, gradient elution), to obtain 240 mg of the title product as a light yellow solid. MS (m/z): 304.1 $[M+H]^+$.

(D) N-(5-((2-chloropyridin-4-yl)oxy)-3-methoxypyridin-2-yl)-1-isopropyl-2-oxo-1,2-dihydropyridine-3-carboxamide Under nitrogen, N-(5-hydroxy-3-methoxypyridin-2-yl)-1-isopropyl-2-oxo-1,2-dihydropyridine-3-carboxamide (240 mg, 0.8 mmol), 2-chloro-4-fluoropyridine (126 mg, 0.96 mmol), potassium t-butoxide (135 mg, 1.2 mmol) and DMSO (6 ml) were successively added to a reaction flask, and the mixture was heated to 90° C. and stirred for 6 hours. The reaction solution was cooled to room temperature, and then added water (40 ml), stirred for half an hour, and then filtered. The solid was washed with water and dried, to obtain 180 mg of the title product as a brown solid. MS (m/z): 415.1 $[M+H]^+$.

(E) 1-isopropyl-N-(3-methoxy-5-((2-(1-methyl-1H-pyrazol-4-yl)pyridin-4-yl)oxy)pyridin-2-yl)-2-oxo-1,2-dihydropyridine-3-carboxamide Under nitrogen, N-(5-((2-chloropyridin-4-yl)oxy)-3-methoxypyridin-2-yl)-1-isopropyl-2-oxo-1,2-dihydropyridine-3-carboxamide (90 mg, 0.22 mmol), 1-methyl-4-pyrazole pinacol borate (69 mg, 0.33 mmol), potassium carbonate (59 mg, 0.43 mmol), dioxane/water (10 ml/2 ml) and $Pd(dppf)Cl_2$ (15 mg, 0.02 mmol) were successively added to a reaction flask, and the mixture was refluxed and stirred overnight. The reaction solution was cooled to room temperature and then concentrated, the residue was purified with flash column chromatography (water (0.5% formic acid):methanol=100:0-0:100, gradient elution), to obtain 70 mg of the title product as a white solid. MS (m/z): 461.2 $[M+H]^+$.

$^1$H NMR (400 MHz, DMSO-d6) δ 12.38 (s, 1H), 8.43 (dd, J=7.2, 1.9 Hz, 1H), 8.40 (d, J=5.7 Hz, 1H), 8.29 (s, 1H), 8.22 (dd, J=6.7, 2.0 Hz, 1H), 7.99 (s, 1H), 7.90 (d, J=2.3 Hz, 1H), 7.48 (d, J=2.2 Hz, 1H), 7.28 (d, J=2.2 Hz, 1H), 6.76 (dd, J=5.7, 2.3 Hz, 1H), 6.70-6.59 (m, 1H), 5.35-5.18 (m, 1H), 3.89 (s, 3H), 3.86 (s, 3H), 1.38 (d, J=6.8 Hz, 6H).

Compound 93

1-isopropyl-N-(6-methyl-5-((2-(1-methyl-1H-pyrazol-4-yl)pyridin-4-yl)oxy)pyridin-2-yl)-2-oxo-1,2-dihydropyridine-3-carboxamide

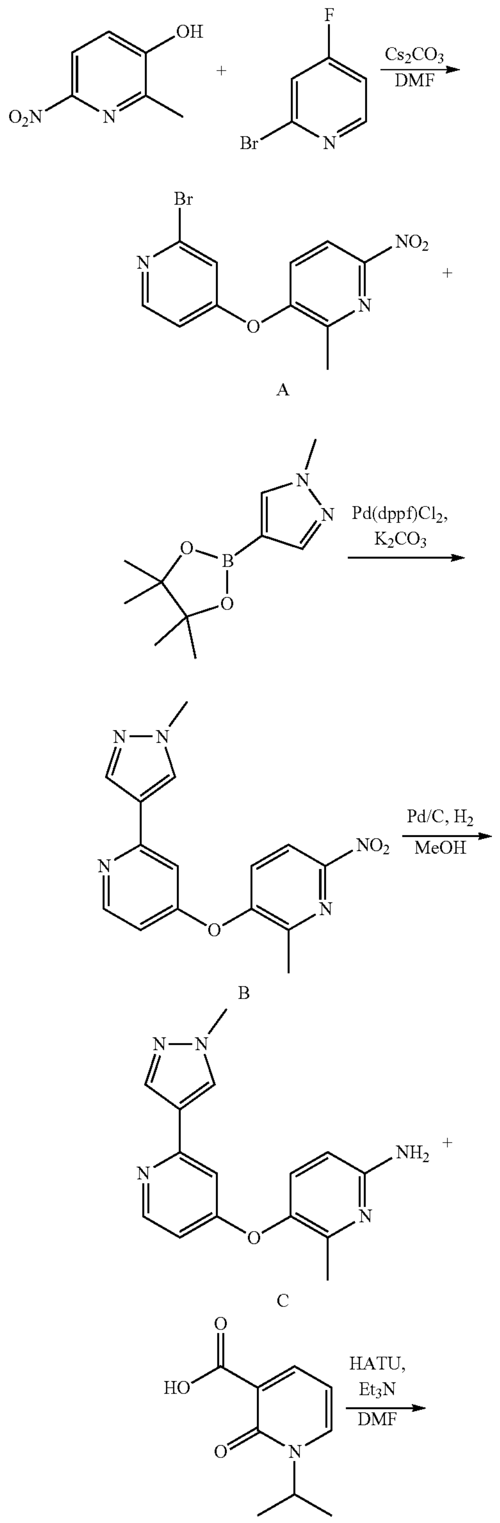

-continued

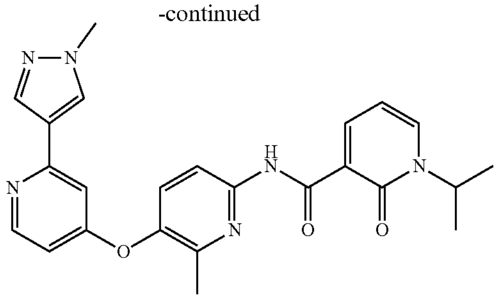

D (A) 3-((2-bromopyridin-4-yl)oxy)-2-methyl-6-nitropyridine

Under nitrogen, 2-methyl-6-nitropyridin-3-ol (616 mg, 4 mmol), 2-bromo-4-fluoropyridine (739 mg, 4.2 mmol), cesium carbonate (1.95 g, 6 mmol) and DMF (15 ml) were successively added to a reaction flask, and the mixture was heated to 90° C. and stirred for 6 hours. The reaction solution was cooled to room temperature, and then added water (80 ml), stirred for half an hour, and then filtered. The solid was washed with water and dried, to obtain 460 mg of the title product as a brown solid. MS (m/z): 310.0 $[M+H]^+$.

(B) 2-methyl-3-((2-(1-methyl-1H-pyrazol-4-yl)pyridin-4-yl)oxy)-6-nitropyridine

The title compound was prepared with corresponding intermediates and reagents with reference to the preparation processes of compound 92(E). MS (m/z): 312.1 $[M+H]^+$.

(C) 6-methyl-5-((2-(1-methyl-1H-pyrazol-4-yl)pyridin-4-yl)oxy)pyridin-2-amine 2-methyl-3-((2-(1-methyl-1H-pyrazol-4-yl)pyridin-4-yl)oxy)-6-nitropyridine (250 mg, 0.8 mmol), methanol (20 ml) and palladium carbon (100 mg) were successively added to a reaction flask, after replacing hydrogen with hydrogen balloon, the reaction solution was stirred under normal pressure at room temperature overnight. The reaction solution was filtered, and the filtrate was concentrated, the residue was purified with flash column chromatography (water (0.5% formic acid):methanol=100:0-0:100, gradient elution), to obtain 180 mg of the title product as a brown solid. MS (m/z): 282.1 $[M+H]^+$.

(D) 1-isopropyl-N-(6-methyl-5-((2-(1-methyl-1H-pyrazol-4-yl)pyridin-4-yl)oxy)pyridin-2-yl)-2-oxo-1,2-dihydropyridine-3-carboxamide The title compound was prepared with corresponding intermediates and reagents with reference to the preparation processes of compound 79(A). MS (m/z): 445.2 $[M+H]^+$.

$^1$H NMR (400 MHz, DMSO-d6) δ 12.65 (s, 1H), 8.49 (dd, J=7.2, 2.0 Hz, 1H), 8.37 (d, J=5.7 Hz, 1H), 8.32-8.17 (m, 3H), 7.98 (s, 1H), 7.66 (d, J=8.8 Hz, 1H), 7.20 (d, J=2.3 Hz, 1H), 6.74-6.58 (m, 2H), 5.30-5.14 (m, 1H), 3.85 (s, 3H), 2.30 (s, 3H), 1.40 (d, J=6.8 Hz, 6H).

Compound 94

N-(5-((2-(1-(2-hydroxyethyl)-1H-pyrazol-4-yl)pyridin-4-yl)oxy)pyridin-2-yl)-1-methyl-2-oxo-1,2-dihydropyridine-3-carboxamide

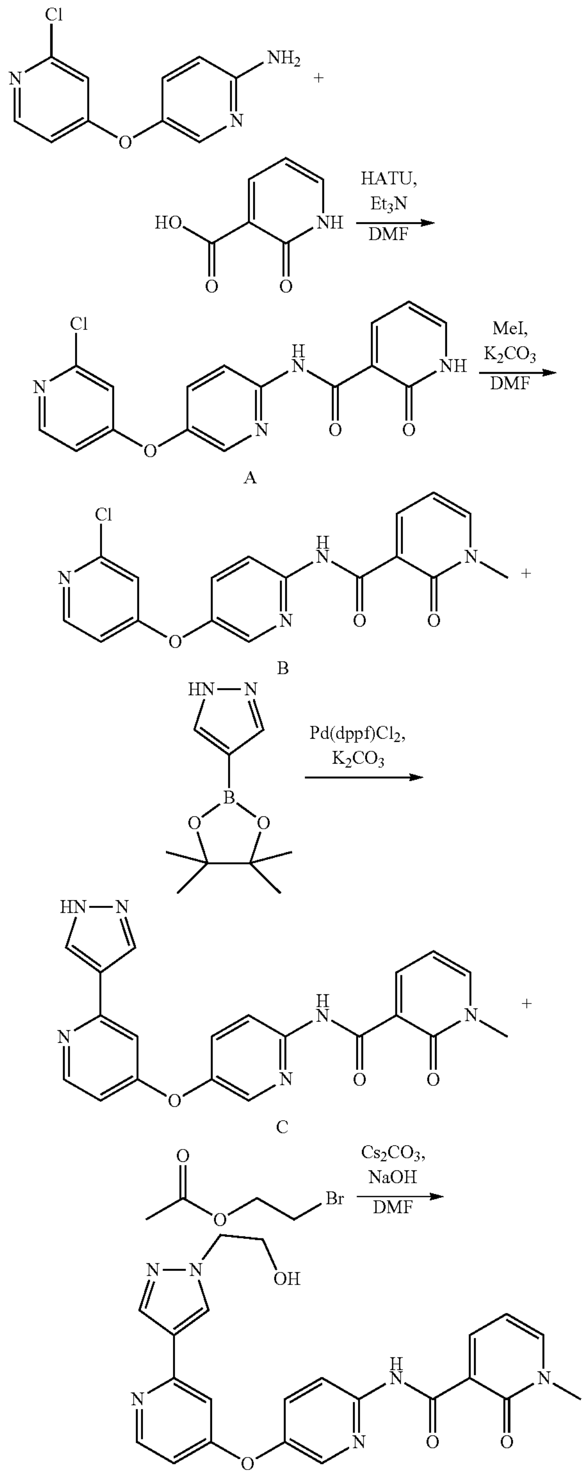

A

B

C

D (A) N-(5-((2-chloropyridin-4-yl)oxy)pyridin-2-yl)-2-oxo-1,2-dihydropyridine-3-carboxamide Under nitrogen, 5-((2-chloropyridin-4-yl)oxy)pyridin-2-amine (850 mg, 3.84 mmol), 2-hydroxynicotinic acid (640 mg, 4.6 mmol), HATU (2.2 g, 5.8 mmol), DMF (12 ml) and TEA (1.3 ml, 9.6 mmol) were successively added to a reaction flask, and the mixture was heated to 40° C. and stirred overnight. The reaction solution was cooled to room temperature, and then added water (80 ml), stirred for two hours, and then filtered. The solid was washed with water and dried, to obtain 900 mg of the title product as a light yellow solid. MS (m/z): 343.0 $[M+H]^+$.

(B) N-(5-((2-chloropyridin-4-yl)oxy)pyridin-2-yl)-1-methyl-2-oxo-1,2-dihydropyridine-3-carboxamide Under nitrogen, N-(5-((2-chloropyridin-4-yl)oxy)pyridin-2-yl)-2-oxo-1,2-dihydropyridine-3-carboxamide (900 mg, 2.6 mmol), iodomethane (479 μl, 7.7 mmol), potassium carbonate (1.06 g, 7.7 mmol) and DMF (10 ml) were successively added to a reaction flask, and the mixture was stirred at room temperature for 1 hour and completely reacted. Water (80 ml) was added, the reaction solution was stirred for 1 hour, and then filtered. The solid was washed with water and dried, to obtain 800 mg of the title product as a light yellow solid. MS (m/z): 357.0 $[M+H]^+$.

(C) N-(5-((2-(1H-pyrazol-4-yl)pyridin-4-yl)oxy)pyridin-2-yl)-1-methyl-2-oxo-1,2-dihydropyridine-3-carboxamide Under nitrogen, N-(5-((2-chloropyridin-4-yl)oxy)pyridin-2-yl)-1-methyl-2-oxo-1,2-dihydropyridine-3-carboxamide (100 mg, 0.28 mmol), 4-pyrazole pinacol borate (82 mg, 0.42 mmol), potassium carbonate (77 mg, 0.56 mmol), dioxane/water (10 ml/2 ml) and $Pd(dppf)Cl_2$ (21 mg, 0.03 mmol) were successively added to a reaction flask, and the mixture was refluxed and stirred for 2 hours. The reaction solution was cooled to room temperature and then concentrated, the residue was purified with flash column chromatography (water (0.5% formic acid):methanol=100:0-0:100, gradient elution), to obtain 80 mg of the title product as a light yellow solid. MS (m/z): 389.1 $[M+H]^+$.

(D) N-(5-((2-(1-(2-hydroxyethyl)-1H-pyrazol-4-yl)pyridin-4-yl)oxy)pyridin-2-yl)-1-methyl-2-oxo-1,2-dihydropyridine-3-carboxamide Under nitrogen, N-(5-((2-(1H-pyrazol-4-yl)pyridin-4-yl)oxy)pyridin-2-yl)-1-methyl-2-oxo-1,2-dihydropyridine-3-carboxamide (80 mg, 0.21 mmol), 2-bromoethyl acetate (167 mg, 1 mmol), cesium carbonate (326 mg, 1 mmol) and DMF (5 ml) were successively added to a reaction flask, and the mixture was heated to 80° C. and stirred overnight. The reaction solution was cooled to room temperature, and then added dropwise 2N sodium hydroxide aqueous solution (2 ml), and stirred at room temperature for 2 hours. The reaction solution was purified with flash column chromatography (water (0.5% formic acid):methanol=100:0-0:100, gradient elution), to obtain 40 mg of the title product as a white solid. MS (m/z): 433.1 $[M+H]^+$.

$^1H$ NMR (400 MHz, DMSO-d6) δ 12.66 (s, 1H), 8.50 (dd, J=7.3, 1.9 Hz, 1H), 8.43-8.35 (m, 2H), 8.35-8.25 (m, 2H), 8.20 (dd, J=6.4, 1.9 Hz, 1H), 8.01 (s, 1H), 7.77 (dd, J=9.0, 2.8 Hz, 1H), 7.29 (d, J=2.1 Hz, 1H), 6.74 (dd, J=5.6, 2.3 Hz,

1H), 6.67-6.57 (m, 1H), 4.94 (t, J=5.2 Hz, 1H), 4.15 (t, J=5.5 Hz, 2H), 3.80-3.69 (m, 2H), 3.64 (s, 3H).

The following compounds were prepared with corresponding intermediates and reagents with reference to the preparation processes of compound 94 (steps A-C) under suitable conditions recognized by the POSITA.

| Compound | Structural formula | MS (M + H)$^+$ | $^1$HNMR |
|---|---|---|---|
| 127 | 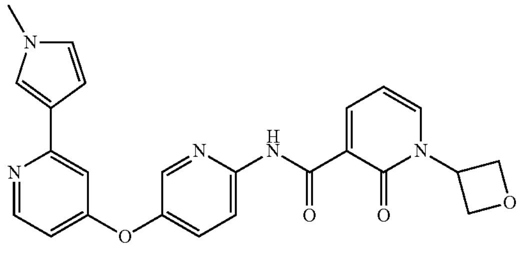 [SMILES: Cn1ccc(-c2cc(Oc3ccc(NC(=O)c4cccn(C5COC5)c4=O)nc3)ccn2)c1] | 444.1 | 1H NMR (400 MHz, DMSO-d6) δ 12.41 (s, 1H), 8.51 (d, J = 7.2 Hz, 1H), 8.34 (d, J = 9.0 Hz, 1H), 8.30 (d, J = 5.7 Hz, 1H), 8.25 (d, J = 2.1 Hz, 1H), 8.17 (d, J = 6.5 Hz, 1H), 7.76-7.69 (m, 1H), 7.34 (s, 1H), 7.08 (s, 1H), 6.68 (d, J = 7.3 Hz, 2H), 6.60 (d, J = 5.5 Hz, 1H), 6.51 (s, 1H), 5.57 (p, J = 7.3 Hz, 1H), 4.90 (t, J = 7.3 Hz, 2H), 4.81 (t, J = 7.0 Hz, 2H), 3.60 (s, 3H). |

Compound 95

N-(5-((2-(1-(2-hydroxyethyl)-1H-pyrazol-4-yl)pyridin-4-yl)oxy)pyridin-2-yl)-1-isopropyl-2-oxo-1,2-dihydropyridine-3-carboxamide

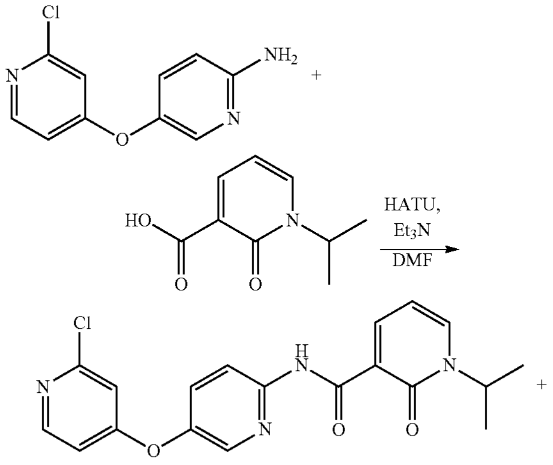

A

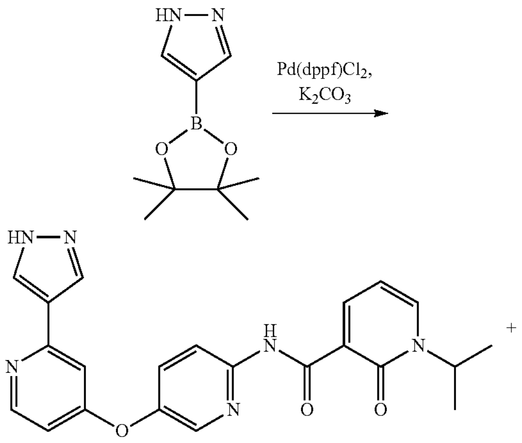

B

-continued

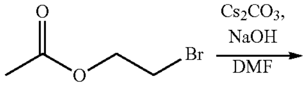

-continued

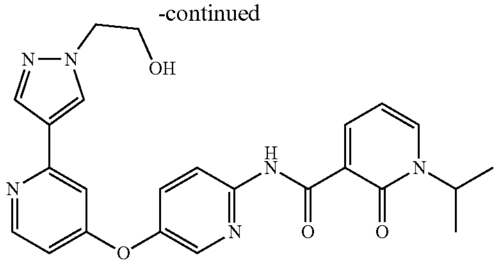

C (A) N-(5-((2-chloropyridin-4-yl)oxy)pyridin-2-yl)-1-isopropyl-2-oxo-1,2-dihydropyridine-3-carboxamide The title compound was prepared with corresponding intermediates and reagents with reference to the preparation processes of compound 94(A). MS (m/z): 385.1 [M+H]$^+$.

(B) N-(5-((2-(1H-pyrazol-4-yl)pyridin-4-yl)oxy)pyridin-2-yl)-1-isopropyl-2-oxo-1,2-dihydropyridine-3-carboxamide The title compound was prepared with corresponding intermediates and reagents with reference to the preparation processes of compound 94(C). MS (m/z): 417.1 [M+H]$^+$.

(C) N-(5-((2-(1-(2-hydroxyethyl)-1H-pyrazol-4-yl)pyridin-4-yl)oxy)pyridin-2-yl)-1-isopropyl-2-oxo-1,2-dihydropyridine-3-carboxamide The title compound was prepared with corresponding intermediates and reagents with reference to the preparation processes of compound 94(D). MS (m/z): 461.2[M+H]$^+$.

$^1$H NMR (400 MHz, DMSO-d6) δ 12.72 (s, 1H), 8.50 (dd, J=7.3, 2.1 Hz, 1H), 8.40 (s, 1H), 8.39 (d, J=2.5 Hz, 1H), 8.31 (d, J=2.9 Hz, 1H), 8.29 (s, 1H), 8.26 (dd, J=6.7, 2.1 Hz, 1H), 8.01 (s, 1H), 7.77 (dd, J=9.0, 2.9 Hz, 1H), 7.29 (d, J=2.3 Hz, 1H), 6.74 (dd, J=5.7, 2.4 Hz, 1H), 6.72-6.66 (m, 1H), 5.30-5.18 (m, 1H), 4.93 (t, J=5.3 Hz, 1H), 4.15 (t, J=5.6 Hz, 2H), 3.79-3.70 (m, 2H), 1.39 (d, J=6.8 Hz, 6H).

Compound 96

1-isopropyl-N-(5-((2-((1-methyl-1H-pyrazol-4-yl)amino)pyridin-4-yl)oxy)pyridin-2-yl)-2-oxo-1,2-dihydropyridine-3-carboxamide

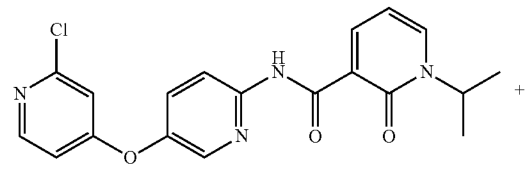

nol=100:0-0:100, gradient elution) and p-TLC plate, to obtain 25 mg of the title product as a light yellow solid. MS (m/z): 446.2 $[M+H]^+$.

$^1$H NMR (400 MHz, DMSO-d6) δ 12.71 (s, 1H), 8.78 (s, 1H), 8.49 (dd, J=7.3, 2.1 Hz, 1H), 8.38 (d, J=9.0 Hz, 1H), 8.28 (d, J=2.8 Hz, 1H), 8.25 (dd, J=6.7, 2.1 Hz, 1H), 8.02 (d, J=5.8 Hz, 1H), 7.89 (s, 1H), 7.76 (dd, J=9.0, 2.9 Hz, 1H), 7.32 (s, 1H), 6.73-6.64 (m, 1H), 6.34 (dd, J=5.8, 2.2 Hz, 1H), 6.04 (d, J=2.2 Hz, 1H), 5.29-5.18 (m, 1H), 3.77 (s, 3H), 1.39 (d, J=6.8 Hz, 6H).

The following compounds were prepared with corresponding intermediates and reagents with reference to the preparation processes of compound 96 under suitable conditions recognized by the POSITA.

| Compound | Structural formula | MS $(M + H)^+$ | $^1$HNMR |
|---|---|---|---|
| 97 | 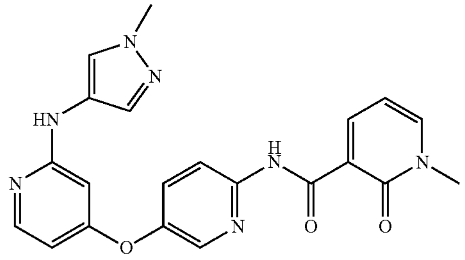 [SMILES: Cn1cc(Nc2cc(Oc3ccc(NC(=O)c4cccn(C)c4=O)nc3)ccn2)cn1] | 418.2 | $^1$H NMR (400 MHz, DMSO-d6) δ 12.65 (s, 1H), 8.77 (s, 1H), 8.50 (dd, J = 7.3, 2.1 Hz, 1H), 8.38 (d, J = 9.0 Hz, 1H), 8.28 (d, J = 2.8 Hz, 1H), 8.20 (dd, J = 6.5, 2.1 Hz, 1H), 8.02 (d, J = 5.8 Hz, 1H), 7.89 (s, 1H), 7.76 (dd, J = 9.0, 2.9 Hz, 1H), 7.32 (s, 1H), 6.67-6.57 (m, 1H), 6.34 (dd, J = 5.8, 2.2 Hz, 1H), 6.03 (d, J = 2.1 Hz, 1H), 3.77 (s, 3H), 3.64 (s, 3H). |

-continued

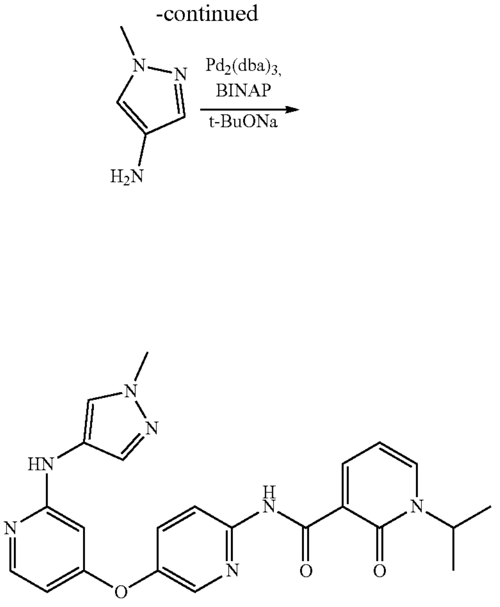

Under nitrogen, N-(5-((2-chloropyridin-4-yl)oxy)pyridin-2-yl)-1-isopropyl-2-oxo-1,2-dihydropyridine-3-carboxamide (50 mg, 0.13 mmol), 1-methyl-1H-pyrazol-4-amine (38 mg, 0.39 mmol), BINAP (8 mg, 0.013 mmol), tert-butoxysodium (25 mg, 0.26 mmol), dioxane (10 ml) and $Pd_2(dba)_3$ (12 mg, 0.013 mmol) were successively added to a reaction flask, and the mixture was refluxed and stirred for 2 hours. The reaction solution was cooled to room temperature and then concentrated, the residue was purified with flash column chromatography (water (0.5% formic acid):metha- Compound 98

N-(5-((2-(4-ethylpiperazin-1-yl)pyridin-4-yl)oxy)pyridin-2-yl)-1-isopropyl-2-oxo-1,2-dihydropyridine-3-carboxamide

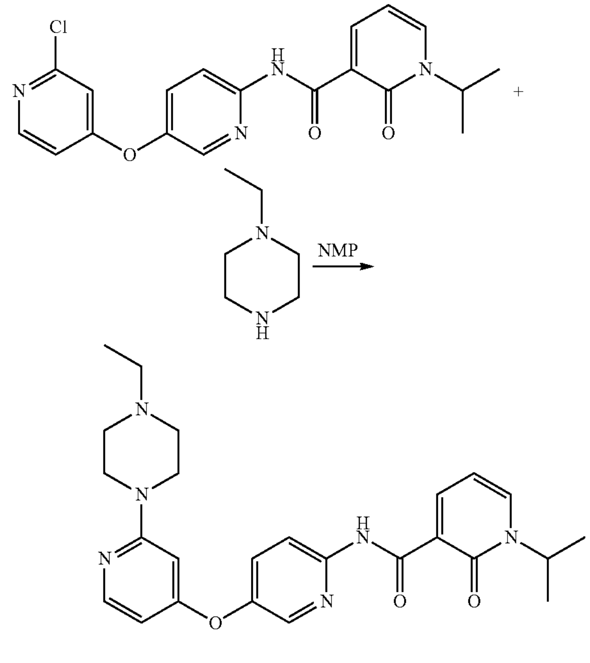

N-(5-((2-chloropyridin-4-yl)oxy)pyridin-2-yl)-1-isopropyl-2-oxo-1,2-dihydropyridine-3-carboxamide (50 mg, 0.13 mmol), 1-ethylpiperazine (74 mg, 0.65 mmol) and NMP (4.0 ml) were added to a microwave tube, and the mixture was reacted at 160° C. under microwave for 1.5 hours, the reaction solution was purified with flash column chromatography ($H_2O$/MeOH=100:0-0:100, gradient elution), to obtain 25 mg of the title product as a yellow solid. MS (m/z): 463.2 $[M+H]^+$.

$^1$H NMR (400 MHz, DMSO-d6) δ 12.64 (s, 1H), 8.44 (s, 1H), 8.39-8.26 (m, 1H), 8.26-8.11 (m, 2H), 7.97 (s, 1H), 7.78-7.56 (m, 1H), 6.75-6.54 (m, 1H), 6.31 (s, 1H), 6.17 (s, 1H), 5.19 (s, 1H), 3.36-3.30 (m, 4H), 2.41-2.20 (m, 6H), 1.35 (s, 6H), 0.97 (s, 3H).

Compound 99

1-methyl-N-(5-((2-(2-methyl-2H-1,2,3-triazol-4-yl)pyridin-4-yl)oxy)pyridin-2-yl)-2-oxo-1,2-dihydropyridine-3-carboxamide

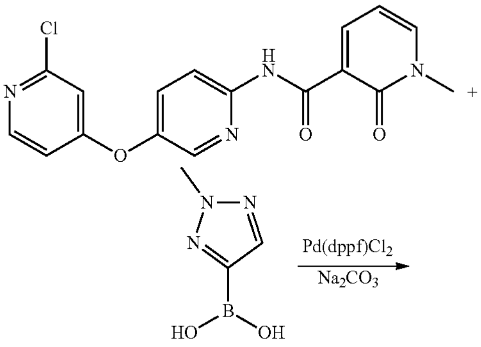

-continued

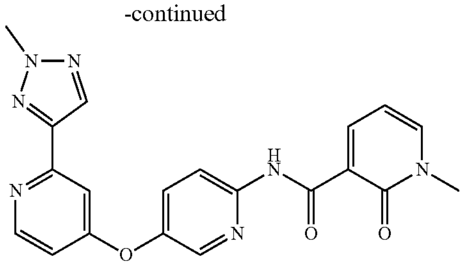

N-(5-((2-chloropyridin-4-yl)oxy)pyridin-2-yl)-1-methyl-2-oxo-1,2-dihydropyridine-3-carboxamide (120 mg, 0.336 mmol), (2-methyl-2H-1,2,3-triazol-4-yl)boronic acid (85 mg, 0.673 mmol), $Na_2CO_3$ (106 mg, 1.008 mmol), Pd(dppf) $Cl_2$—$CH_2Cl_2$ (27 mg, 0.0336 mmol), dioxane (23.0 ml) and water (3.0 ml) were added to a reaction flask, and the mixture was heated to 110° C. and stirred overnight, after cooling, the reaction solution was purified with flash column chromatography ($H_2O$/MeOH=100:0-0:100, gradient elution), to obtain 65 mg of the title product as a white solid. MS (m/z): 404.2 $[M+H]^+$.

$^1$H NMR (400 MHz, DMSO-d6) δ 12.67 (s, 1H), 8.51 (d, J=5.7 Hz, 1H), 8.48 (dd, J=7.4, 2.2 Hz, 1H), 8.39 (d, J=9.0 Hz, 1H), 8.34 (d, J=2.9 Hz, 1H), 8.20-8.15 (m, 2H), 7.81 (dd, J=9.0, 2.9 Hz, 1H), 7.28 (d, J=2.5 Hz, 1H), 7.02 (dd, J=5.7, 2.5 Hz, 1H), 6.64-6.55 (m, 1H), 4.15 (s, 3H), 3.61 (s, 3H).

The following compounds were prepared with corresponding intermediates and reagents with reference to the preparation processes of compound 99 under suitable conditions recognized by the POSITA.

| Compound | Structural formula | MS $(M + H)^+$ | $^1$HNMR |
|---|---|---|---|
| 100 | HCOOH 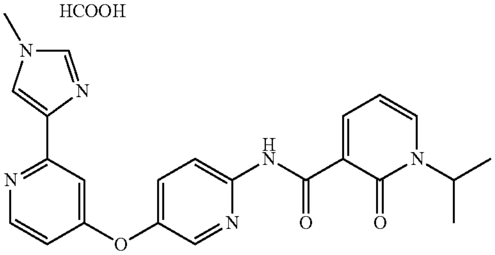 [SMILES: CC(C)n1cccc(C(=O)Nc2ccc(Oc3ccnc(-c4cn(C)cn4)c3)cn2)c1=O ; "HCOOH"] | 431.2 | $^1$H NMR (400 MHz, DMSO-d6) δ 12.70 (s, 1H), 8.46 (dd, J = 7.3, 2.1 Hz, 1H), 8.40-8.33 (m, 2H), 8.30 (d, J = 2.8 Hz, 1H), 8.22 (dd, J = 6.7, 2.1 Hz, 1H), 8.14 (s, 1H), 7.77 (dd, J = 9.0, 2.9 Hz, 1H), 7.66 (s, 1H), 7.58 (s, 1H), 7.24 (d, J = 2.6 Hz, 1H), 6.81 (dd, J = 5.7, 2.6 Hz, 1H), 6.73-6.59 (m, 1H), 5.21 (m, 1H), 3.65 (s, 3H), 1.36 (d, J = 6.8 Hz, 6H). |
| 101 | 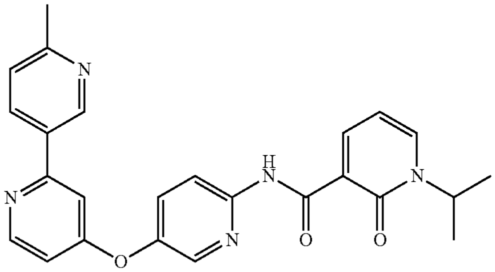 [SMILES: Cc1ccc(-c2cc(Oc3ccc(NC(=O)c4cccn(C(C)C)c4=O)nc3)ccn2)cn1] | 442.2 | $^1$H NMR (400 MHz, DMSO-d6) δ 12.68 (s, 1H), 9.08 (s, 1H), 8.53 (d, J = 5.6 Hz, 1H), 8.45 (d, J = 5.7 Hz, 1H), 8.36 (d, J = 8.9 Hz, 1H), 8.33-8.16 (m, 3H), 7.77 (dd, J = 8.9, 2.6 Hz, 1H), 7.63 (s, 1H), 7.31 (d, J = 8.0 Hz, 1H), 6.95-6.83 (m, 1H), 6.65 (m, 1H), 5.30-5.08 (m, 1H), 2.47 (s, 3H), 1.35 (d, J = 6.7 Hz, 6H). |

-continued

| Compound | Structural formula | MS (M + H)$^+$ | $^1$HNMR |
|---|---|---|---|
| 102 | 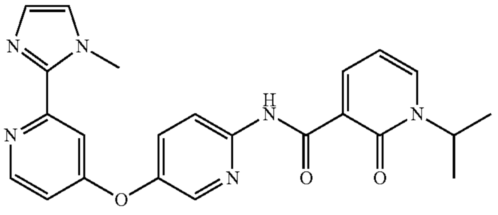 [SMILES: CC(C)n1cccc(C(=O)Nc2ccc(Oc3ccnc(-c4nccn4C)c3)cn2)c1=O] | 431.2 | $^1$H NMR (400 MHz, DMSO-d6) δ 12.71 (s, 1H), 8.70-8.11 (m, 5H), 7.91-7.62 (m, 2H), 7.49 (s, 1H), 7.36 (s, 1H), 6.81 (s, 1H), 6.67 (s, 1H), 5.40-5.08 (m, 1H), 3.91 (s, 3H), 1.60-1.24 (br, 6H). |
| 103 | 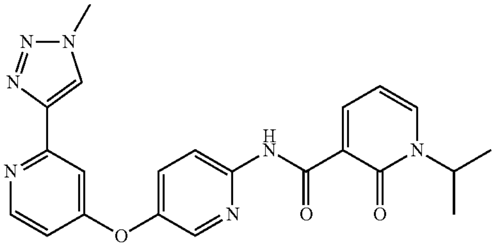 [SMILES: CC(C)n1cccc(C(=O)Nc2ccc(Oc3ccnc(-c4cn(C)nn4)c3)cn2)c1=O] | 432.2 | $^1$H NMR (400 MHz, DMSO-d6) δ 12.72 (s, 1H), 8.54 (s, 1H), 8.49-8.47 (m, 1H), 8.47-8.46 (m, 1H), 8.39 (d, J = 9.1 Hz, 1H), 8.34 (d, J = 2.5 Hz, 1H), 8.23 (dd, J = 6.7, 2.1 Hz, 1H), 7.81 (dd, J = 9.0, 2.9 Hz, 1H), 7.44 (d, J = 2.6 Hz, 1H), 6.95 (dd, J = 5.7, 2.6 Hz, 1H), 6.75-6.58 (m, 1H), 5.33-5.12 (m, 1H), 4.07 (s, 3H), 1.35 (s, 6H). |
| 115 | 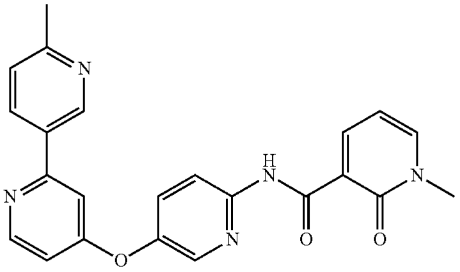 [SMILES: Cc1ccc(-c2cc(Oc3ccc(NC(=O)c4cccn(C)c4=O)nc3)ccn2)cn1] | 414.1 | 1H NMR (400 MHz, DMSO-d6) δ 12.67 (s, 1H), 9.12 (d, J = 1.9 Hz, 1H), 8.57 (d, J = 5.7 Hz, 1H), 8.50 (dd, J = 7.3, 2.0 Hz, 1H), 8.40 (d, J = 9.0 Hz, 1H), 8.35 (d, J = 2.8 Hz, 1H), 8.31 (dd, J = 8.1, 2.3 Hz, 1H), 8.20 (dd, J = 6.5, 2.0 Hz, 1H), 7.81 (dd, J = 9.0, 2.9 Hz, 1H), 7.68 (d, J = 2.2 Hz, 1H), 7.35 (d, J = 8.1 Hz, 1H), 6.93 (dd, J = 5.6, 2.3 Hz, 1H), 6.65-6.58 (m, 1H), 3.64 (s, 3H), 2.51 (s, 3H). |
| 125 | 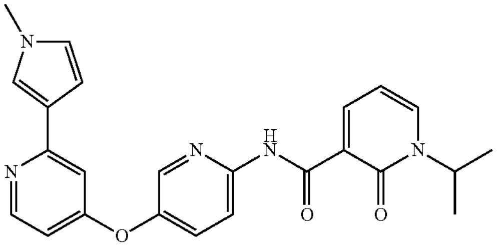 [SMILES: CC(C)n1cccc(C(=O)Nc2ccc(Oc3ccnc(-c4ccn(C)c4)c3)cn2)c1=O] | 430.1 | 1H NMR (400 MHz, DMSO-d6) δ 12.64 (s, 1H), 8.46 (dd, J = 7.3, 2.1 Hz, 1H), 8.36 (d, J = 9.0 Hz, 1H), 8.30 (d, J = 5.7 Hz, 1H), 8.27 (d, J = 2.9 Hz, 1H), 8.22 (dd, J = 6.7, 2.1 Hz, 1H), 7.73 (dd, J = 9.0, 2.9 Hz, 1H), 7.36-7.32 (m, 1H), 7.08 (d, J = 2.4 Hz, 1H), 6.71-6.69 (m, 1H), 6.68-6.63 (m, 1H), 6.61 (dd, J = 5.7, 2.4 Hz, 1H), 6.51 (dd, J = 2.6, 1.8 Hz, 1H), 5.27-5.14 (m, 1H), 3.60 (s, 3H), 1.36 (d, J = 6.8 Hz, 6H). |

Compound 104

1-cyclopropyl-N-(5-((2-(1-methyl-1H-pyrazol-4-yl)pyridin-4-yl)oxy)pyridin-2-yl)-2-oxo-1,2-dihydropyridine-3-carboxamide

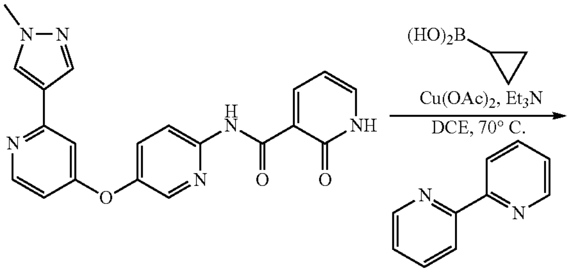

-continued

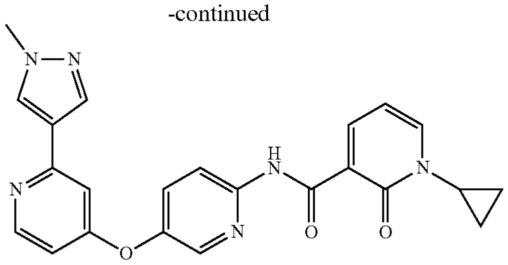

N-(5-((2-(1-methyl-1H-pyrazol-4-yl)pyridin-4-yl)oxy)pyridin-2-yl)-2-oxo-1,2-dihydropyridine-3-carboxamide (100 mg, 0.26 mmol), cyclopropyl boronic acid (66 mg, 0.78 mmol), 2,2'-bipyridine (8 mg, 0.05 mmol), copper acetate (55 mg, 0.30 mmol), triethylamine (53 mg, 0.52 mmol), molecular sieve (200 mg) and 1,2-dichloroethane (10 ml) were successively added to a reaction flask, and the mixture was reacted under oxygen at 70° C. for 24 hours. The reaction solution was filtered, and the filtrate was purified with flash column chromatography (water/methanol=100:0-

0:100, gradient elution), to obtain 10.1 mg of the title product as a yellow solid. MS (m/z): 429.2 [M+H]$^+$.

$^1$H NMR (400 MHz, a mixed solution of $CD_3OD$ and $CDCl_3$) δ 8.54 (dd, J=7.3, 2.1 Hz, 1H), 8.40 (d, J=9.0 Hz, 1H), 8.32 (d, J=5.8 Hz, 1H), 8.19 (d, J=2.9 Hz, 1H), 8.02 (s, 1H), 7.93-7.85 (m, 2H), 7.60 (dd, J=9.0, 2.9 Hz, 1H), 7.13 (d, J=2.4 Hz, 1H), 6.73 (dd, J=5.8, 2.4 Hz, 1H), 6.55 (t, J=7.0 Hz, 1H), 3.90 (s, 3H), 3.49-3.38 (m, 1H), 1.22-1.13 (m, 2H), 0.99-0.95 (m, 2H).

Compound 105

6-amino-1-methyl-N-(5-((2-(1-methyl-1H-pyrazol-4-yl)pyridin-4-yl)oxy)pyridin-2-yl)-2-oxo-1,2-dihydro-pyridine-3-carboxamide

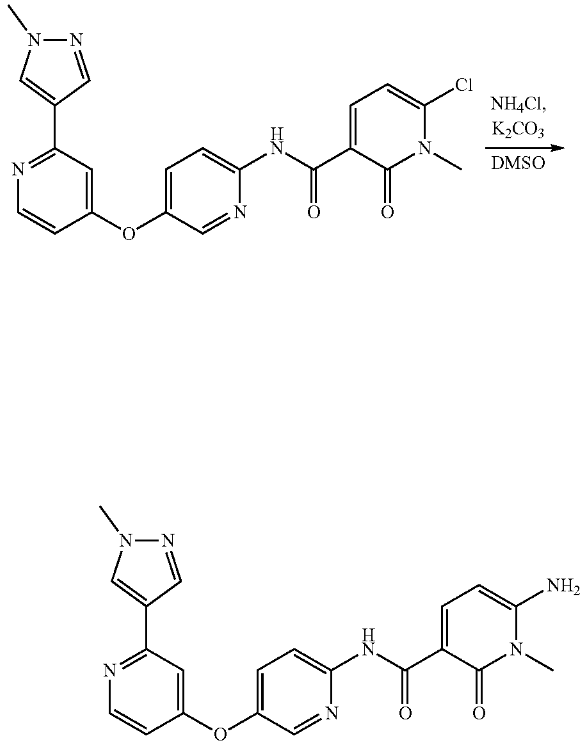

6-chloro-1-methyl-N-(5-((2-(1-methyl-1H-pyrazol-4-yl) pyridin-4-yl)oxy)pyridin-2-yl)-2-oxo-1,2-dihydropyridine-3-carboxamide (80 mg, 0.18 mmol), ammonium chloride (46 mg, 0.90 mmol), potassium carbonate (50 mg, 0.36 mmol) and DMSO (5 ml) were successively added to a reaction flask, and the mixture was reacted at room temperature for 15 hours. The reaction solution was filtered, and the filtrate was purified with flash column chromatography (water/methanol=100:0-0:100, gradient elution), to obtain 6.3 mg of the title product as a yellow solid. MS (m/z): 418.1[M+H]$^+$.

$^1$H NMR (400 MHz, DMSO-d6) δ 12.41 (s, 1H), 8.36-8.33 (m, 2H), 8.24 (s, 1H), 8.20 (d, J=2.7 Hz, 1H), 8.05 (d, J=8.8 Hz, 1H), 7.95 (s, 1H), 7.76-7.61 (m, 3H), 7.21 (d, J=2.1 Hz, 1H), 6.68 (dd, J=5.6, 2.3 Hz, 1H), 5.81 (d, J=8.8 Hz, 1H), 3.82 (s, 3H), 3.39 (s, 3H).

Compound 106

1-methyl-N-(5-((2-(1-methyl-1H-pyrazol-4-yl)pyridin-4-yl)oxy)pyridin-2-yl)-6-(methylamino)-2-oxo-1,2-dihydropyridine-3-carboxamide

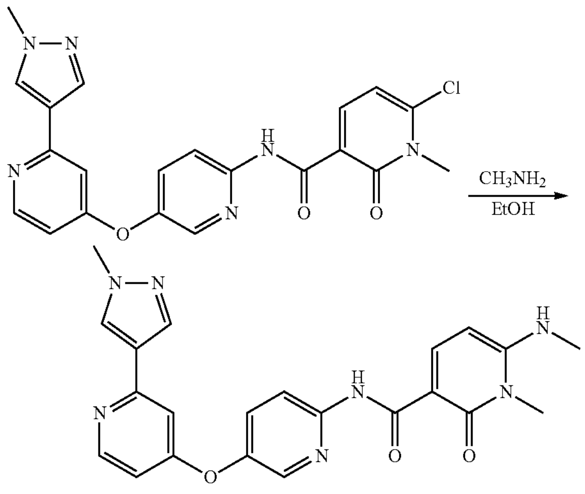

6-chloro-1-methyl-N-(5-((2-(1-methyl-1H-pyrazol-4-yl) pyridin-4-yl)oxy)pyridin-2-yl)-2-oxo-1,2-dihydropyridine-3-carboxamide (80 mg, 0.18 mmol) and methylamine alcohol solution (5 ml) were successively added to a reaction flask, and the mixture was reacted at 80° C. for 2 hours. The reaction solution was filtered, and the filtrate was purified with flash column chromatography (water/methanol=100:0-0:100, gradient elution), to obtain 23.0 mg of the title product as a yellow solid. MS (m/z): 432.1[M+H]$^+$.

$^1$H NMR (400 MHz, DMSO-d6) δ 12.43 (s, 1H), 8.40-8.30 (m, 2H), 8.24 (s, 1H), 8.21 (d, J=2.9 Hz, 1H), 8.17 (d, J=8.9 Hz, 1H), 7.95 (s, 1H), 7.68-7.65 (m, 2H), 7.21 (d, J=2.3 Hz, 1H), 6.68 (dd, J=5.6, 2.2 Hz, 1H), 5.80 (d, J=9.0 Hz, 1H), 3.82 (s, 3H), 3.41 (s, 3H), 2.85 (s, 3H).

Compound 107

1-methyl-N-(5-((2-(1-methyl-1H-imidazol-4-yl)pyridin-4-yl)oxy)pyridin-2-yl)-2-oxo-1,2-dihydropyridine-3-carboxamide

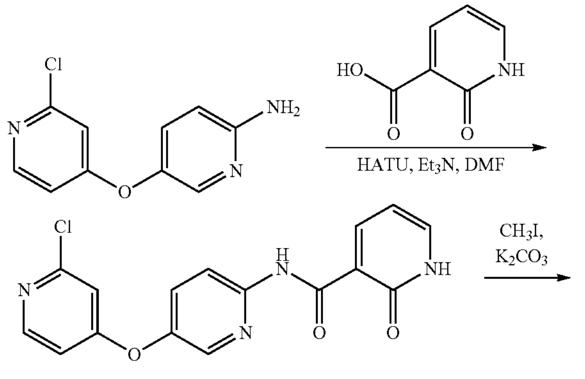

A

-continued

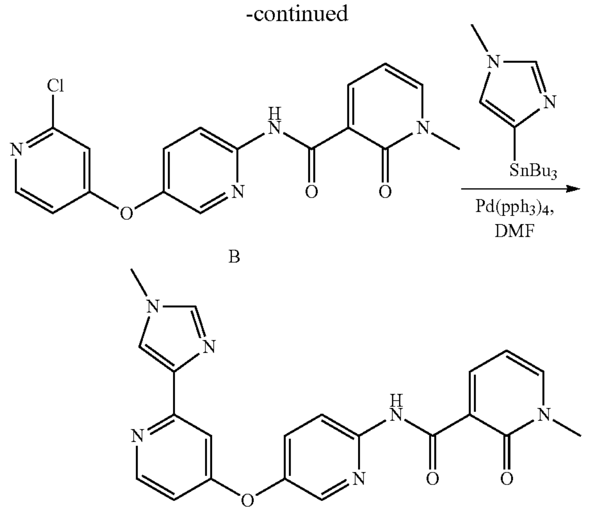

B

C (A) N-(5-((2-chloropyridin-4-yl)oxy)pyridin-2-yl)-2-oxo-1,2-dihydropyridine-3-carboxamide The title compound was prepared with corresponding intermediates and reagents with reference to the preparation processes of compound 79(A). MS (m/z): 343.0 $[M+H]^+$.

(B) N-(5-((2-chloropyridin-4-yl)oxy)pyridin-2-yl)-1-methyl-2-oxo-1,2-dihydropyridine-3-carboxamide Under nitrogen, N-(5-((2-chloropyridin-4-yl)oxy)pyridin-2-yl)-2-oxo-1,2-dihydropyridine-3-carboxamide (387 mg, 1.13 mmol), iodomethane (241 mg, 1.70 mmol), potassium carbonate (312 mg, 2.26 mmol) and DMSO (5 ml) were successively added to a reaction flask, and the mixture was reacted at 60° C. for 1 hour. The reaction solution was purified with flash column chromatography (water/methanol=100:0-0:100, gradient elution), to obtain 203 mg of the title product as a yellow solid. MS (m/z): 356.7$[M+H]^+$.

(C) 1-methyl-N-(5-((2-(1-methyl-1H-imidazol-4-yl)pyridin-4-yl)oxy)pyridin-2-yl)-2-oxo-1,2-dihydropyridine-3-carboxamide Under nitrogen, N-(5-((2-chloropyridin-4-yl)oxy)pyridin-2-yl)-1-methyl-2-oxo-1,2-dihydropyridine-3-carboxamide (130 mg, 0.37 mmol), 1-methyl-4-(tributylstannyl)-1H-imidazole (208 mg, 0.56 mmol), $Pd(PPh_3)_4$ (13 mg, 0.01 mmol) and DMF (5 ml) were successively added to a reaction flask, and the mixture was reacted at 100° C. for 2 hours. The reaction solution was concentrated, and the residue was purified with flash column chromatography (water/methanol=100:0-0:100, gradient elution), to obtain 64.5 mg of the title product as a yellow solid. MS (m/z): 403.0 $[M+H]^+$.

$^1H$ NMR (400 MHz, DMSO-d6) δ 12.65 (s, 1H), 8.47 (d, J=6.9 Hz, 1H), 8.39-8.35 (m, 2H), 8.30 (s, 1H), 8.18 (d, J=5.6 Hz, 1H), 7.78 (d, J=7.7 Hz, 1H), 7.67 (s, 1H), 7.58 (s, 1H), 7.25 (s, 1H), 6.81 (s, 1H), 6.61-6.57 (m, 1H), 3.66 (s, 3H), 3.61 (s, 3H).

The following compounds were prepared with corresponding intermediates and reagents with reference to the preparation processes of compound 107 under suitable conditions recognized by the POSITA.

| Compound | Structural formula | MS $(M + H)^+$ | $^1HNMR$ |
|---|---|---|---|
| 108 | 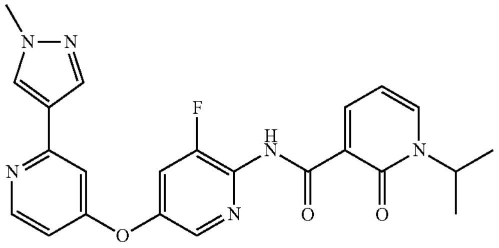 [SMILES: CC(C)n1cccc(C(=O)Nc2ncc(Oc3ccnc(-c4cnn(C)c4)c3)cc2F)c1=O] | 449.0 | $^1H$ NMR (400 MHz, DMSO-d6) δ 12.29 (s, 1H), 8.45-8.37 (m, 2H), 8.27 (s, 1H), 8.25-8.21 (m, 2H), 7.98 (s, 1H), 7.93 (dd, J = 10.4, 1.9 Hz, 1H), 7.32 (d, J = 1.9 Hz, 1H), 6.80 (dd, J = 5.5, 2.1 Hz, 1H), 6.68-6.65 (m, 1H), 5.28-5.13 (m, 1H), 3.84 (s, 3H), 1.36 (d, J = 6.7 Hz, 6H). |
| 114 | 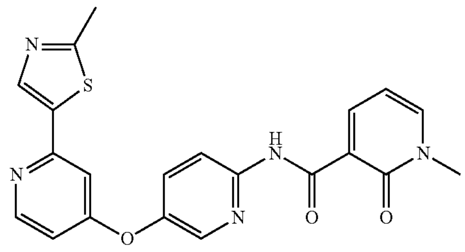 [SMILES: Cc1ncc(-c2cc(Oc3ccc(NC(=O)c4cccn(C)c4=O)nc3)ccn2)s1] | 420.1 | 1H NMR (400 MHz, $CDCl_3$) δ 12.64 (s, 1H), 8.62 (dd, J = 7.3, 2.1 Hz, 1H), 8.48 (d, J = 9.0 Hz, 1H), 8.43 (d, J = 5.8 Hz, 1H), 8.24 (d, J = 2.8 Hz, 1H), 8.03 (s, 1H), 7.62 (dd, J = 6.6, 2.1 Hz, 1H), 7.50 (dd, J = 9.0, 2.9 Hz, 1H), 7.18 (d, J = 2.3 Hz, 1H), 6.73 (dd, J = 5.8, 2.3 Hz, 1H), 6.51-6.46 (m, 1H), 3.71 (s, 3H), 2.74 (s, 3H). |

Compound 109

N-(5-((2-(1-(2-aminoethyl)-1H-pyrazol-4-yl)pyridin-4-yl)oxy)pyridin-2-yl)-1,2-dimethyl-6-oxo-1,6-dihydropyrimidine-5-carboxamide

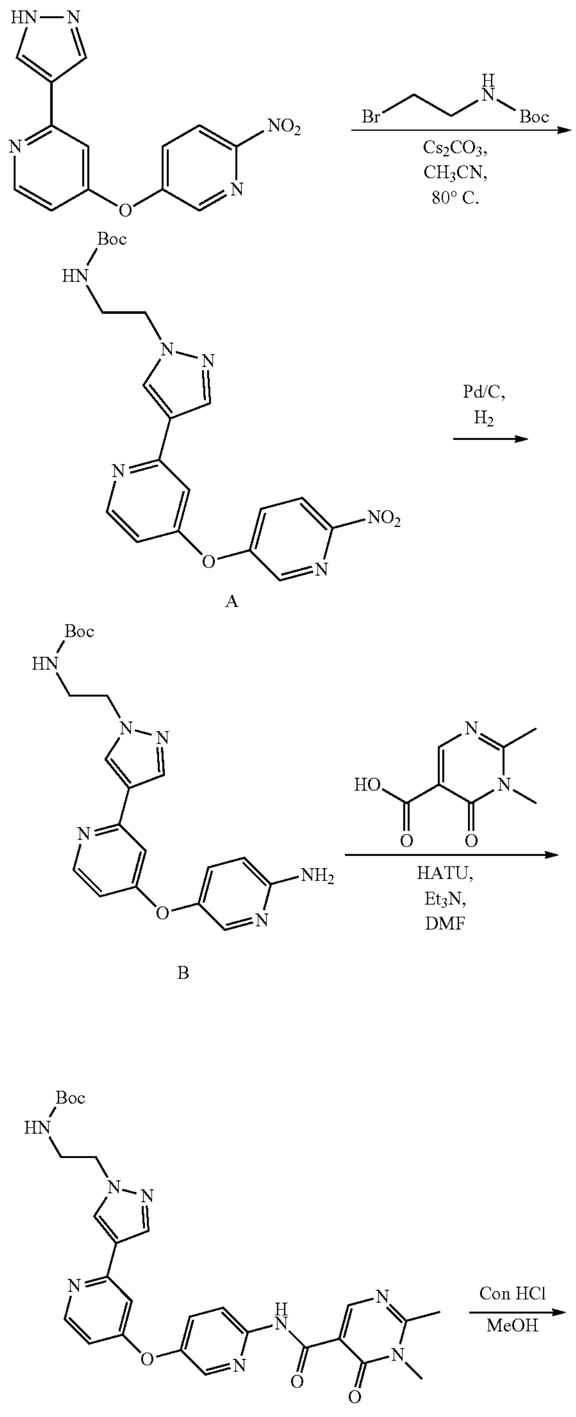

A

B

C

-continued

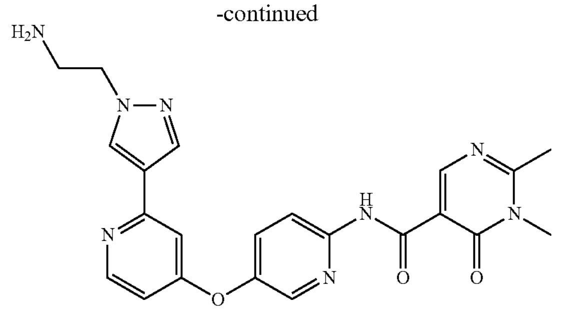

D (A) tert-butyl (2-(4-(4-((6-nitropyridin-3-yl)oxy)pyridin-2-yl)-1H-pyrazol-1-yl)ethyl)carbamate 4-((6-nitropyridin-3-yl)oxy)-2-(1H-pyrazol-4-yl)pyridine (350 mg, 1.24 mmol), tert-butyl (2-bromoethyl)carbamate (415 mg, 1.85 mmol), cesium carbonate (601 mg, 1.85 mmol) and acetonitrile (20 ml) were successively added to a reaction flask, and the mixture was reacted at 80° C. for 5 hours. The reaction solution was purified with flash column chromatography (dichloromethane/methanol=100:0-0:100, gradient elution), to obtain 362 mg of the title product as a yellow solid. MS (m/z): 427.2[M+H]$^+$.

(B) tert-butyl (2-(4-(4-((6-aminopyridin-3-yl)oxy)pyridin-2-yl)-1H-pyrazol-1-yl)ethyl)carbamate Tert-butyl (2-(4-(4-((6-nitropyridin-3-yl)oxy)pyridin-2-yl)-1H-pyrazol-1-yl)ethyl)carbamate (110 mg, 0.26 mmol) and palladium carbon (11 mg) were dissolved in methanol (10 ml), and the mixture was stirred under hydrogen at room temperature for 5 hours. The reaction solution was filtered to remove palladium carbon, and the filtrate was concentrated, which was purified with flash column chromatography (water/methanol=100:0-0:100, gradient elution), to obtain 93 mg of the title product. MS (m/z): 397.2[M+H]$^+$.

(C) tert-butyl (2-(4-(4-((6-(1,2-dimethyl-6-oxo-1,6-dihydropyrimidine-5-carboxamido)pyridin-3-yl)oxy)pyridin-2-yl)-1H-pyrazol-1-yl)ethyl)carbamate Tert-butyl (2-(4-(4-((6-aminopyridin-3-yl)oxy)pyridin-2-yl)-1H-pyrazol-1-yl)ethyl)carbamate (93 mg, 0.23 mmol), 1,2-dimethyl-6-oxo-1,6-dihydropyrimidine-5-carboxylic acid (35 mg, 0.23 mmol), HATU (86 mg, 0.23 mmol), triethylamine (70 mg, 0.69 mmol) and DMF (4 ml) were successively added to a reaction flask, and the mixture was reacted at 45° C. for 15 hours. The reaction solution was purified with flash column chromatography (water/methanol=100:0-0:100, gradient elution), to obtain 37 mg of the title product as a yellow solid. MS (m/z): 547.2[M+H]$^+$.

(D) N-(5-((2-(1-(2-aminoethyl)-1H-pyrazol-4-yl)pyridin-4-yl)oxy)pyridin-2-yl)-1,2-dimethyl-6-oxo-1,6-dihydropyrimidine-5-carboxamide In a reaction flask, tert-butyl (2-(4-(4-((6-(1,2-dimethyl-6-oxo-1,6-dihydropyrimidine-5-carboxamido)pyridin-3-yl)oxy)pyridin-2-yl)-1H-pyrazol-1-yl)ethyl)carbamate (37 mg, 0.07 mmol) was dissolved in concentrated hydrochloric acid (1 ml) and methanol (5 ml), and the mixture was reacted at room temperature for half an hour, the reaction solution was concentrated at 50° C., which was purified with flash column chromatography (water/methanol=100:0-0:100, gradient elution), to obtain 7 mg of the title product as a yellow solid. MS (m/z): 447.1 [M+H]$^+$.

$^1$H NMR (400 MHz, CD3OD) δ 8.89 (s, 1H), 8.71 (s, 1H), 8.58 (d, J=6.5 Hz, 1H), 8.49-8.45 (m, 2H), 8.35 (s, 1H), 7.97 (d, J=8.5 Hz, 1H), 7.77 (s, 1H), 7.36 (d, J=6.0 Hz, 1H), 4.62-4.57 (m, 2H), 3.77 (s, 3H), 3.53-3.48 (m, 2H), 2.90-2.67 (m, 3H).

The following compounds were prepared with corresponding intermediates and reagents with reference to the preparation processes of compound 109 under suitable conditions recognized by the POSITA.

| Compound | Structural formula | MS (M + H)$^+$ | $^1$HNMR |
|---|---|---|---|
| 110 | 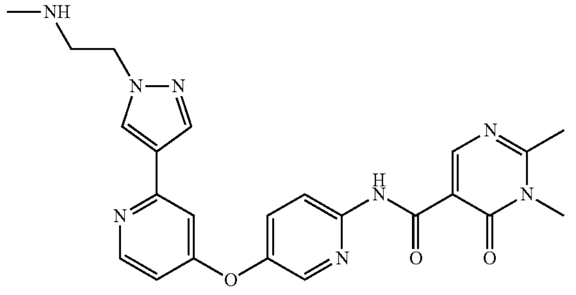 | 461.1 | $^1$H NMR (400 MHz, CD3OD) δ 8.78 (s, 1H), 8.43-8.38 (m, 2H), 8.23 (d, J = 2.8 Hz, 1H), 8.22 (s, 1H), 8.08 (s, 1H), 7.69 (dd, J = 9.0, 2.8 Hz, 1H), 7.25 (d, J = 2.4 Hz, 1H), 6.82 (dd, J = 5.8, 2.4 Hz, 1H), 4.57-4.49 (m, 2H), 3.67 (s, 3H), 3.58-3.49 (m, 2H), 2.75 (s, 3H), 2.68 (s, 3H). |

Compound 111

1,2-dimethyl-N-(5-((2-((5-methyl-1H-pyrazol-3-yl)amino)pyridin-4-yl)oxy)pyridin-2-yl)-6-oxo-1,6-dihydropyrimidine-5-carboxamide

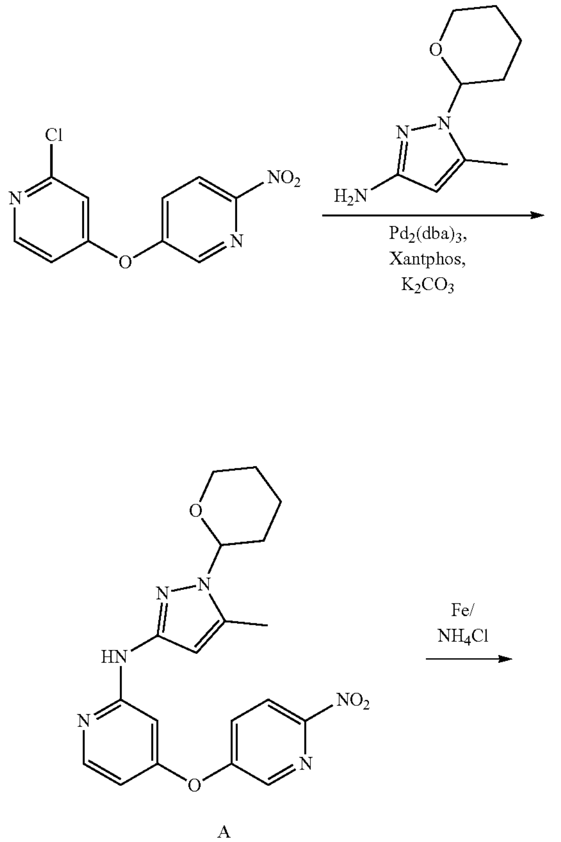

-continued

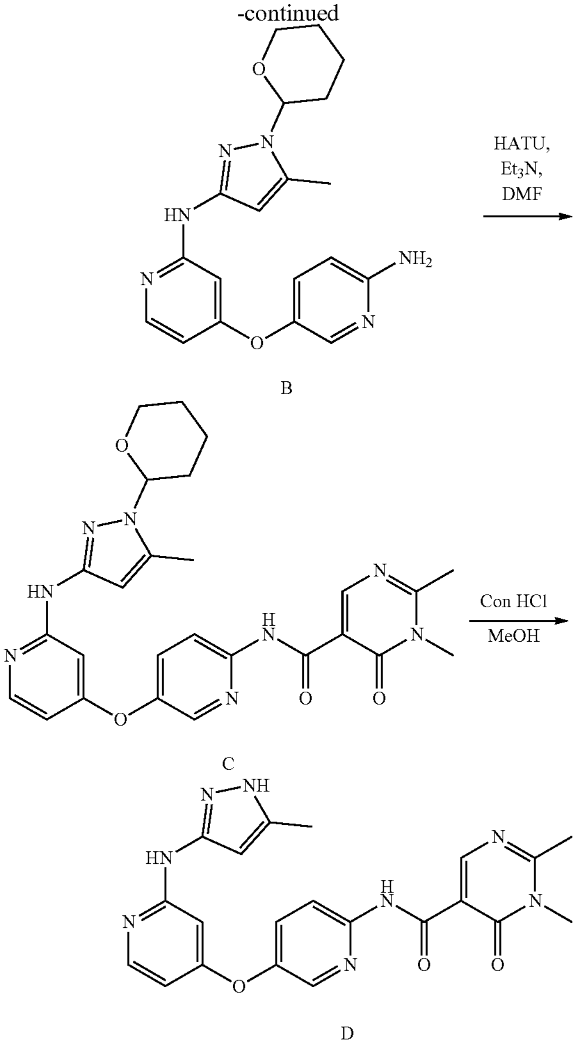

(A) N-(5-methyl-1-(tetrahydro-2H-pyran-2-yl)-1H-pyrazol-3-yl)-4-((6-nitropyridin-3-yl)oxy)pyridin-2-amine 2-chloro-4-((6-nitropyridin-3-yl)oxy)pyridine (500 mg, 2.0 mmol), 5-methyl-1-(tetrahydro-2H-pyran-2-yl)-1H-pyrazol-3-amine (540 mg, 3.0 mmol), $Pd_2(dba)_3$ (186 mg, 0.2 mmol), Xantphos (116 mg, 0.2 mmol), potassium carbonate (420 mg, 3.0 mmol) and dioxane (20 ml) were successively added to a reaction flask, and the mixture was reacted under nitrogen at 100° C. for 15 hours. The reaction solution was purified with flash column chromatography (dichloromethane/methanol=100:0-0:100, gradient elution), to obtain 320 mg of the title product as a yellow solid. MS (m/z): 397.0[M+H]$^+$.

(B) 4-((6-aminopyridin-3-yl)oxy)-N-(5-methyl-1-(tetrahydro-2H-pyran-2-yl)-1H-pyrazol-3-yl)pyridin-2-amine N-(5-methyl-1-(tetrahydro-2H-pyran-2-yl)-1H-pyrazol-3-yl)-4-((6-nitropyridin-3-yl)oxy)pyridin-2-amine (320 mg, 0.81 mmol), iron powder (168 mg, 3.24 mmol) and ammonium chloride (214 mg, 4.05 mmol) were dissolved in ethanol (8 ml) and water (2 ml), and the mixture was refluxed and reacted for 1 hour. The reaction solution was filtered to remove iron powder, and the filtrate was concentrated, which was purified with flash column chromatography (water/methanol=100:0-0:100, gradient elution), to obtain 227 mg of the title product. MS (m/z): 367.1 [M+H]$^+$.

(C) 1,2-dimethyl-N-(5-((2-((5-methyl-1-(tetrahydro-2H-pyran-2-yl)-1H-pyrazol-3-yl)amino)pyridin-4-yl)oxy)pyridin-2-yl)-6-oxo-1,6-dihydropyrimidine-5-carboxamide The title compound was prepared with corresponding intermediates and reagents with reference to the preparation processes of compound 1(A). MS (m/z): 517.2[M+H]$^+$.

(D) 1,2-dimethyl-N-(5-((2-((5-methyl-1H-pyrazol-3-yl)amino)pyridin-4-yl)oxy)pyridin-2-yl)-6-oxo-1,6-dihydropyrimidine-5-carboxamide The title compound was prepared with corresponding intermediates and reagents with reference to the preparation processes of compound 109(D). MS (m/z): 433.1 [M+H]$^+$.

$^1$H NMR (400 MHz, DMSO-d6) δ 11.83 (s, 1H), 9.09 (s, 1H), 8.73 (s, 1H), 8.32 (d, J=9.0 Hz, 1H), 8.26 (d, J=2.8 Hz, 1H), 7.99 (d, J=5.7 Hz, 1H), 7.73 (dd, J=9.0, 2.9 Hz, 1H), 6.88 (s, 1H), 6.35-6.28 (m, 1H), 5.93 (s, 1H), 3.57 (s, 3H), 2.63 (s, 3H), 2.13 (s, 3H).

The following compounds were prepared with corresponding intermediates and reagents with reference to the preparation processes of compound 111 under suitable conditions recognized by the POSITA.

| Compound | Structural formula | MS (M + H)$^+$ | $^1$HNMR |
|---|---|---|---|
| 112 | 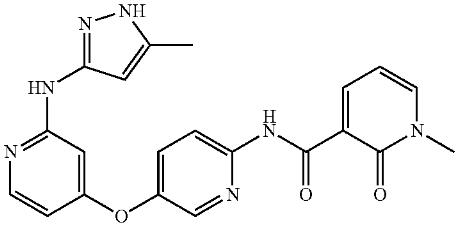 [SMILES: Cc1cc(Nc2cc(Oc3ccc(NC(=O)c4cccn(C)c4=O)nc3)ccn2)n[nH]1] | 418.1 | $^1$H NMR (400 MHz, DMSO-d6) δ 12.61 (s, 1H), 9.16 (s, 1H), 8.53-8.41 (m, 1H), 8.35 (d, J = 9.0 Hz, 1H), 8.25 (d, J = 2.6 Hz, 1H), 8.17 (d, J = 4.7 Hz, 1H), 8.11 (s, 1H), 8.00 (d, J = 5.8 Hz, 1H), 7.71 (dd, J = 8.9, 2.6 Hz, 1H), 6.87 (s, 1H), 6.61-6.57 (m, 1H), 6.34 (d, J = 3.9 Hz, 1H), 5.93 (s, 1H), 3.62 (s, 3H), 2.13 (s, 3H). |

Compound 113

N-(5-((2-(1-(2-hydroxyethyl)-1H-pyrazol-4-yl)pyridin-4-yl)oxy)pyridin-2-yl)-1,2-dimethyl-6-oxo-1,6-dihydropyrimidine-5-carboxamide

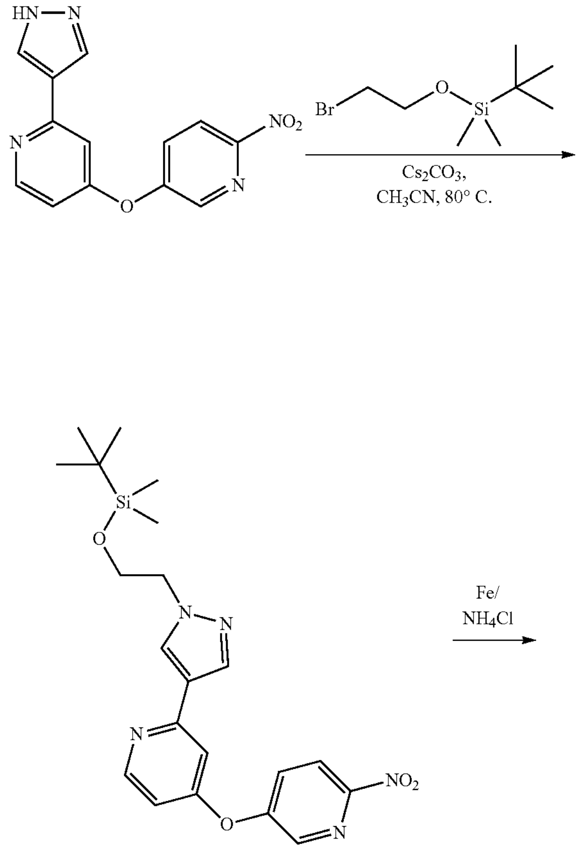

A

-continued

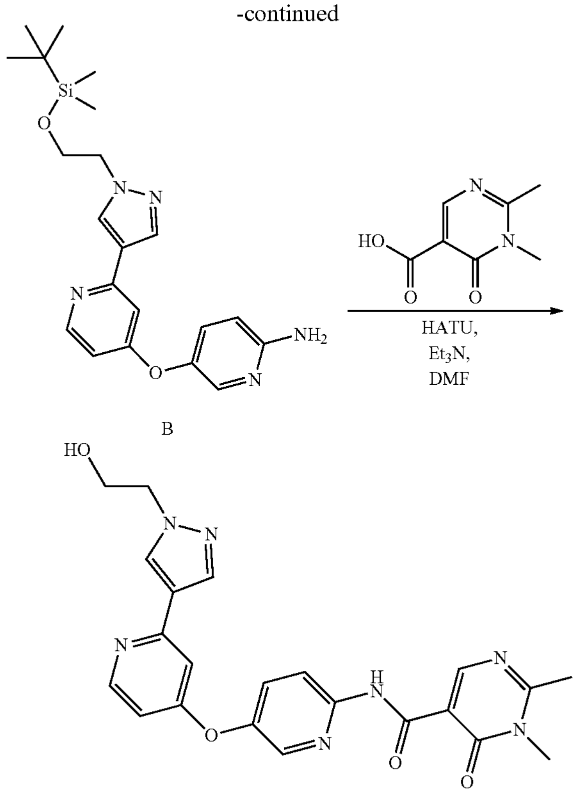

B

C (A) 2-(1-(2-((tert-butyldimethylsilyl)oxy)ethyl)-1H-pyrazol-4-yl)-4-((6-nitropyridin-3-yl)oxy)pyridine 4-((6-nitropyridin-3-yl)oxy)-2-(1H-pyrazol-4-yl)pyridine (100 mg, 0.35 mmol), (2-bromoethoxy)(tert-butyl) dimethylsilane (101 mg, 0.42 mmol) and cesium carbonate (172 mg, 0.53 mmol) were dissolved in acetonitrile (10 ml), and the mixture was stirred at 80° C. for 5 hours. The reaction solution was concentrated to obtain a crude product, which was purified with flash column chromatography (dichloromethane/methanol=100:0-90:10, gradient elution), to obtain 139 mg of the title product. MS (m/z): 442.2[M+H]$^+$.

(B) 5-((2-(1-(2-((tert-butyldimethylsilyl)oxy)ethyl)-1H-pyrazol-4-yl)pyridin-4-yl)oxy)pyridin-2-amine The title compound was prepared with corresponding intermediates and reagents with reference to the preparation processes of compound 111(B). MS (m/z): 412.2[M+H]$^+$.

(C) N-(5-((2-(1-(2-hydroxyethyl)-1H-pyrazol-4-yl)pyridin-4-yl)oxy)pyridin-2-yl)-1,2-dimethyl-6-oxo-1,6-dihydropyrimidine-5-carboxamide 5-((2-(1-(2-((tert-butyldimethylsilyl)oxy)ethyl)-1H-pyrazol-4-yl)pyridin-4-yl)oxy)pyridin-2-amine (83 mg, 0.20 mmol), 1,2-dimethyl-6-oxo-1,6-dihydropyrimidine-5-carboxylic acid (34 mg, 0.20 mmol), HATU (76 mg, 0.20 mmol), triethylamine (60 mg, 0.60 mmol) and DMF (3 ml) were successively added to a reaction flask, and the mixture was reacted at 40° C. for 15 hours. The reaction solution was purified with flash column chromatography (water/methanol=100:0-0:100, gradient elution), to obtain 23.3 mg of the title product as a yellow solid. MS (m/z): 448.2 [M+H]$^+$.

$^1$H NMR (400 MHz, DMSO-d6) δ 11.85 (s, 1H), 8.74 (s, 1H), 8.43-8.22 (m, 4H), 8.00 (s, 1H), 7.79-7.75 (m, 1H), 7.29-7.25 (m, 1H), 6.75-6.72 (m, 1H), 4.93 (s, 1H), 4.17-4.14 (m, 2H), 3.77-3.72 (m, 2H), 3.59 (s, 3H), 2.64 (s, 3H).

Compound 117

1,2-dimethyl-N-(5-((2-(1-methyl-1H-pyrrol-3-yl)pyridin-4-yl)oxy)pyridin-2-yl)-6-oxo-1,6-dihydropyrimidine-5-carboxamide

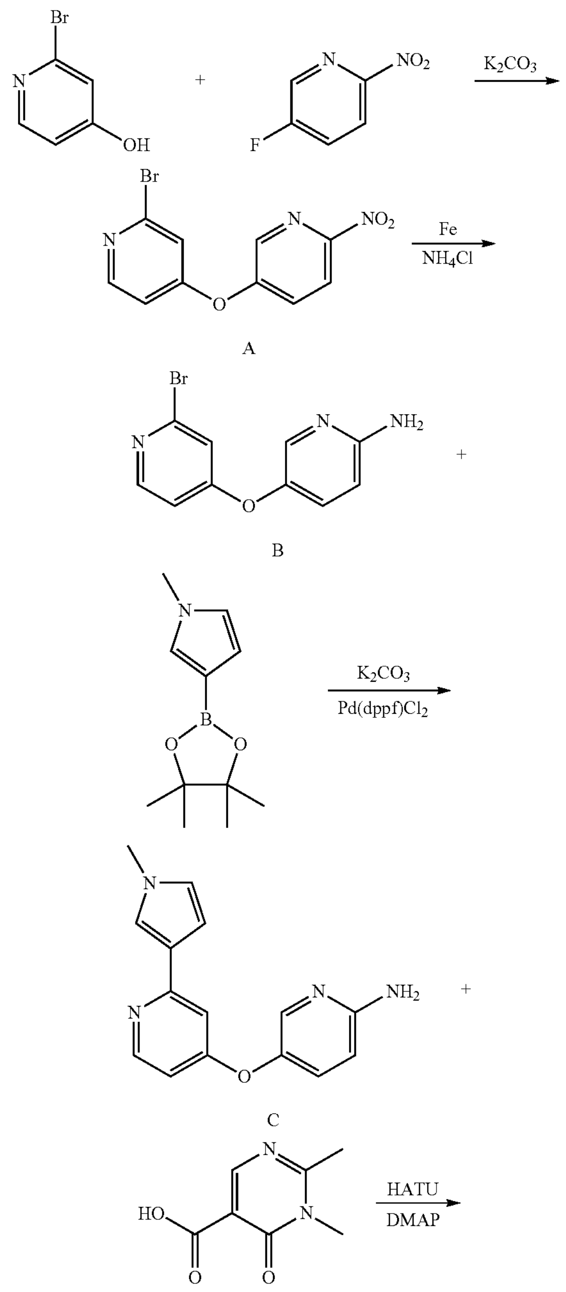

-continued

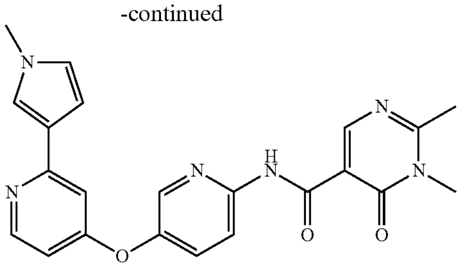

D (A) 2-bromo-4-((6-nitropyridin-3-yl)oxy)pyridine 2-bromo-4-hydroxyl pyridine (5.22 g, 30 mmol), 5-fluoro-2-nitropyridine (4.263 g, mmol) and potassium carbonate (4.975 g, 36 mmol) were dissolved in DMF (40 ml), and the mixture was heated at 90° C. for 4 hours. The reaction was cooled to room temperature, and quenched with water (200 ml). The reaction solution was filtered, and the solid was collected, to obtain 8.1 g of the title product. MS (m/z): 296.0, 298.0 $[M+H]^+$.

(B) 5-((2-bromopyridin-4-yl)oxy)pyridin-2-amine 2-bromo-4-((6-nitropyridin-3-yl)oxy)pyridine (5 g, 16.89 mmol), iron powder (3.773 g, 67.56 mmol), ammonium chloride (4.517 g, 84.45 mmol), ethanol (60 ml) and water (15 ml) were successively added to a reaction flask, and the mixture was heated to reflux and reacted for 1 hour. The reaction solution was concentrated, and the residue was purified with flash column chromatography (petroleum ether/ethyl acetate=100:0-0:100, gradient elution), to obtain 4.3 g of the title product. MS (m/z): 266.0, 268.0 $[M+H]^+$.

(C) 5-((2-(1-methyl-1H-pyrrol-3-yl)pyridin-4-yl)oxy)pyridin-2-amine 5-((2-bromopyridin-4-yl)oxy)pyridin-2-amine (532 mg, 2.0 mmol), 1-methyl-3-(4,4,5,5-tetramethyl-1,3,2-dioxaborolan-2-yl)-1H-pyrrole (414 mg, 2.0 mmol), Pd(dppf)$Cl_2$ (73 mg, 0.1 mmol), $K_2CO_3$ (552 mg, 4.0 mmol), dioxane (20 ml) and water (4 ml) were successively added to a reaction flask, and the mixture was heated to 100° C. under nitrogen and reacted for 15 hours. The reaction solution was concentrated, and then purified with flash column chromatography (petroleum ether/ethyl acetate=100:0-0:100, gradient elution), to obtain 410 mg of the title product. MS (m/z): 267.1$[M+H]^+$.

(D) 1,2-dimethyl-N-(5-((2-(1-methyl-1H-pyrrol-3-yl)pyridin-4-yl)oxy)pyridin-2-yl)-6-oxo-1,6-dihydropyrimidine-5-carboxamide 5-((2-(1-methyl-1H-pyrrol-3-yl)pyridin-4-yl)oxy)pyridin-2-amine (410 mg, 1.54 mmol), 1,2-dimethyl-6-oxo-1,6-dihydropyrimidine-5-carboxylic acid (388 mg, 2.31 mmol), HATU (878 mg, 2.31 mmol), DMAP (282 mg, 2.31 mmol) and DMF (3 ml) were successively added to a reaction flask, and the mixture was heated to 40° C. and reacted for 15 hours. The reaction solution was purified with flash column chromatography (water/methanol=100:0-0:100, gradient elution), and the resulting crude product was further purified with flash column chromatography (dichloromethane/methanol=100:0-70:30, gradient elution), to obtain the title product (180 mg). MS (m/z): 417.1$[M+H]^+$. 1H NMR (400 MHz, DMSO-d6) δ 11.84 (s, 1H), 8.73 (s, 1H), 8.35-8.25 (m, 3H), 7.74 (dd, J=9.1, 2.9 Hz, 1H), 7.34 (s, 1H), 7.08 (d, J=2.4 Hz, 1H), 6.72-6.67 (m, 1H), 6.61 (dd, J=5.7, 2.4 Hz, 1H), 6.53-6.48 (m, 1H), 3.60 (s, 3H), 3.56 (s, 3H), 2.62 (s, 3H).

The following compounds were prepared with corresponding intermediates and reagents with reference to the preparation processes of compound 117(D) under suitable conditions recognized by the POSITA.

| Compound | Structural formula | MS $(M + H)^+$ | $^1$HNMR |
|---|---|---|---|
| 120 | 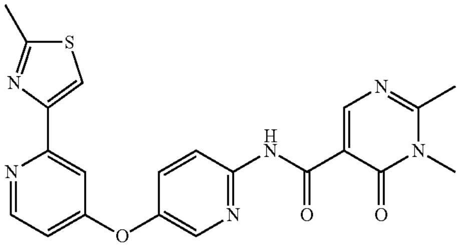 | 435.1 | 1H NMR (400 MHz, DMSO-d6) δ 11.86 (s, 1H), 8.72 (s, 1H), 8.48 (d, J = 5.6 Hz, 1H), 8.39-8.31 (m, 2H), 8.10 (s, 1H), 7.81 (dd, J = 8.9, 2.8 Hz, 1H), 7.45 (d, J = 2.4 Hz, 1H), 6.97 (dd, J = 5.6, 2.4 Hz, 1H), 3.57 (s, 3H), 2.65 (s, 3H), 2.62 (s, 3H). |
| 121 | 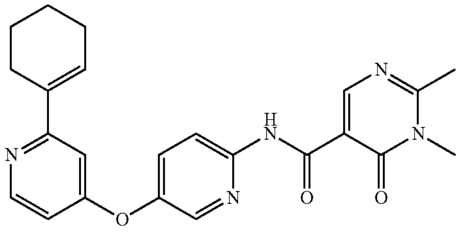 [SMILES: Cc1ncc(C(=O)Nc2ccc(Oc3ccnc(C4=CCCCC4)c3)cn2)c(=O)n1C] | 418.1 | 1H NMR (400 MHz, DMSO-d6) δ 11.84 (s, 1H), 8.72 (d, J = 3.0 Hz, 1H), 8.37 (d, J = 5.6 Hz, 1H), 8.32 (d, J = 9.0 Hz, 1H), 8.27 (d, J = 2.9 Hz, 1H), 7.74 (dd, J = 9.0, 2.9 Hz, 1H), 7.00 (d, J = 2.4 Hz, 1H), 6.77 (dd, J = 5.6, 2.3 Hz, 1H), 6.69-6.63 (m, 1H), 3.56 (s, 3H), 2.62 (s, 3H), 2.40-2.32 (m, 2H), 2.20-2.11 (m, 2H), 1.70-1.62 (m, 2H), 1.61-1.50 (m, 2H). |

-continued
| Compound | Structural formula | MS (M + H)+ | $^1$HNMR |
|---|---|---|---|
| 122 | 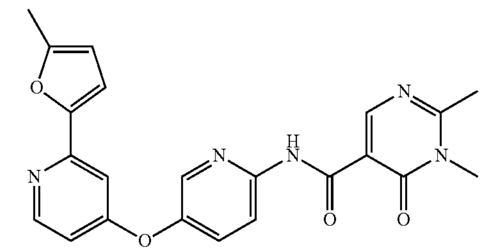 | 418.1 | 1H NMR (400 MHz, DMSO-d6) δ 11.86 (s, 1H), 8.72 (s, 1H), 8.41 (d, J = 5.7 Hz, 1H), 8.34 (d, J = 9.0 Hz, 1H), 8.32 (d, J = 2.9 Hz, 1H), 7.79 (dd, J = 9.0, 2.9 Hz, 1H), 7.10 (d, J = 2.5 Hz, 1H), 6.99 (d, J = 3.3 Hz, 1H), 6.82 (dd, J = 5.6, 2.3 Hz, 1H), 6.25-6.20 (m, 1H), 3.56 (s, 3H), 2.62 (s, 3H), 2.30 (s, 3H). |
| 126 | 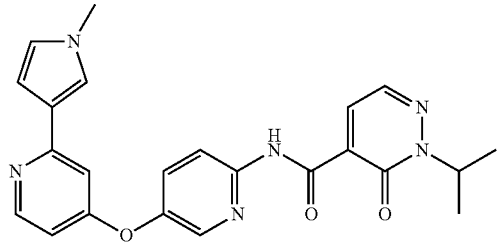 [SMILES: CC(C)n1nccc(C(=O)Nc2ccc(Oc3ccnc(-c4ccn(C)c4)c3)cn2)c1=O] | 431.1 | 1H NMR (400 MHz, DMSO-d6) δ 12.35 (s, 1H), 8.40-8.30 (m, 4H), 8.23 (d, J = 4.2 Hz, 1H), 7.79 (dd, J = 9.0, 2.9 Hz, 1H), 7.40-7.35 (m, 1H), 7.13 (d, J = 2.4 Hz, 1H), 6.77-6.70 (m, 1H), 6.65 (dd, J = 5.7, 2.4 Hz, 1H), 6.57-6.51 (m, 1H), 5.42-5.27 (m, 1H), 3.63 (s, 3H), 1.36 (d, J = 6.6 Hz, 6H). |
Compound 123
1,2-dimethyl-N-(5-((2-(1-methyl-1H-pyrazol-4-yl)pyridin-4-yl)methyl)pyridin-2-yl)-6-oxo-1,6-dihydropyrimidine-5-carboxamide
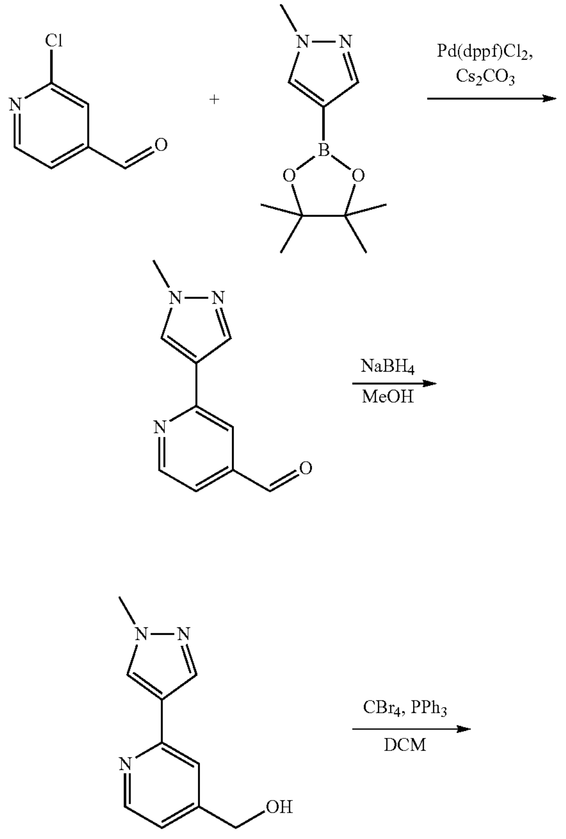
-continued
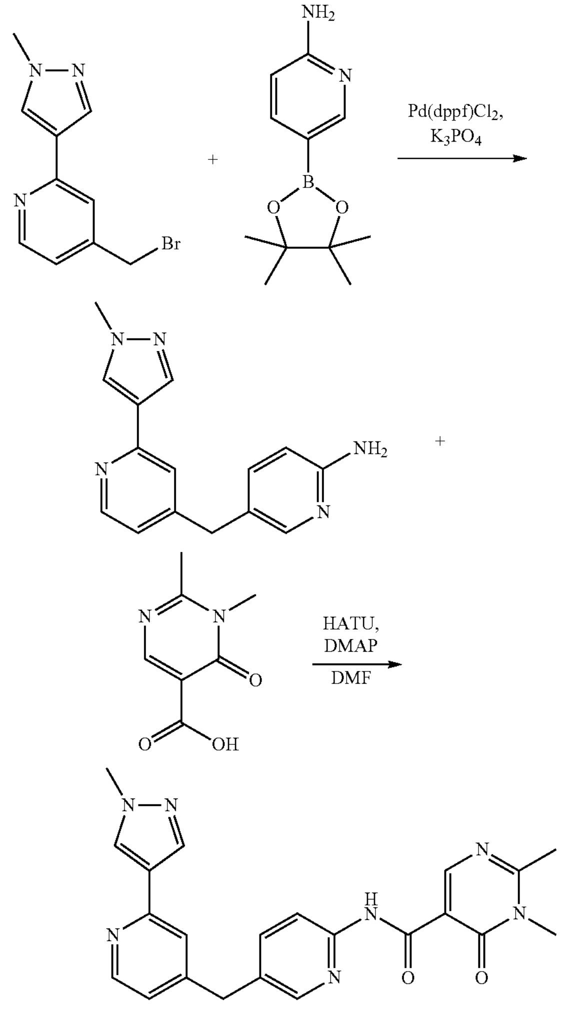

(A) 2-(1-methyl-1H-pyrazol-4-yl)isonicotinaldehyde

Under nitrogen, 2-chloroisonicotinaldehyde (1 g, 7.1 mmol), 1-methyl pyrazol-4-boronic acid pinacol ester (1.8 g, 8.5 mmol), cesium carbonate (1.95 g, 14.2 mmol), dioxane/water (20 ml/2 ml) and $Pd(dppf)Cl_2$ (512 mg, 0.7 mmol) were successively added to a reaction flask, and the mixture was heated to 90° C. and stirred overnight. The reaction solution was cooled to room temperature and then concentrated, the residue was purified with flash column chromatography (water (0.5% formic acid):methanol=100:0-0:100, gradient elution), to obtain 1 g of the title product as a brown solid. MS (m/z): 220.1 $[M+MeOH+H]^+$.

(B) (2-(1-methyl-1H-pyrazol-4-yl)pyridin-4-yl) methanol

Under nitrogen, 2-(1-methyl-1H-pyrazol-4-yl)isonicotinaldehyde (1 g, 5.3 mmol) and methanol (20 ml) were added to a reaction flask, and then sodium borohydride (1 g, 26.5 mmol) was slowly added batchwise, the mixture was stirred at room temperature for 1 hour and completely reacted. Water (2 ml) was slowly added dropwise, and the reaction was quenched and concentrated, the residue was purified with flash column chromatography (water:methanol=100:0-0:100, gradient elution), to obtain 800 mg of the title product as a light yellow solid. MS (m/z): 190.1 $[M+H]^+$.

(C) 4-(bromomethyl)-2-(1-methyl-1H-pyrazol-4-yl) pyridine

Under nitrogen, (2-(1-methyl-1H-pyrazol-4-yl)pyridin-4-yl)methanol (800 mg, 4.2 mmol), carbon tetrabromide (2.1 g, 6.3 mmol) and dichloromethane (30 ml) were successively added to a reaction flask, and then triphenylphosphine (1.7 g, 6.3 mmol) was added batchwise, the mixture was stirred at room temperature for 1 hour and completely reacted. The reaction solution was concentrated, and then the residue was purified with flash column chromatography (dichloromethane:methanol=100:0-90:10, gradient elution), to obtain 1.06 g of the title product as a light yellow solid. MS (m/z): 252.0 $[M+H]^+$.

(D) 5-((2-(1-methyl-1H-pyrazol-4-yl)pyridin-4-yl) methyl)pyridin-2-amine

Under nitrogen, 4-(bromomethyl)-2-(1-methyl-1H-pyrazol-4-yl)pyridine (200 mg, 0.79 mmol), 2-aminopyridin-5-boronic acid pinacol ester (262 mg, 1.2 mmol), tripotassium phosphate (503 mg, 2.4 mmol), dioxane/water (10 ml/2 ml) and $Pd(dppf)Cl_2$ (58 mg, 0.08 mmol) were successively added to a reaction flask, and the mixture was heated to 90° C. and stirred overnight. The reaction solution was cooled to room temperature and then concentrated, the residue was purified with flash column chromatography (water:methanol=100:0-0:100, gradient elution) and flash column chromatography (dichloromethane:methanol=100:0-90:10, gradient elution), to obtain 50 mg of the title product as a white solid. MS (m/z): 266.1 $[M+H]^+$.

(E) 1,2-dimethyl-N-(5-((2-(1-methyl-1H-pyrazol-4-yl)pyridin-4-yl)methyl)pyridin-2-yl)-6-oxo-1,6-dihydropyrimidine-5-carboxamide Under nitrogen, 5-((2-(1-methyl-1H-pyrazol-4-yl)pyridin-4-yl)methyl)pyridin-2-amine (50 mg, 0.19 mmol), 1,2-dimethyl-6-oxo-1,6-dihydropyrimidine-5-carboxylic acid (64 mg, 0.38 mmol), HATU (144 mg, 0.38 mmol), DMF (5 ml) and DMAP (116 mg, 0.95 mmol) were successively added to a reaction flask, and the mixture was heated to 40° C. and stirred for two days, water (2 ml) was added, and then the reaction solution was purified with flash column chromatography (water (0.5% formic acid):methanol=100:0-0:100, gradient elution), to obtain 30 mg of the title product as a white solid. MS (m/z): 416.1 $[M+H]^+$.

1H NMR (400 MHz, DMSO-d6) δ 11.73 (s, 1H), 8.72 (s, 1H), 8.38 (d, J=5.0 Hz, 1H), 8.34 (d, J=2.1 Hz, 1H), 8.24 (s, 1H), 8.19 (d, J=8.5 Hz, 1H), 7.96 (s, 1H), 7.76 (dd, J=8.4, 2.0 Hz, 1H), 7.57 (s, 1H), 7.04 (d, J=4.9 Hz, 1H), 3.96 (s, 2H), 3.87 (s, 3H), 3.57 (s, 3H), 2.63 (s, 3H).

Compound 128

2-methyl-1-(methyl-d3)-N-(5-((2-(1-methyl-1H-pyrazol-4-yl)pyridin-4-yl)oxy)pyridin-2-yl)-6-oxo-1,6-dihydropyrimidine-5-carboxamide

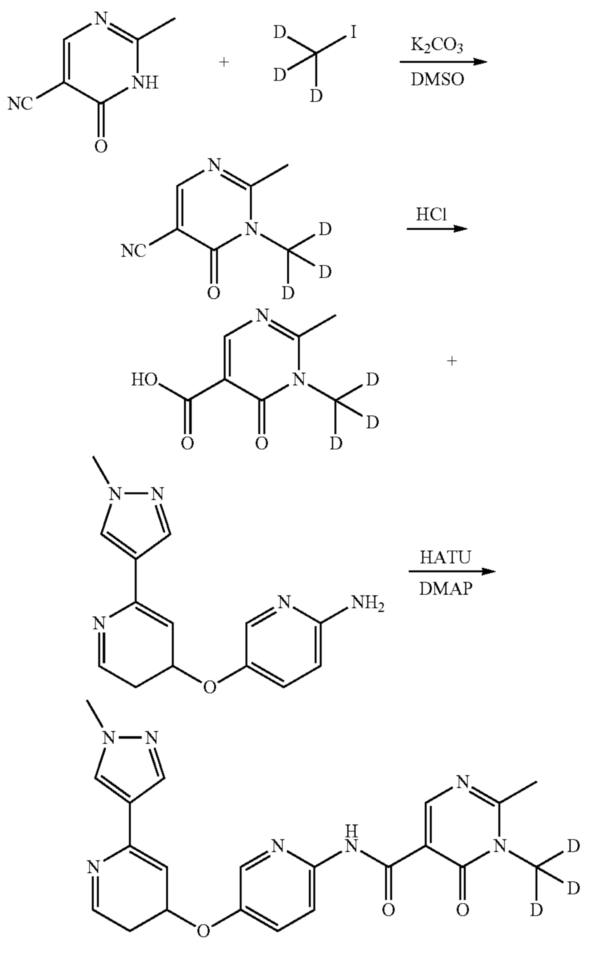

(A) 2-methyl-1-(methyl-d3)-6-oxo-1,6-dihydropyrimidine-5-carbonitrile

In a reaction flask, 2-methyl-6-oxo-1,6-dihydropyrimidine-5-carbonitrile (2702 mg, 20.0 mmol), deuterated iodomethane (3189 mg, 22.0 mmol) and potassium carbonate (4146 mg, 30.0 mmol) were dissolved in dimethyl sulfoxide (10 ml). The reaction solution was stirred at room temperature for 15 hours, and then purified with flash column chromatography (water:methanol=100:0-0:100, gradient elution), to obtain the title product (2.05 g, yield 67.3%) as a white solid. MS (m/z): 153.0 [M+H]$^+$ (B) 2-methyl-1-(methyl-d3)-6-oxo-1,6-dihydropyrimidine-5-carboxylic acid In a reaction flask, 2-methyl-1-(methyl-d3)-6-oxo-1,6-dihydropyrimidine-5-carbonitrile (2.05 g, 13.47 mmol) was dissolved in concentrated hydrochloric acid (10 ml), and the reaction solution was heated and refluxed for 2 hours. The reaction solution was concentrated to dryness, and the residue was purified with flash column chromatography (water/methanol=100:0-0:100, gradient elution), to obtain the title product (1.6 g, yield 69.4%) as a white solid. MS (m/z): 172.0 [M+H]+

(C) 2-methyl-1-(methyl-d3)-N-(5-((2-(1-methyl-1H-pyrazol-4-yl)pyridin-4-yl)oxy)pyridin-2-yl)-6-oxo-1,6-dihydropyrimidine-5-carboxamide 5-((2-(1-methyl-1H-pyrazol-4-yl)pyridin-4-yl)oxy)pyridin-2-amine (1.92 g, 7.18 mmol), 2-methyl-1-(methyl-d3)-6-oxo-1,6-dihydropyrimidine-5-carboxylic acid (1.60 g, 9.34 mmol), HATU (3.55 g, 9.34 mmol), 4-dimethylaminopyridine (1.14 g, 9.34 mmol) and N,N-dimethylformamide (20 ml) were successively added to a reaction flask, and the mixture was reacted at room temperature and stirred for 15 hours. After the reaction was completed, water (2 ml) was added, and then the reaction solution was concentrated, the residue was purified with flash column chromatography (water (0.05% formic acid)/methanol=100:0-0:100, gradient elution), to obtain a white solid, the white solid was recrystallized with dichloromethane and methanol to obtain the title product (2.4 g, yield 79.5%) as a white solid. MS (m/z): 421.0[M+H]+

$^1$H NMR (400 MHz, DMSO-d6) δ 11.85 (s, 1H), 8.73 (d, J=0.7 Hz, 1H), 8.36 (d, J=5.7 Hz, 1H), 8.33 (d, J=9.0 Hz, 1H), 8.29 (d, J=2.9 Hz, 1H), 8.25 (s, 1H), 7.96 (s, 1H), 7.76 (dd, J=9.0, 2.9 Hz, 1H), 7.24 (d, J=2.4 Hz, 1H), 6.76-6.67 (m, 1H), 3.83 (s, 3H), 2.62 (s, 3H).

Compound 129

1,2-dimethyl-N-(5-((2-(1-(methyl-d3)-1H-pyrazol-4-yl)pyridin-4-yl)oxy)pyridin-2-yl)-6-oxo-1,6-dihydropyrimidine-5-carboxamide

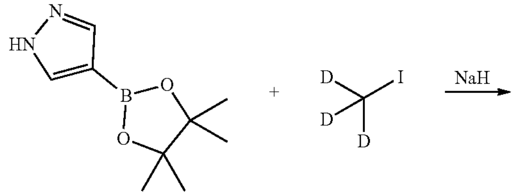

-continued

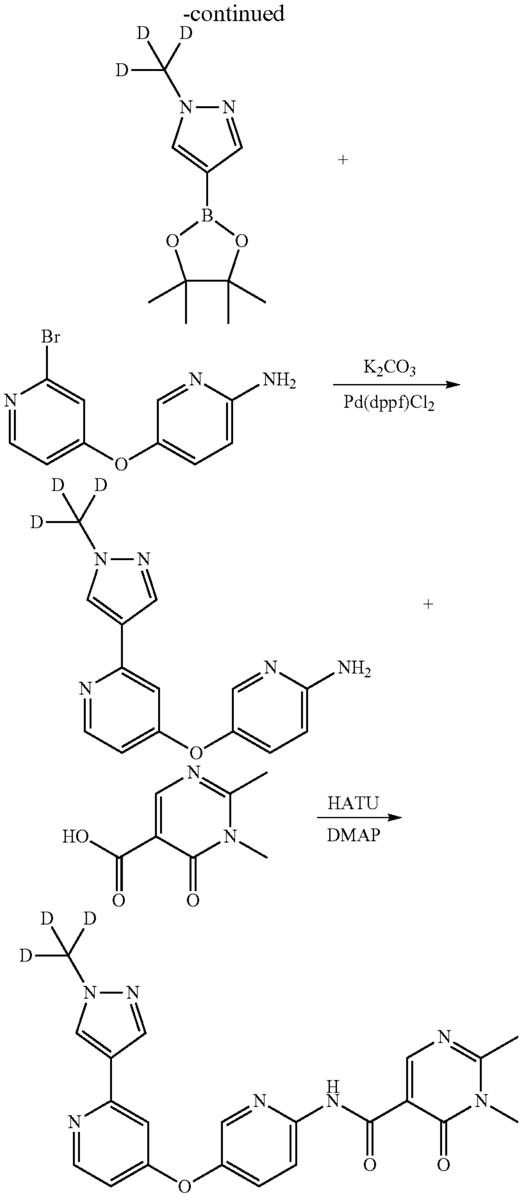

(A) 1-(methyl-d3)-4-(4,4,5,5-tetramethyl-1,3,2-dioxaborolan-2-yl)-1H-pyrazole

In a reaction flask, 4-(4,4,5,5-tetramethyl-1,3,2-dioxaborolan-2-yl)-1H-pyrazole (582 mg, 3.0 mmol) was dissolved in N,N-dimethylformamide (5 ml), and sodium hydride (132 mg, 3.3 mmol) was added batchwise to a reaction solution at room temperature, after this, the reaction solution was stirred at room temperature for 10 minute, and then added deuterated iodomethane (522 mg, 3.6 mmol), the reaction solution was stirred at room temperature for another 4 hours. After the reaction was completed, the reaction solution was quenched with water, and extracted with ethyl acetate, the organic phases were combined, and concentrated, and then purified with flash column chromatography (water/methanol=100:0-0:100, gradient elution), to obtain the title product (420 mg, yield 66%) as a white solid. MS (m/z): 212.1 [M+H]+

(B) 5-((2-(1-(methyl-d3)-1H-pyrazol-4-yl)pyridin-4-yl)oxy)pyridin-2-amine 1-(methyl-d3)-4-(4,4,5,5-tetramethyl-1,3,2-dioxaborolan-2-yl)-1H-pyrazole (441 mg, 1.99 mmol), 5-((2-bromopyridin-4-yl)oxy)pyridin-2-amine (447 mg, 1.66 mmol), $Pd(dppf)Cl_2$ (124 mg, 0.17 mmol) and potassium carbonate (458 mg, 3.32 mmol) were dissolved in the mixed solution of 1,4-dioxane (20 ml) and water (5 ml), and the mixture was heated to reflux and stirred for 15 hours. The reaction solution was cooled to room temperature, and concentrated to obtain a crude product, which was purified with flash column chromatography (water (0.05% formic acid)/methanol=100:0-0:100, gradient elution), to obtain the title product (370 mg, yield 82.5%) as a white solid. MS (m/z): $271.1[M+H]^+$ (C) 1,2-dimethyl-N-(5-((2-(1-(methyl-d3)-1H-pyrazol-4-yl)pyridin-4-yl)oxy)pyridin-2-yl)-6-oxo-1,6-dihydropyrimidine-5-carboxamide 5-((2-(1-(methyl-d3)-1H-pyrazol-4-yl)pyridin-4-yl)oxy)pyridin-2-amine (135 mg, 0.5 mmol), 1,2-dimethyl-6-oxo-1,6-dihydropyrimidine-5-carboxylic acid (126 mg, 0.75 mmol), HATU (285 mg, 0.75 mmol), 4-dimethylaminopyridine (92 mg, 0.75 mmol) and N,N-dimethylformamide (3 ml) were successively added to a reaction flask, and the reaction solution was stirred at room temperature for 15 hours. After the reaction was completed, the reaction solution was quenched with 2 ml of water, and concentrated to obtain a crude product, which was purified with flash column chromatography (water (0.05% formic acid)/methanol=100:0-0:100, gradient elution), to obtain the title product (85 mg, yield 40.47%) as a white solid. MS (m/z): 421.0[M+H]+

$^1$H NMR (400 MHz, DMSO-d6) δ 11.84 (s, 1H), 8.72 (s, 1H), 8.42-8.27 (m, 3H), 8.24 (s, 1H), 7.95 (s, 1H), 7.76 (d, J=6.7 Hz, 1H), 7.23 (s, 1H), 6.71 (d, J=3.6 Hz, 1H), 3.56 (s, 3H), 2.61 (s, 3H).

Compound 130

N-(5-((2-(1H-pyrazol-4-yl)pyridin-4-yl)oxy)pyridin-2-yl)-1,2-dimethyl-6-oxo-1,6-dihydropyrimidine-5-carboxamide

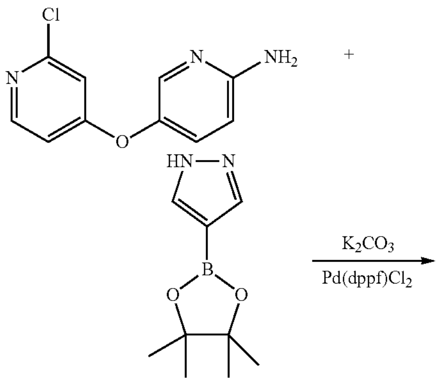

-continued

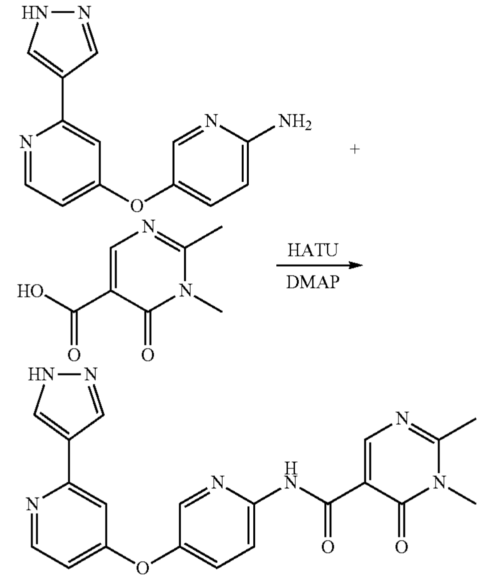

(A) 5-((2-(1H-pyrazol-4-yl)pyridin-4-yl)oxy)pyridin-2-amine

In a reaction flask, 5-((2-chloropyridin-4-yl)oxy)pyridin-2-amine (222 mg, 1.0 mmol), 4-(4,4,5,5-tetramethyl-1,3,2-dioxaborolan-2-yl)-1H-pyrazole (388 mg, 2.0 mmol), $Pd(dppf)Cl_2$ (73 mg, 0.1 mmol) and potassium carbonate (276 mg, 2.0 mmol) were dissolved in the mixed solution of 1,4-dioxane (20 ml) and water (5 ml), and the mixture was heated to reflux and stirred for 15 hours. The reaction was cooled to room temperature, and concentrated to obtain a crude product, which was purified with flash column chromatography (water (0.05% formic acid)/methanol=100:0-0:100, gradient elution), to obtain the title product (120 mg, yield 47.4%) as a white solid. MS (m/z): $254.0[M+H]^+$ (B) N-(5-((2-(1H-pyrazol-4-yl)pyridin-4-yl)oxy)pyridin-2-yl)-1,2-dimethyl-6-oxo-1,6-dihydropyrimidine-5-carboxamide 5-((2-(1H-pyrazol-4-yl)pyridin-4-yl)oxy)pyridin-2-amine (120 mg, 0.47 mmol), 1,2-dimethyl-6-oxo-1,6-dihydropyrimidine-5-carboxylic acid (128 mg, 0.76 mmol), HATU (289 mg, 0.76 mmol), 4-dimethylaminopyridine (93 mg, 0.76 mmol) and N,N-dimethylformamide (3 ml) were successively added to a reaction flask, and the reaction solution was heated at 45° C. for 15 hours. After the reaction was completed, the reaction solution was quenched with 2 ml of water, and concentrated to obtain a crude product, which was purified with flash column chromatography (water (0.05% formic acid)/methanol=100:0-0:100, gradient elution), to obtain the title product (18 mg, yield 9.5%) as a white solid. MS (m/z): $404.0[M+H]^+$ $^1$H NMR (400 MHz, DMSO-d6) δ 12.99 (s, 1H), 11.85 (s, 1H), 8.73 (s, 1H), 8.37 (d, J=5.7 Hz, 1H), 8.34 (d, J=9.0 Hz, 1H), 8.30 (d, J=2.9 Hz, 1H), 8.03 (s, 1H), 7.76 (dd, J=9.0, 2.9 Hz, 1H), 7.34 (d, J=2.4 Hz, 1H), 6.70 (dd, J=5.7, 2.4 Hz, 1H), 3.57 (s, 3H), 2.63 (s, 3H).

Compound 131

2-methyl-N-(5-((2-(1-methyl-1H-pyrazol-4-yl)pyridin-4-yl)oxy)pyridin-2-yl)-6-oxo-1,6-dihydropyrimidine-5-carboxamide

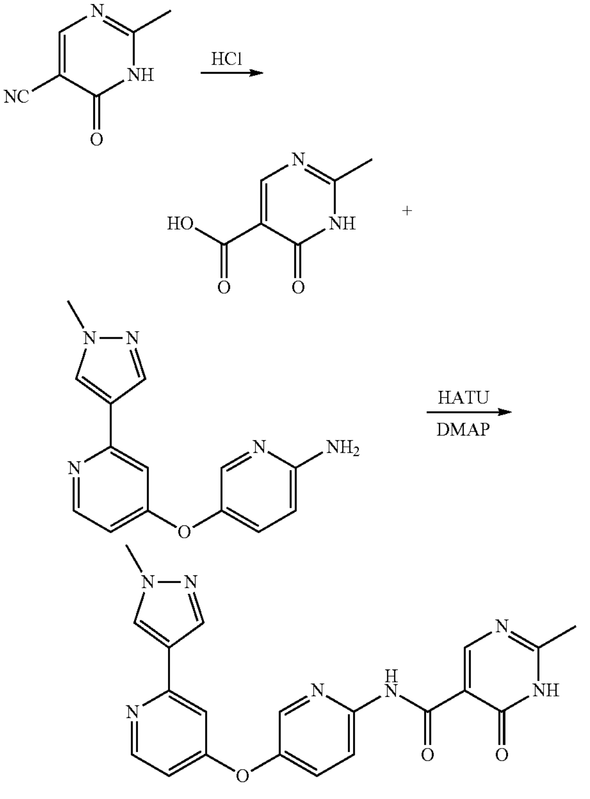

(A) 2-methyl-6-oxo-1,6-dihydropyrimidine-5-carboxylic acid

In a reaction flask, 2-methyl-6-oxo-1,6-dihydropyrimidine-5-carbonitrile (1.35 g, 10.0 mmol) was dissolved in concentrated hydrochloric acid (10 ml). The reaction solution was heated and refluxed for 2 hours. The reaction solution was concentrated to dryness, and the residue was purified with flash column chromatography (water/methanol=100:0-0:100, gradient elution), to obtain the title product (1.1 g, yield 71.4%) as a white solid. MS (m/z): 155.0 $[M+H]^+$ (B) 2-methyl-N-(5-((2-(1-methyl-1H-pyrazol-4-yl)pyridin-4-yl)oxy)pyridin-2-yl)-6-oxo-1,6-dihydropyrimidine-5-carboxamide 5-((2-(1-methyl-1H-pyrazol-4-yl)pyridin-4-yl)oxy)pyridin-2-amine (134 mg, 0.5 mmol), 2-methyl-6-oxo-1,6-dihydropyrimidine-5-carboxylic acid (123 mg, 0.8 mmol), HATU (304 mg, 0.8 mmol), 4-dimethylaminopyridine (98 mg, 0.8 mmol) and N,N-dimethylformamide (3 ml) were successively added to a reaction flask. The reaction solution was heated at 45° C. for 15 hours. After the reaction was completed, the reaction solution was quenched with 2 ml of water, and concentrated to obtain a crude product, which was purified with flash column chromatography (water (0.05% formic acid)/methanol=100:0-0:100, gradient elution), to obtain the title product (130 mg, yield 64%) as a white solid. MS (m/z): 404.0 $[M+H]^+$ $^1$H NMR (400 MHz, DMSO-d6) δ 12.02 (s, 1H), 8.71 (s, 1H), 8.36 (d, J=5.7 Hz, 1H), 8.33 (d, J=9.0 Hz, 1H), 8.28 (d, J=2.8 Hz, 1H), 8.24 (s, 1H), 7.95 (s, 1H), 7.75 (dd, J=9.0, 2.9 Hz, 1H), 7.23 (d, J=2.3 Hz, 1H), 6.71 (dd, J=5.7, 2.4 Hz, 1H), 3.83 (s, 3H), 2.40 (s, 3H).

Compound 132

2-(2-hydroxyethyl)-N-(5-((2-(1-methyl-1H-pyrazol-4-yl)pyridin-4-yl)oxy)pyridin-2-yl)-6-oxo-1,6-dihydropyrimidine-5-carboxamide

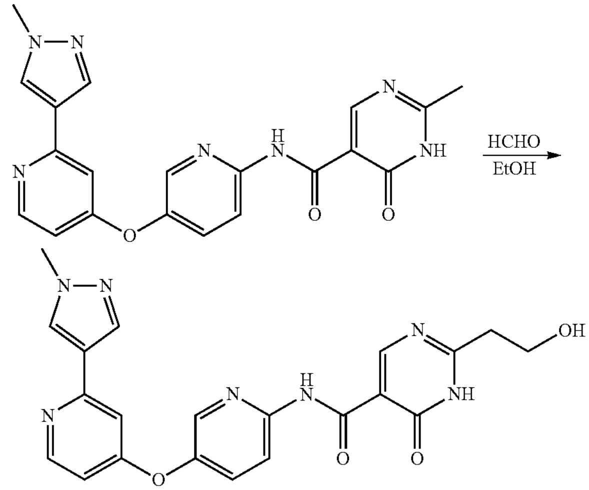

2-methyl-N-(5-((2-(1-methyl-1H-pyrazol-4-yl)pyridin-4-yl)oxy)pyridin-2-yl)-6-oxo-1,6-dihydropyrimidine-5-carboxamide (100 mg, 0.248 mmol), formaldehyde aqueous solution (1 ml) and ethanol (3 ml) were successively added to a microwave tube, the microwave tube was sealed, and the reaction solution was reacted in a microwave reactor at 140° C. for 1 hour. After the reaction was completed, the reaction solution was concentrated to dryness, and the residue was purified with flash column chromatography (water (0.05% formic acid)/methanol=100:0-0:100, gradient elution), and further purified with preparative thin layer chromatography, to obtain the title product (9 mg, yield 8.4%) as a white solid. MS (m/z): 434.0 $[M+H]^+$ $^1$H NMR (400 MHz, DMSO-d6) δ 12.13 (s, 1H), 8.74 (s, 1H), 8.36 (dd, J=9.9, 7.4 Hz, 2H), 8.28 (d, J=2.9 Hz, 1H), 8.25 (s, 1H), 8.15 (s, 1H), 7.96 (s, 1H), 7.75 (dd, J=9.0, 2.9 Hz, 1H), 7.23 (d, J=2.4 Hz, 1H), 6.72 (dd, J=5.7, 2.4 Hz, 1H), 3.83 (s, 3H), 3.78 (t, J=6.2 Hz, 2H), 2.80 (t, J=6.2 Hz, 2H).

Compound 133

2-(hydroxymethyl)-N-(5-((2-(1-methyl-1H-pyrazol-4-yl)pyridin-4-yl)oxy)pyridin-2-yl)-6-oxo-1,6-dihydropyrimidine-5-carboxamide

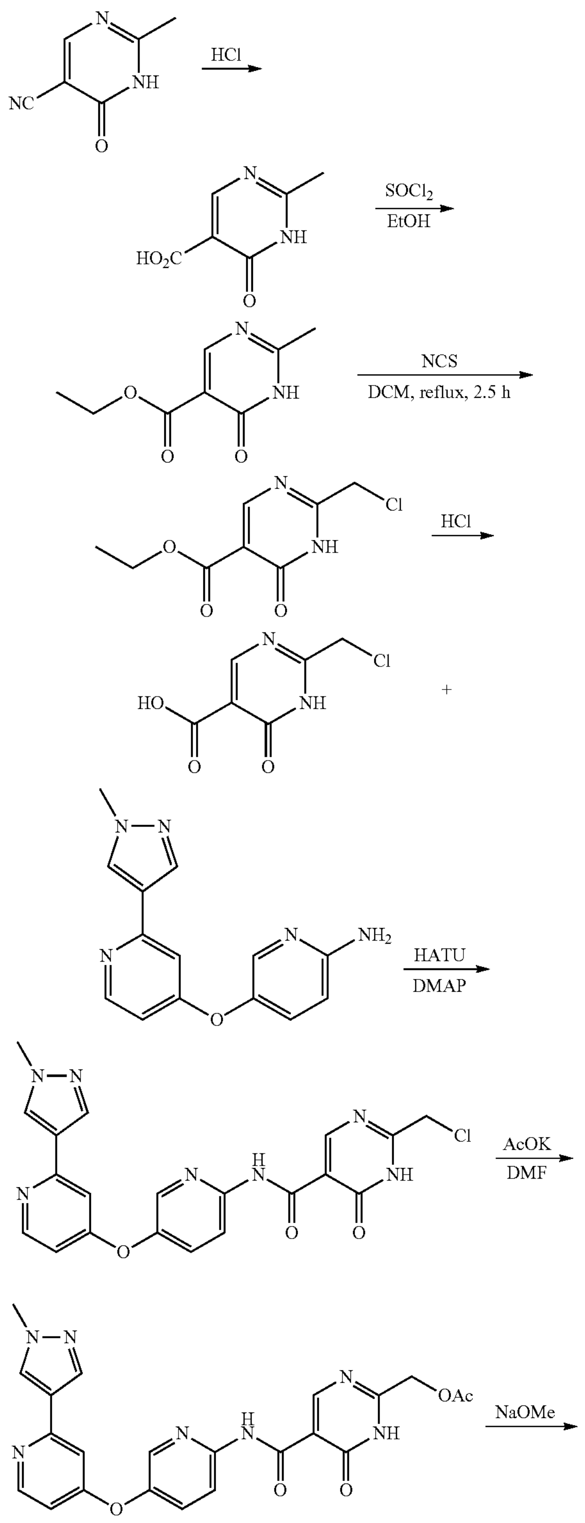

-continued

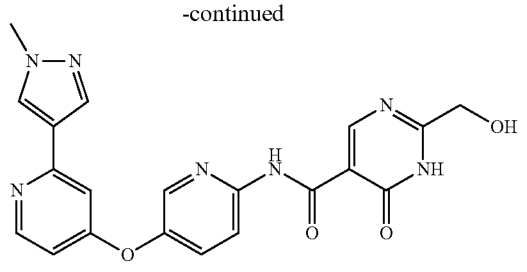

(A) 2-methyl-6-oxo-1,6-dihydropyrimidine-5-carboxylic acid

In a reaction flask, 2-methyl-6-oxo-1,6-dihydropyrimidine-5-carbonitrile (6.0 g, 44.4 mmol) was dissolved in concentrated hydrochloric acid (15 ml). The reaction solution was heated and refluxed for 2 hours. The reaction solution was concentrated to dryness, and the crude product was directly used in the next step without purification (6.84 g, yield 100%). MS (m/z): 155.2 $[M+H]^+$ (B) Ethyl 2-methyl-6-oxo-1,6-dihydropyrimidine-5-carboxylate In a reaction flask, the acid intermediate 2-methyl-6-oxo-1,6-dihydropyrimidine-5-carboxylic acid (6.84 g, 44.4 mmol) prepared in the previous step was dissolved in ethanol (100 ml). Thionyl chloride (5 ml) was added dropwise to the mixture in an ice bath, after the dropwise addition was completed, the reaction solution was heated and refluxed for 15 hours. After the reaction was completed, the reaction solution was concentrated, and the residue was purified with flash column chromatography (water (0.05% formic acid)/methanol=100:0-0:100, gradient elution), to obtain the title product (4.5 g, two-step reaction yield 55.6%) as a white solid. MS (m/z): 183.2 $[M+H]^+$ (C) Ethyl 2-(chloromethyl)-6-oxo-1,6-dihydropyrimidine-5-carboxylate Ethyl 2-methyl-6-oxo-1,6-dihydropyrimidine-5-carboxylate (4500 mg, 24.7 mmol), N-chlorosuccinimide (3298 mg, 24.7 mmol) and dichloromethane (100 ml) were successively added to a reaction flask, and the mixture was heated and refluxed for 2.5 hours. After the reaction was completed, the reaction solution was cooled to room temperature and quenched with water, the reaction solution was concentrated to dryness, and the residue was purified with flash column chromatography (water (0.05% formic acid)/methanol=100:0-0:100, gradient elution), to obtain the title product (1.7 g, yield 37.7%) as a white solid. MS (m/z): 217.0$[M+H]^+$ (D) 2-(chloromethyl)-6-oxo-1,6-dihydropyrimidine-5-carboxylic acid In a reaction flask, ethyl 2-(chloromethyl)-6-oxo-1,6-dihydropyrimidine-5-carboxylate (1.7 g, 7.85 mmol) was dissolved in concentrated hydrochloric acid (15 ml), and the reaction solution was heated and refluxed for 2 hours. The reaction solution was concentrated to dryness, and the residue was purified with flash column chromatography (water/methanol=100:0-0:100, gradient elution), to obtain the title product (1.2 g, yield 81%) as a white solid. MS (m/z): 189.0[M+H]+

(E) 2-(chloromethyl)-N-(5-((2-(1-methyl-1H-pyrazol-4-yl)pyridin-4-yl)oxy)pyridin-2-yl)-6-oxo-1,6-dihydropyrimidine-5-carboxamide 5-((2-(1-methyl-1H-pyrazol-4-yl)pyridin-4-yl)oxy)pyridin-2-amine (1742 mg, 6.52 mmol), 2-(chloromethyl)-6-oxo-1,6-dihydropyrimidine-5-carboxylic acid (1.23 g, 6.52 mmol), HATU (2.73 g, 7.17 mmol), 4-dimethylaminopyridine (876 mg, 7.17 mmol) and N,N-dimethylformamide (15 ml) were successively added to a reaction flask, and the reaction solution was stirred at room temperature for 15 hours. After the reaction was completed, the reaction solution was quenched with 2 ml of water, and concentrated, the crude product was purified with flash column chromatography (water (0.05% formic acid)/methanol=100:0-0:100, gradient elution), to obtain the title product (1.8 g, yield 63%) as a white solid. MS (m/z): 438.1[M+H]+

(F) (5-((5-((2-(1-methyl-1H-pyrazol-4-yl)pyridin-4-yl)oxy)pyridin-2-yl)carbamoyl)-6-oxo-1,6-dihydropyrimidin-2-yl)methyl acetate 2-(chloromethyl)-N-(5-((2-(1-methyl-1H-pyrazol-4-yl)pyridin-4-yl)oxy)pyridin-2-yl)-6-oxo-1,6-dihydropyrimidine-5-carboxamide (500 mg, 1.14 mmol), potassium acetate (500 mg, 5.1 mmol) and N,N-dimethylformamide (4 ml) were successively added to a reaction flask. The reaction solution was heated at 80° C. for 15 hours. After the reaction was completed, the reaction solution was cooled to room temperature, and quenched with water (1 ml). The reaction solution was concentrated, and the crude product was purified with flash column chromatography (water (0.05% formic acid)/methanol=100:0-0:100, gradient elution), to obtain the title product (290 mg, yield 55.1%) as a white solid. MS (m/z): 462.2 [M+H]+

(G) 2-(hydroxymethyl)-N-(5-((2-(1-methyl-1H-pyrazol-4-yl)pyridin-4-yl)oxy)pyridin-2-yl)-6-oxo-1,6-dihydropyrimidine-5-carboxamide (5-((5-((2-(1-methyl-1H-pyrazol-4-yl)pyridin-4-yl)oxy)pyridin-2-yl)carbamoyl)-6-oxo-1,6-dihydropyrimidin-2-yl)methyl acetate (30 mg, 0.065 mmol), methanol (3 ml) and sodium methoxide (14 mg, 0.26 mmol) were successively added to a reaction flask, and the reaction solution was stirred at room temperature for 1 hour. After the reaction was completed, the PH of the reaction solution is adjusted to about 5 with dilute hydrochloric acid (2M). The reaction solution was concentrated, and the crude product was purified with flash column chromatography (water (0.05% formic acid)/methanol=100:0-0:100, gradient elution), to obtain the title product (15 mg, yield 55.5%) as a white solid. MS (m/z): 420.1[M+H]+

$^1$H NMR (400 MHz, DMSO-d6) δ 12.19 (s, 1H), 8.65 (s, 1H), 8.36 (d, J=5.7 Hz, 1H), 8.33 (d, J=9.0 Hz, 1H), 8.28 (d, J=2.8 Hz, 1H), 8.24 (s, 1H), 7.95 (s, 1H), 7.74 (dd, J=9.0, 2.9 Hz, 1H), 7.22 (d, J=2.3 Hz, 1H), 6.71 (dd, J=5.7, 2.4 Hz, 1H), 5.86 (s, 1H), 4.44 (s, 2H), 3.82 (s, 3H).

Compound 134

2-hydroxy-1-methyl-N-(5-((2-(1-methyl-1H-pyrazol-4-yl)pyridin-4-yl)oxy)pyridin-2-yl)-6-oxo-1,6-dihydropyrimidine-5-carboxamide

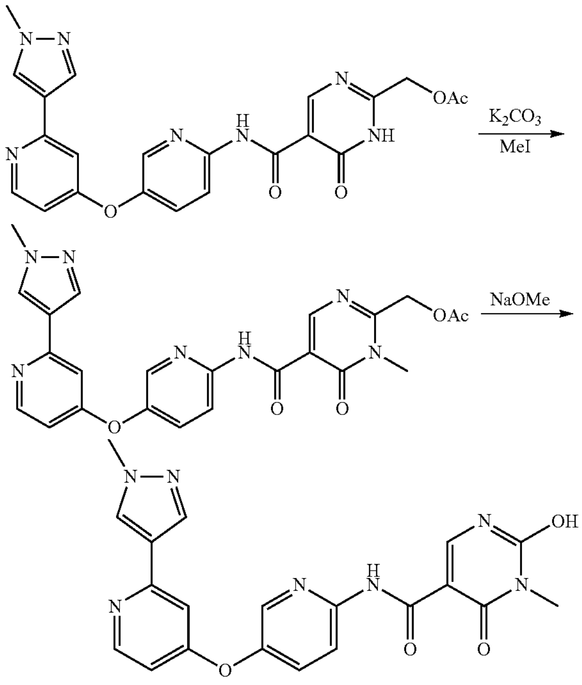

(A) (1-methyl-5-((5-((2-(1-methyl-1H-pyrazol-4-yl)pyridin-4-yl)oxy)pyridin-2-yl)carbamoyl)-6-oxo-1,6-dihydropyrimidin-2-yl)methyl acetate (5-((5-((2-(1-methyl-1H-pyrazol-4-yl)pyridin-4-yl)oxy)pyridin-2-yl)carbamoyl)-6-oxo-1,6-dihydropyrimidin-2-yl)methyl acetate (200 mg, 0.433 mmol), potassium carbonate (72 mg, 0.519 mmol), N,N-dimethylformamide (3 ml) and iodomethane (62 mg, 0.433 mmol) were successively added to a reaction flask. The reaction solution was stirred continuously at room temperature for 4 hours. After the reaction was completed, the reaction solution was quenched with water, and extracted with ethyl acetate, the organic phases were combined, and concentrated, and then purified with flash column chromatography (water/methanol=100:0-0:100, gradient elution), to obtain the title product (140 mg, yield 67.96%) as a white solid. MS (m/z): 476.1 [M+H]+

(B) 2-hydroxy-1-methyl-N-(5-((2-(1-methyl-1H-pyrazol-4-yl)pyridin-4-yl)oxy)pyridin-2-yl)-6-oxo-1,6-dihydropyrimidine-5-carboxamide (1-methyl-5-((5-((2-(1-methyl-1H-pyrazol-4-yl)pyridin-4-yl)oxy)pyridin-2-yl)carbamoyl)-6-oxo-1,6-dihydropyrimidin-2-yl)methyl acetate (48 mg, 0.1 mmol), methanol (3 ml) and sodium methoxide (216 mg, 0.4 mmol) were successively added to a reaction flask, and the reaction solution was stirred at room temperature for 1 hour. After the reaction was completed, the PH of the reaction solution is adjusted to about 5 with dilute hydrochloric acid (2M). The reaction solution was concentrated, and the crude product was purified with flash column chromatography (water (0.05% formic acid)/methanol=100:0-0:100, gradient elution), to obtain the title product (10 mg, yield 23.8%) as a white solid. MS (m/z): 420.1 $[M+H]^+$ $^1$H NMR (400 MHz, DMSO-d6) δ 11.69 (s, 1H), 8.45 (s, 1H), 8.35 (d, J=5.6 Hz, 1H), 8.31 (d, J=8.9 Hz, 1H), 8.24 (s, 2H), 7.95 (s, 1H), 7.70 (d, J=9.0 Hz, 1H), 7.22 (d, J=2.0 Hz, 1H), 6.70 (dd, J=5.5, 2.0 Hz, 1H), 3.82 (s, 3H), 3.21 (s, 3H).

Compound 135

N-(5-((2-(3-hydroxy-1-methyl-1H-pyrazol-4-yl)pyridin-4-yl)oxy)pyridin-2-yl)-1,2-dimethyl-6-oxo-1,6-dihydropyrimidine-5-carboxamide

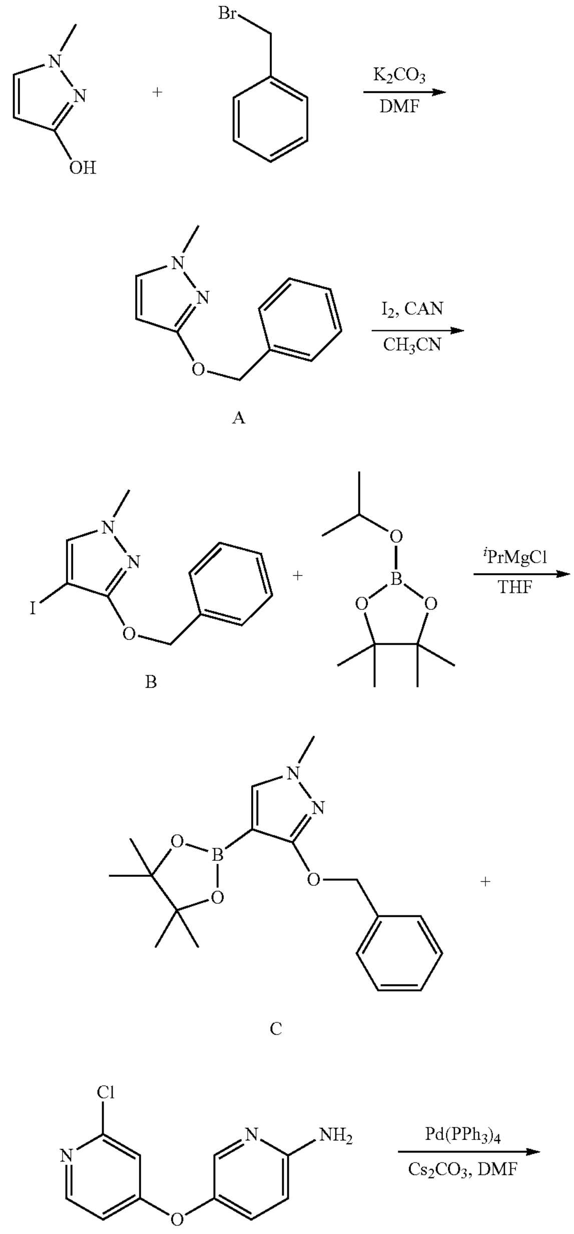

-continued

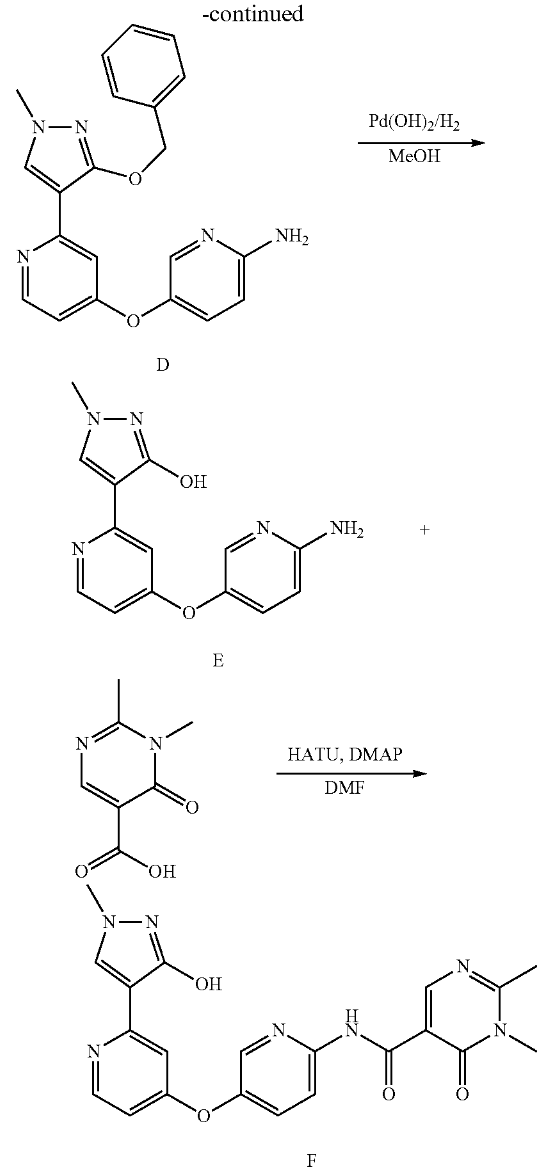

(A) 3-(benzyloxy)-1-methyl-1H-pyrazole

Under nitrogen, 1-methyl-1H-pyrazol-3-ol (4 g, 41 mmol), potassium carbonate (6.8 g, 49 mmol) and DMF (50 ml) were successively added to a reaction flask, and benzyl bromide (8.4 g, 49 mmol) was added dropwise in an ice bath, the mixture was warmed to room temperature and stirred for 1.5 hours, and then heated to 50° C. and stirred for another 4 hours. The reaction solution was cooled to room temperature, and then water (100 ml) and ethyl acetate (150 ml) were added, after layering, the organic phase was washed with saturated brine (100 ml) two times, dried with anhydrous sodium sulfate and filtered, concentrated. The residue was purified with flash column chromatography (petroleum ether:ethyl acetate=100:0-0:100, gradient elution), to obtain 4.7 g of the title product as a colorless oil. MS (m/z): 189.1 $[M+H]^+$ (B) 3-(benzyloxy)-4-iodo-1-methyl-1H-pyrazole Under nitrogen, 3-(benzyloxy)-1-methyl-1H-pyrazole (4.7 g, 25 mmol), acetonitrile (60 ml), cerium ammonium nitrate (8.22 g, 15 mmol) and elemental iodine (3.8 g, 15 mmol) were successively added to a reaction flask, and the mixture was stirred at room temperature for 2 hours. The reaction solution was cooled in an ice bath, and then 5% sodium bisulfite (100 ml) was added dropwise, and the mixture was extracted with ethyl acetate (100 ml). The organic phase was washed with saturated brine (100 ml), dried with anhydrous sodium sulfate and filtered, concentrated. The residue was purified with flash column chromatography (petroleum ether:ethyl acetate=100:0-0:100, gradient elution), to obtain 5.1 g of the title product as a brown oil. MS (m/z): 315.0 $[M+H]^+$ (C) 3-(benzyloxy)-1-methyl-4-(4,4,5,5-tetramethyl-1,3,2-dioxaborolan-2-yl)-1H-pyrazole Under nitrogen, 3-(benzyloxy)-4-iodo-1-methyl-1H-pyrazole (5.1 g, 16 mmol) and anhydrous tetrahydrofuran (80 ml) were successively added to a reaction flask, and the mixture was cooled to −10° C. in an ice salt bath, and then isopropyl magnesium chloride (12 ml, 24 mmol) was added dropwise, the reaction solution was warmed to 0° C. and stirred for 1.5 hours, and then cooled to −10° C. again in an ice salt bath, 2-isopropoxy-4,4,5,5-tetramethyl-1,3,2-dioxaborolan (5.95 g, 32 mmol) was added dropwise, and then the reaction solution was slowly warmed to room temperature and stirred for 4 hours. Saturated ammonium chloride (100 ml) was added, and the reaction solution was extracted with ethyl acetate (100 ml), and the organic phase was washed with saturated brine (100 ml), dried with anhydrous sodium sulfate and filtered, and concentrated. The residue was purified with flash column chromatography (petroleum ether:ethyl acetate=100:0-0:100, gradient elution), to obtain 4.6 g of the title product as a colorless oil. MS (m/z): 315.2 $[M+H]^+$ (D) 5-((2-(3-(benzyloxy)-1-methyl-1H-pyrazol-4-yl)pyridin-4-yl)oxy)pyridin-2-amine Under nitrogen, 3-(benzyloxy)-1-methyl-4-(4,4,5,5-tetramethyl-1,3,2-dioxaborolan-2-yl)-1H-pyrazole (1.57 g, 5 mmol), 5-((2-chloropyridin-4-yl)oxy)pyridin-2-amine (742 mg, 3.33 mmol), cesium carbonate (2.7 g, 8.3 mmol), tetra(triphenylphosphine)palladium (380 mg, 0.33 mmol) and DMF/$H_2O$ (18 ml/6 ml) were successively added to a reaction flask, and the mixture was heated to 90° C. and then stirred overnight. The reaction solution was cooled to room temperature and then concentrated, the residue was purified with flash column chromatography (water (0.1% formic acid):acetonitrile=100:0 0:100, gradient elution), to obtain 1.2 g of the title product as a light yellow solid. MS (m/z): 374.2 $[M+H]^+$ (E) 4-(4-((6-aminopyridin-3-yl)oxy)pyridin-2-yl)-1-methyl-1H-pyrazol-3-ol 5-((2-(3-(benzyloxy)-1-methyl-1H-pyrazol-4-yl)pyridin-4-yl)oxy)pyridin-2-amine (1.2 g, 3.33 mmol), methanol (60 ml), dichloromethane (6 ml) and palladium hydroxide (600 mg) were successively added to a reaction flask, under hydrogen, the mixture was stirred at room temperature overnight. The reaction solution was filtered, and the filter cake was washed with methanol, the filtrate was combined and then concentrated, and the residue was purified with flash column chromatography (dichloromethane:methanol=100:0-90:10, gradient elution), to obtain 590 mg of the title product as a white solid. MS (m/z): 284.1 $[M+H]^+$ (F) N-(5-((2-(3-hydroxy-1-methyl-1H-pyrazol-4-yl)pyridin-4-yl)oxy)pyridin-2-yl)-1,2-dimethyl-6-oxo-1,6-dihydropyrimidine-5-carboxamide Under nitrogen, 4-(4-((6-aminopyridin-3-yl)oxy)pyridin-2-yl)-1-methyl-1H-pyrazol-3-ol (283 mg, 1 mmol), 1,2-dimethyl-6-oxo-1,6-dihydropyrimidine-5-carboxylic acid (202 mg, 1.2 mmol), HATU (570 mg, 1.5 mmol), DMF (10 ml) and DMAP (183 mg, 1.5 mmol) were successively added to a reaction flask, and the mixture was heated to 40° C. and then stirred overnight. Water (2 ml) was added, and the reaction solution was purified with flash column chromatography (water (0.1% formic acid):acetonitrile=100:0-0:100, gradient elution) and preparative thin layer chromatography, to obtain 75 mg of the title product as a white solid. MS (m/z): 434.2 $[M+H]^+$ $^1H$ NMR (400 MHz, DMSO-d6) δ 11.89 (s, 1H), 10.96 (s, 1H), 8.76 (s, 1H), 8.45-8.28 (m, 3H), 8.07 (s, 1H), 7.81 (dd, J=9.0, 2.9 Hz, 1H), 7.24 (d, J=2.4 Hz, 1H), 6.76 (dd, J=5.8, 2.5 Hz, 1H), 3.65 (s, 3H), 3.59 (s, 3H), 2.65 (s, 3H).

Example 3

Measurement of CSF1R Kinase Activity at Molecular Level

1. Reagents and materials:
   Z-LYTE™ Tyr 1 peptide substrate: Invitrogen, PV3190;
   5× kinase buffer: Invitrogen, PV3189;
   10 mM ATP: Invitrogen, PV3227;
   Development reagent B: Invitrogen, PV3295;
   Development buffer: Invitrogen, P3127;
   Stopping solution: Invitrogen, P3094;
   Recombinant human CSF1R kinase: Invitrogen, PR4598A;
   384 well plate, black: Corning, 3575;
   Envision: Perkin Elmer.
2. Preparation of reaction solutions 1) 1.33× kinase buffer: 5× kinase buffer was diluted to a 1.33× kinase buffer with $ddH_2O$.

2) Dilution of a 4× test compound: The test compound was diluted in gradient to 4-fold the reaction concentration and the concentration of DMSO was kept at 8%. The final concentration of the compound in reaction was: 1, 0.33, 0.11, 0.037, 0.012, 0.004, 0.0014, 0.00046 μM, and the final concentration of DMSO was 2%.

3) A mixture of kinase/peptide substrate: In 1.33× kinase buffer, the kinase and Z-LYTE™ Tyr 1 peptide substrate were diluted to 0.12 μg/mL and 4 μM, respectively, to prepare a mixture of kinase/peptide substrate. The mixture was mixed gently with a pipette.

4) A phosphorylated peptide substrate solution (PP solution): 0.4 μL of Z-LYTE™ Tyr1 phosphorylated peptide substrate was added to 99.6 μL of 1.33× kinase buffer.

5) ATP solution: 10 mM of ATP was diluted to 760 μM with 1.33× kinase buffer to prepare ATP solution.

6) Development solution: Development reagent B was diluted with Development buffer at a ratio of 1:200.

3. Methods

1) Kinase reaction (10 μL system)

2.5 μL of 4× test compound was added to each reaction well of the 384 plate, and the corresponding volume of 8% DMSO was added to the control well. The plate was placed on ice. 5 μL of a mixture of kinase/peptide substrate, 2.5 μL of kinase buffer and ATP solution were successively added to each well. Three control groups were set up: Group C1 contains only kinase buffer, group C2 contains the mixture of kinase/peptide substrate, kinase buffer and ATP, and group C3 contains 5 μL of PP solution. After adding the reaction components, the 384-well plate was sealed and incubated at 25-30° C. for 1 h in dark.

2) Development reaction

5 μL of Development solution was added to each well, sealed and incubated at 25-30° C. for another 1 h in dark.

3) Reaction stopping and plate reading

5 μL of stopping solution was added to each well. The Coumarin value (excitation at 400 nm, emission at 445 nm) and Fluorescein value (excitation at 400 nm, emission at 520 nm) were measured, respectively.

4. Data Analysis $$\% \text{ phosphorylation rate}=100\%-100\%\times[ER\times C3\ 520\ nm-C3\ 445\ nm]/[(C1\ 445\ nm-C3\ 445\ nm)+ER\times(C3\ 520\ nm-C1\ 520\ nm)]$$

wherein

ER (emission ratio): Coumarin emission read-out (445 nm)/Fluorescein emission read-out (520 nm);

C3 445 nm: 100% phosphorylated Coumarin emission read-out;

C3 520 nm: 100% phosphorylated Fluorescein emission read-out;

C1 445 nm: 0% phosphorylated Coumarin emission read-out;

C1 520 nm: 0% phosphorylated Fluorescein emission read-out.

$$\text{Inhibition rate \% (IR)}=[1-\% \text{ phosphorylation rate}_{test\ sample}/100\% \text{ phosphorylation rate}_{control}]\times 100\%$$

wherein

% phosphorylation rate$_{test\ sample}$: phosphorylation rate of the test compound;

100% phosphorylation rate$_{control}$: phosphorylation rate of C3 control group.

5. $IC_{50}$ values: calculated by using software XL-Fit™ (version 5.3) supplied by ID Business Solutions (Guildford, UK), which is an additional software to Microsoft Excel.

6. Test results

| Compound No. | $IC_{50}$ (μM) | Compound No. | $IC_{50}$ (μM) | Compound No. | $IC_{50}$ (μM) |
|---|---|---|---|---|---|
| 1 | 0.217 | 38 | 0.012 | 77 | 0.006 |
| 2 | 0.008 | 39 | 0.033 | 78 | 0.015 |
| 3 | 0.005 | 40 | 0.016 | 79 | 0.307 |
| 4 | 0.066 | 41 | 0.027 | 80 | 0.004 |
| 5 | 0.022 | 42 | 0.005 | 81 | 0.034 |
| 6 | 0.007 | 43 | 0.006 | 82 | 0.006 |
| 7 | 0.067 | 44 | 0.007 | 83 | 0.009 |
| 8 | 0.004 | 45 | 0.009 | 84 | 0.006 |
| 9 | 0.012 | 46 | 0.012 | 85 | 0.005 |
| 10 | 0.015 | 47 | 0.005 | 86 | 0.005 |
| 11 | 0.005 | 48 | 0.005 | 87 | 0.008 |
| 12 | 0.009 | 49 | 0.023 | 88 | 0.003 |
| 13 | 0.091 | 50 | 0.078 | 89 | 0.008 |
| 14 | 0.063 | 51 | 0.056 | 90 | 0.006 |
| 15 | 0.034 | 53 | 0.135 | 91 | 0.003 |
| 16 | 0.088 | 55 | 0.003 | 92 | 0.029 |
| 17 | 0.019 | 56 | 0.004 | 93 | 0.017 |
| 18 | 0.013 | 57 | 0.024 | 94 | 0.025 |
| 19 | 0.274 | 58 | 0.069 | 95 | 0.008 |
| 20 | 0.008 | 59 | 0.121 | 96 | 0.008 |
| 21 | 0.028 | 60 | 0.008 | 97 | 0.018 |
| 22 | 0.011 | 61 | 0.045 | 98 | 0.484 |
| 23 | 0.022 | 62 | 0.020 | 99 | 0.070 |

-continued

| Compound No. | $IC_{50}$ (μM) | Compound No. | $IC_{50}$ (μM) | Compound No. | $IC_{50}$ (μM) |
|---|---|---|---|---|---|
| 24 | 0.030 | 63 | 0.009 | 100 | 0.008 |
| 25 | 0.016 | 64 | 0.016 | 101 | 0.007 |
| 26 | 0.005 | 65 | 0.005 | 102 | 0.036 |
| 27 | 0.008 | 66 | 0.054 | 103 | 0.006 |
| 28 | 0.015 | 67 | 0.033 | 104 | 0.005 |
| 29 | 0.173 | 68 | 0.007 | 105 | 0.009 |
| 30 | 0.035 | 69 | 0.003 | 106 | 0.007 |
| 31 | 0.689 | 70 | 0.032 | 107 | 0.009 |
| 32 | 0.059 | 71 | 0.010 | 108 | 0.011 |
| 33 | 0.062 | 72 | 0.014 | 109 | 0.177 |
| 34 | 0.079 | 73 | 0.011 | 110 | 0.111 |
| 35 | 0.113 | 74 | 0.009 | 111 | 0.019 |
| 36 | 0.028 | 75 | 0.008 | 112 | 0.019 |
| 37 | 0.169 | 76 | 0.005 | 113 | 0.034 |
| 114 | 0.042 | 119 | 0.467 | 124 | 0.016 |
| 115 | 0.046 | 120 | 0.052 | 125 | 0.007 |
| 116 | 0.105 | 121 | 0.413 | 126 | 0.025 |
| 117 | 0.007 | 122 | 0.055 | 127 | 0.017 |
| 118 | 0.019 | 123 | 0.019 | 128 | 0.005 |
| 129 | 0.004 | 130 | 0.021 | 131 | 0.076 |
| 132 | 0.198 | 133 | 0.548 | 134 | 0.078 |
| 135 | 0.012 | | | | |

Example 4

Detection of CSF1R Phosphorylation Activity at Cell Level

1. Cell line

THP-1 (ATCC), human acute monocytic leukemia cells. The cells were cultured in an RPMI 1640 medium containing 10% FBS.

2. Reagents and instruments

Human phosphorylation-CSF1R ELISA kit: R&D, #DYC3268-2;

RPMI 1640 culture solution: GIBCO, 910491;

Human M-CSF recombinant cytokine: R&D, 9216-MC-500;

Cell lysis buffer: Cell Signal, 99803S;

1×PBS buffer (1 L): 8.0 g of NaCl, 0.2 g of KCl, 3.58 g of $Na_2HPO_4$-$12H_2O$, 0.24 g of $KH_2PO_4$ were dissolved in 1 L of dd $H_2O$, and the pH was adjusted to 7.4;

Blocking solution: PBS buffer containing 1% BSA;

PBST washing liquid: PBS buffer containing 0.05% Tween-20;

Chromogenic substrate: R&D, #DY999;

2N $H_2SO_4$;

Microwell plate reader: Labsystems Multiskan K3: Thermo; Envision: Perkin Elmer;

ELISA plate: Corning, #9018;

Cell culture plate: Facol, #353027.

3. Treatment of cells and preparation of lysis buffer

THP-1 cells were resuspended in RPMI-1640 culture solution containing 2% FBS, and the culture was added to a 96-well plate at a density of $5\times10^4$/well, 50 μL/well, and cultured in a cell incubator at 5% $CO_2$ and 37° C. overnight; The test compound was diluted with a serum-free RPMI-1640 medium to 3, 1.1, 0.37, 0.12, 0.04, 0.014, 0.005 and 0.002 μM, and the concentration of DMSO was 5%. 5 μL of the diluted compound was added to the 50 μL cell culture system, the culture was cultured in a 5% $CO_2$, 37° C. cell incubator for 60 min, 300 ng/mL of M-CSF was added to the cells, and the mixture was stimulated in the 37° C. cell incubator for 1 min, added 50 μL of cell lysis buffer, and stored in a refrigerator at −80° C.

4. ELISA detection steps

100 μL/well of the p-CSF1R capture antibody diluted to 0.8 μg/mL with PBS was added to the ELISA plate, and the plate was coated on a shaker at room temperature overnight. The culture was washed with PBST, and then added blocking solution and incubated at room temperature for 2 h. The culture was washed with PBST, added 90 μL of cell lysis buffer, and incubated on a shaker at 25° C. for 2 h. The plate was washed with PBST three times, added 100 μL of anti-p-tyrosine-HRP detection antibody diluted with 0.1% PBS-BSA diluent, and incubated on a shaker at 25° C. for 2 h. The plate was washed with PBST washing liquid, added 100 μL of chromogenic substrate and incubated at room temperature for 10-20 min. The reaction was stopped by adding 50 μL of 2N $H_2SO_4$. The optical density signal (450/570 nm) of each well was detected in Labsystems Multiskan K3 or Envision.

5. Data Analysis $$\text{Inhibition rate (\%)} = 100\% - \frac{\text{Drug-treated well read-out} - \text{background read-out}}{\text{Cell well read-out} - \text{background read-out}} \times 100\%$$

wherein

Drug-treated well read-out: indicating the optical density signal of a cell well with the test compound treatment.

Background read-out: indicating the optical density signal of a well without cells but with cell lysis buffer.

Cell well read-out: indicating the optical density signal of a cell well not treated with the compound.

6. Calculation of $IC_{50}$: obtained by using XL-Fit 5.3 software.

7. Test results

| Compound No. | $IC_{50}$ (μM) | Compound No. | $IC_{50}$ (μM) | Compound No. | $IC_{50}$ (μM) |
|---|---|---|---|---|---|
| 2 | 0.022 | 40 | 0.296 | 77 | 0.010 |
| 3 | 0.063 | 41 | 0.019 | 78 | 0.011 |
| 4 | 0.028 | 42 | 0.006 | 80 | 0.003 |
| 5 | 0.011 | 43 | 0.006 | 81 | 0.145 |
| 6 | 0.021 | 44 | 0.003 | 82 | 0.011 |
| 7 | 0.025 | 45 | 0.003 | 83 | 0.013 |
| 8 | 0.004 | 46 | 0.009 | 84 | 0.01 |
| 9 | 0.105 | 47 | 0.003 | 85 | 0.005 |
| 10 | 0.062 | 48 | 0.005 | 86 | 0.007 |
| 11 | 0.006 | 49 | 0.014 | 87 | 0.017 |
| 12 | 0.143 | 50 | 0.054 | 88 | 0.01 |
| 13 | 0.042 | 51 | 0.067 | 89 | 0.016 |
| 14 | 0.021 | 55 | 0.007 | 90 | 0.01 |
| 15 | 0.215 | 56 | 0.021 | 91 | 0.009 |
| 16 | 0.020 | 57 | 0.043 | 92 | 0.307 |
| 17 | 0.256 | 58 | 0.126 | 93 | 0.061 |
| 18 | 0.060 | 60 | 0.014 | 94 | 0.033 |
| 20 | 0.109 | 61 | 0.075 | 95 | 0.016 |
| 21 | 0.043 | 62 | 0.009 | 96 | 0.008 |
| 22 | 0.01 | 63 | 0.005 | 97 | 0.007 |
| 23 | 0.038 | 64 | 0.021 | 99 | 0.748 |
| 24 | 0.059 | 65 | 0.010 | 100 | 0.015 |
| 25 | 0.038 | 66 | 0.023 | 101 | 0.022 |
| 26 | 0.003 | 67 | 0.009 | 102 | 0.132 |
| 27 | 0.018 | 68 | 0.006 | 103 | 0.007 |
| 28 | 0.012 | 69 | 0.003 | 104 | 0.014 |
| 30 | 0.014 | 70 | 0.203 | 105 | 0.069 |
| 32 | 0.015 | 71 | 0.036 | 106 | 0.010 |
| 33 | 0.015 | 72 | 0.016 | 107 | 0.017 |
| 34 | 0.024 | 73 | 0.031 | 108 | 0.024 |
| 36 | 0.008 | 74 | 0.015 | 111 | 0.010 |
| 38 | 0.007 | 75 | 0.014 | 112 | 0.010 |
| 39 | 0.012 | 76 | 0.018 | 113 | 0.017 |

-continued

| Compound No. | $IC_{50}$ (μM) | Compound No. | $IC_{50}$ (μM) | Compound No. | $IC_{50}$ (μM) |
|---|---|---|---|---|---|
| 114 | 0.035 | 118 | 0.021 | 125 | 0.024 |
| 115 | 0.022 | 120 | 0.021 | 126 | 0.030 |
| 116 | 0.021 | 123 | 0.016 | 127 | 0.026 |
| 117 | 0.008 | 124 | 0.019 | 128 | 0.006 |
| 129 | 0.007 | 130 | 0.007 | 131 | 0.056 |
| 132 | 2.115 | 133 | >3 | 134 | 0.295 |

Example 5

Cell Proliferation Experiment

1. Cell line

Ba/F3$^{BCR\text{-}FMS\text{-}11}$, mouse primary B lymphocytes stably expressing the BCR-FMS fusion gene. The cells were cultured in an RPMI 1640 medium containing 10% FBS.

2. Reagents and instruments cckit-8 kit: Dojindo, 9 CK04;

Envision: Perkin Elmer;

Cell culture plate: Facol, 9353027.

3. Experimental steps

The BCR-FMS fusion gene was transfected into Ba/F3 cells, and the cell line Ba/F3$^{BCR\text{-}FMS\text{-}11}$ that stably expresses BCR-FMS and grows depending on CSF-1R was screened. Ba/F3$^{BCR\text{-}FMS\text{-}11}$ cell proliferation experiments is completed by using the Cell Counting kit cckit-8 in a 96-well plate. In a 96-well plate, 5000/well of Ba/F3$^{BCR\text{-}FMS\text{-}11}$ cells were inoculated at 100 μL/well. After 24 hours, the test compound was diluted to 10, 3.33, 1.11, 0.37, 0.12, 0.037, 0.012, and 0.004 μM, the concentration of DMSO was kept at 5%. 10 μL of the compound dilutions with the above 8 concentrations were added to the culture cell wells. The culture was incubated in a 37° C. and 5% $CO_2$ cell incubator for 72 hours. 10 μL of Cell Counting kit cckit-8 detection reagent was added to each well, and incubated at 37° C. and 5% $CO_2$ in a cell incubator for another 1 h. The optical density absorption value at 450 nm of each well was detected by using Perkin Elmer Envision instrument.

4. Data Analysis $$\text{Inhibition rate (\%)} = 100\% - \frac{\text{Drug-treated well read-out} - \text{background read-out}}{\text{Cell well read-out} - \text{background read-out}} \times 100\%$$

wherein

Drug-treated well read-out: indicating the optical density signal of a cell well with the test compound treatment.

Cell well read-out: indicating the optical density signal of a cell well not treated with the test compound (only 0.5% DMSO).

Background read-out: indicating the optical density signal of a well with the cell medium.

5. Calculation of $IC_{50}$: obtained by using XL-Fit 5.3 software.

6. Test results

| Compound No. | $IC_{50}$ (μM) | Compound No. | $IC_{50}$ (μM) | Compound No. | $IC_{50}$ (μM) |
|---|---|---|---|---|---|
| 2 | 0.011 | 40 | 0.046 | 77 | 0.005 |
| 3 | 0.012 | 41 | 0.052 | 78 | 0.011 |
| 4 | 0.060 | 42 | 0.006 | 80 | 0.005 |
| 5 | 0.047 | 43 | 0.005 | 81 | 0.143 |
| 6 | 0.015 | 44 | 0.006 | 82 | 0.009 |
| 7 | 0.039 | 45 | 0.009 | 83 | 0.007 |
| 8 | 0.007 | 46 | 0.02 | 84 | 0.008 |
| 9 | 0.107 | 47 | 0.006 | 85 | 0.007 |
| 10 | 0.088 | 48 | 0.005 | 86 | 0.007 |
| 11 | 0.006 | 49 | 0.024 | 87 | 0.006 |
| 12 | 0.066 | 50 | 0.112 | 88 | 0.008 |
| 13 | 0.231 | 51 | 0.097 | 89 | 0.008 |
| 14 | 0.044 | 55 | 0.005 | 90 | 0.002 |
| 15 | 0.493 | 56 | 0.008 | 91 | 0.003 |
| 16 | 0.045 | 57 | 0.012 | 92 | 0.567 |
| 17 | 0.072 | 58 | 0.179 | 93 | 0.013 |
| 18 | 0.057 | 60 | 0.015 | 94 | 0.142 |
| 20 | 0.044 | 61 | 0.087 | 95 | 0.014 |
| 21 | 0.073 | 62 | 0.032 | 96 | 0.010 |
| 22 | 0.014 | 63 | 0.008 | 97 | 0.015 |
| 23 | 0.045 | 64 | 0.040 | 99 | 0.534 |
| 24 | 0.037 | 65 | 0.008 | 100 | 0.015 |
| 25 | 0.066 | 66 | 0.055 | 101 | 0.031 |
| 26 | 0.01 | 67 | 0.025 | 102 | 0.151 |
| 27 | 0.008 | 68 | 0.012 | 103 | 0.009 |
| 28 | 0.014 | 69 | 0.004 | 104 | 0.006 |
| 30 | 0.024 | 70 | 0.225 | 105 | 0.084 |
| 32 | 0.099 | 71 | 0.051 | 106 | 0.007 |
| 33 | 0.058 | 72 | 0.007 | 107 | 0.035 |
| 34 | 0.125 | 73 | 0.017 | 108 | 0.012 |
| 36 | 0.023 | 74 | 0.012 | 111 | 0.008 |
| 38 | 0.017 | 75 | 0.007 | 112 | 0.022 |
| 39 | 0.063 | 76 | 0.004 | 113 | 0.048 |
| 114 | 0.079 | 118 | 0.006 | 125 | 0.017 |
| 115 | 0.038 | 120 | 0.039 | 126 | 0.028 |
| 116 | 0.201 | 123 | 0.025 | 127 | 0.011 |
| 117 | 0,009 | 124 | 0.011 | 128 | 0.002 |
| 129 | 0.002 | 130 | 0.015 | 131 | 0.396 |
| 132 | 1.189 | 133 | >3.3 | 134 | 0.526 |
| 135 | 0.007 | | | | |

The invention claimed is:

1. A compound of formula (I):

(I)

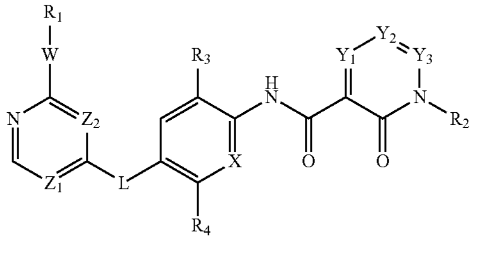

or a pharmaceutically acceptable salt thereof, and/or a deuterate, a solvate, a racemic mixture, an enantiomer, a diastereomer and a tautomer thereof, wherein X is N;

$Z_1$ and $Z_2$ are both CH;

$Y_1$ is $CR_7$; $Y_2$ is N; $Y_3$ is $CR_9$;

L is O;

W is absent;

$R_1$ is 5-12 membered heteroaryl, which is optionally substituted with one or more groups chosen from: halogen, $C_{1-6}$ alkyl, $C_{1-6}$ haloalkyl, —($C_{1-6}$ alkylene)$_n$-$NH_2$, —($C_{1-6}$ alkylene)$_n$-NH ($C_{1-6}$ alkyl), —($C_{1-6}$ alkylene)$_n$-N($C_{1-6}$ alkyl)$_2$, or —($C_{1-6}$ alkylene)$_n$-OH;

$R_2$ is $C_{1-6}$ alkyl;

$R_3$, $R_4$, and $R_7$ are each independently chosen from: hydrogen, halogen, $C_{1-6}$ alkyl, or —O ($C_{1-6}$ alkyl);

$R_9$ is hydrogen, $C_{1-6}$ alkyl, $C_{1-6}$ haloalkyl, or $C_{3-8}$ cycloalkyl;

n is 0 or 1.

2. The compound of claim 1, or a pharmaceutically acceptable salt thereof, and/or a deuterate, a solvate, a racemic mixture, an enantiomer, a diastereomer and a tautomer thereof, wherein $R_7$ is hydrogen, $C_{1-6}$ alkyl or —O ($C_{1-6}$ alkyl); $R_9$ is hydrogen, $C_{1-6}$ alkyl, $C_{1-6}$ haloalkyl or $C_{3-6}$ cycloalkyl.

3. The compound of claim 2, or a pharmaceutically acceptable salt thereof, and/or a deuterate, a solvate, a racemic mixture, an enantiomer, a diastereomer and a tautomer thereof, wherein $R_7$ is hydrogen; $R_9$ is hydrogen, $C_{1-6}$ alkyl or $C_{3-6}$ cycloalkyl.

4. The compound of claim 3, or a pharmaceutically acceptable salt thereof, and/or a deuterate, a solvate, a racemic mixture, an enantiomer, a diastereomer and a tautomer thereof, wherein $R_7$ is hydrogen; $R_9$ is hydrogen or methyl.

5. The compound of claim 1, or a pharmaceutically acceptable salt thereof, and/or a deuterate, a solvate, a racemic mixture, an enantiomer, a diastereomer and a tautomer thereof, wherein $R_1$ is pyrazolyl, pyrrolyl, furanyl, thienyl, pyridyl, thiazolyl, 1,2,3-triazolyl, 1,2,4-triazolyl, imidazolyl, or imidazo [1,2-a]pyridyl, each of which is optionally substituted with one or more groups chosen from: halogen, $C_{1-6}$ alkyl, $C_{1-6}$ haloalkyl, —($C_{1-6}$ alkylene)$_n$-$NH_2$, —($C_{1-6}$ alkylene)$_n$-NH ($C_{1-6}$ alkyl), —($C_{1-6}$ alkylene)$_n$-N ($C_{1-6}$ alkyl)$_2$ or —($C_{1-6}$ alkylene)$_n$-OH.

6. The compound of claim 1, or a pharmaceutically acceptable salt thereof, and/or a deuterate, a solvate, a racemic mixture, an enantiomer, a diastereomer and a tautomer thereof, wherein $R_1$ is furanyl, thienyl, pyridyl, thiazolyl, 1,2,3-triazolyl, 1,2,4-triazolyl, imidazolyl, or imidazo [1,2-a]pyridyl, each of which is optionally substituted with one or more $C_{1-6}$ alkyl.

7. The compound of claim 1 or a pharmaceutically acceptable salt thereof, and/or a deuterate, a solvate, a racemic mixture, an enantiomer, a diastereomer and a tautomer thereof, wherein $R_2$ is methyl, ethyl or i-propyl.

8. The compound of claim 1, or a pharmaceutically acceptable salt thereof, and/or a deuterate, a solvate, a racemic mixture, an enantiomer, a diastereomer and a tautomer thereof, wherein $R_3$ is hydrogen, or halogen; and $R_4$ is hydrogen.

9. The compound of formula (I) of claim 1, or a pharmaceutically acceptable salt thereof, which is chosen from:

| No. | Structural formula |
|---|---|
| 8 | 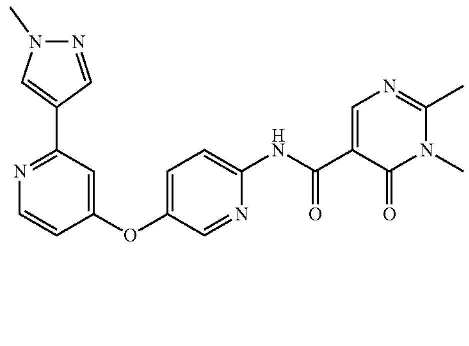 |

-continued
| No. | Structural formula |
| --- | --- |
| 10 | 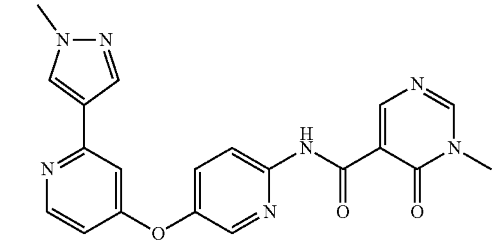 |
| 13 | 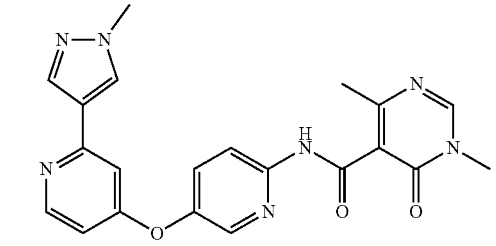 [SMILES: Cc1ncn(C)c(=O)c1C(=O)Nc1ccc(Oc2ccnc(-c3cnn(C)c3)c2)cn1] |
| 14 | 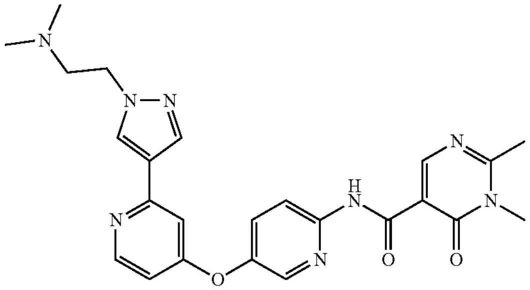 |
| 23 | 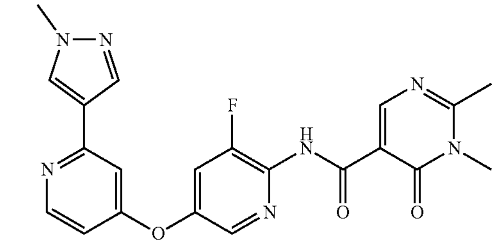 |
| 30 | 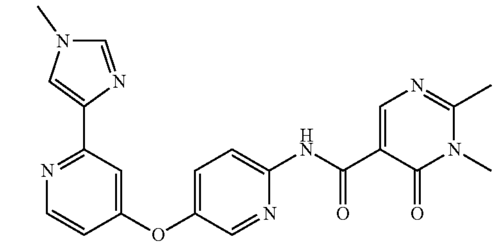 |
| 31 | 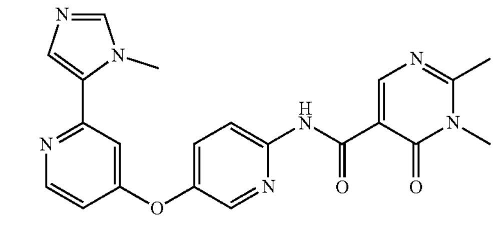 [SMILES: Cc1ncc(C(=O)Nc2ccc(Oc3ccnc(-c4cncn4C)c3)cn2)c(=O)n1C] |
-continued
| No. | Structural formula |
| --- | --- |
| 32 | 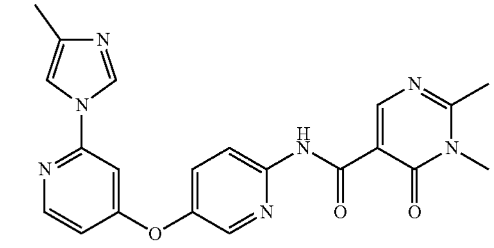 |
| 33 | 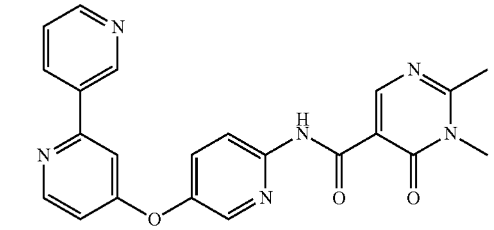 [SMILES: Cc1ncc(C(=O)Nc2ccc(Oc3ccnc(-c4cccnc4)c3)cn2)c(=O)n1C] |
| 34 | 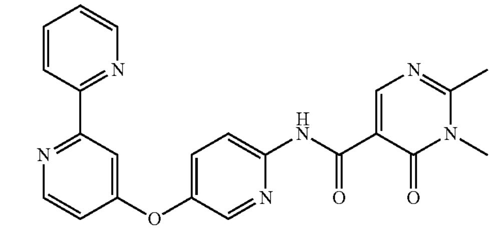 [SMILES: Cc1ncc(C(=O)Nc2ccc(Oc3ccnc(-c4ccccn4)c3)cn2)c(=O)n1C] |
| 38 | 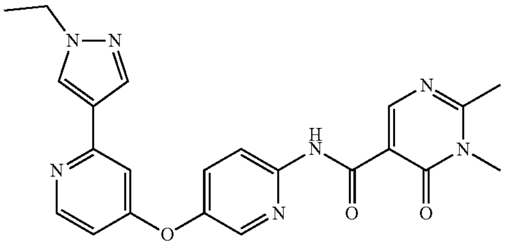 [SMILES: CCn1cc(-c2cc(Oc3ccc(NC(=O)c4cnc(C)n(C)c4=O)nc3)ccn2)cn1] |
| 39 | 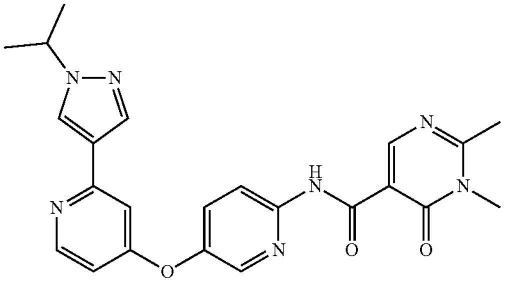 [SMILES: Cc1ncc(C(=O)Nc2ccc(Oc3ccnc(-c4cnn(C(C)C)c4)c3)cn2)c(=O)n1C] |
| 41 | 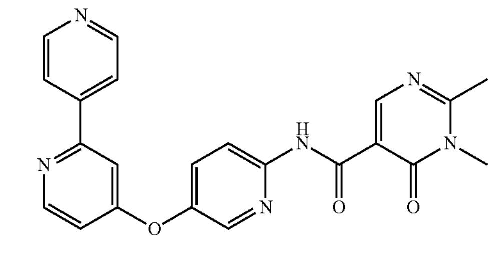 [SMILES: Cc1ncc(C(=O)Nc2ccc(Oc3ccnc(-c4ccncc4)c3)cn2)c(=O)n1C] |

-continued
| No. | Structural formula |
| --- | --- |
| 49 | 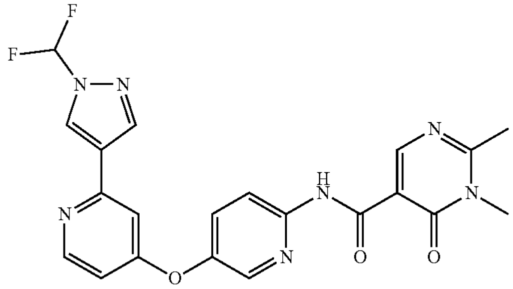 [SMILES: Cc1ncc(C(=O)Nc2ccc(Oc3ccnc(-c4cnn(C(F)F)c4)c3)cn2)c(=O)n1C] |
| 56 | 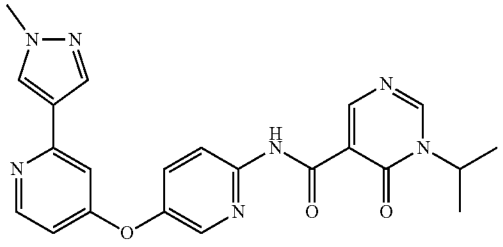 [SMILES: CC(C)n1cncc(C(=O)Nc2ccc(Oc3ccnc(-c4cnn(C)c4)c3)cn2)c1=O] |
| 62 | 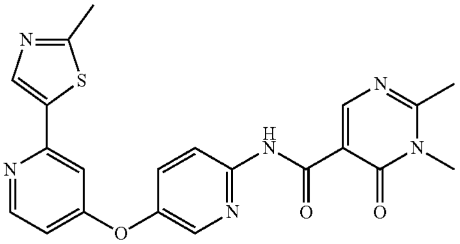 [SMILES: Cc1ncc(-c2cc(Oc3ccc(NC(=O)c4cnc(C)n(C)c4=O)nc3)ccn2)s1] |
| 64 | 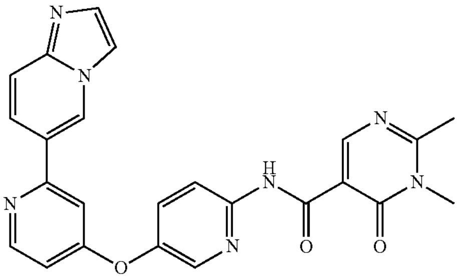 [SMILES: Cc1ncc(C(=O)Nc2ccc(Oc3ccnc(-c4ccc5nccn5c4)c3)cn2)c(=O)n1C] |
| 66 | 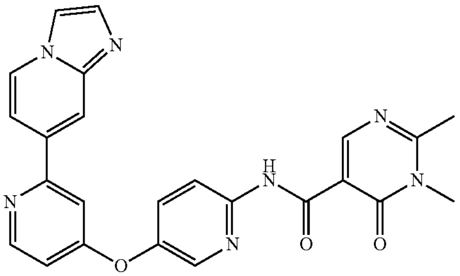 [SMILES: Cc1ncc(C(=O)Nc2ccc(Oc3ccnc(-c4ccn5ccnc5c4)c3)cn2)c(=O)n1C] |
| 73 | 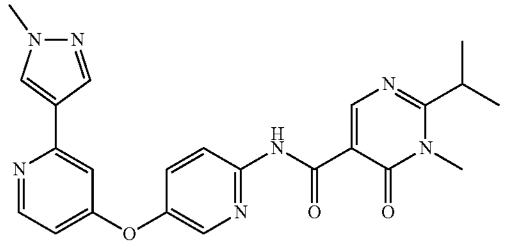 [SMILES: CC(C)c1ncc(C(=O)Nc2ccc(Oc3ccnc(-c4cnn(C)c4)c3)cn2)c(=O)n1C] |
| 74 | 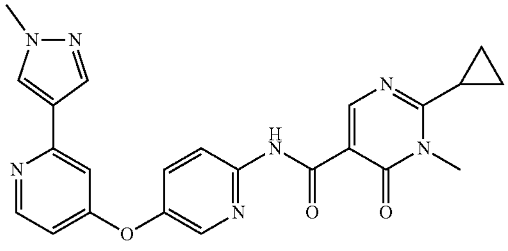 [SMILES: Cn1cc(-c2cc(Oc3ccc(NC(=O)c4cnc(C5CC5)n(C)c4=O)nc3)ccn2)cn1] |
| 109 | 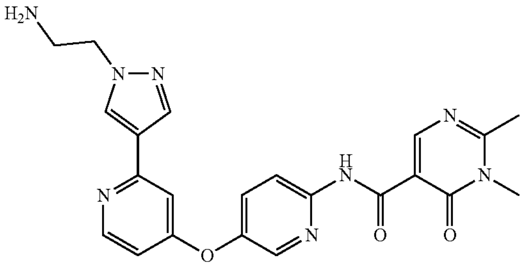 [SMILES: Cc1ncc(C(=O)Nc2ccc(Oc3ccnc(-c4cnn(CCN)c4)c3)cn2)c(=O)n1C] |
| 110 | 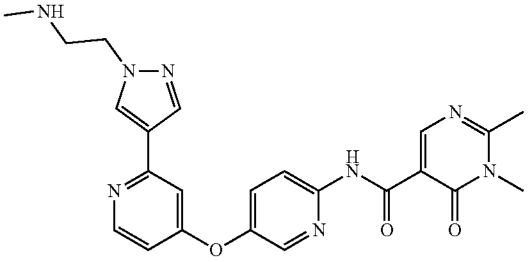 |
| 113 | 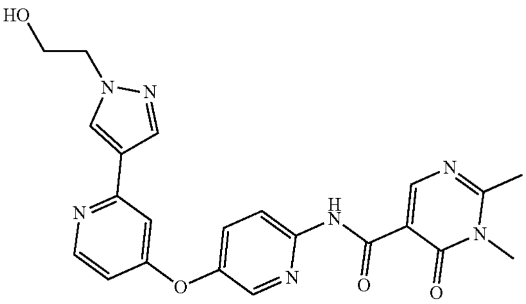 [SMILES: Cc1ncc(C(=O)Nc2ccc(Oc3ccnc(-c4cnn(CCO)c4)c3)cn2)c(=O)n1C] |
| 116 | 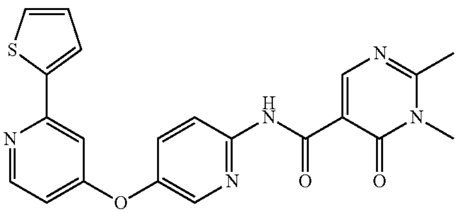 |

-continued

| No. | Structural formula |
|---|---|
| 117 | 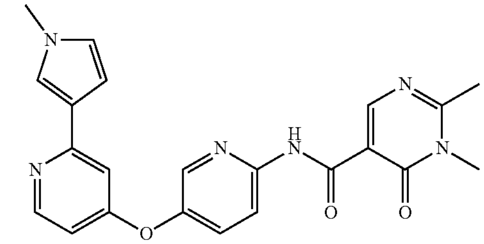 |
| 119 | 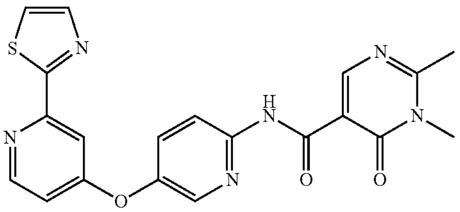 [SMILES: Cc1ncc(C(=O)Nc2ccc(Oc3ccnc(-c4nccs4)c3)cn2)c(=O)n1C] |
| 120 | 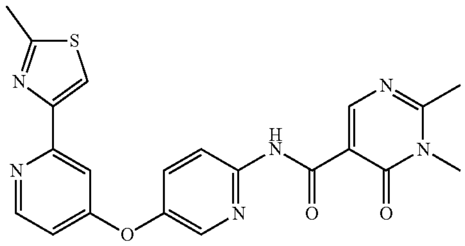 |
| 122 | 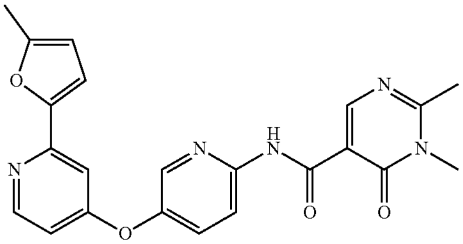 |
| 128 | 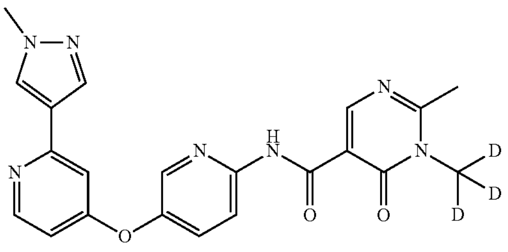 [SMILES: [2H]C([2H])([2H])n1c(C)ncc(C(=O)Nc2ccc(Oc3ccnc(-c4cnn(C)c4)c3)cn2)c1=O] |
| 129 | 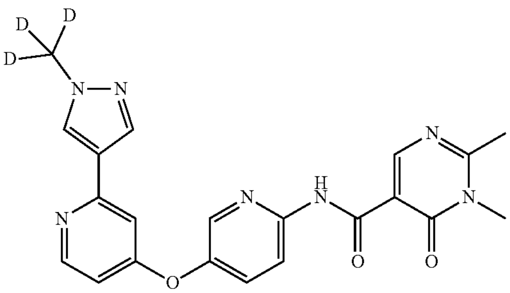 [SMILES: [2H]C([2H])([2H])n1cc(-c2cc(Oc3ccc(NC(=O)c4cnc(C)n(C)c4=O)nc3)ccn2)cn1] |

-continued

| No. | Structural formula |
|---|---|
| 130 | 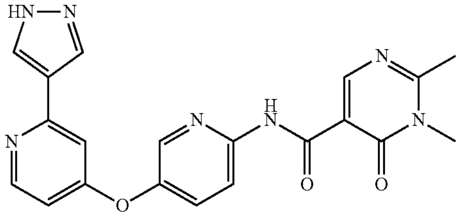 [SMILES: Cc1ncc(C(=O)Nc2ccc(Oc3ccnc(-c4cn[nH]c4)c3)cn2)c(=O)n1C] |
| 135 | 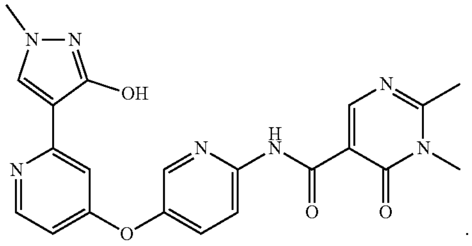 |

10. The compound of claim 1, or a pharmaceutically acceptable salt thereof, and/or a deuterate, a solvate, a racemic mixture, an enantiomer, a diastereomer and a tautomer thereof, wherein $R_1$ is pyrazolyl or pyrrolyl, each of which is optionally substituted with one or more groups chosen from: $C_{1-6}$ alkyl, $C_{1-6}$ haloalkyl, —($C_{1-6}$ alkylene)-$NH_2$, —($C_{1-6}$ alkylene)-NH ($C_{1-6}$ alkyl), —($C_{1-6}$ alkylene)-N($C_{1-6}$ alkyl)$_2$ or —($C_{1-6}$ alkylene)-OH.

11. The compound of claim 1, or a pharmaceutically acceptable salt thereof, and/or a deuterate, a solvate, a racemic mixture, an enantiomer, a diastereomer and a tautomer thereof, wherein $R_1$ is pyrazolyl or pyrrolyl, each of which is optionally substituted with one or more $C_{1-6}$ alkyl.

12. A pharmaceutical composition, comprising the compound of claim 1, or a pharmaceutically acceptable salt thereof, and optionally comprising a pharmaceutically acceptable excipient.

13. A combination, comprising the compound of claim 1, or a pharmaceutically acceptable salt thereof, and at least one additional therapeutic agent.

14. The combination of claim 13 wherein the additional therapeutic agent is selected from an anti-neoplastic agent, an immune checkpoint inhibitor or agonist, and a targeted therapeutic agent.

15. The combination of claim 14, wherein the antineoplastic agent is a chemotherapeutic agent.

16. A method of in vivo or in vitro inhibiting the activity of CSF-1R, comprising contacting CSF-1R with an effective amount of the compound of claim 1, or a pharmaceutically acceptable salt thereof.

17. A method of treating cancer in a subject, comprising administering to the subject in need thereof an effective amount of the compound of claim 1, or a pharmaceutically acceptable salt thereof.

18. The method of claim 17, wherein the cancer is chosen from solid tumor or hematologic malignancy.

19. The method of claim 17, wherein the cancer is chosen from ovarian cancer, lung cancer, brain tumor, tenosynovial giant cell tumor, gastrointestinal stromal tumor (GIST), gastric cancer, esophageal cancer, colon cancer, colorectal cancer, pancreatic cancer, prostate cancer, breast cancer, cervical cancer, melanoma, mesothelioma, mesothelial carcinoma, renal cancer, liver cancer, thyroid carcinoma, head and neck cancer, urothelial carcinoma, bladder cancer, endometrial cancer, choriocarcinoma, adrenal carcinoma, sarcoma, leukemia, lymphoma or myeloma.

20. The method of claim 17, wherein the cancer is chosen from non-small cell lung cancer and glioblastoma.

* * * * *